(12) United States Patent
Hull et al.

(10) Patent No.: US 11,981,953 B2
(45) Date of Patent: May 14, 2024

(54) METHOD TO SCREEN COMPOUNDS FOR ANTIFUNGAL ACTIVITY AND PHARMACEUTICAL COMPOSITIONS AND METHODS TO TREAT FUNGAL DISEASES BY INHIBITING SPORE GERMINATION

(71) Applicant: WISCONSIN ALUMNI RESEARCH FOUNDATION, Madison, WI (US)

(72) Inventors: Christina Marie Hull, Middleton, WI (US); Mingwei Huang, Madison, WI (US); Sebastien Claude Ortiz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1447 days.

(21) Appl. No.: 16/369,939

(22) Filed: Mar. 29, 2019

(65) Prior Publication Data
US 2019/0300926 A1 Oct. 3, 2019

Related U.S. Application Data

(60) Provisional application No. 62/649,802, filed on Mar. 29, 2018.

(51) Int. Cl.
| | |
|---|---|
| *C12Q 1/18* | (2006.01) |
| *A01N 33/10* | (2006.01) |
| *A01N 37/44* | (2006.01) |
| *A01N 41/12* | (2006.01) |
| *A01N 47/40* | (2006.01) |
| *A61K 31/137* | (2006.01) |
| *A61K 31/145* | (2006.01) |
| *A61K 31/155* | (2006.01) |
| *A61K 31/24* | (2006.01) |
| *A61P 31/10* | (2006.01) |
| *C12Q 1/66* | (2006.01) |

(52) U.S. Cl.
CPC ............... *C12Q 1/18* (2013.01); *A01N 33/10* (2013.01); *A01N 37/44* (2013.01); *A01N 41/12* (2013.01); *A01N 47/40* (2013.01); *A61K 31/137* (2013.01); *A61K 31/145* (2013.01); *A61K 31/155* (2013.01); *A61K 31/24* (2013.01); *A61P 31/10* (2018.01); *C12Q 1/66* (2013.01); *G01N 2333/375* (2013.01)

(58) Field of Classification Search
CPC ....................................................... C12Q 1/18
See application file for complete search history.

(56) References Cited

U.S. PATENT DOCUMENTS

2005/0119306 A1* 6/2005 Trail ...................... C12N 15/80
435/32

FOREIGN PATENT DOCUMENTS

| EP | 0174477 A1 * | 3/1986 | ............... C12Q 1/18 |
| WO | WO-0029610 A1 * | 5/2000 | ........... G01N 33/533 |

OTHER PUBLICATIONS

Huang ("Protein Composition of Infectious Spores Reveals Novel Sexual Development and Germination Factors in Cryptococcus" PLoS Genet 11(8), 2015, 1-28) (Year: 2015).*
Abhyankar ("Spore proteomics: the past, present and the fucture" FEMS Microbiol Lett, 2014, 358, 137-144. (Year: 2014).*
Zhao, (Cytological adn proteomic analyses of horsetail (*Equisetum arvense* L.) spore germination), Fronteirs in Plant Science, 2015, 17:44, 1-20) (Year: 2015).*
Alspaugh JA, Perfect JR, Heitman J. (1998) "Signal transduction pathways regulating differentiation and pathogenicity of *Cryptococcus neoformans*," Fungal Genet Biol. 25:1-14 (pmid:9806801).
Barkal LJ, Walsh NM, Botts MR, Beebe DJ, Hull CM. 2016. Leveraging a high resolution microfluidic assay reveals insights into pathogenic fun- gal spore germination. Integr Biol 8:603-615. https://doi.org/10.1039/c6ib00012f.
Botts et al., Isolation and characterization of Cryptococcus neoformans spores reveal a critical role for capsule biosynthesis genes in spore biogenesis. Eukaryotic Cell. Apr. 2009; 8(4):595-605. doi: 10.1128/EC.00352-08.
Davidson RC, Blankenship JR, Kraus PR, De J Berrios M, Hull CM, D'Souza C, et al., A PCR-based strategy to generate integrative targeting alleles with large regions of homology. *Microbiology*. 2002; 148: 2607-2615. PMID: 12177355.
Giles SS, Dagenais TRT, Botts MR, Keller NP, Hull CM (2009) "Elucidating the pathogenesis of spores from the human fungal pathogen *Cryptococcus neoformans*," Infect Immun 77(8):3491-3500 (pmid:19451235).

(Continued)

*Primary Examiner* — Robert J Yamasaki
*Assistant Examiner* — Charles Z Constantine
(74) *Attorney, Agent, or Firm* — Joseph T. Leone; DeWitt LLP

(57) ABSTRACT

A method of testing compounds for activity to inhibit germination of spores. The method includes the steps of providing bacterial, fungal, or plant spores transformed to contain and express a detectable marker, wherein the marker when expressed, is operationally linked to a spore-specific or yeast-specific protein, in a medium and under environmental conditions in which the spores will germinate, and measuring a first signal output generated by the marker prior to the spores initiating germination; contacting the spores of step (a) with a compound whose activity to inhibit germination of spores is to be measured; incubating the spores of step (b) under environmental conditions and for a time wherein spores not treated with the compound will germinate; and determining extent of germination of the spores by measuring a second signal output generated by the marker, wherein a difference between the first signal output and the second signal output is proportional to the extent of germination of the spores. Also described are compositions of matter for inhibiting spore germination in vitro and in vivo.

16 Claims, 13 Drawing Sheets
Specification includes a Sequence Listing.

(56) References Cited

OTHER PUBLICATIONS

Handbook of Pharmaceutical Salts, Properties, Selection, and Use, P.H. Stahl and C.G. Wermuch, Eds., © 2008, Wiley-VCH (Zurich, Switzerland), ISBN: 978-3-90639-058-1 (Book—Copy Not Provided).

Huang M, Hebert AS, Coon JJ, Hull CM, (2015) Protein Composition of Infectious Spores Reveals Novel Sexual Development and Germination Factors in *Cryptococcus*, PLoS Genet 11(8): e1005490 (https://doi.org/10.1371/journal.pgen.1005490).

Kwon-Chung KJ, Edman JC, Wickes BL, (1992) "Genetic association of mating types and virulence in *Cryptococcus neoformans*," *Infect Immun*.60:602-605 (pmid:1730495).

Moore TD, Edman JC, (1993) "The alpha-mating type locus of *Cryptococcus neoformans* contains a peptide pheromone gene," *Mol Cell Biol*. 13:1962-1970 (pmid:8441425).

Rajasingjam R, Smith RM, Park BJ, Jarvis JM, Govender N, Chiller TM, Denning DW, Loyse A, Boulware DR, (2017) "Global burden of disease of HIV-associated cryptococcal meningitis: and updated analysis" *Lancet Infectious Disease* 17: 873-881 (pmid:2848341).

Sherman F, Fink GR, Hicks JB. Laboratory course manual for methods in yeast genetics. Cold Spring Harbor Laboratory; 1987 (Book—Copy Not Provided).

Sherman F. (2002) "Getting started with yeast," *Methods Enzymol*. 350:3-41(pmid:12073320).

Toffaletti DL, Rude TH, Johnston SA, Durack DT, Perfect JR. Gene transfer in Cryptococcus neoformans by use of biolistic delivery of DNA. *J Bacteriol*. 1993; 175: 1405-1411. PMID: 8444802.

Velagapudi R, Hsueh Y-P, Geunes-Boyer S, Wright JR, Heitman J, (2009) "Spores as infectious propagules of *Cryptococcus neoformans*," *Infect Immun*. 77:4345-4355 (pmid:19620339).

Walsh NM, Wuthrich M, Wang H, Klein B, and Hull CM. 2017. Characterization of C-type lectins reveals an unexpectedly limited interaction between *Cryptococcus neoformans* spores and Dectin-1. *PloS One* 12(3):e0173866.

\* cited by examiner

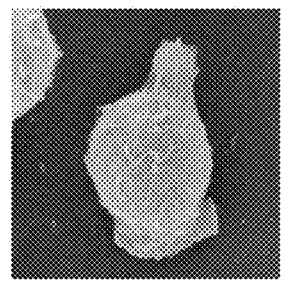
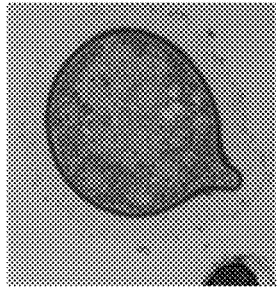
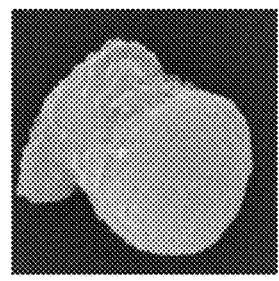
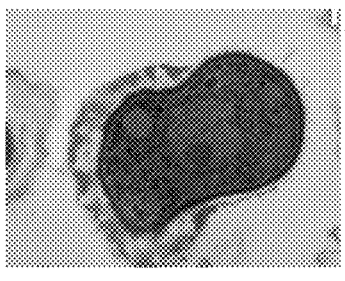
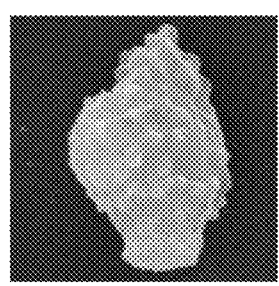
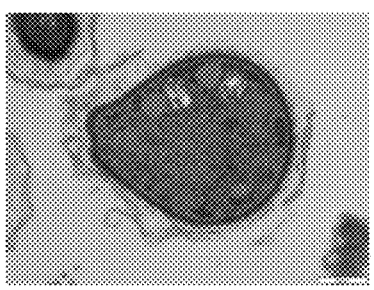
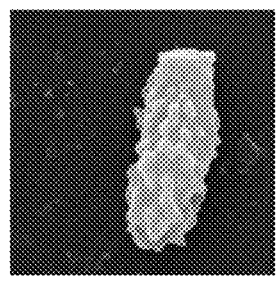
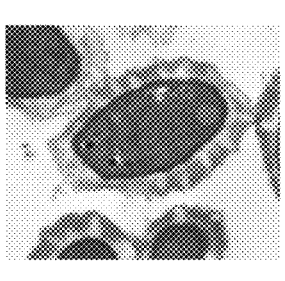
FIG. 2A
FIG. 2B

METHOD TO SCREEN COMPOUNDS FOR ANTIFUNGAL ACTIVITY AND PHARMACEUTICAL COMPOSITIONS AND METHODS TO TREAT FUNGAL DISEASES BY INHIBITING SPORE GERMINATION

CROSS-REFERENCE TO RELATED APPLICATIONS

Priority is hereby claimed to provisional application Ser. No. 62/649,802, filed Mar. 29, 2018, which is incorporated herein by reference.

FEDERAL FUNDING STATEMENT

This invention was made with government support under AI089370 awarded by the National Institutes of Health. The government has certain rights in the invention.

BACKGROUND

Spores are an essential cell type required for long-term survival across diverse organisms and are a hallmark of fungal reproduction, persistence, and dispersal. Among human fungal pathogens, spores are presumed infectious particles, but relatively little is known about this robust cell type. Sporulation enables a relative quiescence—a type of hibernation—that contributes to the survival of fungi. However, sporulation also requires a transition back into a vegetative form so that the fungi can replicate—i.e., germination. Germination, despite its central importance in fungal reproduction and pathology in plants and animals, is not well understood.

Spores are a particularly successful cell type used by many microorganisms, including bacteria, fungi, and protozoa to survive unsuitable growth conditions and/or to disperse to new environments. Among eukaryotes, some of the most environmentally resistant spores are those of fungi, and much of our current understanding of spores comes from studies in model fungi such as *Saccharomyces cerevisiae* and *Aspergillus nidulans*. There are two general categories of fungal spores—sexual and asexual, and both forms occur across diverse fungal species via myriad developmental strategies. For example, in the budding yeast *S. cerevisiae* sexual spores are formed when yeast diploids are subject to nitrogen starvation and a non-fermentable carbon source, resulting in four haploid ascospores; *S. cerevisiae* does not produce asexual spores. In contrast, the filamentous fungus *Aspergillus nidulans* produces both asexual and sexual spores via the development of multicellular fruiting structures with thousands of spores per structure. In all instances, however, spores are adapted for general survivability.

As a consequence, fungal spores share three basic characteristics: First, mature spores are relatively metabolically quiescent, allowing them to remain dormant for long periods of time under sub-optimal growth conditions (e.g. in the absence of nutrients). Second, spores are resistant to environmental stresses, such as high temperatures, desiccation, and UV radiation, thus facilitating long-term survival and/or dispersal across great distances. Third, upon encountering growth-promoting environments, spores rapidly escape quiescence and germinate to resume vegetative growth. As a result, fungi are ubiquitous across all ecosystems on earth.

Spore-producing fungi commonly generate spores with thick, protective coats and robust stress resistance. Spores respond to different environmental signals to initiate germination, depending on their adapted niches. For example, spores of *S. cerevisiae* germinate readily in response to the presence of a fermentable carbon source. In contrast, spores of *Talaromyces macrosporus* require nutrients and a rigorous external trigger of very high temperature or pressure. These triggers generally result in responses such as water uptake, cell wall remodeling, and activation of nutrient metabolism and protein synthesis, leading to active fungal growth.

The transition from dormant particle to actively growing cell is particularly important because fungal survival cannot occur in the absence of the ability to germinate when (and only when) appropriate for vegetative growth. Environmental fungi are well adapted to their niches, and interestingly, these adaptations have led to a handful of fungi with the ability to cause life-threatening diseases in humans. *Histoplasma capsulatum, Blastomyces dermatitidis, Aspergillus fumigatus, Coccidioides immitis, Sporothrix schenkii, Penicillium marneffei,* and *Cryptococcus neoformans* are the most common environmental fungi that can cause disease in humans. The general route of infection is by inhaling cells from environmental sources. Spores (sexual or asexual, depending on the fungus) are the most likely infectious particles for all of these pathogens; however, very little is known about their basic spore biology, making the development of disease prevention and treatment strategies challenging.

Among human fungal pathogens, the most common cause of fatal fungal disease (and a well-developed model for study) is *Cryptococcus neoformans*, a primarily opportunistic pathogenic yeast that causes meningoencephalitis. People with AIDS are particularly susceptible, and there are an over 200,000 cases and nearly as many deaths annually worldwide from cryptococcosis. Rajasingjam R, Smith R M, Park B J, Jarvis J M, Govender N, Chiller T M, Denning D W, Loyse A, Boulware D R (2017) "Global burden of disease of HIV-associated cryptococcal meningitis: and updated analysis" *Lancet Infectious Disease* 17: 873-881 (pmid:2848341). *C. neoformans* is ubiquitous in the environment, and inhalation of aerosolized spores and/or yeast is the most common route of infection of humans. Under laboratory conditions, spores are produced through sexual development between haploid yeast of opposite mating types (a and α) or by α fruiting. In response to specific environmental conditions, cells form filaments and fruiting bodies (basidia) from which haploid, recombinant spores bud in chains.

Spores of *C. neoformans* exhibit the fundamental properties of most fungal spores, such as stability in the absence of nutrients and resistance to a variety of environmental stresses, including high temperature, desiccation, and oxidative stress. These spores have also been shown to germinate efficiently and synchronously in response to nutrients, and they germinate and cause disease in a mouse inhalation model of infection. See Velagapudi R, Hsueh Y-P, Geunes-Boyer S, Wright J R, Heitman J (2009) "Spores as infectious propagules of *Cryptococcus neoformans*," *Infect Immun.* 77:4345-4355 (pmid:19620339) and Giles S S, Dagenais T R T, Botts M R, Keller N P, Hull C M (2009) "Elucidating the pathogenesis of spores from the human fungal pathogen *Cryptococcus neoformans*," *Infect Immun* 77:3491-3500 (pmid:19451235). These findings indicate that *C. neoformans* spores harbor intrinsic properties that facilitate survival in the environment, maintain spore viability and stability, and initiate germination in response to external signals, including those of a mammalian host.

Current antifungal therapeutics are relatively limited because of high toxicity or insufficient efficacy. These issues arise because, unlike bacteria, fungi are eukaryotes. Thus, fungi are far more similar (metabolically and biochemically)

to plants and animals than are bacteria. In short, compounds that interfere with fungal biology or are toxic to fungi, tend also to interfere with or be toxic to humans and animals.

A comparatively small number of antifungal compounds are approved for human, veterinary, and agricultural use in the United States. Focusing on antifungal drugs approved for use in humans, the gold standard by which all other antifungal pharmaceuticals are measured in terms of systemic antifungal activity is the polyene amphotericin B, first marketed in 1955. It is widely used to treat life-threatening fungal infections such as invasive mucormycosis, cryptococcal meningitis, aspergillosis, and candidiasis. While highly effective against fungi, amphotericin B itself has a slew of well-known and potentially life-threatening side effects. When administered intravenously, amphotericin B typically induces a debilitating set of symptoms, including high fever, shaking chills, hypotension, anorexia, nausea, vomiting, headache, dyspnea and tachypnea, drowsiness, and generalized weakness. Kidney damage is a commonly reported side effect. As a result, amphotericin B is administered with very close monitoring of the patient by healthcare professionals.

Other antifungal compounds approved for use in humans include imidazoles (e.g., miconazole), triazoles (e.g., fluconazole), and thiazole antifungals (e.g., abafungin). Most of these types of antifungal compounds, however, are used topically, rather than systemically. They are much less toxic that amphotericin B, but not as efficacious.

Echinocandins are a much newer class of systemic antifungal compounds approved for use in humans. The echinocandins are macrocyclic lipopeptides. Their structure is characterized by (typically) a 6-mer macrocyclic peptoid moiety bonded to a long (e.g., >C10) hydrocarbon tail. Echinocandins inhibit the synthesis of glucan in the cell wall of fungi via noncompetitive inhibition of the enzyme 1,3-β glucan synthase. In this sense, they exert a pharmacological activity against fungi that is analogous to the pharmacological activity of beta-lactam antibiotics against bacteria. Echinocandins are also far less toxic than amphotericin B, but again, not as effective.

Thus, there remains a long-felt and unmet need for a method to test new and existing compounds for their ability to inhibit fungal growth.

SUMMARY

While vegetative fungi are similar metabolically and biochemically to other eukaryotic cells, fungi also sporulate and germinate. Thus, chemical inhibitors of fungal germination are potentially highly useful compounds in antifungal compositions (i.e., human and veterinary pharmaceuticals, topical and systemic pharmaceuticals, and agricultural and industrial fungicides). Thus, disclosed herein is a fluorescence-based quantitative germination assay suitable for high throughput screening. Using the subject germination assay, a screening of a 75,000-compound library yielded 108 germination-inhibiting compounds. Some of these compounds exhibited specific activity to inhibit germination of *Cryptococcus* spores (as contrasted to inhibiting vegetative cell growth). This indicates that germination itself is an effective target in developing antifungal drugs for prophylactic use in at-risk patients.

Thus, disclosed hererin is a method of testing compounds for activity to inhibit germination of spores. The method comprises providing bacterial, fungal, or plant spores transformed to contain and express a detectable marker, wherein the marker is operationally linked to a spore-specific or yeast-specific protein, in a medium and under environmental conditions in which the spores will germinate, and measuring a first signal output generated by the marker prior to the spores initiating germination. The spores are then contacted with a compound whose activity to inhibit germination of spores is to be measured. The spores are then incubated under environmental conditions and for a time wherein spores not treated with the compound will germinate. The extent of germination of the spores is determined by measuring a second signal output generated by the marker, wherein a difference between the first signal output and the second signal output is proportional to the extent of germination of the spores.

In certain versions of the method, the marker is operationally linked to a spore-specific protein selected from the group consisting of XP_567740.1 (SEQ. ID. NO: 2), XP_566791.1 (SEQ. ID. NO: 4), XP_570303.1 (SEQ. ID. NO: 6), XP_571089.1 (SEQ. ID. NO: 8), XP_571997.1 (SEQ. ID. NO: 10), XP_569295.1 (SEQ. ID. NO: 12), XP_569173.1 (SEQ. ID. NO: 14), XP_569068.1 (SEQ. ID. NO: 16), XP_569336.1 (SEQ. ID. NO: 18), XP_567136.1 (SEQ. ID. NO: 20), XP_568990.1 (SEQ. ID. NO: 22), XP_570610.1 (SEQ. ID. NO: 24), XP_571921.1 (SEQ. ID. NO: 26), XP_572925.1 (SEQ. ID. NO: 28), XP_570796.1 (SEQ. ID. NO: 30), XP_571548.1 (SEQ. ID. NO: 32), XP_570447.1 (SEQ. ID. NO: 34), and XP_571343.1 (SEQ. ID. NO: 36).

Another version of the method comprises the steps described previously, and further comprising plotting the area and aspect ratio of the spores and any germinated cells after the incubation of step (c). Because spores tend to be smaller and have a more oblong aspect ratio than do germinated, vegetative cells, the extent of germination can be determined by measuring the distribution of the cells' area versus aspect ratio. Again, in this version of the method, the marker, if present, is operationally linked to a spore-specific protein selected from the group consisting of XP_567740.1 (SEQ. ID. NO: 2), XP_566791.1 (SEQ. ID. NO: 4), XP_570303.1 (SEQ. ID. NO: 6), XP_571089.1 (SEQ. ID. NO: 8), XP_571997.1 (SEQ. ID. NO: 10), XP_569295.1 (SEQ. ID. NO: 12), XP_569173.1 (SEQ. ID. NO: 14), XP_569068.1 (SEQ. ID. NO: 16), XP_569336.1 (SEQ. ID. NO: 18), XP_567136.1 (SEQ. ID. NO: 20), XP_568990.1 (SEQ. ID. NO: 22), XP_570610.1 (SEQ. ID. NO: 24), XP_571921.1 (SEQ. ID. NO: 26), XP_572925.1 (SEQ. ID. NO: 28), XP_570796.1 (SEQ. ID. NO: 30), XP_571548.1 (SEQ. ID. NO: 32), XP_570447.1 (SEQ. ID. NO: 34), and XP_571343.1 (SEQ. ID. NO: 36), Also disclosed herein are antifungal compositions and method of using them as topical and systemic fungicides for industrial, agricultural, and pharmaceutical uses. Disclosed herein is a composition of matter for inhibiting germination of fungal spores, the composition comprising a spore germination-inhibiting concentration of a compound selected from the group consisting of

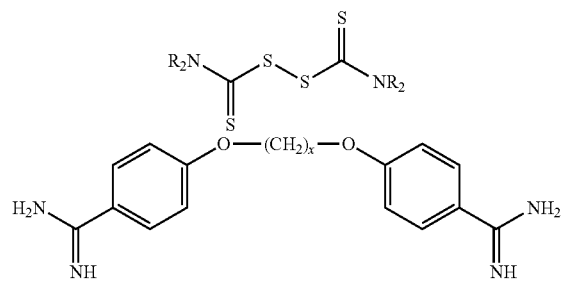

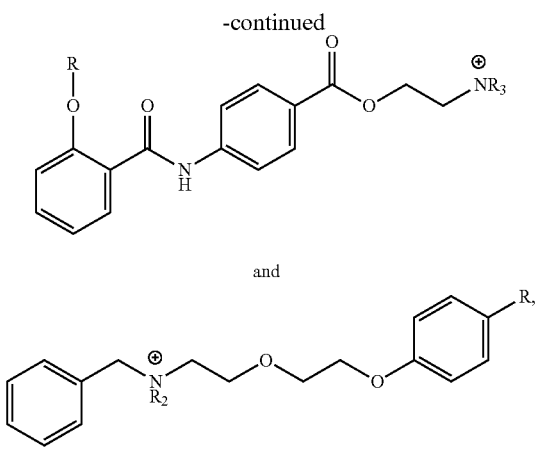

and salts thereof, in combination with a vehicle.

Also disclosed herein is a pharmaceutical composition for inhibiting fungal infection in mammals (as well as the corresponding method of inhibiting topical or systemic fungal infections in mammals, including humans), the composition comprising a spore germination-inhibiting amount of a compound selected from the group consisting of:

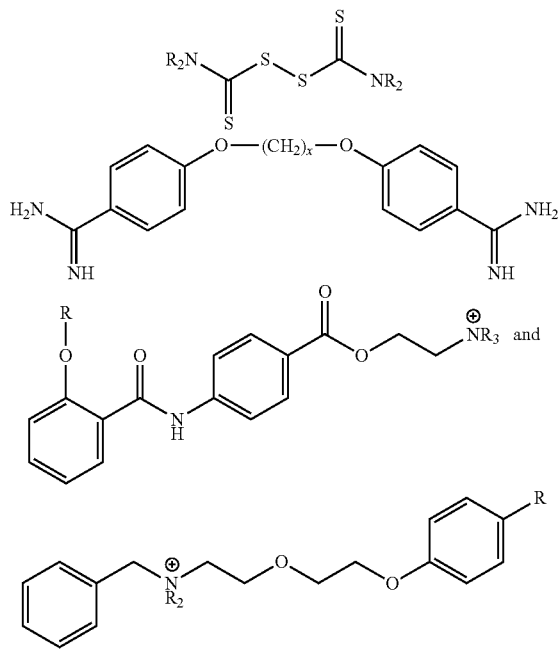

wherein R is linear or branched $C_{1-12}$ alkyl and "x" is an integer of from 1 to 12, and salts thereof, in combination with a pharmaceutically suitable vehicle.

BRIEF DESCRIPTION OF THE DRAWINGS

FIG. 2A is a series of scanning electron micrographs showing morphological transitions during germination. The germinating spore is false-colored green; the emerging yeast wall is false-colored yellow, and the resulting daughter cell is false-colored orange. Bar=1 μm for 0, 4, and 8 Hr; bar=2 μm for 12 Hr.

FIG. 2B is a series of micrographs analogous to those in FIG. 2A using transmission electron microscopy rather than scanning electron microscopy. Bars=500 nm.

Figure 7A:
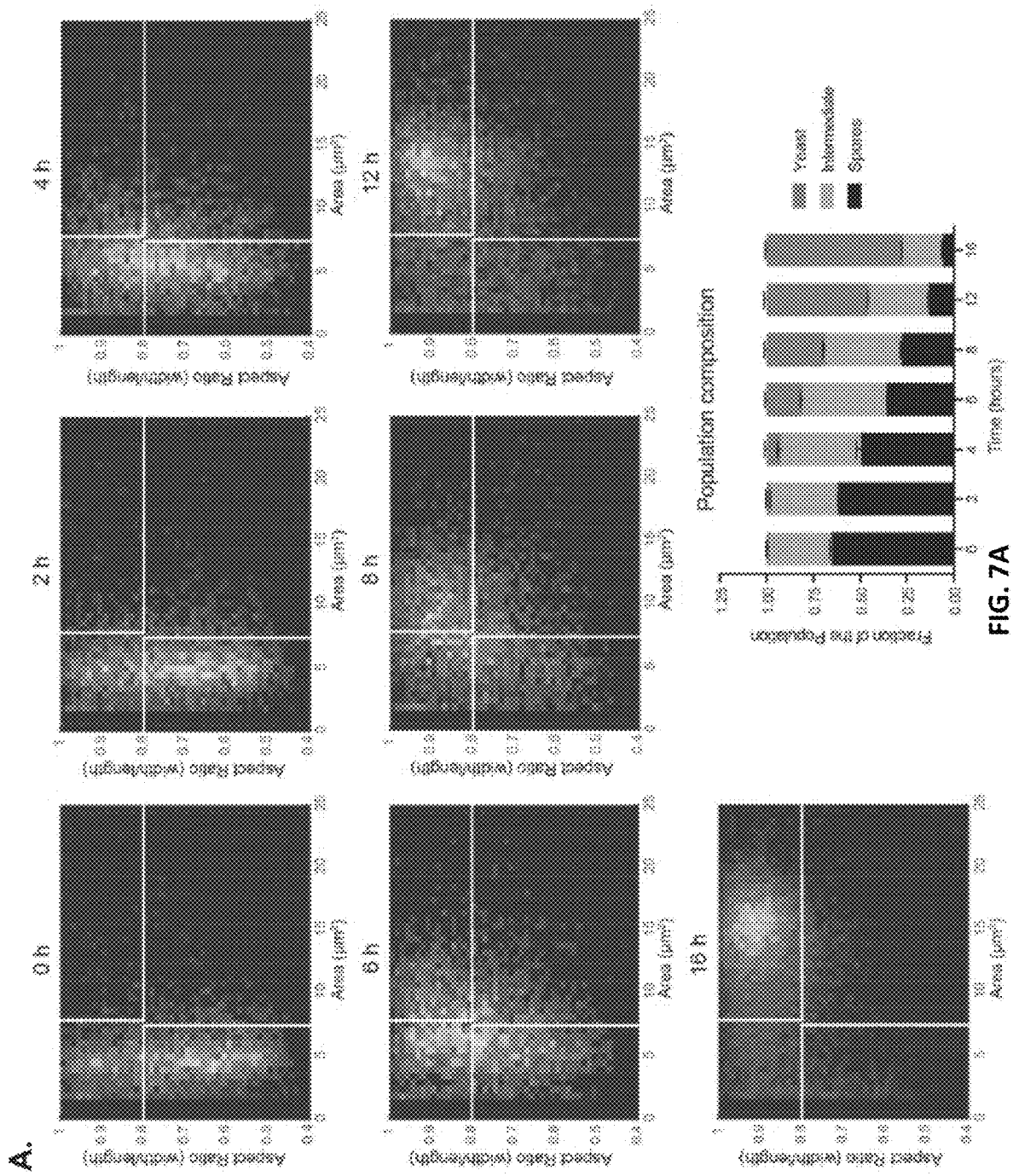
FIG. 7A depicts a series of photographic analyses showing that germination in microscale devices as described herein can be determined by cell area versus aspect ratio.

Thus, each panel in FIG. 7A depicts the germination dynamics of spores visualized by 2D histograms of cell area vs. aspect ratio. Data are also shown as a stacked bar plot of the population composition over time (at lower right). Colors are normalized on each plot such that yellow represents the area and aspect ratio combination with the most cells observed and dark blue represents area and aspect ratio combinations that were not observed. Cells in the lower left quadrant are defined as spores; cells in the upper right quadrant as yeast; all remaining cells are classified as intermediates.

Figure 7B:
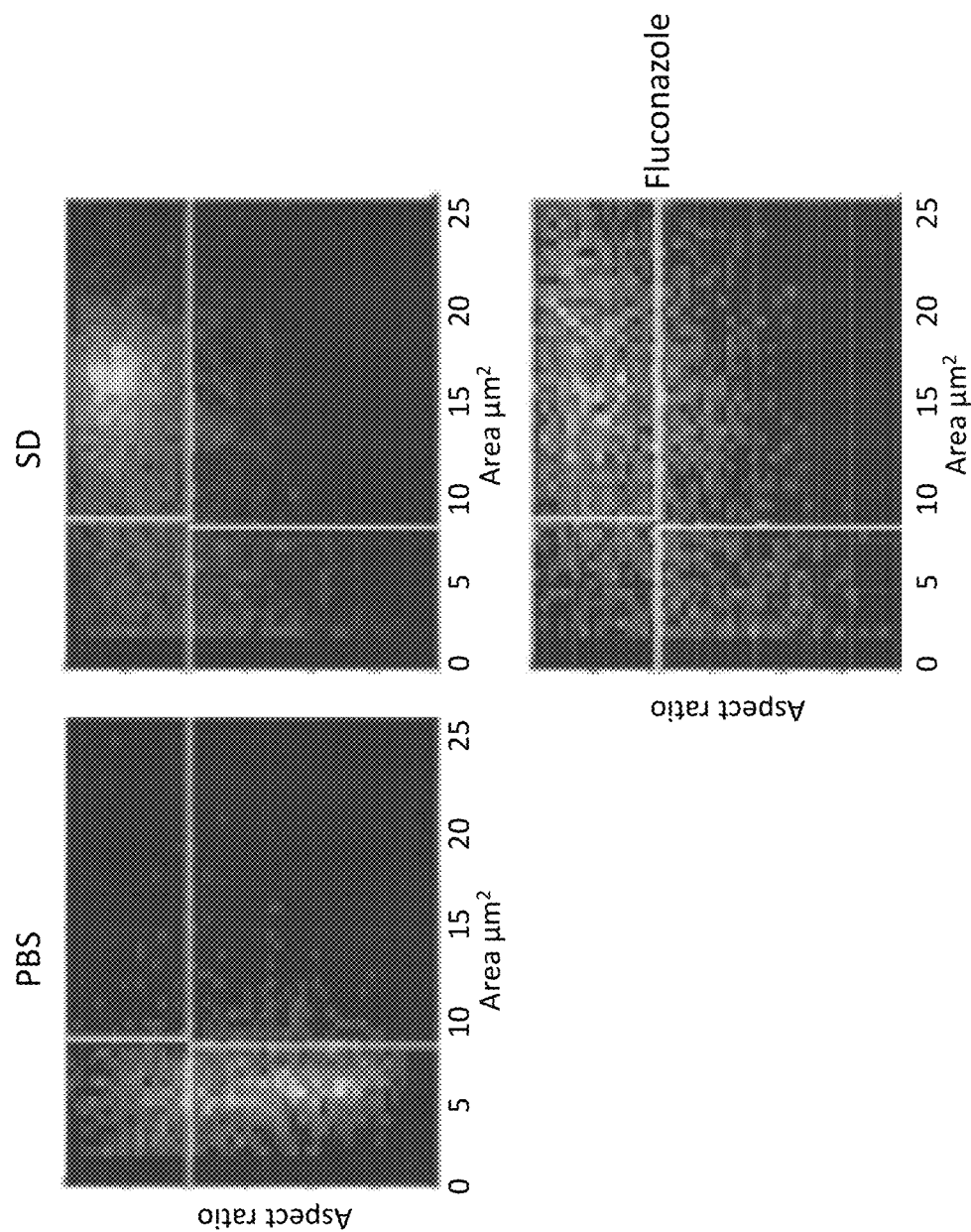

FIG. 7B shows 2D histograms as in FIG. 7A, but for a 16-hour germination of *Cryptococcus* spores using PBS as a control (no germination), synthetic dextrose growth medium (SD) alone (full germination in the absence of compounds), and fluconazole (16 mg/mL) in the presence of growth medium.

Figure 8A:
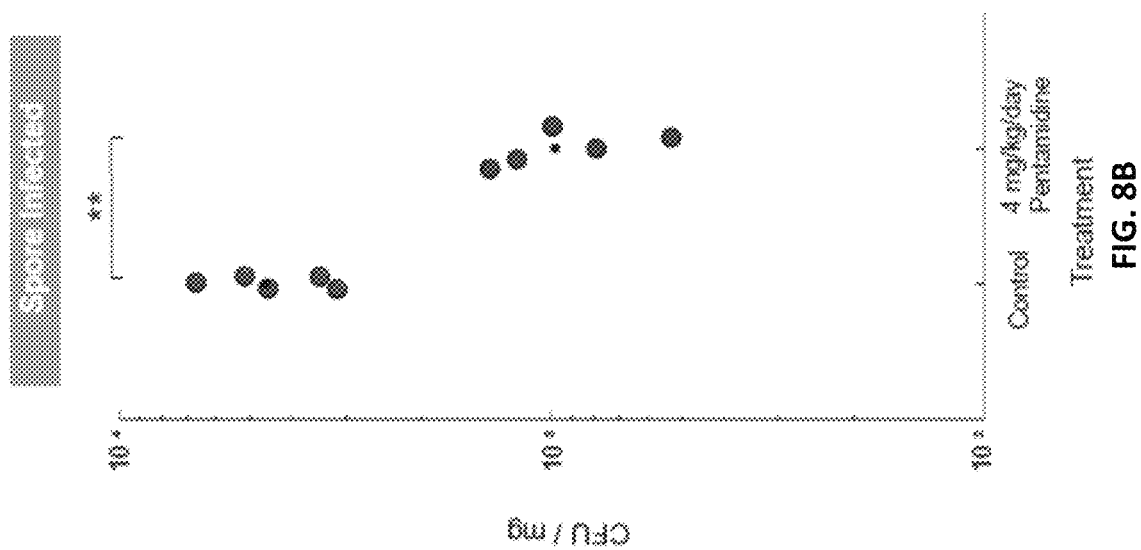
Figure 8B:
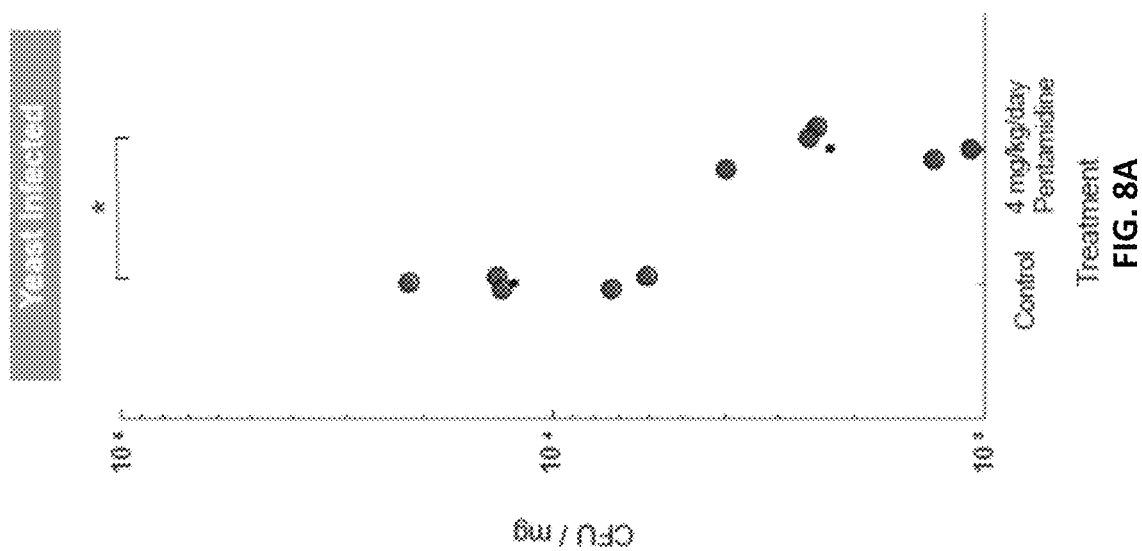

FIGS. 8A and 8B show that pentamidine treatment lowers fungal burden in mouse lung. FIG. 8A is a graph showing lung colony-forming units quantified for each mouse infected with JEC20×JEC21 yeast. The test group of mice were treated with 4 mg/kg/day pentamidine; the control group of mice were treated with 1×PBS; *$p<0.05$ for two-tailed paired t-test.

FIG. 8B is a graph depicting lung colony-forming units quantified for each mouse infected with JEC20×JEC21. Again, the test mice were treated with 4 mg/kg/day pentamidine; the control mice were given 1×PBS; **$p<0.01$ for two-tailed paired t-test.

Figure 9:
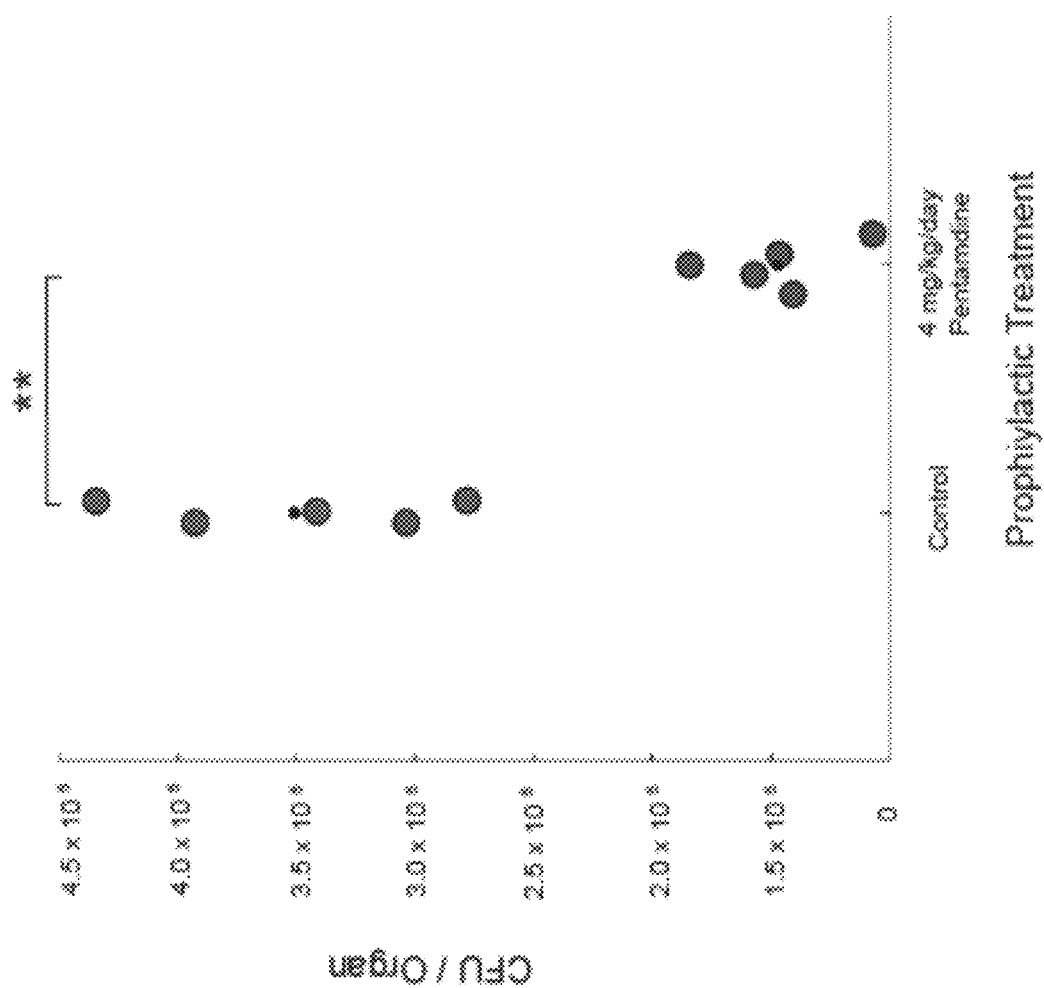

FIG. 9 is a graph showing that pentamidine prophylactically inhibits fungal spore germination in vivo. FIG. 9 depicts lung colony-forming units quantified for each mouse infected with JEC20×JEC21 spores. The test group of mice were treated with 4 mg/kg/day pentamidine; the control group of mice were treated with 1×PBS. **$p<0.01$ for two-tailed paired t-test. See Examples for complete details.

DETAILED DESCRIPTION

Abbreviations and Definitions:

The term "pharmaceutically-suitable salt" refers to any acid or base addition salt whose counter-ions are non-toxic to the patient in pharmaceutical doses of the salts, so that the beneficial inhibitory effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydro-halides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, gentisates, isethionates, di-p-toluoyltartrates, methane sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N-methylmorpholine, and the like. See, for example, "Handbook of Pharmaceutical Salts, Properties, Selection, and Use," P. H. Stahl and C. G. Wermuch, Eds., © 2008, Wiley-VCH (Zurich, Switzerland), ISBN: 978-3-90639-058-1.

"Spore-specific molecule" refers to any molecule, moiety, or protein that is highly overrepresented in abundance in spores relative to yeast. Conversely, "Yeast-specific molecule" refers to any molecule, moiety, or protein that is highly overrepresented in abundance in yeast relative to spores. Specifically included in the terms are the proteins identified in Huang M, Hebert A S, Coon J J, Hull C M (2015) "Protein Composition of Infectious Spores Reveals Novel Sexual Development and Germination Factors in *Cryptococcus*, PLoS Genet 11(8): e1005490 (https://doi.org/10.1371/journal.pgen.1005490). These spore-specific proteins were repeatedly identified by mass spectrometry in spore samples and never in yeast samples and are encoded by the following genes:

TABLE 1

Genes encoding spore-specific proteins.

| Gene | JEC21 ID | Predicted functions/domains | Deletion phenotype(s) |
|---|---|---|---|
| Group 1: Replication and Chromosome Biology | | | |
| TOP1 | CNI03280 | topoisomerase1 | sporulation defects |
| IRR1 | CNA07890 | nuclear cohesion complex component | inviable |
| Group 2: Transcription and Splicing | | | |
| RSC9 | CNB00580 | chromatin remodeling complex component | cell fusion defect |
| DST1 | CNF01160 | general transcription elongation factor TFIIS | sporulation defect |
| PRP31 | CNB05520 | U4/U6-U5 snRNP complex component | inviable |
| PRP11 | CND02290 | SF3a splicing factor complex component | inviable |
| Group 3: Cellular Transport | | | |
| BCH1 | CNG02530 | specialized cargo export from Golgi | filamentation defect |
| SFH5 | CNE04320 | non-classical phosphatidylinositol transfer protein | no phenotype |
| DDI1 | CNC00460 | vSNARE binding protein | sporulation defect |
| EMC3 | CNF02470 | protein folding in the ER | decreased spore yield |
| Group 4: Carbohydrate Metabolism | | | |
| GRE202 | CNG01830 | D-lactaldehyde dehydrogenase | decreased spore yield |
| ISP1[a] | CNB02490 | conserved in fungi/short chain dehydrogenase | filamentation defect |

TABLE 1-continued

Genes encoding spore-specific proteins.

| Gene | JEC21 ID | Predicted functions/domains | Deletion phenotype(s) |
|---|---|---|---|
| ISP3 | CND04560 | conserved in fungi/mannose-6-phosphate isomerase | no phenotype |
| ISP4 | CNK01510 | conserved in fungi/glycosyl hydrolase | no phenotype |
| | | Group 5: Proteins of Unknown Function | |
| ISP2 | CNE01730 | *Cryptococcus*-specific/no conserved domains | increased sporulation; slow germination |
| ISP5 | CNB04980 | conserved in fungi/ferritin-like superfamily domain | no phenotype |
| ISP6 | CNA04360 | *Cryptococcus*-specific/transmembrane domain | no phenotype |
| ISP7 | CND00650 | *Cryptococcus*-specific/no conserved domains | no phenotype |

[a]Genes encoding proteins with no obvious homologs were named ISP for identified Spore Protein.
dDoi: 10.1371/journal.pgen.1005490.t003

The spore-specific genes and proteins identified in the above table have the nucleotide and amino acid sequences and protein ID's shown in the Sequence Listing at SEQ. ID. NOS 1-36.

Yeast-specific proteins include, but are not limited to, CND06170, XP_570090.1 (SEQ. ID. NOS. 37 and 38); CND01050, XP_570422.1 (SEQ. ID. NOS. 39 and 40); CNH01340, XP_572322.1 (SEQ. ID. NOS. 41 and 42); CNN02360, XP_568723.1 (SEQ. ID. NOS. 43 and 44); CNB01440, XP_568816.1 (SEQ. ID. NOS. 45 and 46); CNG00410, XP_571739.1 (SEQ. ID. NOS. 47 and 48); CNH02740, XP_572447.1 (SEQ. ID. NOS. 49 and 50); CNJ01750, XP_567350.1 (SEQ. ID. NOS. 51 and 52); CNI02030, XP_572658.1 (SEQ. ID. NOS. 53 and 54); CNB05750, XP_569316.1 (SEQ. ID. NOS. 55 and 56); CNI03560, XP_572607.1 (SEQ. ID. NOS. 57 and 58); CNK01820, XP_567661.1 (SEQ. ID. NOS. 59 and 60); CNI00900, XP_572819.1 (SEQ. ID. NOS. 61 and 62); CNK02880, XP_567883.1 (SEQ. ID. NOS. 63 and 64); CNF00610, XP_571239.1 (SEQ. ID. NOS. 65 and 66); and CNI00870, XP_572850.1 (SEQ. ID. NOS. 66 and 67). These yeast-specific proteins, which are shown in the Sequence Listing, can be utilized as markers of germination.

The gene and encoded protein encoded by CNK01510 (SEQ. ID. NOS. 1 and 2, respectively) is the preferred spore-specific molecule to be labeled in accordance with the assay disclosed herein.

The terms "label," "marker," "probe," "reporter," and "tag" are used interchangeable and mean a molecular moiety or probe of any structure or configuration, that can be detected by any means, now known or developed in the future, by which a vegetative cell, spore, or molecule bearing such a "label," "marker," "probe," "reporter," or "tag" can be distinguished from cells, spores, or molecules not bearing such a "label," "marker," "probe," "reporter," or "tag." The terms include, without limitation, radioactive labels, fluorescent labels, chromophoric labels, affinity-based labels (such as antibody-type markers), chemiluminescent labels, and the like. Conventional radioactive isotopes used for detection include, without limitation, $^{32}P$, $^{2}H$ and many others. A huge number of fluorescent and chromophoric probes are known in the art and commercially available from numerous worldwide suppliers, including Life Technologies (Carlsbad, Calif., USA), Enzo Life Sciences (Farmingdale, N.Y., USA), and Sigma-Aldrich (St. Louis, Mo., USA). Luciferase is the preferred marker. Complete kits for accomplishing luciferase labeling to a desired substrate are commercially available from several suppliers, including Promega Corporation, Madison, Wis. (e.g., Promega's NanoLuc®-brand vectors and NanoGlo®-brand luciferase assay systems).

The term "operationally linked" or "operationally connected" when referring to joined polynucleotide sequences denotes that the sequences are in the same reading frame and upstream regulatory sequences will perform as such in relation to downstream structural sequences. Polynucleotide sequences which are operationally linked are not necessarily physically linked directly to one another but may be separated by intervening nucleotides which do not interfere with the operational relationship of the linked sequences. Similarly, when referring to joined polypeptide sequences, operationally linked means that the functionality of the individual joined segments are substantially identical as compared to their functionality prior to being operationally linked. For example, a fluorescent protein or chemiluminescent protein can be fused to a polypeptide of interest and in the fused state retain its fluorescence or chemiluminscence, while the fused polypeptide of interest also retains its original biological activity.

All strains used in the working examples were of the serotype D background (*Cryptococcus neoformans* var. *neoformans* strains JEC20 (ATCC 96909) and JEC21 (ATCC 96910 and ATCC MYA-565). See Kwon-Chung K J, Edman J C, Wickes B L (1992) "Genetic association of mating types and virulence in *Cryptococcus neoformans*," *Infect Immun.* 60:602-605 (pmid:1730495) and Moore T D, Edman J C (1993) "The alpha-mating type locus of *Cryptococcus neoformans* contains a peptide pheromone gene," *Mol Cell Biol.* 13:1962-1970 (pmid:8441425). All were handled using standard techniques and media as described in Sherman F. (2002) "Getting started with yeast," *Methods Enzymol.* 350:3-41(pmid:12073320) and Alspaugh J A, Perfect J R, Heitman J. (1998) "Signal transduction pathways regulating differentiation and pathogenicity of *Cryptococcus neoformans*," *Fungal Genet Biol.* 25:1-14 (pmid:9806801).

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite articles "a" and "an" mean "one or more" unless explicitly stated otherwise.

All combinations of method or process steps as used herein can be performed in any order, unless otherwise specified or clearly implied to the contrary by the context in which the referenced combination is made.

The methods disclosed herein can comprise, consist of, or consist essentially of the essential elements and limitations of the method described, as well as any additional or optional ingredients, components, or limitations described herein or otherwise useful in microbiology, biochemistry, and/or mycology.

Figure 1:
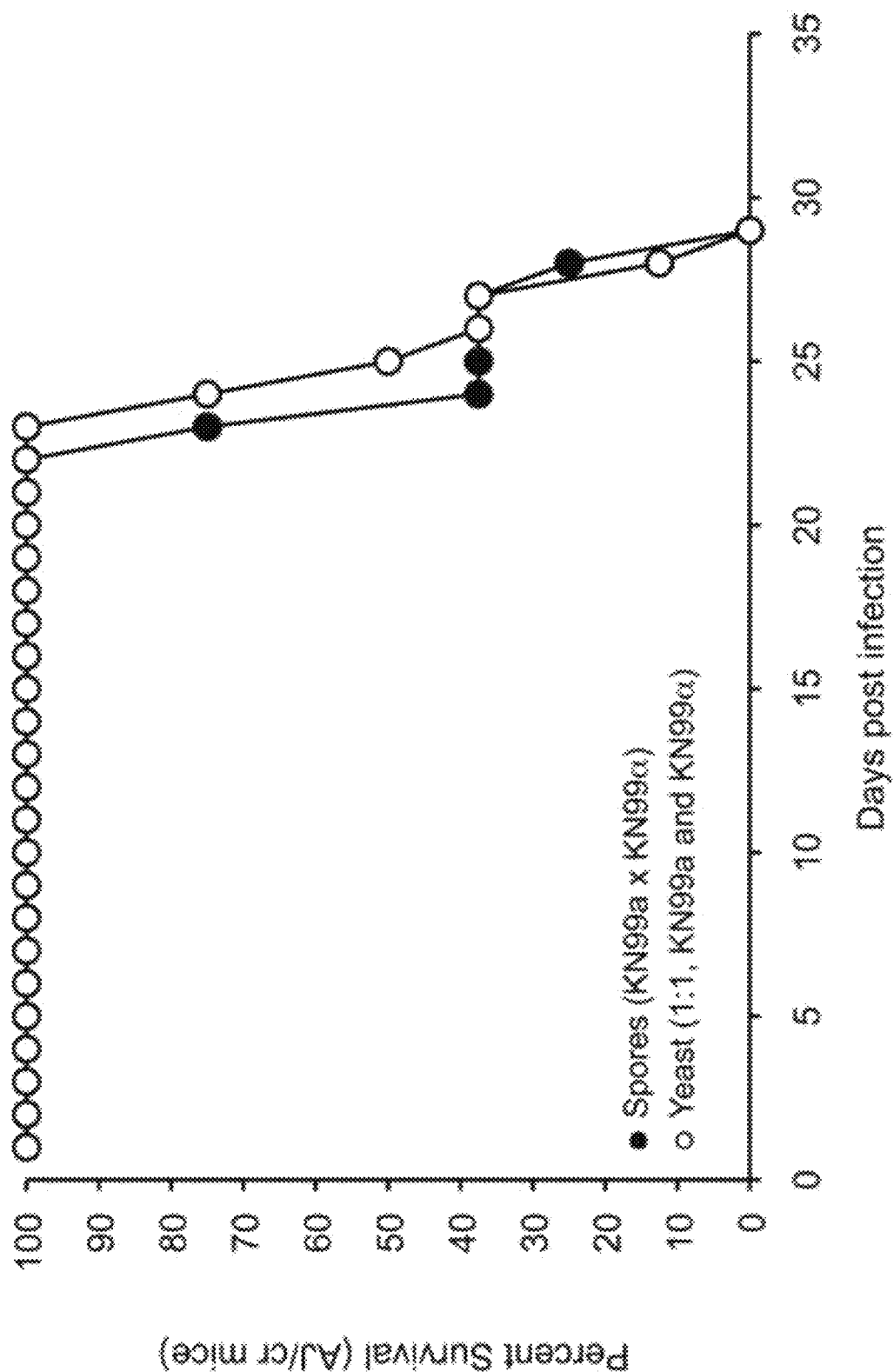
FIG. 1 is a graph showing that *C. neoformans* var. grubii spores are pathogenic in a murine model of cryptococcosis. Groups of eight AJ/Cr mice were infected with *C. neoformans* var. grubii spores ($10^5$) or yeast ($10^5$) via intranasal inhalation. See Giles et al. *Infect. Immun.* 2009, 77(8):3491. Time post-infection (in days) is shown in the X-axis; percent of surviving mice is shown on the Y-axis.

The Method:

At the core of the present invention is the realization that targeting a cellular process that is specific to organisms that sporulate—namely, spore germination—is likely to yield highly effective antifungal compositions that exhibit fewer side-effects than conventional antifungal drugs when used in humans. (Organisms that produce spores include fungi, bacteria, protists, plant seeds, ferns, and the like.) What then is needed then is a high-throughput assay that can evaluate compounds for their ability to inhibit fungal spore germination. As shown in FIG. 1, it is known that spores are infectious agents. FIG. 1 is a graph showing survivability in a widely accepted mouse model of cryptococcosis. See Giles et al. *Infect. Immun.* 2009, 77(8):3491. Here, mice were infected with spores or yeast of *C. neoformans* var. grubii. Spores ($10^5$) or yeast ($10^5$) were administered to the test animals via intranasal inhalation. Mice infected with spores are shown in black circles; mice infected with yeast are shown in white circles. As can be seen in FIG. 1, the mice died at virtually identical rates. In other words, *Cryptococcus* spores are just as virulent as the yeast form.

The method functions on two principles. The first principle is that the vegetative form of organisms, especially fungi, are very different, morphologically than their corresponding spores. This is shown quite convincingly in FIGS. 2A and 2B. FIG. 2A is a series of scanning electron micrographs showing the morphological transitions that take place during germination of *C. neoformans* spores. A *C. neoformans* spore is shown in the far left photo. The germinating spore is false-colored green. The emerging yeast wall is false-colored yellow. This can been seen initially in the photo second from the left and then in a much more pronounced fashion in the third photo of the series. The daughter cell is false-colored orange and is seen clearly in the far right photo. A simple visual comparison between the far left and far right photos in FIG. 2A illustrates the significant morphological differences between a spore of *C. neoformans* (on the left) and a yeast (vegetative form, on the right). As can be seen from FIG. 2A, the spore is roughly cylindrical and clearly has a major axis that is much longer than its minor axis. The vegetative yeast form, in contrast is more nearly spherical or globular. Its major and minor axes are much closer in physical length. FIG. 2B shows the same phenomenon using using transmission electron microscopy rather than scanning electron microscopy. Spores are quantitatively smaller and more oblong than yeast.

The second principle is that the inventors have identified 18 proteins that are expressed at far greater levels in the spore form as contrasted to the yeast form. Thus, by affixing a marker to one or more of these spore-specific proteins, the extent of germination can be tracked by following changes in the signal generated by the marker as the spore-specific protein is degraded during the germination process.

The first step of the method is to provide bacterial, fungal, or plant spores transformed to contain and express a detectable marker, wherein the marker is operationally linked to a spore-specific or a yeast-specific protein. The marker is preferably a protein fluorophore or protein chemiluminescent marker, such as luciferase, fluorescent protein A, green fluorescent protein, etc. The marker protein is incorporated into spores or yeast by fusing the gene encoding the marker protein to a spore-specific or yeast-specific target gene. The spore then produces the spore-specific protein with the marker attached. (Or the yeast then produces the yeast-specific protein with the marker attached.) The marker will thus generate a first signal associated with the spores. That first signal remains unchanged for as long as the spores remain intact. However, when the spore germinates, the spore-specific protein and its attached marker are degraded, which then alters the signal generated by the attached marker (or the yeast-specific marker is increased). A second signal measurement taken after germination is thus proportional to the extent of germination.

Figure 3A:
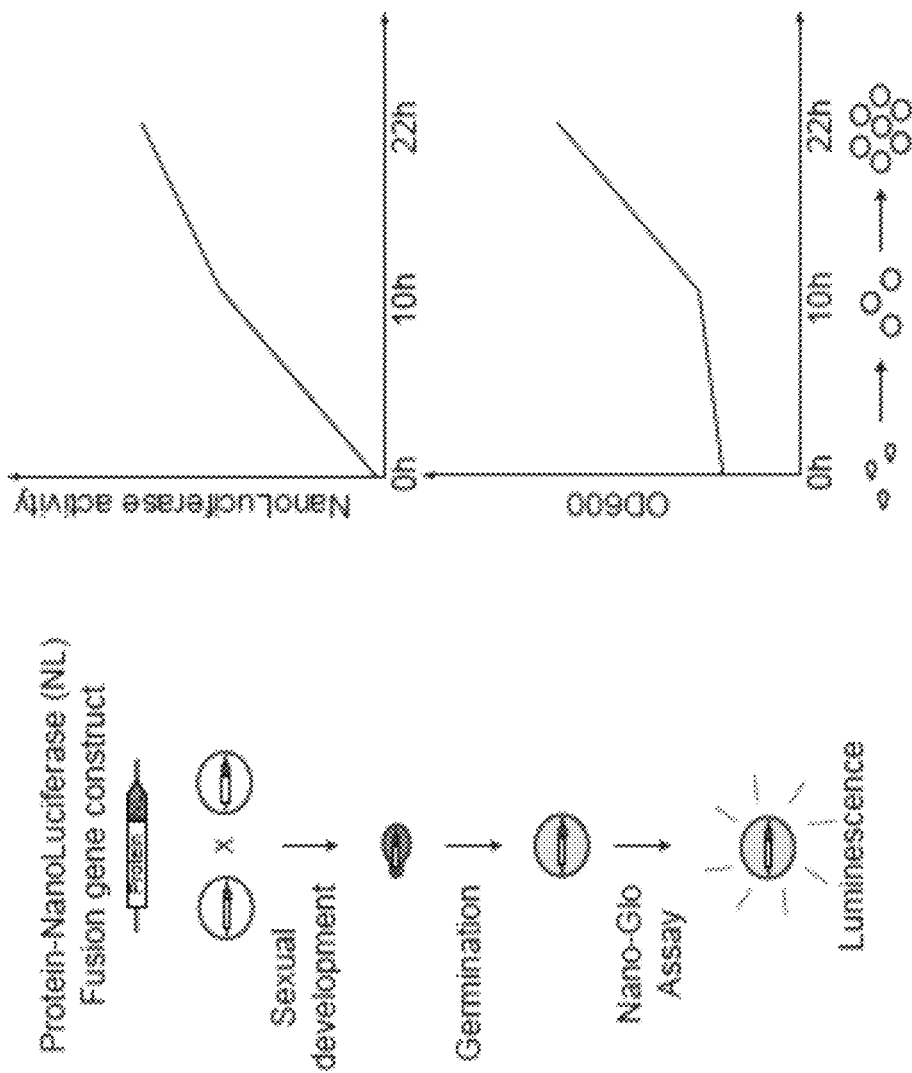
FIG. 3A is a schematic diagram of a screening assay for an uninhibited germination reporter strain as it undergoes germination (left-hand panel) and graphs depicting germination as reported by NanoLuciferase (NL) activity (top right, NanoLuc®-brand luciferace, Promega Corporation, Madison, Wis.), and as measured by optical density (OD) (bottom right). The schematic pictures below show the morphology and number of cells over time. This example depicts a yeast-specific protein.

This process is shown schematically in FIG. 3A. As shown in the left-hand side of the figure, the yeast form of the organism (in this case *C. neoformans*) was transformed to contain a fusion construct comprising a spore-specific protein fused to a luciferase gene. The transformed yeast were cultured to yield a population of propagating yeast that include the fusion construct. The yeast were then induced to sporulate. A first measure of the signal generated by the luciferase marker generated by the fusion construct is taken. This is shown at Time=0 in the two right-hand graphs depicted in FIG. 3A. The upper graph show the signal generated by the reporter as the spore germinate. The lower graph shows the optical density of the culture solution at 600 nm ($OD_{600}$) over the same time period. As can be seen from the two graphs, as the spore germinate and multiply, the optical density increases (as the number of cells increases). In a corresponding fashion, the signal generated by the marker displays a proportional rise. The schematic pictures below show the morphology and number of cells over time.

Figure 3B:
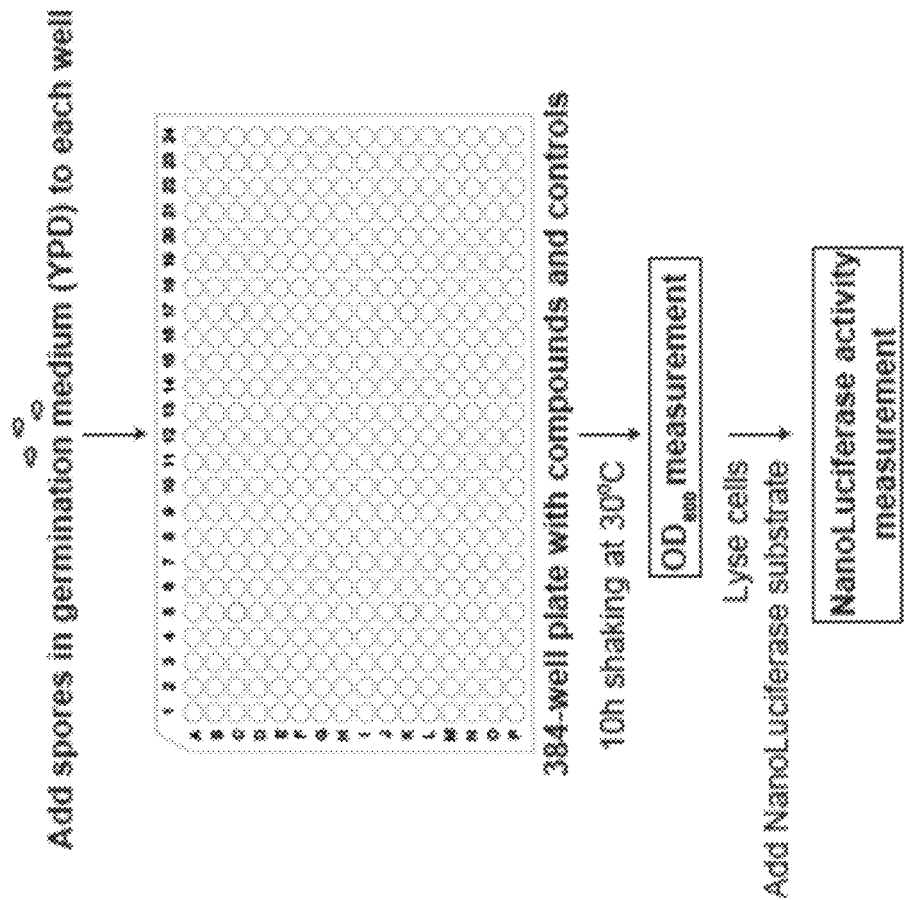
FIG. 3B is a schematic diagram showing the workflow for the screening assay.

The assay can be implemented in a massively redundant, massively high-throughput format that is easily automated using conventional multiwall plates and robotic equipment. (Laboratory robotics for handling multiwall culture plates are available from a host of international commercial suppliers, including Agilent Technologies (Santa Clara, Calif.), Beckman Coulter (Grants Pass, Oreg.), Hudson Robotics (Springfield, N.J.), and many others.) For a non-limiting example, see FIG. 3B, which is a schematic diagram showing the workflow for a high-throughput screening assay according to the present disclosure. As shown in FIG. 3B, the method can be implemented using conventional 384-well incubation plates. Spores to be studied are modified to contain a suitable marker, as described earlier. The spores are then incubated in a multiwall plate in a suitable germination medium. For many fungi, yeast extract-peptone-dextrose growth medium (YPD or YEPD) is suitable. (YPD is a well known medium for fungal germination and contains roughly 2% w/v bacto-peptone, 1% w/v yeast extract, and 2% w/v dextrose. A 1 L batch is made by combining 20 g bacto-peptone, 10 g yeast extract, and 20 g dextrose, adding water to 1 L and then autoclaving before use.)

A first signal from each well of the multiwall plate is then taken at the start of the incubation period. The contents of each well can be arranged in any suitably logical fashion, with positive and negative control wells, and wells containing compounds to be tested for their ability to inhibit germination of the spores, perhaps in appropriate serial dilutions of the compounds. The entire multiwall plate is then cultured for a time, temperature, humidity, etc. that is conducive to germination of the spores. After a set time, and OD600 measurement may optionally be taken to confirm that in the control wells the spores responded appropriately. The cells are then lysed, luciferase substrate is added, and a second measurement of the signal generated by the marker is taken. The extent of germination can then be determined by comparing the first signal to the second.

Figure 3C:
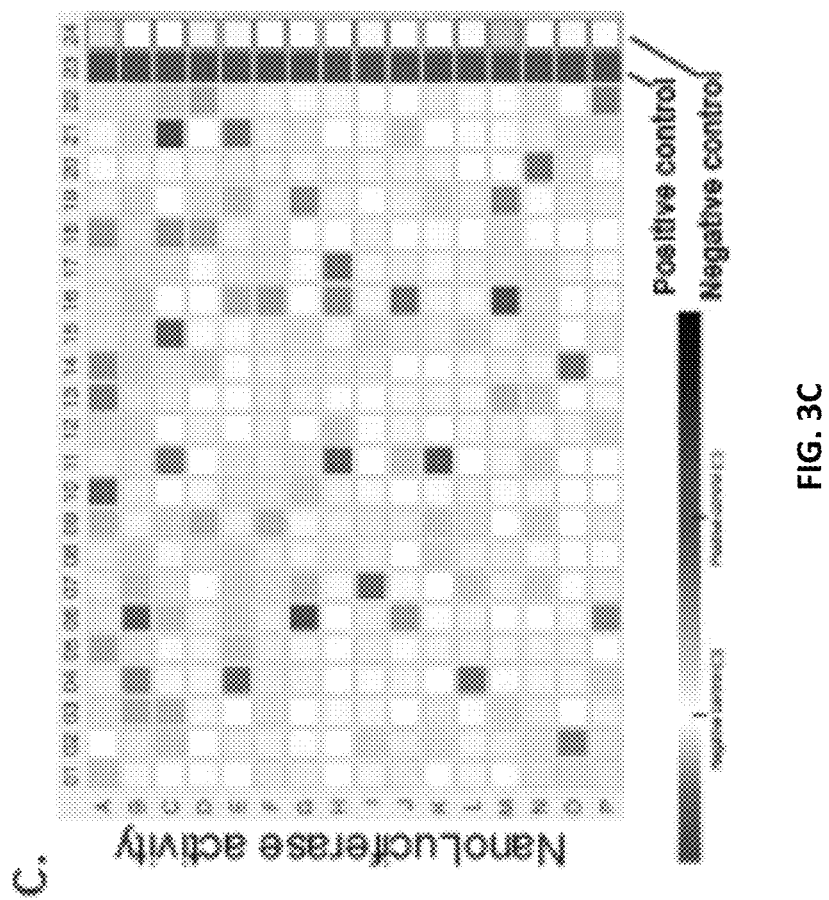
FIG. 3C shows representative plates from the screening assay described in FIGS. 3A and 3B, showing wells that contain germination-inhibiting compounds in red.

FIG. 3C shows a representative multiwall plate from the resulting from the method just described. Positve and negative control wells are in columns 23 and 24, respectively. Wells that contain germination-inhibiting compounds in various shades of pink/red, with the darker red hues indicating great inhibitory activity. The signals can be gathered, digitized, recorded, and compared using a photomultiplier tube, in conventional fashion. Thus, wells H11, K11, C15, M16, and C21 all appear to contain very effective germination-inhibiting compounds.

Figure 3D:
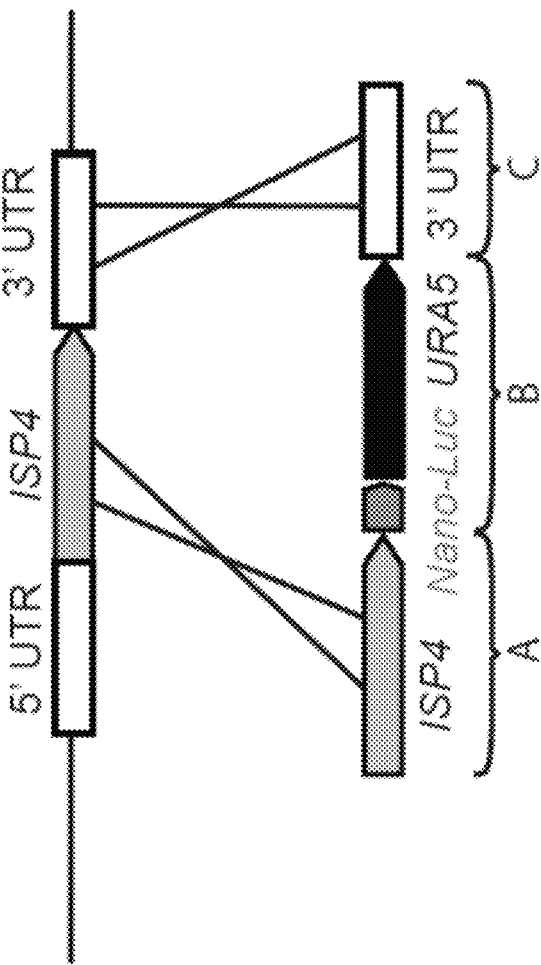
FIG. 3D is a schematic diagram of the transformation construct containing a marker, in this case a gene encoding luciferase ("Nano-Luc").

FIG. 3D shows a schematic diagram of a vector used to transform a spore so that it includes a marker responsive to germination An exemplary protocol, using luciferase as the marker, can be accomplished using commercial kits and largely following the manufacture's instructions on how to use the kit. A preferred kit for is Promega's Nano-Luc®-brand vectors and Nano-Glo®-brand luciferase assay system.

Briefly, homologous recombination is utilized to tag spore proteins with luciferase under their endogenous promoters. See FIG. 3D. In this fashion, their expression levels in the spores will remain undisturbed by tagging. As illustrated in FIG. 3D, the transformation construct contains three parts (A, B, and, C). Part A includes the sequence that encodes ISP4 but without a stop codon. Part B includes NanoLuc sequence (GeneBank sequence number KM359770) and *C. neoformans* URAS gene (GenBank sequence number AE017347.1), the latter of which serves as a selection marker for cell transformation. Part C includes the 3' UTR of ISP4, so that together with Part A, the transformation construct will be more favorably integrated into the genome through homologous recombination. Individual parts were generated by regular PCR and the full-length transformation construct was created using fusion PCR. See Davidson R C, Blankenship J R, Kraus P R, de J Berrios M, Hull C M, D'Souza C, et al. A PCR-based strategy to generate integrative targeting alleles with large regions of homology. *Microbiology.* 2002; 148: 2607-2615. PMID: 12177355. The construct was transformed into cells by biolistic transformation before selection. See Toffaletti D L, Rude T H, Johnston S A, Durack D T, Perfect J R. Gene transfer in *Cryptococcus neoformans* by use of biolistic delivery of DNA. *J Bacteriol.* 1993; 175: 1405-1411. PMID: 8444802.

The present inventors have identified a signicant number of proteins in *C. neoformans* that were detected in spores only. Thus, these proteins are all candidates for labelling in the present invention. In *C. neoformans* and in other fungi where the correspnding genes are conserved, one or more of the following proteins can be labelled with the marker: XP_567740.1 (SEQ. ID. NO: 2), XP_566791.1 (SEQ. ID. NO: 4), XP_570303.1 (SEQ. ID. NO: 6), XP_571089.1 (SEQ. ID. NO: 8), XP_571997.1 (SEQ. ID. NO: 10), XP_569295.1 (SEQ. ID. NO: 12), XP_569173.1 (SEQ. ID. NO: 14), XP_569068.1 (SEQ. ID. NO: 16), XP_569336.1 (SEQ. ID. NO: 18), XP_567136.1 (SEQ. ID. NO: 20), XP_568990.1 (SEQ. ID. NO: 22), XP_570610.1 (SEQ. ID. NO: 24), XP_571921.1 (SEQ. ID. NO: 26), XP_572925.1 (SEQ. ID. NO: 28), XP_570796.1 (SEQ. ID. NO: 30), XP_571548.1 (SEQ. ID. NO: 32), XP_570447.1 (SEQ. ID. NO: 34), XP_571343.1 (SEQ. ID. NO: 36).

Figure 4:
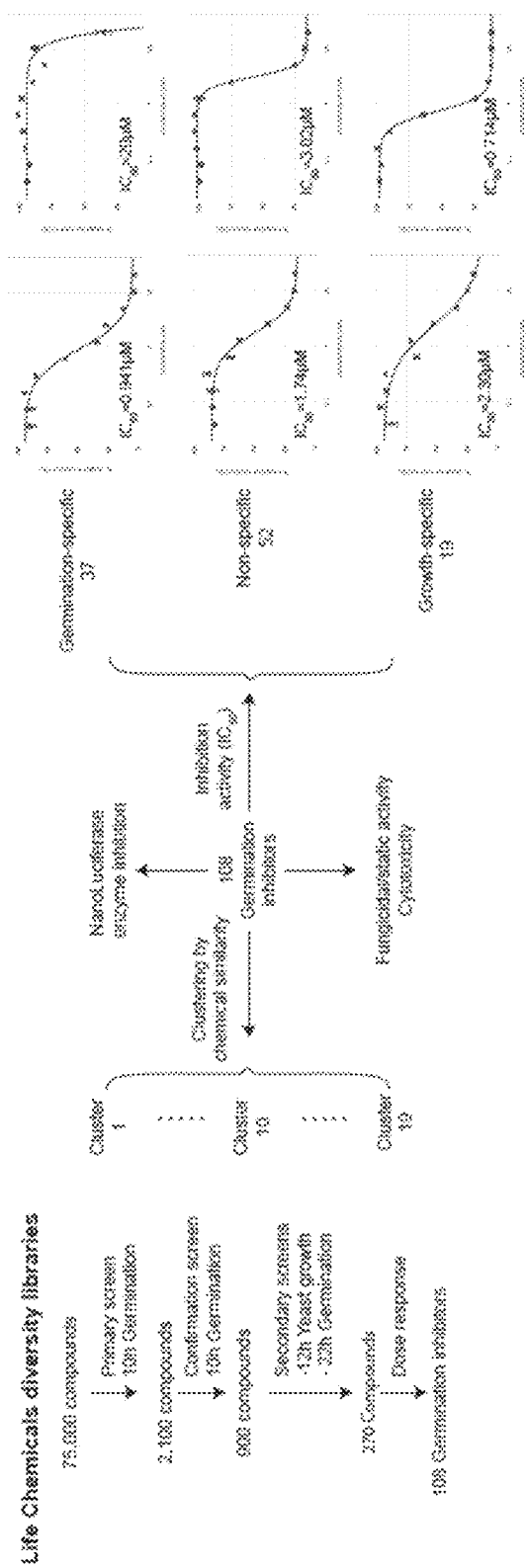
FIG. 4 is a flow chart showing the workflow of a high-throughput screening assay according to the present disclosure.

FIG. 4 is a flow chart showing the workflow of a high-throughput screening assay according to the present disclosure. Here, the figure shows how a large library of 75,000 compounds was screened using the present method set up in high-throughput format. As shown on the left-hand side of the figure, the full library was first subjected to a primary screening comprising a 10-hour germination, followed by evaluating which compounds showed initial interested as germination inhibitors. This yielded 2,100 putative "hits," i.e., compounds that at least initially showed promise as germination inhibitors. These 2,100 hits were then re-screened and the upper 900 best performing inhibitors were tested further. These 900 compounds were then re-screened using longer germination and yeast growth incubation times. This resulted in 270 compounds being advanced for further study. This group of 270 compounds was then studied using the method described herein to determine if any of the compounds inhibited spore germation and/or fungal growth in a dose-dependent fashion. This final screen yielded 108 compounds from the original 75,000 compounds that inhibited fungal spore germination and/or yeast grown in a dose-depedent fashion.

As shown in the middle panel of FIG. 4, the 108 compounds that were "hits" were then clustered by structural similarity and further tested to see if their anti-fungal properties were germination specific (i.e., primarily germination inhibitory), non-specific, or primarily growth specific. As shown in the right-hand graphs of FIG. 4, 37 of the compounds specifically inhibited germination in a dose-dependent manner; 52 of the compounds were non-specific, dose-dependent inhibitors; and 19 of the compounds specifically inhibited vegetative fungal growh in a dose-dependent manner.

Figures 5A, 5B:
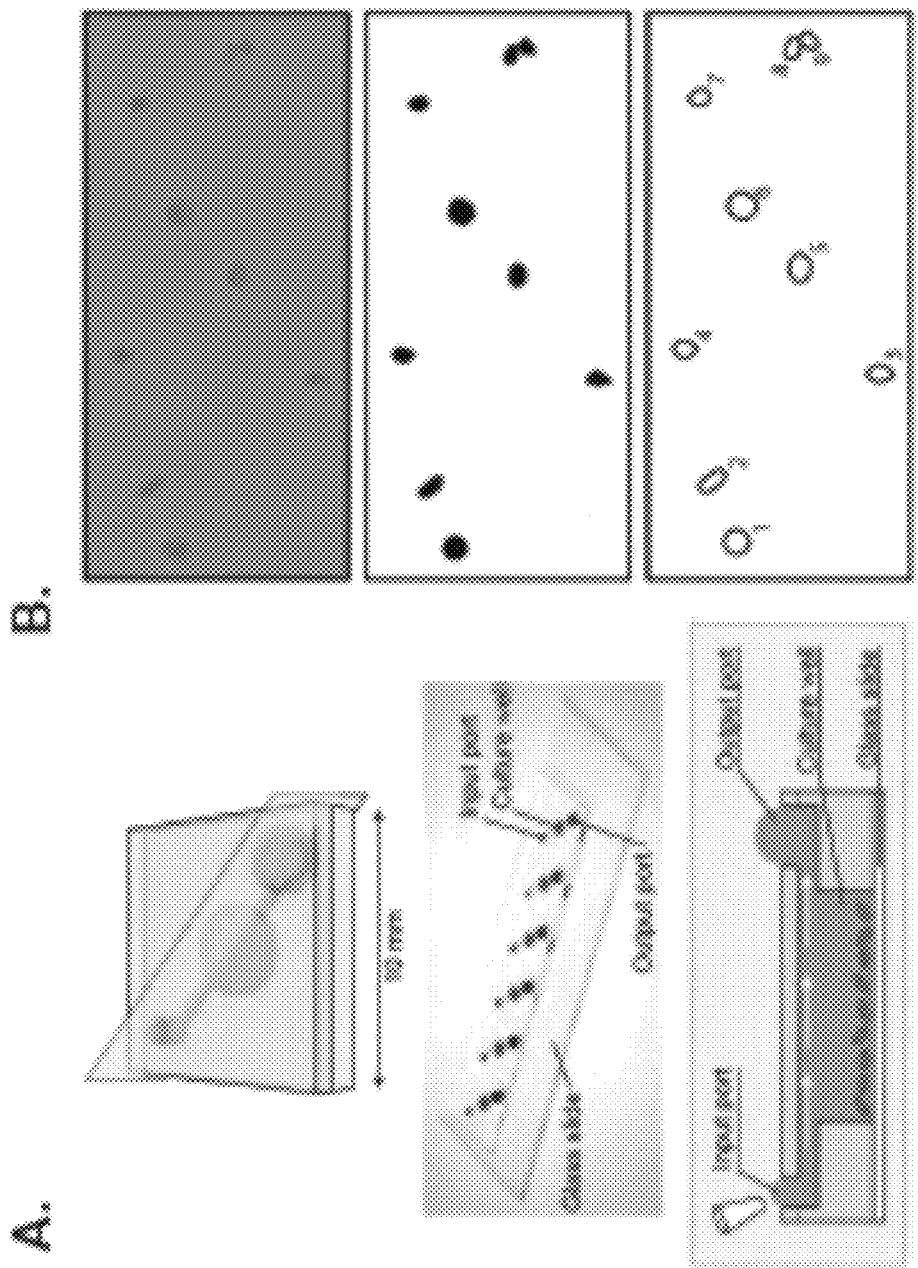
FIG. 5A shows schematic views of a microliter-scale well device and how it operates. The microfluidic device includes an input port connected to a culture well connected to an output port. Each microfluidic chamber is built upon a transparent support, such as a glass microscope slide. The microfluidic device is dimensioned and configured to culture and image non-adherent cells, such as spores and germinated fungi, yeast, and the like. The top panel of FIG. 5A shows a perspective view of a single microfluidic culturing device. The middle panel of FIG. 5A shows six (6) such devices disposed on a glass slide. Each of the six devices shown is filled with 10 μL of blue dye. The bottom panel of FIG. 5A shows a front elevation cutaway of the device shown in the top panel.
FIG. 5B depicts representative raw images of the fungal cells (spores and germinated cells) in the device shown in FIG. 5A. Image processing steps are then applied to the raw images to discriminate between spores and germinated cells. These process steps may include, without limitation, applying a density threshold to the raw images and then automatically detecting and measuring the cells 2-D area and aspect ratio.

As shown in FIGS. 5A and 5B, the method described herein can also be formatted for continuous studies using a microfluidic test bed. The test bed, depicted schematically in FIG. 5A, comprises a microliter-scale culture well having an input port and an output port. That is, the device includes an input port operationally linked in fluid connection to to a culture well which is operationally linked in fluid connection to an output port. Each microfluidic chamber is built upon a transparent support, such as a glass microscope slide. The microfluidic device is dimensioned and configured to culture and image non-adherent cells, such as spores and germinated fungi, yeast, and the like. The top panel of FIG. 5A shows a perspective view of a single microfluidic culturing device. The middle panel of FIG. 5A shows six (6) such devices disposed on a glass slide. These six devices held 10 µL blue dye. The bottom panel of FIG. 5A shows a front elevation cutaway of the device shown in the top panel. In this bottom panel, fluid flow is depicted as moving from left-to-right. Non-adherent cells are retained within the culture well, while the medium gently flows above them. Compounds to be tested are introduced through the input port, where they then flow to the culture well to interact with the cells therein. When built on an optically transparent substrate, the cells can be visualized and photographed in real time, as shown in the photos in FIG. 5B.

FIG. 5B depicts representative raw images of the fungal cells (spores, germinating cells, and yeast) in the device shown in FIG. 5A. Various imaging processing steps, described in detail below, are then applied to the raw images to discriminate among spores, germinating cells, and yeast. These process steps may include, without limitation, applying a density threshold to the raw images and then automatically detecting and measuring the cells' 2-D area and aspect ratio.

Figure 6:
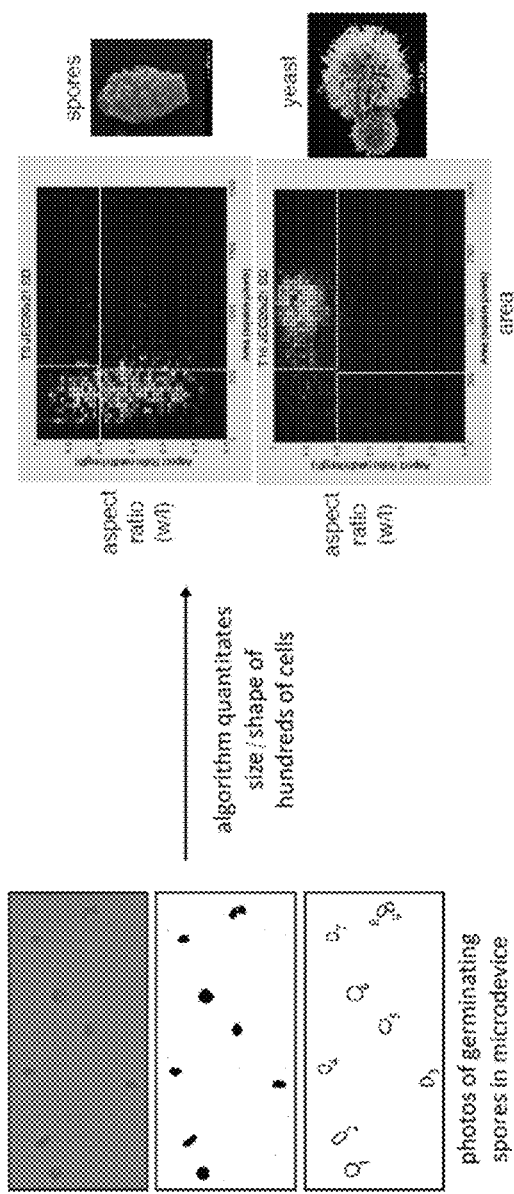
FIG. 6 depicts how photos of germinating spores in the micro-device depicted in FIG. 5A were analyzed for the size and shape of the cells and the aspect ratio calculated. This was done using modified algorithms of ImageJ, a public domain, open-source, Java-based image processing program, which was developed originally by Wayne Rasband at the Research Services Branch of the National Institutes of Health. ImageJ can be downloaded free of charge at https://imagej.nih.gov/ij/download.html. The images of the cells are then plotted based on their 2-D area (X-axis) versus their aspect ratio (Y-axis) as shown in the right-hand panels of FIG. 6. Spores, because they are more oblong and smaller in area, plot to the bottom left-hand side of the histogram; germinated cells, because they are more spherical and larger in area, plot to the upper right quadrant of the plots.

FIG. 6 shows how computer processing can be brought to bear to automatically discriminate between ungerminated spores and vegetative yeast after a culture period has been completed. The left-hand side of FIG. 6 shows the three raw photographs from FIG. 5B. These are raw photographs of the germinating spores in the microfluidic device showin in FIG. 5A. The photos are digitized from the outset. The digitized images were analyzed for the size and shape of each cell in each image. The area of each cell, as well as its aspect ratio can be determined using a public domain, open-source, Java-based image processing program called ImageJ. Several other commercial image processing software packages can also accomplish this task. For example, Stream-brand image analysis sotware from Olympus Corporation (Waltham, Mass.) and PAX-it brand image analysis software from MIS, Inc. (Villa Park, Ill.). The images of the cells are then plotted based on their 2-D area (X-axis) versus their aspect ratio (Y-axis) as shown in the right-hand panels of FIG. 6. As can be seen from the plots in FIG. 6, the spores (upper plot) cluster in a distinctly different location and with a distinctly different distribution as compared to the vegetative yeast (lower plot). This is because spores, being more oblong and smaller in area, plot to the left-hand side of the histogram—indicating smaller average area and ovoid nature in the photographs. Spores tend to toward a wider distribution of their aspect ratios and areas. This may be due to the fact that the spores settle in the device at many angles. When photographed, spore aspect ratios and sizes are are more variable than in reality. Yeast, because they are more spherical and larger in area regardless of the position from which they are photographed, plot in a tight cluster in the upper right quadrant of the histograms.

Futher examples of how spores, germinating cells, and yeast can be compared is shown in FIGS. 7A and 7B. FIG. 7A depicts a series of photographic analyses further demonstrating that germination in microscale devices as described herein can be determined by cell area versus aspect ratio. Each panel in FIG. 7A depicts the germination dynamics of spores visualized by 2D histograms of cell area vs aspect ratio, as well as a stacked bar plot of the population composition over time (at lower right). Colors are normalized on each plot such that yellow represents the area and aspect ratio combination with the most cells observed and dark blue represents area and aspect ratio combinations that were not observed. Cells in the lower left quadrant are defined as spores; cells in the upper right quadrant as yeast; all remaining cells are classified as intermediates undergoing germination. FIG. 7B shows 2D histograms as in FIG. 7A, but for a 16-hour germination of *Cryptococcus* spores using PBS as a control (no germination), synthetic dextrose growth medium (SD) alone (full germination in the absence of compounds), and the antifungal compound fluconazole (16 mg/mL) in the presence of growth medium. In this study, we demonstrate that spore germination is a viable target for antifungal development by identifying and characterizing FDA approved drugs able to inhibit both spore germination and yeast replication. These inhibitors have the potential of becoming tools to probe the essential fungal process of spore germination, or repurposed into antifungal therapies. Importantly, we determined that one of the drugs, Pentamidine, was effective at lowering fungal burden in vivo and could be repurposed as a prophylactic treatment against *Cryptococcus* pathogens.

Germination Provides a Suitable Target for the Development of Novel Antifungals:

Limited therapies exist to combat fungal disease. Humans and fungi share many biological processes due to their eukaryotic nature. Because fungi-specific drug targets are difficult to find, potent antifungal agents often have toxic side-effects in humans. In the quest to find novel fungal-specific targets, the field has mainly focused on the cell membrane processes (ergosterol biosynthesis), and the fungal cell wall (β(1,3)-glucan synthesis). While these targets have been effective in the discovery of antifungals in the past; the lack of novel antifungal therapies is an indication that these targets currently have limited success. It is critical that novel fungi-specific targets are identified for the development of new antifungals. This requires identifying new cell processes to probe that are unique to fungi. Fungal spore germination provides one of these novel targets.

Fungal spore germination has been previously suggested to be a modified cell cycle. Recently discovered evidence suggests otherwise. In previous studies we identified and characterized spore-enriched proteins. One of these proteins (Isp2) was found to stall germination for two hours prior to initiating vegetative growth. Isp2 showed no apparent phenotype in vegetatively growing yeast. Isp2, along with other spore germination-specific results, indicate that it is unlikely that germination is simply a modified cell cycle. Spore germination in not only a unique fungal process but is also unlike any process defined in humans. The uniqueness of fungal spore germination makes it a prime process to probe in the effort to develop novel antifungals. The examples below show that using germination inhibition as a signal can identify drugs that could be repurposed in the treatment of invasive fungal diseases.

Targeting Hermination Provides a Mechanism for Prevention:

In addition to providing a fungal-specific drug targets, targeting germination provides a unique opportunity for preventing fungal disease. Spores are stress-resistant cell types that are known infectious particles of many fungal pathogens, and have distinct phenotypes compared to yeast when interacting with hosts. Developing antifungals that target all potential infectious particles could be used to protect against fungal pathogens through prophylaxis treatment. If a low toxicity antifungal is found, prophylactic treatment could be administered to immunocompromised individuals, the population most at risk of developing invasive fungal infections.

Screening Characterized Drugs Allows for the Potential Development of Tools:

The screening of already approved FDA drugs provides a unique opportunity to screen drugs that often have known targets. By screening compounds with known inhibition targets, pathways can be identified that could be potentially important to fungal spore germination. These compounds can be used to probe fungal spore germination to help understand this critical fungal differentiation process. One of the clearest examples of a potential tool in this study was alexidine hydrochloride, which had strong antifungal activity and was a potent inhibitor of fungal spore germination. See the Examples section. This drug has previously been reported to inhibit phospholipases of *Cryptococcus* (Ganendren et al., 2004). This may suggest that phospholipases are important for viability of fungal spores. The ability of alexidine to inhibit other fungal processes, however, is unclear. In the future, we will use alexidine as a tool to probe the molecular events of phospholipid biosynthesis in fungal spore germination.

Pentamidine, a Potential Antifungal Prophylactic Against *Cryptococcus* Infection:

Screening FDA-approved drugs has the benefit of potential repurposing as these drugs could reach patients in need sooner than novel compounds. The Examples section shows that pentamidine has huge promise in repurposing for a variety of reasons. Pentamidine, an antiparasitic, is only approved for use against one fungal pathogen, Pneumocystis. Pentamidine is approved for use in immunocompromised individuals, which is the primary group of individuals infected by *Cryptococcus* pathogens. Pentamidine already exists in an aerosolized formulation which allows for the drug to build up in the lung, which is the main site where *Cryptococcus* pathogens establish infections. Finally, this drug is already approved for use prophylactically against Pneumocystis, which would suggest that pentamidine could be used to protect immunocompromised individuals from cryptococcosis.

The Examples section shows that pentamidine was able to inhibit *Cryptococcus* infectious particles in vitro, was effective at lowering fungal burden in a mouse model of infection and, when used prophylactically, was able to inhibit spore germination in vivo, suggesting that pentamidine can build up in the lung sufficiently to inhibit this stress resistant cell type. The ability to inhibit both cell types, and the nature of this drug, suggest that it could make an ideal prophylactic against *Cryptococcus* pathogens which cause hundreds of thousands of deaths per year in immunocompromised individuals. While pentamidine is often not the first choice for prophylaxis against Pneumocystis, the data presented herein shows that pentamidine can be used to protect patients against other fungal pathogens generally and *Cryptococcus*. spp. specifically.

Pharmaceutical Compositions:

Using the method disclosed herein, the inventors identified four (4) FDA-approved compounds with germination-inhibiting properties that are effective antifungal therapeutics. These four compounds are disulfiram, pentamidine, otilonium bromide, and benzethonium chloride.

Thus, also disclosed herein are pharmaceutical compositions for inhibiting topical and systemic fungal infection in mammals. The compositions comprise a spore germination-inhibiting amount of a compound selected from the group consisting of:

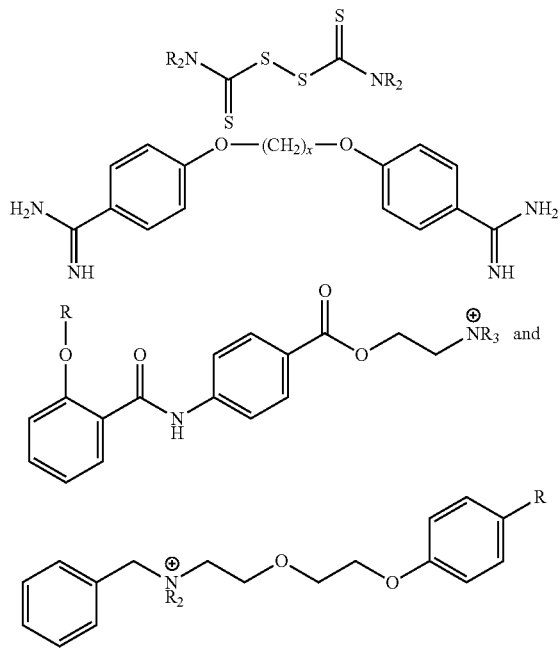

wherein R is linear or branched $C_{1-12}$ alkyl and "x" is an integer of from 1 to 12, and pharmaceutically suitable salts thereof, in combination with a pharmaceutically suitable vehicle.

The active ingredients may be used in combination with a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectible, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, compounds as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant active agent.

For intravenous administration, the compounds may be incorporated into commercial formulations such as Intralipid©-brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative compound as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical state of the subject being treated. The dosage of the composition to be administered to the patient may be determined by one of ordinary skill in the art and depends upon various factors such as weight of the patient, age of the patient, immune status of the patient, etc., and is ultimately at the discretion of the medical professional administering the treatment.

With respect to form, the composition may be, for example, a solution, a dispersion, a suspension, an emulsion or a sterile powder which is then reconstituted. The composition may be administered in a single daily dose or multiple doses.

The present disclosure also includes treating fungal infections (topical and systemic) in mammals, including humans, by administering a spore germination-inhibiting amount of one or more compounds described herein. In particular, the compositions of the present invention may be used to treat fungal infections of any and all description.

The above-described pharmaceutical compositions may be utilized in connection with non-human animals, both domestic and non-domestic, as well as humans.

EXAMPLES

The following examples are included to provide a more complete description of the methods and compositions disclosed and claimed herein. The examples are not intended to limit the scope of the claims in any fashion.

Strain Manipulation, Media and Spore Isolation:

The following strains were used and handled using standard techniques and media as previously described. (Sherman et al., 1987). *Cryptococcus neoformans* serotype D: JEC20, JEC21, JEC20-GFP, JEC21-GFP (Walsh et al. 2018), serotype A: H99, *Candida albicans*: SC5314 and *Aspergillus fumigatus*: AF293. Spores were isolated from cultures as previously described. (Botts et al., 2009). Briefly, yeast of both mating types (JEC20 and JEC21) were grown on YPD for 2 days at 30° C. combined in phosphate buffered saline (PBS) mixed to a 1:1 ratio and spotted onto V8 pH 7 agar plates. Plates were incubated for 5 days at 25° C. and spots were resuspended in 70% Percoll in 1×PBS. Spores were counted using a hemocytometer.

MIC/MFC Experiments:

All minimum inhibitory concentration (MIC) experiments were based on EUCAST methodology. (European Committee on Antimicrobial Susceptibility Testing, a standards-setting committee of the European Society of Clinical Microbiology and Infectious Diseases; EUCAST Development Laboratory for fungi, Statens Serum Institut, Building 211, Artillerivej 5, DK-2300 Copenhagen, Denmark; www.eucast.org.) Yeast cells were grown overnight in liquid YPD and used to inoculate fresh YPD. After 6-hour incubation, yeast cells were washed in 1×PBS and quantified using a hemocytometer. For each drug, $1.25 \times 10^5$ yeast cells were incubated in RPMI, and 0.33M MOPS, pH 7 at varying concentrations of inhibitors, with a final volume of 200 µL. *Cryptococcus neoformans* cells were incubated for 2 days at 30° C. while *Candida albicans* strains were incubated for 2 days at 35° C. $OD_{600}$ readings were used to assess the MIC values for each drug. To determine minimum fungicidal concentrations (MFC) values, 3 µL per well were plated on YPD and allowed to grow for 2 days. Spinning down of 96-well plates and washing did not alter the read outs of the MFC experiment.

For *Aspergillus fumigatus* MIC, conidia were collected using 0.01% Tween 80 in PBS after 3 days of growth on glucose medium media plates. Conidia at a final concentration of $2 \times 10^4$ cells were incubated in RPMI, 0.33 M MOPS, and 2% glucose at pH 7 at varying concentrations of inhibitors, with a final volume of 200 µL. MIC values were assessed based on the lowest concentration of drug that had complete absence of germ tubes or hyphae.

Quantitative Germination Assay:

All germination assays are based on Barkal et al., 2016. Briefly, microfluidic devices were loaded with $1 \times 10^5$ spores, and at 0 hours, SD media with drug of interest, were added to the sample. Spores were allowed to germinated at 30° C. in a humidified chamber and cells were monitored every two (2) hours for 16 hours. Each assay was performed in two (2) individual wells with three (3) field of views acquired from each well. All images were analyzed as previously described based on cell shape and size. Population ratio of spores, intermediate, and yeast cells were determined. Error bars in plots are based on variation between all fields of view acquired. All experiments were able to be reproduced independently. After the 16-hour experiment, samples were plated on YPD and allowed to grow at 30° C. to determine if drugs were completely germicidal or not based on lack of growth. If assays were unable to be performed in microfluidic devices, the $2 \times 10^5$ spores were incubated in identical conditions outside of PDMS devices and only loaded into devices for image acquisition.

Fungal Burden Animal Studies:

All yeast cells were cultured overnight in YPD, washed and diluted to $5 \times 10^6$ cells. For JEC20 and JEC21, $2.5 \times 10^6$ cells of each were combined. Spores were cultured as previously described and diluted to $2 \times 10^6$ cells. All experiments were performed on 8- to 10-week old C57BL/6J (Jackson Laboratory, Bar Harbor, Me., USA) female mice (5 mice per group). All mice were infected intranasally with a total of 50 µL. All dosing was performed with 4 mg/kg/day or 1×PBS for three (3) days either prior to infection or 1-day post-infection. Mice were sacked day-4 post-infection and lungs were collected, processed, and fungal burden was assessed.

In Vivo Germination:

Female mice, 8- to 10-week-old C57BL/6J (Jackson Laboratory) female mice (3 mice per group) were used. Mice were dosed with either 4mg/kg/day or 1×PBS (50 µL) for three (3) consecutive days. Mice were intranasally infected with $2 \times 10^6$ JEC20-GFPxJEC21-GFP spores, strains described in Walsh et al., 2018. After 8 hours post-infection, mice were sacked and lavaged with 0.05% TirtonX in 1×PBS. Lavage suspension underwent a series of treatments and washes, in order: red blood cell lysis (ACK lysing buffer, 2 mL, 5 minutes), formaldehyde fixation (4%, 500 µL, 30 minutes) and calcofluor white staining (25 µg/mL, 20 µL for 1 minute). Cells (50-100 per mouse) were imaged, and identified as *Cryptococcus neoformans* cells based on green fluorescent signal or cyan staining from calcofluor staining. Cells surface area and aspect ratio were measured in ImageJ and cells were classified as spores, intermediates, or yeast based on size and shapes parameters used in the quantitative germination assay.

Identifying Inhibitors of Germination and Growth

To identify inhibitors of *Cryptococcus neoformans* spore germination, a high throughput screen was developed that utilizes a nanoluciferase construct to monitor whether spores germinate in the presence of inhibitor. Briefly a protein luciferase construct was created resulting in a low luciferase signal for non-germinated spores and a high signal from germinated and replicating cells. The screen was coupled with $OD_{600}$ readings to monitor the ability of compounds to inhibit yeast replication. The examples focused on FDA-approved drugs, as these drugs have the potential of being repurposed into antifungal therapeutics. To determine whether any FDA-approved drugs were able to inhibit *Cryptococcus neoformans* spore germination and yeast replication, the aforementioned high throughput screen was performed on the L1300 Selleck FDA-Approved Drug Library containing an array of 1108 compounds. This library of compounds is available commercially from Selleck Chemicals, 14408 W Sylvanfield Drive, Houston, Tex. 77014, USA.

The screening was successful at identifying known antifungal drugs as inhibitors of yeast replication as indicated by an $OD_{600}$ signal of less than 75% of the negative control (Table 2). For the purpose of these examples, antifungal drugs were defined as any FDA-approved drug used in the treatment of fungal infections. Of these 23 known antifungal drugs, only six (6) were identified as inhibitors of spore germination, indicated by a luciferase signal of less than 30% of the negative control. These germination inhibitors demonstrated normal nanoluciferase signal dose response curves (data not shown).

TABLE 2

Antifungal drugs used to treat fungal infections and their ability to inhibit *Cryptococcus neoformans* spore germination (based on luciferase signal) and yeast replication (based on $OD_{600}$).

| | Drugs | Germination Percent Luciferase Signal | Replication Percent $OD_{600}$ |
|---|---|---|---|
| Inhibitors of Germination (6) Less than 30% Luciferase Signal | Pentamidine HCl | 6.5 | 38.3 |
| | Bifonazole | 13.6 | 33.4 |
| | Econazole nitrate | 16.1 | 33.1 |
| | Isoconazole nitrate | 16.8 | 37.0 |
| | Tioconazoie | 25.0 | 36.8 |
| | Miconazole nitrate | 25.5 | 38.2 |
| Non-inhibitors of Germination (17) | Butoconazole nitrate | 41.5 | 33.4 |
| | Fenticonazole nitrate | 49.1 | 36.4 |
| | Naftifine HCl | 55.5 | 34.5 |
| | Sulconazole nitrate | 57.8 | 40.9 |
| | Butenafine HCl | 57.5 | 32.9 |
| | Tolnaftate | 60.2 | 47.3 |
| | Liranaftate | 64.8 | 37.6 |
| | Clotrimazole | 65.9 | 34.1 |

TABLE 2-continued

Antifungal drugs used to treat fungal infections and their ability to inhibit *Cryptococcus neoformans* spore germination (based on luciferase signal) and yeast replication (based on $OD_{600}$).

| Drugs | Germination Percent Luciferase Signal | Replication Percent $OD_{600}$ |
|---|---|---|
| Fluconazole | 84.0 | 72.2 |
| Amphotericin B | 84.6 | 45.7 |
| Amorolfine HCl | 88.6 | 41.4 |
| Caspofungin acetate | 89.7 | 48.5 |
| Climbazole | 151.5 | 38.9 |
| Ketoconazole | 154.8 | 35.4 |
| Itraconazole | 159.6 | 58.9 |
| Posaconazole | 167.2 | 46.7 |
| Voriconazole | 173.9 | 35.8 |

In addition to the antifungal drugs from the screen, 60 other inhibitors of yeast replication were identified, 16 of which were also inhibitors of spore germination (Table 3). These inhibitors have a wide range of clinical functions, including quaternary ammonium compounds ("QACs") and mammalian target of rapamycin ("mTOR") inhibitors (i.e.,) which are known to have broad effects on eukaryotic processes. Some drugs used in treating neurological diseases were also identified. Finally, antimicrobial and antihelminth drugs were also identified to inhibit germination. All compounds, with the exception of doxercalciferol, demonstrated appropriate nanoluciferase dose response curves (data not shown). Only a handful of compounds were pursued further in the examples due to limited availability of certain drugs. Representatives from each group, however, were selected for further characterization. Finally, five inhibitors of only germination were identified (see below).

TABLE 3

FDA-approved drugs able to inhibit spore germination and yeast replication. List of drugs, their ability to inhibit *Cryptococcus neoformans* spore germination (based on luciferase signal) and yeast replication (based on OD600), as well as their function as listed by L1300 Selleck FDA Approved Drug Library.

| | | Germination Percent Luciferase Signal | Replication Percent $OD_{600}$ | Function |
|---|---|---|---|---|
| Germination and Growth Inhibitors | Cetylpyridinium chloride | 4.2 | 31.9 | Infection |
| | Domiphen bromide | 4.4 | 63.9 | Infection |
| | Cetrimonium bromide | 4.4 | 63.2 | Infection |
| | Alexidine Hcl | 4.6 | 29.6 | |
| | Otilonium bromide | 6.9 | 29.0 | Cardiovascular Disease |
| | Benzethonium chloride | 6.9 | 30.3 | Neurological Disease |
| | Niclosamide | 7.8 | 43.4 | |
| | PCI-32765 | 10.6 | 70.3 | Neurological Disease |
| | Everolimus | 15.7 | 67.7 | Cancer |
| | Doxercalciferol | 17.1 | 55.2 | Endocrinology |
| | Rapamycin | 18.5 | 61.8 | Immunology |
| | Temsirolimus | 21.3 | 59.2 | Cancer |
| | Ezetimibe | 22.0 | 51.3 | Cardiovascular Disease |
| | Dequalinium chloride | 22.3 | 47.9 | |
| | Disulfiram | 22.7 | 65.6 | Neurological Disease |
| | Biperiden HCl | 23.4 | 56.6 | Neurological Disease |

Together these results give a set of compounds that are germination inhibitors and replication inhibitors that can be further investigated as potential targets for repurposing or to elucidate germination processes. Inhibitors of both germination and yeast replication were prioritized for further study.

Antifungal Drugs are Inhibitors of Fungal Pathogen Vegetative Growth:

To confirm the ability of the known antifungals to inhibit yeast replication, minimum inhibitory concentration (MIC) and minimum fungicidal concentration (MFC) testing was performed on the top three germination inhibition hits. All three antifungal compounds inhibited replication of *Cryptococcus neoformans* yeast of both serotype A and D, while being less potent against *Candida albicans* (Table 4). All of the antifungal drugs were fungicidal with the exception of bifonazole against H99.

TABLE 4

Ability to inhibit fungal pathogens of antifungal drug germination-inhibitor hits. MIC/MFC values of top three germination inhibitors against prominent human fungal pathogens.

| | *Cryptococcus neoformans* (JEC21) | | *Cryptococcus neoformans* (H99) | |
|---|---|---|---|---|
| | MIC (µg/mL) | MFC (µg/mL) | MIC (µg/mL) | MFC (µg/mL) |
| Pentamidine isethionate | 1.56 | 3.13 | 6.25 | 6.25 |
| Bifonazole | 6.25 | 6.25 | 6.25 | >100 |
| Econazole nitrate | <0.78 | 6.25 | <0.78 | 6.25 |

| | *Candida albicans* (SC5314) | | *Aspergillus Fumigatus* (AF293) |
|---|---|---|---|
| | MIC (µg/mL) | MFC (µg/mL) | MIC (µg/mL) |
| Pentamidine isethionate | 50 | 50 | >100 |
| Bifonazole | >100 | >100 | >100 |
| Econazole nitrate | 6.25 | 12.5 | 3.13 |

Pentamidine and bifonazole were unable to inhibit *Aspergillus fumigatus* while econazole nitrate was able to inhibit its growth. It is important to note the *Aspergillus fumigatus* inhibition testing is performed on conidia, their asexual spore (Table 4). Together these results confirm the ability of these antifungals to inhibit fungal growth in a fungicidal manner.

Antifungal Drugs are Inhibitors of Fungal Spore Germination:

Once yeast replication inhibition was confirmed, the ability of the drugs to inhibit spore germination was characterized using a quantified microfluidics-based germination assay where the changes in size and morphology are monitored as small ovoid spores germinate into large circular yeast.

Pentamidine isethionate was able to successfully inhibit spore germination as seen by a decrease in morphology transition (data not shown). While germination is not completely halted, the spores were only able to circularize partially and unable to transition into the yeast state. It is important to note that all of the spores were inhibited, indicating that none of the ~10,000 spores showed inherent resistance and escape from inhibition. Due to the hydrophobic nature of bifonazole and econazole nitrate, the PDMS devices resulted in sequestration of the compounds and the assays could not be performed in the microfluidic devices. To determine if these compounds had an effect on spore germination, the assay was performed outside of the microfluidic device and imaged at 0 and 16 hours. Both econazole nitrate and bifonazole were able to inhibit spore germination effectively with spore escape apparent in bifonazole-treated spores as determined by a yeast population increase. None of these drugs were fully germicidal at these concentrations. These assays confirm that the high throughput screen identified antifungal drugs that are potent inhibitors of spore germination.

FDA Drug Hits are Inhibitors of Fungal Pathogen Vegetative Growth:

To determine the ability of the 16 non-antifungal drugs to inhibit yeast growth, MIC and MFC testing was performed on nine of the 16 drugs. The nine drugs were selected based on dose response curves, drug availability and ensuring that all classes of inhibitors were tested. Seven inhibitors were able to inhibit yeast replication to varying degrees (Table 5) while biperiden HCl and ezetimibe, were unable to inhibit yeast growth (data not shown). All drugs were tested against *Aspergillus fumigatus* with varying degrees of success. Notably alexidine was extremely potent against *A. fumigatus*. Additionally, cetylpyridinium bromide, otilonium bromide, benzethonium chloride and disulfiram were all able to inhibit *A. fumigatus*. (Table 5)

TABLE 5

Ability to inhibit fungal pathogens of FDA drugs germination-inhibitor hits. MIC/MFC values of germination inhibitors against prominent human fungal pathogens.

| | *Cryptococcus neoformans* (JEC21) | | *Cryptococcus neoformans* (H99) | |
|---|---|---|---|---|
| | MIC (µg/mL) | MFC (µg/mL) | MIC (µg/mL) | MFC (µg/mL) |
| Cetylpyridinium chloride | <0.78 | <0.78 | <0.78 | <0.78 |
| Alexidine HCl | <0.78 | <0.78 | <0.78 | <0.78 |
| Otilonium bromide | 3.13 | 3.13 | 3.13 | 3.13 |
| Benzethonium chloride | 3.13 | 3.13 | 3.13 | 3.13 |
| Niclosamide | <0.78 | 1.56 | 1.56 | >100 |
| Temsirolimus | 6.25 | 6.25 | 6.25 | 6.25 |
| Disulfiram | 3.13 | 3.13 | 6.25 | 6.25 |

| | *Candida albicans* (SC5314) | | *Aspergillus Fumigatus* (AF293) |
|---|---|---|---|
| | MIC (µg/mL) | MFC (µg/mL) | MIC (µg/mL) |
| Cetylpyridinium chloride | 1.56 | 3.13 | 1.56 |
| Alexidine HCl | <0.78 | <0.78 | <0.78 |
| Otilonium bromide | 3.13 | 3.13 | 6.25 |
| Benzethonium chloride | 6.25 | 12.5 | 12.5 |
| Niclosamide | >100 | >100 | >100 |
| Temsirolimus | 1.56 | 1.56 | >100 |
| Disulfiram | 6.25 | 12.5 | 25 |

These results indicate that these FDA-approved drugs have the ability to inhibit fungal pathogen vegetative growth and kill fungal cells. While some of these drugs have previously been shown to have antifungal activities, some have not.

FDA Drug Hits are Inhibitors of Fungal Spore Germination:

To determine the ability of these seven drugs, which inhibit fungal vegetative growth, to inhibit spore germination; germination assays were performed on the drugs at a concentration of 25 µg/mL. All seven of these drugs were able to inhibit germination to different extents (data not shown).

Five of the seven drugs were tested in microfluidic devices. Alexidine hydrochloride, an antimicrobial, and otilonium bromide, an antimuscarinic used to treat irritable bowel syndrome, were both able to completely inhibit spore germination, as seen by the lack of change in morphology. Both of these drugs were fully germicidal. Niclosamide, an antihelminth that inhibits oxidative phosphorylation, was also able to completely inhibit germination, but was not fully germicidal. Temsirolimus, an mTOR inhibitor used in some cancer treatments, was able to partially inhibit germination and appeared to stall germination strongly between 6 and 8 hours. When spores were exposed to temsirolimus they were able to circularize but appeared to have difficulty growing in size. Finally, disulfiram, an alcohol dehydrogenase inhibitor used in the treatment of alcoholism, was a weak inhibitor of germination leading to about a 2-hour stall in germination overall at this concentration. At higher concentrations, a similar stall to that observed with temsirolimus was observed (data not shown). Neither temsirolimus nor disulfiram were germicidal.

Cetylpyridinium chloride and benzethonium chloride, both quaternary ammonium salts, were unable to be tested in the microfluidic devices due to their viscosity and were therefore tested in outside the devices and imaged at 0 and 16 hours. Both drugs were able to inhibit spore germination completely and were fully germicidal at this concentration. These assays confirm that the method discloed herein has utility to identify a variety of non-antifungal, FDA-approved drugs that are able to inhibit fungal spore germination to varying degrees. These results also start to elucidate potential molecular processes crucial for fungal spore germination.

Pentamidine Ubiquitously Slows Germination:

Pentamidine was selected for further study due to many factors that make it a good candidate for repurposing. A range of concentrations of pentamidine isethionate was tested in a germination assay. As concentrations of pentamidine increased, spore germination became slower. However, no individual spores were able to escape inhibition, as seen by the lack of spores in the yeast state at higher concentrations. While pentamidine was not germicidal at lower concentration, at 50 µg/mL pentamidine showed germicidal activity. These results suggest that pentamidine slows the germination of spores ubiquitously and at high enough concentrations is sporicidal.

Pentamidine Treatment Lowers Fungal Burden in Mouse Lung:

Pentamidine is a successful inhibitor of *Cryptococcus neoformans* yeast replication in vitro. For repurposing potential, it is important to determine drug efficacy in vivo. For this purpose, the ability of pentamidine to lower the fungal burden in mouse lungs infected by both spores and yeast was determined. One-day post-infection intranasal dosing was begun at 4 mg/kg/day and the mice were treated for three consecutive days. On the fourth day post-infection, lungs were collected and fungal burden was determined. Pentamidine-treated mice had significantly lower fungal burdens in the lung than PBS-treated mice, in both yeast- and spore-infected mice. See FIG. 8A and FIG. 8B, respectively. These results indicate that pentamidine is able to inhibit yeast replication in vivo.

Prophylactic Pentamidine Inhibits Spore Germination In Vivo:

Pentamidine is a successful inhibitor of spore germination in vitro. It is important, though, to determine drug efficacy in vivo. Therefore, the ability of pentamidine to inhibit germination of spores in mouse lungs was determined. To determine if prophylactic pentamidine had an effect on fungal lung burden, mice were treated with 4 mg/kg/day of pentamidine or 1×PBS for three consecutive days. After three days of infection, mice were infected with JEC20× JEC21 spores and 4-days post infection, mouse lungs were collected and lung fungal burden was determined. The results are shown in FIG. 9. As evidenced by data in FIG. 9, pentamidine prophylaxis was successful in decreasing spore-mediated lung burden. These results indicate that spore germination was inhibited in vivo.

In vivo spore germination has never been characterized mainly due to technical hurdles. Using a novel assay, *Cryptococcus neoformans* cells were recovered from prophylactically treated, spore-infected mouse lungs 8 hours post infection. This was an early enough time point where no budding yeast were recovered from mouse lungs, ensuring that all cells were spore derived and not budding derived. Based on size and shape of the cells, the level of in vivo spore germination was quantified. Prophylactic pentamidine was able to inhibit spore germination as indicated by a higher spore percent and a lower yeast percent in pentamidine-treated mice. Together these results demonstrate that prophylactic pentamidine has in vivo activity against *Cryptococcus neoformans* spores, indicating it is useful to prophylactically treat (i.e., prevent) fungal infection.

What is claimed is:

1. A method of testing compounds for activity to inhibit germination of spores, the method comprising:
   (a) providing bacterial, fungal, or plant spores transformed to contain and express a detectable marker, wherein the marker when expressed, is operationally linked to a spore-specific or yeast-specific protein, in a medium and under environmental conditions in which the spores will germinate, and measuring a first signal output generated by the marker prior to the spores initiating germination;
   (b) contacting the spores of step (a) with a compound whose activity to inhibit germination of spores is to be measured;
   (c) incubating the spores of step (b) under environmental conditions and for a time wherein spores not treated with the compound will germinate; and
   (d) determining extent of germination of the spores by measuring a second signal output generated by the marker, wherein a difference between the first signal output and the second signal output is proportional to the extent of germination of the spores.

2. The method of claim 1, wherein the spores of step (a) are of a genus selected from the group consisting of *Histoplasma, Blastomyces, Aspergillus, Coccidioides, Sporothrix, Penicillium*, and *Cryptococcus*.

3. The method of claim 1, wherein the spores of step (a) are a species selected from the group consisting of *Histoplasma capsulatum, Blastomyces dermatitidis, Aspergillus fumigatus, Coccidioides immitis, Sporothrix schenkii, Penicillium marneffei*, and *Cryptococcus neoformans*.

4. The method of claim 1, wherein the detectable marker, when expressed, is a fluorophore or a chemiluminescent marker.

5. A method of testing compounds for activity to inhibit germination of spores, the method comprising:
   (a) providing bacterial, fungal, or plant spores transformed to contain and express a detectable marker, wherein the marker when expressed, is operationally linked to a gene selected from the group consisting of SEQ. ID. NOS: 1, 3, 5, 7, 9, 11, 13, 15, 17, 19, 21, 23, 25, 27, 29, 30, 31, 33, and 35, in a medium and under environmental conditions in which the spores will germinate, and measuring a first signal output generated by the marker prior to the spores initiating germination, wherein the detectable marker, when expressed, is a fluorophore or a chemiluminescent marker;
   (b) contacting the spores of step (a) with a compound whose activity to inhibit germination of spores is to be measured;
   (c) incubating the spores of step (b) under environmental conditions and for a time wherein spores not treated with the compound will germinate; and
   (d) determining extent of germination of the spores by measuring a second signal output generated by the marker, wherein a difference between the first signal output and the second signal output is proportional to the extent of germination of the spores.

6. The method of claim 4, wherein the spores of step (a) are of a genus selected from the group consisting of *Histoplasma, Blastomyces, Aspergillus, Coccidioides, Sporothrix, Penicillium*, and *Cryptococcus*.

7. The method of claim 4, wherin the spores of step (a) are a species selected from the group consisting of *Histoplasma capsulatum, Blastomyces dermatitidis, Aspergillus fumigatus, Coccidioides immitis, Sporothrix schenkii, Penicillium marneffei*, and *Cryptococcus neoformans*.

8. The method of claim 1, wherein the detectable marker, when expressed, is a fluorophore or a chemiluminescent marker.

9. The method of claim 1, wherein the detectable marker, when expressed, is luciferase.

10. The method of claim 1, wherein the detectable marker, when expressed, is luciferase.

11. A method of testing compounds for activity to inhibit germination of spores, the method comprising:
    (a) providing bacterial, fungal, or plant spores transformed to contain and express a detectable marker, wherein the marker when expressed, is operationally linked to a gene encoding a spore-specific protein selected from the group consisting of XP_567740.1 (SEQ. ID. NO: 2), XP_566791.1 (SEQ. ID. NO: 4), XP_570303.1 (SEQ. ID. NO: 6), XP_571089.1 (SEQ. ID. NO: 8), XP_571997.1 (SEQ. ID. NO: 10), XP_569295.1 (SEQ. ID. NO: 12), XP_569173.1 (SEQ. ID. NO: 14), XP_569068.1 (SEQ. ID. NO: 16), XP_569336.1 (SEQ. ID. NO: 18), XP_567136.1 (SEQ. ID. NO: 20), XP_568990.1 (SEQ. ID. NO: 22), XP_570610.1 (SEQ. ID. NO: 24), XP_571921.1 (SEQ. ID. NO: 26), XP_572925.1 (SEQ. ID. NO: 28), XP_570796.1 (SEQ. ID. NO: 30), XP_571548.1 (SEQ. ID. NO: 32), XP_570447.1 (SEQ. ID. NO: 34), and XP_571343.1 (SEQ. ID. NO: 36), in a medium and under environmental conditions in which the spores will germinate, and measuring a first signal output generated by the marker prior to the spores initiating germination;
    (b) contacting the spores of step (a) with a compound whose activity to inhibit germination of spores is to be measured;
    (c) incubating the spores of step (b) under environmental conditions and for a time wherein spores not treated with the compound will germinate; and
    (d) determining extent of germination of the spores by measuring a second signal output generated by the marker, wherein a difference between the first signal output and the second signal output is proportional to the extent of germination of the spores.

12. A method of testing compounds for activity to inhibit germination of spores, the method comprising:
 (a) providing bacterial, fungal, or plant spores transformed to contain and express a detectable marker, wherein the marker when expressed, is operationally linked to a gene selected from the group consisting of SEQ. ID. NOS: 1, 3, 5, 7, 9, 11, 13, 15, 17, 19, 21, 23, 25, 27, 29, 30, 31, 33, and 35, in a medium and under environmental conditions in which the spores will germinate, and measuring a first signal output generated by the marker prior to the spores initiating germination;
 (b) contacting the spores of step (a) with a compound whose activity to inhibit germination of spores is to be measured;
 (c) incubating the spores of step (b) under environmental conditions and for a time wherein spores not treated with the compound will germinate; and
 (d) determining extent of germination of the spores by measuring a second signal output generated by the marker, wherein a difference between the first signal output and the second signal output is proportional to the extent of germination of the spores.

13. The method of claim 12, wherein the marker, when expressed, is operationally connected to a protein encoded by gene CNK01510 (SEQ. ID. NO: 1).

14. A method of testing compounds for activity to inhibit germination of spores, the method comprising:
 (a) providing bacterial, fungal, or plant spores transformed to contain and express a detectable marker, wherein the marker is operationally linked to a spore-specific or yeast-specific protein, in a medium and under environmental conditions in which the spores will germinate, and measuring a first signal output generated by the marker prior to the spores initiating germination;
 (b) contacting the spores of step (a) with a compound whose activity to inhibit germination of spores is to be measured;
 (c) incubating the spores of step (b) under environmental conditions and for a time wherein spores not treated with the compound will germinate;
 (d) determining extent of germination of the spores by measuring a second signal output generated by the marker, wherein a difference between the first signal output and the second signal output is proportional to the extent of germination of the spores, and
 (e) plotting area and aspect ratio of the spores and any germinated cells after the incubation of step (c).

15. A method of testing compounds for activity to inhibit germination of spores, the method comprising:
 (a) providing bacterial, fungal, or plant spores transformed to contain and express a detectable marker, wherein the marker when expressed, is operationally linked to a gene encoding a spore-specific protein selected from the group consisting of XP_567740.1 (SEQ. ID. NO: 2), XP_566791.1 (SEQ. ID. NO: 4), XP_570303.1 (SEQ. ID. NO: 6), XP_571089.1 (SEQ. ID. NO: 8), XP_571997.1 (SEQ. ID. NO: 10), XP_569295.1 (SEQ. ID. NO: 12), XP_569173.1 (SEQ. ID. NO: 14), XP_569068.1 (SEQ. ID. NO: 16), XP_569336.1 (SEQ. ID. NO: 18), XP_567136.1 (SEQ. ID. NO: 20), XP_568990.1 (SEQ. ID. NO: 22), XP_570610.1 (SEQ. ID. NO: 24), XP_571921.1 (SEQ. ID. NO: 26), XP_572925.1 (SEQ. ID. NO: 28), XP_570796.1 (SEQ. ID. NO: 30), XP_571548.1 (SEQ. ID. NO: 32), XP_570447.1 (SEQ. ID. NO: 34), and XP_571343.1 (SEQ. ID. NO: 36)), in a medium and under environmental conditions in which the spores will germinate, and measuring a first signal output generated by the marker prior to the spores initiating germination, wherein the detectable marker, when expressed, is a fluorophore or a chemiluminescent marker;
 (b) contacting the spores of step (a) with a compound whose activity to inhibit germination of spores is to be measured;
 (c) incubating the spores of step (b) under environmental conditions and for a time wherein spores not treated with the compound will germinate; and
 (d) determining extent of germination of the spores by measuring a second signal output generated by the marker, wherein a difference between the first signal output and the second signal output is proportional to the extent of germination of the spores.

16. The method of claim 5, wherein the marker, when expressed, is operationally connected to a protein encoded by gene CNK01510 (SEQ. ID. NO: 1).

* * * * *

```
SEQUENCE LISTING

<160> NUMBER OF SEQ ID NOS: 68

<210> SEQ ID NO 1
<211> LENGTH: 804
<212> TYPE: DNA
<213> ORGANISM: Cryptococcus neoformans
<220> FEATURE:
<221> NAME/KEY: CDS
<222> LOCATION: (1)..(804)

<400> SEQUENCE: 1 atg tct gac gac gga caa gta caa agg gga aag gcc ggc att agc tgg      48
Met Ser Asp Asp Gly Gln Val Gln Arg Gly Lys Ala Gly Ile Ser Trp
1               5                   10                  15 ccg gct caa gaa cta acc tcg gat ccc att gcc aaa ttc ttc cag tac      96
Pro Ala Gln Glu Leu Thr Ser Asp Pro Ile Ala Lys Phe Phe Gln Tyr
```

```
                20                  25                  30
ggc tct aaa ctc tca tgg cac tgg aac tgg acc aag cat tgg aag ggc       144
Gly Ser Lys Leu Ser Trp His Trp Asn Trp Thr Lys His Trp Lys Gly
         35                  40                  45 cct ctg gtg ccg gag acc tct gac gac ctt gag att gac gca gaa ttt       192
Pro Leu Val Pro Glu Thr Ser Asp Asp Leu Glu Ile Asp Ala Glu Phe
 50                  55                  60 gtg ccc atg atc tgg tca ccc caa tct tta gat gat ggt tgc gac ttg       240
Val Pro Met Ile Trp Ser Pro Gln Ser Leu Asp Asp Gly Cys Asp Leu
 65                  70                  75                  80 caa gaa gga tgg aat ctt ctc ttg ggt ttc aac gag cct gac ctc gac       288
Gln Glu Gly Trp Asn Leu Leu Leu Gly Phe Asn Glu Pro Asp Leu Asp
                 85                  90                  95 aac gaa gct gtt gca agc cat cgc tct ccg cag gaa gct gca gac gcg       336
Asn Glu Ala Val Ala Ser His Arg Ser Pro Gln Glu Ala Ala Asp Ala
            100                 105                 110 tgg atc cag ctg gca caa ctc cgt acc gat cca gac aac cag cac ctc       384
Trp Ile Gln Leu Ala Gln Leu Arg Thr Asp Pro Asp Asn Gln His Leu
        115                 120                 125 gtt tcc ccc gct gta gca tcc aac gtg gaa tgg ctt aaa gag ttc ctc       432
Val Ser Pro Ala Val Ala Ser Asn Val Glu Trp Leu Lys Glu Phe Leu
    130                 135                 140 tcc ctg att cca gaa gac act tat ccc gcc tac ttg gct gtg cac ctc       480
Ser Leu Ile Pro Glu Asp Thr Tyr Pro Ala Tyr Leu Ala Val His Leu
145                 150                 155                 160 tac aca acc act ttt gat gat ttt gtc ggc aag atg gag atg tac cac       528
Tyr Thr Thr Thr Phe Asp Asp Phe Val Gly Lys Met Glu Met Tyr His
                165                 170                 175 aac gag ttt gga ttg cct att atc ttg act gaa ttc tgc atg cag agt       576
Asn Glu Phe Gly Leu Pro Ile Ile Leu Thr Glu Phe Cys Met Gln Ser
            180                 185                 190 tgg gac gaa ggt gtt cca ggc cca gag gac cag cag caa gtc cat gat       624
Trp Asp Glu Gly Val Pro Gly Pro Glu Asp Gln Gln Gln Val His Asp
        195                 200                 205 tac atg ggc caa aca aca aaa tgg ctt gat gaa act gac tat gtt att       672
Tyr Met Gly Gln Thr Thr Lys Trp Leu Asp Glu Thr Asp Tyr Val Ile
    210                 215                 220 aag tac tgt tgg ttt ggc gct gtt cgt gat acg gcg aac ttg cac gac       720
Lys Tyr Cys Trp Phe Gly Ala Val Arg Asp Thr Ala Asn Leu His Asp
225                 230                 235                 240 gtc cac ccc ttc aac cga ctc atg gat gaa aac ggc gag att acc cca       768
Val His Pro Phe Asn Arg Leu Met Asp Glu Asn Gly Glu Ile Thr Pro
                245                 250                 255 ttg ggt ttc caa tac atg tat ggt ggg cat gag taa                       804
Leu Gly Phe Gln Tyr Met Tyr Gly Gly His Glu
            260                 265
```

<210> SEQ ID NO 2
<211> LENGTH: 267
<212> TYPE: PRT
<213> ORGANISM: Cryptococcus neoformans

<400> SEQUENCE: 2

```
Met Ser Asp Asp Gly Gln Val Gln Arg Gly Lys Ala Gly Ile Ser Trp
1               5                   10                  15

Pro Ala Gln Glu Leu Thr Ser Asp Pro Ile Ala Lys Phe Phe Gln Tyr
            20                  25                  30

Gly Ser Lys Leu Ser Trp His Trp Asn Trp Thr Lys His Trp Lys Gly
        35                  40                  45
```

```
Pro Leu Val Pro Glu Thr Ser Asp Asp Leu Glu Ile Asp Ala Glu Phe
    50                  55                  60

Val Pro Met Ile Trp Ser Pro Gln Ser Leu Asp Asp Gly Cys Asp Leu
65                  70                  75                  80

Gln Glu Gly Trp Asn Leu Leu Gly Phe Asn Glu Pro Asp Leu Asp
                85                  90                  95

Asn Glu Ala Val Ala Ser His Arg Ser Pro Gln Glu Ala Ala Asp Ala
            100                 105                 110

Trp Ile Gln Leu Ala Gln Leu Arg Thr Asp Pro Asp Asn Gln His Leu
                115                 120                 125

Val Ser Pro Ala Val Ala Ser Asn Val Glu Trp Leu Lys Glu Phe Leu
    130                 135                 140

Ser Leu Ile Pro Glu Asp Thr Tyr Pro Ala Tyr Leu Ala Val His Leu
145                 150                 155                 160

Tyr Thr Thr Thr Phe Asp Asp Phe Val Gly Lys Met Glu Met Tyr His
                165                 170                 175

Asn Glu Phe Gly Leu Pro Ile Ile Leu Thr Glu Phe Cys Met Gln Ser
            180                 185                 190

Trp Asp Glu Gly Val Pro Gly Pro Glu Asp Gln Gln Val His Asp
                195                 200                 205

Tyr Met Gly Gln Thr Thr Lys Trp Leu Asp Glu Thr Asp Tyr Val Ile
    210                 215                 220

Lys Tyr Cys Trp Phe Gly Ala Val Arg Asp Thr Ala Asn Leu His Asp
225                 230                 235                 240

Val His Pro Phe Asn Arg Leu Met Asp Glu Asn Gly Glu Ile Thr Pro
                245                 250                 255

Leu Gly Phe Gln Tyr Met Tyr Gly Gly His Glu
            260                 265
```

<210> SEQ ID NO 3
<211> LENGTH: 1821
<212> TYPE: DNA
<213> ORGANISM: Cryptococcus neoformans
<220> FEATURE:
<221> NAME/KEY: CDS
<222> LOCATION: (1)..(1821)

<400> SEQUENCE: 3

```
atg tcg acc ctt ccc att tat cac ccc gtt cca acg gac gag aaa cac     48
Met Ser Thr Leu Pro Ile Tyr His Pro Val Pro Thr Asp Glu Lys His
1               5                   10                  15 cca ata tct gcc act ttg gta gac ggc gag ttt gac cct cgc tac att     96
Pro Ile Ser Ala Thr Leu Val Asp Gly Glu Phe Asp Pro Arg Tyr Ile
                20                  25                  30 cat ccc gcc gca atc ggc tct caa tac ctt tat att ggc ggt ccc cgc    144
His Pro Ala Ala Ile Gly Ser Gln Tyr Leu Tyr Ile Gly Gly Pro Arg
            35                  40                  45 agc gcc tat cag gcc gcg aag gac aag tac gct ggc ttg tcc aaa gtc    192
Ser Ala Tyr Gln Ala Ala Lys Asp Lys Tyr Ala Gly Leu Ser Lys Val
    50                  55                  60 aag aaa ggt ctc ctc gct ctt gcc gtt gtt tgg ttc ggt ctt gtc gtt    240
Lys Lys Gly Leu Leu Ala Leu Ala Val Val Trp Phe Gly Leu Val Val
65                  70                  75                  80 ggc cat cag gct gcg cgt ctt gct ggc ggc aaa tgc cac cag gac gct    288
Gly His Gln Ala Ala Arg Leu Ala Gly Gly Lys Cys His Gln Asp Ala
                85                  90                  95 cat cat gct ccc gcc gaa ttt ggc gtg aag cag tgg aga gac cac tca    336
His His Ala Pro Ala Glu Phe Gly Val Lys Gln Trp Arg Asp His Ser
```

```
                100                 105                 110
tct cat cga ttt ggt ggc cct atc ttc ctc gag gat ggt cca ctt gac      384
Ser His Arg Phe Gly Gly Pro Ile Phe Leu Glu Asp Gly Pro Leu Asp
        115                 120                 125 tgt cat ggt ggc cgt aaa gac cgt gct cct gag gag ctt tct tcc gtt      432
Cys His Gly Gly Arg Lys Asp Arg Ala Pro Glu Glu Leu Ser Ser Val
130                 135                 140 gcc act gtc tac gag tcc atc aac gtt gtc ggg agc aac gat gct acc      480
Ala Thr Val Tyr Glu Ser Ile Asn Val Val Gly Ser Asn Asp Ala Thr
145                 150                 155                 160 gac att ctc tcc gcc aac gcc tct ttc cct ctc aaa ctt ggc cgt ggc      528
Asp Ile Leu Ser Ala Asn Ala Ser Phe Pro Leu Lys Leu Gly Arg Gly
                165                 170                 175 aag cac ttt gat ctc acc ttc caa ggt gag ggt aac gtc atc atc tcg      576
Lys His Phe Asp Leu Thr Phe Gln Gly Glu Gly Asn Val Ile Ile Ser
            180                 185                 190 agg gct gag gag gag tct gaa gac tct act gtc aac gtt ttt gtt gag      624
Arg Ala Glu Glu Glu Ser Glu Asp Ser Thr Val Asn Val Phe Val Glu
        195                 200                 205 tct act tgg tcc ggt gag gag gct gaa ggg gtc aag atg ttg tct gga      672
Ser Thr Trp Ser Gly Glu Glu Ala Glu Gly Val Lys Met Leu Ser Gly
    210                 215                 220 aaa cac tct cac gct ctc tct gtt gct tct tct caa tcc tcg tct cat      720
Lys His Ser His Ala Leu Ser Val Ala Ser Ser Gln Ser Ser Ser His
225                 230                 235                 240 att gtc cac ctt gtt ctt cct gcc aac aag aag cgt ctt cct tcc atc      768
Ile Val His Leu Val Leu Pro Ala Asn Lys Lys Arg Leu Pro Ser Ile
                245                 250                 255 tct atc ttt tct acc aag gac ctt act ctt gat atc cat cca tct gtt      816
Ser Ile Phe Ser Thr Lys Asp Leu Thr Leu Asp Ile His Pro Ser Val
            260                 265                 270 cag gac atc cac gtg gga aag ctc tcc ctc aag tct gag agc ggt gat      864
Gln Asp Ile His Val Gly Lys Leu Ser Leu Lys Ser Glu Ser Gly Asp
        275                 280                 285 atc aag ctt cct acc ctc gct gtc aac aag ctc gtg gct gag acc gta      912
Ile Lys Leu Pro Thr Leu Ala Val Asn Lys Leu Val Ala Glu Thr Val
    290                 295                 300 acc ggt gac gtc ggc ggt aac ttc aac gtc agc aac tct ttc gtt gtc      960
Thr Gly Asp Val Gly Gly Asn Phe Asn Val Ser Asn Ser Phe Val Val
305                 310                 315                 320 aag aca gtc aca ggt aac att aac gcc att gtt aac gtt gtt cct cac     1008
Lys Thr Val Thr Gly Asn Ile Asn Ala Ile Val Asn Val Val Pro His
                325                 330                 335 tcc cca cct aag gac aag ctt aac ctt cat aac gtt gat gcc aag cac     1056
Ser Pro Pro Lys Asp Lys Leu Asn Leu His Asn Val Asp Ala Lys His
            340                 345                 350 gag cac aag aag ttt gac agc cgt cac gga gaa cac aat cac gag aag     1104
Glu His Lys Lys Phe Asp Ser Arg His Gly Glu His Asn His Glu Lys
        355                 360                 365 aag cac ttc gga ggg cgt ttc cac tct gaa gaa gag cga cct tcc aag     1152
Lys His Phe Gly Gly Arg Phe His Ser Glu Glu Glu Arg Pro Ser Lys
    370                 375                 380 tgg tct ctc aat att ttc aag tct aag aaa gag gat gag cct gaa cac     1200
Trp Ser Leu Asn Ile Phe Lys Ser Lys Lys Glu Asp Glu Pro Glu His
385                 390                 395                 400 cct ccc ccc cct ccg gtc ttt atc ggc gct ttc tcc acc tct ggc aac     1248
Pro Pro Pro Pro Pro Val Phe Ile Gly Ala Phe Ser Thr Ser Gly Asn
                405                 410                 415 att ctt ctc aag gtc ttc ggt tct ccc aac gtc tct act gat act aat     1296
```

```
Ile Leu Leu Lys Val Phe Gly Ser Pro Asn Val Ser Thr Asp Thr Asn
            420                 425                 430 gtc ttc tcc cat acc ggt gac gtc gac gtt acc cat gac aag tca ttc    1344
Val Phe Ser His Thr Gly Asp Val Asp Val Thr His Asp Lys Ser Phe
            435                 440                 445 cac ggt ttg tac gag gtc ggc agc tta aag ggc acc tat gat gtt gtc    1392
His Gly Leu Tyr Glu Val Gly Ser Leu Lys Gly Thr Tyr Asp Val Val
            450                 455                 460 gtg agg gac ggc aag gtg cat cga gtc ctg gag gaa tac gtc act gag    1440
Val Arg Asp Gly Lys Val His Arg Val Leu Glu Glu Tyr Val Thr Glu
465                 470                 475                 480 gag gga ggc aag cag aag ggc ctt gcc ttc gtt ccc aag aac aga aag    1488
Glu Gly Gly Lys Gln Lys Gly Leu Ala Phe Val Pro Lys Asn Arg Lys
                485                 490                 495 act gag ggc tcc cac gag aag agg cac ttc cgc aat gct gaa agc gtt    1536
Thr Glu Gly Ser His Glu Lys Arg His Phe Arg Asn Ala Glu Ser Val
            500                 505                 510 gat ggc gag ctt ccc cct ccc cct ggt aag ggc cac ggt cct gat        1584
Asp Gly Glu Leu Pro Pro Pro Pro Gly Lys Gly His Gly Pro Asp
            515                 520                 525 ggt ccc gat ggt cct gat ggt cct gga ggt cct agt ggt cct gga ggt    1632
Gly Pro Asp Gly Pro Asp Gly Pro Gly Gly Pro Ser Gly Pro Gly Gly
530                 535                 540 cct ggt ggt cct gat ggt cct ggt ggt cct ggt ggt cct ggt ggc cct    1680
Pro Gly Gly Pro Asp Gly Pro Gly Gly Pro Gly Gly Pro Gly Gly Pro
545                 550                 555                 560 gga ggt ccc ggt ggt ccc ggt ggt ccc ggt ggt ccc ggc ccc gac cac    1728
Gly Gly Pro Gly Gly Pro Gly Gly Pro Gly Gly Pro Gly Pro Asp His
                565                 570                 575 ccc cgt ggt cct cct cct tgg gtt gtc ttc ccc ccc ggt cac tca gaa    1776
Pro Arg Gly Pro Pro Pro Trp Val Val Phe Pro Pro Gly His Ser Glu
            580                 585                 590 gtc ttc gtc cac act gaa gtt ggc aac gcc aag att gtc ctc taa        1821
Val Phe Val His Thr Glu Val Gly Asn Ala Lys Ile Val Leu
            595                 600                 605

<210> SEQ ID NO 4
<211> LENGTH: 606
<212> TYPE: PRT
<213> ORGANISM: Cryptococcus neoformans

<400> SEQUENCE: 4

Met Ser Thr Leu Pro Ile Tyr His Pro Val Pro Thr Asp Glu Lys His
1               5                   10                  15

Pro Ile Ser Ala Thr Leu Val Asp Gly Glu Phe Asp Pro Arg Tyr Ile
                20                  25                  30

His Pro Ala Ala Ile Gly Ser Gln Tyr Leu Tyr Ile Gly Gly Pro Arg
            35                  40                  45

Ser Ala Tyr Gln Ala Ala Lys Asp Lys Tyr Ala Gly Leu Ser Lys Val
        50                  55                  60

Lys Lys Gly Leu Leu Ala Leu Ala Val Val Trp Phe Gly Leu Val Val
65                  70                  75                  80

Gly His Gln Ala Ala Arg Leu Ala Gly Gly Lys Cys His Gln Asp Ala
                85                  90                  95

His His Ala Pro Ala Glu Phe Gly Val Lys Gln Trp Arg Asp His Ser
            100                 105                 110

Ser His Arg Phe Gly Gly Pro Ile Phe Leu Glu Asp Gly Pro Leu Asp
        115                 120                 125
```

```
Cys His Gly Gly Arg Lys Asp Arg Ala Pro Glu Glu Leu Ser Ser Val
130                 135                 140
Ala Thr Val Tyr Glu Ser Ile Asn Val Val Gly Ser Asn Asp Ala Thr
145                 150                 155                 160
Asp Ile Leu Ser Ala Asn Ala Ser Phe Pro Leu Lys Leu Gly Arg Gly
                165                 170                 175
Lys His Phe Asp Leu Thr Phe Gln Gly Glu Gly Asn Val Ile Ile Ser
            180                 185                 190
Arg Ala Glu Glu Ser Glu Asp Ser Thr Val Asn Val Phe Val Glu
        195                 200                 205
Ser Thr Trp Ser Gly Glu Glu Ala Glu Gly Val Lys Met Leu Ser Gly
210                 215                 220
Lys His Ser His Ala Leu Ser Val Ala Ser Ser Gln Ser Ser Ser His
225                 230                 235                 240
Ile Val His Leu Val Leu Pro Ala Asn Lys Lys Arg Leu Pro Ser Ile
                245                 250                 255
Ser Ile Phe Ser Thr Lys Asp Leu Thr Leu Asp Ile His Pro Ser Val
            260                 265                 270
Gln Asp Ile His Val Gly Lys Leu Ser Leu Lys Ser Glu Ser Gly Asp
        275                 280                 285
Ile Lys Leu Pro Thr Leu Ala Val Asn Lys Leu Val Ala Glu Thr Val
290                 295                 300
Thr Gly Asp Val Gly Gly Asn Phe Asn Val Ser Asn Ser Phe Val Val
305                 310                 315                 320
Lys Thr Val Thr Gly Asn Ile Asn Ala Ile Val Asn Val Val Pro His
                325                 330                 335
Ser Pro Pro Lys Asp Lys Leu Asn Leu His Asn Val Asp Ala Lys His
            340                 345                 350
Glu His Lys Lys Phe Asp Ser Arg His Gly Glu His Asn His Glu Lys
        355                 360                 365
Lys His Phe Gly Gly Arg Phe His Ser Glu Glu Glu Arg Pro Ser Lys
370                 375                 380
Trp Ser Leu Asn Ile Phe Lys Ser Lys Lys Glu Asp Glu Pro Glu His
385                 390                 395                 400
Pro Pro Pro Pro Val Phe Ile Gly Ala Phe Ser Thr Ser Gly Asn
                405                 410                 415
Ile Leu Leu Lys Val Phe Gly Ser Pro Asn Val Ser Thr Asp Thr Asn
            420                 425                 430
Val Phe Ser His Thr Gly Asp Val Asp Val Thr His Asp Lys Ser Phe
        435                 440                 445
His Gly Leu Tyr Glu Val Gly Ser Leu Lys Gly Thr Tyr Asp Val Val
450                 455                 460
Val Arg Asp Gly Lys Val His Arg Val Leu Glu Glu Tyr Val Thr Glu
465                 470                 475                 480
Glu Gly Gly Lys Gln Lys Gly Leu Ala Phe Val Pro Lys Asn Arg Lys
                485                 490                 495
Thr Glu Gly Ser His Glu Lys Arg His Phe Arg Asn Ala Glu Ser Val
            500                 505                 510
Asp Gly Glu Leu Pro Pro Pro Pro Gly Lys Gly His Gly Pro Asp
        515                 520                 525
Gly Pro Asp Gly Pro Asp Gly Pro Gly Pro Ser Gly Pro Gly Gly
530                 535                 540
Pro Gly Gly Pro Asp Gly Pro Gly Gly Pro Gly Gly Pro Gly Gly Pro
```

```
                545                 550                 555                 560
Gly Gly Pro Gly Gly Pro Gly Gly Pro Gly Gly Pro Gly Pro Asp His
                    565                 570                 575

Pro Arg Gly Pro Pro Trp Val Val Phe Pro Pro Gly His Ser Glu
                580                 585                 590

Val Phe Val His Thr Glu Val Gly Asn Ala Lys Ile Val Leu
            595                 600                 605

<210> SEQ ID NO 5
<211> LENGTH: 594
<212> TYPE: DNA
<213> ORGANISM: Cryptococcus neoformans
<220> FEATURE:
<221> NAME/KEY: CDS
<222> LOCATION: (1)..(594)

<400> SEQUENCE: 5 atg cgt ttt act tct atc atc gtt gcc gct ctt ccg ctt gtc ggc tct     48
Met Arg Phe Thr Ser Ile Ile Val Ala Ala Leu Pro Leu Val Gly Ser
1               5                   10                  15 gtc ttc gct gcc ccc ttc gct gag aag gat tct atc gct tct tcc ccc     96
Val Phe Ala Ala Pro Phe Ala Glu Lys Asp Ser Ile Ala Ser Ser Pro
            20                  25                  30 gac ttg gtc aag aag gag gtt aac gtc ctc tct gtc gtc aat gaa gtc    144
Asp Leu Val Lys Lys Glu Val Asn Val Leu Ser Val Val Asn Glu Val
        35                  40                  45 cag tct agg gtt aat gct gct gcc gcc atg ccc cgc cag tct caa gcg    192
Gln Ser Arg Val Asn Ala Ala Ala Ala Met Pro Arg Gln Ser Gln Ala
    50                  55                  60 gat gtt gag gcc tgt ctc aac act gtc att gat gcc ttt aac tgg tgc    240
Asp Val Glu Ala Cys Leu Asn Thr Val Ile Asp Ala Phe Asn Trp Cys
65                  70                  75                  80 ggt ggc cag ctc ggt att gac gtt tcc gcc agc gcc agc gcc aat gcc    288
Gly Gly Gln Leu Gly Ile Asp Val Ser Ala Ser Ala Ser Ala Asn Ala
                85                  90                  95 ggt gct agc atc cat tac ttg cgt cgt gag att att gcc cgt gat gac    336
Gly Ala Ser Ile His Tyr Leu Arg Arg Glu Ile Ile Ala Arg Asp Asp
            100                 105                 110 gac aag gag gct gtt gct cag gca ctc tct agc gtt gtt cag acc gtt    384
Asp Lys Glu Ala Val Ala Gln Ala Leu Ser Ser Val Val Gln Thr Val
        115                 120                 125 aat gtc ggc atc gtc cag cag atc ccc agc caa ttc atc aac atc cct    432
Asn Val Gly Ile Val Gln Gln Ile Pro Ser Gln Phe Ile Asn Ile Pro
    130                 135                 140 ggc gtc tcc aac ctt gtt aac cag ctt gac att gct ctc agt ctc atc    480
Gly Val Ser Asn Leu Val Asn Gln Leu Asp Ile Ala Leu Ser Leu Ile
145                 150                 155                 160 ctt aag ggt gtt gac gct att ctc gcc ggt gtc ctc tac ctc gtc aag    528
Leu Lys Gly Val Asp Ala Ile Leu Ala Gly Val Leu Tyr Leu Val Lys
                165                 170                 175 gcc ctt ctc atc gat gtt ggc atc atc ctc gac tcg ctt ctc ggc ggt    576
Ala Leu Leu Ile Asp Val Gly Ile Ile Leu Asp Ser Leu Leu Gly Gly
            180                 185                 190 ctc ctt tcc atc ctt taa                                            594
Leu Leu Ser Ile Leu
        195

<210> SEQ ID NO 6
<211> LENGTH: 197
<212> TYPE: PRT
<213> ORGANISM: Cryptococcus neoformans
```

<400> SEQUENCE: 6

```
Met Arg Phe Thr Ser Ile Ile Val Ala Ala Leu Pro Leu Val Gly Ser
1               5                   10                  15

Val Phe Ala Ala Pro Phe Ala Glu Lys Asp Ser Ile Ala Ser Ser Pro
            20                  25                  30

Asp Leu Val Lys Lys Glu Val Asn Val Leu Ser Val Val Asn Glu Val
        35                  40                  45

Gln Ser Arg Val Asn Ala Ala Ala Met Pro Arg Gln Ser Gln Ala
    50                  55                  60

Asp Val Glu Ala Cys Leu Asn Thr Val Ile Asp Ala Phe Asn Trp Cys
65                  70                  75                  80

Gly Gly Gln Leu Gly Ile Asp Val Ser Ala Ser Ala Ser Ala Asn Ala
                85                  90                  95

Gly Ala Ser Ile His Tyr Leu Arg Arg Glu Ile Ile Ala Arg Asp Asp
            100                 105                 110

Asp Lys Glu Ala Val Ala Gln Ala Leu Ser Ser Val Val Gln Thr Val
        115                 120                 125

Asn Val Gly Ile Val Gln Gln Ile Pro Ser Gln Phe Ile Asn Ile Pro
    130                 135                 140

Gly Val Ser Asn Leu Val Asn Gln Leu Asp Ile Ala Leu Ser Leu Ile
145                 150                 155                 160

Leu Lys Gly Val Asp Ala Ile Leu Ala Gly Val Leu Tyr Leu Val Lys
                165                 170                 175

Ala Leu Leu Ile Asp Val Gly Ile Leu Asp Ser Leu Leu Gly Gly
            180                 185                 190

Leu Leu Ser Ile Leu
        195
```

<210> SEQ ID NO 7
<211> LENGTH: 894
<212> TYPE: DNA
<213> ORGANISM: Cryptococcus neoformans
<220> FEATURE:
<221> NAME/KEY: CDS
<222> LOCATION: (1)..(894)

<400> SEQUENCE: 7

```
atg tct gcc gtc gaa gca ccc tcc gcc tcg cag gcc atc tgg ccc gag     48
Met Ser Ala Val Glu Ala Pro Ser Ala Ser Gln Ala Ile Trp Pro Glu
1               5                   10                  15 ctc act gaa gac cac ccc ctt tcg cag ctc aac tct cgc ctc cct act     96
Leu Thr Glu Asp His Pro Leu Ser Gln Leu Asn Ser Arg Leu Pro Thr
            20                  25                  30 atc ctt tca gag gct ggt cac tcc caa atc tgg ggc gtt act ctt act    144
Ile Leu Ser Glu Ala Gly His Ser Gln Ile Trp Gly Val Thr Leu Thr
        35                  40                  45 tac tcc act ccc cca acc ttc tct agc ctt att att ctg caa aaa ttc    192
Tyr Ser Thr Pro Pro Thr Phe Ser Ser Leu Ile Ile Leu Gln Lys Phe
    50                  55                  60 ctt cgt tcc gtg gat aat aac gtg gat gag gct gcc acg gct cta ggc    240
Leu Arg Ser Val Asp Asn Asn Val Asp Glu Ala Ala Thr Ala Leu Gly
65                  70                  75                  80 aag aca ctc aag tgg cgg aag gac tgg gga ttg gac gcg cgg gcg gac    288
Lys Thr Leu Lys Trp Arg Lys Asp Trp Gly Leu Asp Ala Arg Ala Asp
                85                  90                  95 aaa aaa gag aag gaa aac ttt ggg ccc gat ttt gaa ggc tta gga tat    336
Lys Lys Glu Lys Glu Asn Phe Gly Pro Asp Phe Glu Gly Leu Gly Tyr
```

```
                    100                 105                 110
gtg acc aag atc aag aaa aat gat ggc gga gat gag atc gtg act tgg       384
Val Thr Lys Ile Lys Lys Asn Asp Gly Gly Asp Glu Ile Val Thr Trp
            115                 120                 125 aac gtt tat gga gct gtg aag gat ttg aaa tcg acc ttt ggg gat ctt       432
Asn Val Tyr Gly Ala Val Lys Asp Leu Lys Ser Thr Phe Gly Asp Leu
    130                 135                 140 gac cga ttc ctt cga tgg cgt gtc aat ctt atg gag gag gct atc gcc       480
Asp Arg Phe Leu Arg Trp Arg Val Asn Leu Met Glu Glu Ala Ile Ala
145                 150                 155                 160 cat ctt cat ctc gct acc acc tct act ccc atc cca gac ttt aac gcc       528
His Leu His Leu Ala Thr Thr Ser Thr Pro Ile Pro Asp Phe Asn Ala
                165                 170                 175 ggt att gat ccc cat cgc atg gca caa gtc cat cta tat gaa ggt gtc       576
Gly Ile Asp Pro His Arg Met Ala Gln Val His Leu Tyr Glu Gly Val
            180                 185                 190 tca ttc ctt cgc atg gat cct cat gtg aaa gct gcc tcc aag gca acc       624
Ser Phe Leu Arg Met Asp Pro His Val Lys Ala Ala Ser Lys Ala Thr
    195                 200                 205 att gag ctt atg gcg gcc aac tat ccc gaa ctt ctt tct cgc aaa ttc       672
Ile Glu Leu Met Ala Ala Asn Tyr Pro Glu Leu Leu Ser Arg Lys Phe
210                 215                 220 ttt gtg ggc gtg cct ttg ata atg agc tgg atg ttt cag gcc gtg cga       720
Phe Val Gly Val Pro Leu Ile Met Ser Trp Met Phe Gln Ala Val Arg
225                 230                 235                 240 atg ttc gtt tcc gct gag act gcc aag aag ttt gtg gtc att agc tac       768
Met Phe Val Ser Ala Glu Thr Ala Lys Lys Phe Val Val Ile Ser Tyr
                245                 250                 255 aag gag aat ctg gcg aat gag ctg gga gaa ctt gaa ggt gtg ccc aag       816
Lys Glu Asn Leu Ala Asn Glu Leu Gly Glu Leu Glu Gly Val Pro Lys
            260                 265                 270 gag tat ggt gga aag ggt ctc agt ttg ggc gaa ctt cag aac cag ctg       864
Glu Tyr Gly Gly Lys Gly Leu Ser Leu Gly Glu Leu Gln Asn Gln Leu
    275                 280                 285 cga ggg gag gac gcg gtg act tct tcg taa                               894
Arg Gly Glu Asp Ala Val Thr Ser Ser
    290                 295

<210> SEQ ID NO 8
<211> LENGTH: 297
<212> TYPE: PRT
<213> ORGANISM: Cryptococcus neoformans

<400> SEQUENCE: 8

Met Ser Ala Val Glu Ala Pro Ser Ala Ser Gln Ala Ile Trp Pro Glu
1               5                   10                  15

Leu Thr Glu Asp His Pro Leu Ser Gln Leu Asn Ser Arg Leu Pro Thr
            20                  25                  30

Ile Leu Ser Glu Ala Gly His Ser Gln Ile Trp Gly Val Thr Leu Thr
        35                  40                  45

Tyr Ser Thr Pro Pro Thr Phe Ser Ser Leu Ile Ile Leu Gln Lys Phe
    50                  55                  60

Leu Arg Ser Val Asp Asn Asn Val Asp Glu Ala Ala Thr Ala Leu Gly
65                  70                  75                  80

Lys Thr Leu Lys Trp Arg Lys Asp Trp Gly Leu Asp Ala Arg Ala Asp
                85                  90                  95

Lys Lys Glu Lys Glu Asn Phe Gly Pro Asp Phe Glu Gly Leu Gly Tyr
            100                 105                 110
```

```
Val Thr Lys Ile Lys Lys Asn Asp Gly Gly Asp Glu Ile Val Thr Trp
            115                 120                 125

Asn Val Tyr Gly Ala Val Lys Asp Leu Lys Ser Thr Phe Gly Asp Leu
        130                 135                 140

Asp Arg Phe Leu Arg Trp Arg Val Asn Leu Met Glu Glu Ala Ile Ala
145                 150                 155                 160

His Leu His Leu Ala Thr Thr Ser Thr Pro Ile Pro Asp Phe Asn Ala
                165                 170                 175

Gly Ile Asp Pro His Arg Met Ala Gln Val His Leu Tyr Glu Gly Val
            180                 185                 190

Ser Phe Leu Arg Met Asp Pro His Val Lys Ala Ala Ser Lys Ala Thr
        195                 200                 205

Ile Glu Leu Met Ala Ala Asn Tyr Pro Glu Leu Leu Ser Arg Lys Phe
    210                 215                 220

Phe Val Gly Val Pro Leu Ile Met Ser Trp Met Phe Gln Ala Val Arg
225                 230                 235                 240

Met Phe Val Ser Ala Glu Thr Ala Lys Lys Phe Val Val Ile Ser Tyr
                245                 250                 255

Lys Glu Asn Leu Ala Asn Glu Leu Gly Glu Leu Glu Gly Val Pro Lys
            260                 265                 270

Glu Tyr Gly Gly Lys Gly Leu Ser Leu Gly Glu Leu Gln Asn Gln Leu
        275                 280                 285

Arg Gly Glu Asp Ala Val Thr Ser Ser
    290                 295

<210> SEQ ID NO 9
<211> LENGTH: 2094
<212> TYPE: DNA
<213> ORGANISM: Cryptococcus neoformans
<220> FEATURE:
<221> NAME/KEY: CDS
<222> LOCATION: (1)..(2094)

<400> SEQUENCE: 9 atg tca gag cta ttc aag gac atc cca gag ttt gta gag acc gac atc      48
Met Ser Glu Leu Phe Lys Asp Ile Pro Glu Phe Val Glu Thr Asp Ile
1               5                   10                  15 gga gag agc ctt gca gcc aga acg gaa acc ctt ggc tcc ttc aga gaa      96
Gly Glu Ser Leu Ala Ala Arg Thr Glu Thr Leu Gly Ser Phe Arg Glu
                20                  25                  30 cta ggc cct cca gac ctc tgc cat gtt atg aaa gtt tat ggg aaa ccg     144
Leu Gly Pro Pro Asp Leu Cys His Val Met Lys Val Tyr Gly Lys Pro
            35                  40                  45 ccg act caa cga gag atc ggg tcc tat cac tac tgc tct gga ata gag     192
Pro Thr Gln Arg Glu Ile Gly Ser Tyr His Tyr Cys Ser Gly Ile Glu
        50                  55                  60 gct tcg tcc tct gcg tca ctc gct gcc tat ctc aac tct ttg cag ttt     240
Ala Ser Ser Ser Ala Ser Leu Ala Ala Tyr Leu Asn Ser Leu Gln Phe
65                  70                  75                  80 tca gtg gaa gat tcg tct gca tgg ttt ggc aag ggg tcg gca tgg aaa     288
Ser Val Glu Asp Ser Ser Ala Trp Phe Gly Lys Gly Ser Ala Trp Lys
                85                  90                  95 gtt cga agc ggg acg tat tgc tgc ttc aat gcc ttt tca cgg gta gat     336
Val Arg Ser Gly Thr Tyr Cys Cys Phe Asn Ala Phe Ser Arg Val Asp
            100                 105                 110 atg cgg gtg gaa gcc aat att ccc ggc ggt gtc gac gct ttt gtg gtt     384
Met Arg Val Glu Ala Asn Ile Pro Gly Gly Val Asp Ala Phe Val Val
        115                 120                 125
```

```
gat ctt cac ggt caa aga cac cct gcg acc ccc gag ctc tgg caa gag        432
Asp Leu His Gly Gln Arg His Pro Ala Thr Pro Glu Leu Trp Gln Glu
        130                 135                 140 acg tac ctg tct gcg atc ctg cgt gct att aga tat gcg gac gat gcc        480
Thr Tyr Leu Ser Ala Ile Leu Arg Ala Ile Arg Tyr Ala Asp Asp Ala
145                 150                 155                 160 tcc tat agg ttg gca ggg tat aga aag ctg gat ccg atc aca acg cca        528
Ser Tyr Arg Leu Ala Gly Tyr Arg Lys Leu Asp Pro Ile Thr Thr Pro
                165                 170                 175 gaa gca gag gaa aga ttc ctc aaa gcc gcc gaa gcg ctg ttc ttc aag        576
Glu Ala Glu Glu Arg Phe Leu Lys Ala Ala Glu Ala Leu Phe Phe Lys
            180                 185                 190 ggc tgg cag ctt ggc tca gat ccc gaa ata cag gtc gcc aca gtt gtc        624
Gly Trp Gln Leu Gly Ser Asp Pro Glu Ile Gln Val Ala Thr Val Val
        195                 200                 205 acc aac cac ctg acc tct gcc att ctt aaa tac ttt tcc gac tct ttc        672
Thr Asn His Leu Thr Ser Ala Ile Leu Lys Tyr Phe Ser Asp Ser Phe
210                 215                 220 aga ctt cat cga gcc gcc aac ctt ttc gaa agg atg atg gac aag gag        720
Arg Leu His Arg Ala Ala Asn Leu Phe Glu Arg Met Met Asp Lys Glu
225                 230                 235                 240 cca gag gta gcc gct cta gtg gcg aag agt tac atc ggc atg aac gag        768
Pro Glu Val Ala Ala Leu Val Ala Lys Ser Tyr Ile Gly Met Asn Glu
                245                 250                 255 gag atc aaa gct gtc aag atc atg aac gct gcc ctt gcc gcc aat cct        816
Glu Ile Lys Ala Val Lys Ile Met Asn Ala Ala Leu Ala Ala Asn Pro
            260                 265                 270 caa tcc tat ccc atc ctt cat gcc caa gtc gat ttc ctc ctt tcc aag        864
Gln Ser Tyr Pro Ile Leu His Ala Gln Val Asp Phe Leu Leu Ser Lys
        275                 280                 285 cac aaa tac gaa tgg gcc cag caa gtc gcc cag cag gcg gtc aat tct        912
His Lys Tyr Glu Trp Ala Gln Gln Val Ala Gln Gln Ala Val Asn Ser
290                 295                 300 gca ccc agc gag ttc acg act tgg gcc aaa ctc acg gag acg tac atc        960
Ala Pro Ser Glu Phe Thr Thr Trp Ala Lys Leu Thr Glu Thr Tyr Ile
305                 310                 315                 320 gag ttg ggg caa ctc gac cag gct ttg ttg aca ctc aac tca tgt cca       1008
Glu Leu Gly Gln Leu Asp Gln Ala Leu Leu Thr Leu Asn Ser Cys Pro
                325                 330                 335 atg ttt act tat aac gaa aga gat ctc cat cgg atg cct acc cct gca       1056
Met Phe Thr Tyr Asn Glu Arg Asp Leu His Arg Met Pro Thr Pro Ala
            340                 345                 350 aag tcc aat atg cca gtc aag aag ttt atc gca gac tcc aat ttg gtg       1104
Lys Ser Asn Met Pro Val Lys Lys Phe Ile Ala Asp Ser Asn Leu Val
        355                 360                 365 gat gaa gat tcg tca cga gag aac gag gcc gat atc gct ctc ctc cgt       1152
Asp Glu Asp Ser Ser Arg Glu Asn Glu Ala Asp Ile Ala Leu Leu Arg
370                 375                 380 ctc ccc gct ccc aac ctc cgc ggc aca ttc gcc aaa gcg tac tcc ctc       1200
Leu Pro Ala Pro Asn Leu Arg Gly Thr Phe Ala Lys Ala Tyr Ser Leu
385                 390                 395                 400 ctc act ctc ctt gtc tct aag att ggt tgg gat gag ctt ctc aaa att       1248
Leu Thr Leu Leu Val Ser Lys Ile Gly Trp Asp Glu Leu Leu Lys Ile
                405                 410                 415 aga tcc tcc gtc ttc gtc atg gaa gag gaa tat cgg ctg cat aaa acg       1296
Arg Ser Ser Val Phe Val Met Glu Glu Glu Tyr Arg Leu His Lys Thr
            420                 425                 430 aac gtt tct gtt gat atg aat ggc gaa gcg ggt gac ggc gcg tcc att       1344
Asn Val Ser Val Asp Met Asn Gly Glu Ala Gly Asp Gly Ala Ser Ile
        435                 440                 445
```

| | | | | | | | | | | | | | | | |
|---|---|---|---|---|---|---|---|---|---|---|---|---|---|---|---|
| gcg | ggc | ttg | aag | agg | acc | tcg | tcc | gaa | gag | gtc | aac | act | ccc | agc | gat | 1392 |
| Ala | Gly | Leu | Lys | Arg | Thr | Ser | Ser | Glu | Glu | Val | Asn | Thr | Pro | Ser | Asp |
| | 450 | | | | | 455 | | | | 460 | | | | | | ata cct acc atc agg ata tca agc gag tcg atg cgc act cct aat acg 1440
Ile Pro Thr Ile Arg Ile Ser Ser Glu Ser Met Arg Thr Pro Asn Thr
465                 470                 475                 480 gct cca gga cca ggg ttc agc gaa aag gca agt act cac aag ccc gct 1488
Ala Pro Gly Pro Gly Phe Ser Glu Lys Ala Ser Thr His Lys Pro Ala
            485                 490                 495 ctg gag aag ccc gag aca gca caa gcg aat gaa gat ccc aat tcg cct 1536
Leu Glu Lys Pro Glu Thr Ala Gln Ala Asn Glu Asp Pro Asn Ser Pro
        500                 505                 510 ttg ggg atg aag agt gaa ggg gaa cag ccg gtt tcg gcg ttt tct cat 1584
Leu Gly Met Lys Ser Glu Gly Glu Gln Pro Val Ser Ala Phe Ser His
    515                 520                 525 aag cga tta tgt gag aga tgg tta gat aac ctc ttt tta gtt ctg tat 1632
Lys Arg Leu Cys Glu Arg Trp Leu Asp Asn Leu Phe Leu Val Leu Tyr
530                 535                 540 gaa gac ttg aga gtc tac acc att tgg aga gca gag ata tct cat ttc 1680
Glu Asp Leu Arg Val Tyr Thr Ile Trp Arg Ala Glu Ile Ser His Phe
545                 550                 555                 560 aaa acc cag cac atg tca tac cga aag act ggt acc gag tgg gag atc 1728
Lys Thr Gln His Met Ser Tyr Arg Lys Thr Gly Thr Glu Trp Glu Ile
                565                 570                 575 ctt ggt gaa ctt gcc aca cgt ttg cat cac aaa gaa gaa gcc aag gac 1776
Leu Gly Glu Leu Ala Thr Arg Leu His His Lys Glu Glu Ala Lys Asp
            580                 585                 590 gcg tac caa cgc tgt ctc gac tcc aaa ttc agc gca aaa gca ctt atg 1824
Ala Tyr Gln Arg Cys Leu Asp Ser Lys Phe Ser Ala Lys Ala Leu Met
        595                 600                 605 aag ctt ctt gaa acg tat gcg aat gag ggc gat ctt caa aag acc ttg 1872
Lys Leu Leu Glu Thr Tyr Ala Asn Glu Gly Asp Leu Gln Lys Thr Leu
    610                 615                 620 acg gcg gct gtg agg ctg aca acc tat cac cat cga tgg tat atg gac 1920
Thr Ala Ala Val Arg Leu Thr Thr Tyr His His Arg Trp Tyr Met Asp
625                 630                 635                 640 gcg tca tac ccg tcc atg gtc gcg cat tat ttg tac aag gtc gga ctc 1968
Ala Ser Tyr Pro Ser Met Val Ala His Tyr Leu Tyr Lys Val Gly Leu
                645                 650                 655 ata cat gga cat gcc aaa tta caa tac aca atg ctc agt atg aac ctg 2016
Ile His Gly His Ala Lys Leu Gln Tyr Thr Met Leu Ser Met Asn Leu
            660                 665                 670 ccg gtc ggg atc ttt gaa ata atg caa ggc tat atg aaa tac ggg gcg 2064
Pro Val Gly Ile Phe Glu Ile Met Gln Gly Tyr Met Lys Tyr Gly Ala
        675                 680                 685 acg ttc aac gtc gaa ggt tca gaa ttc tag 2094
Thr Phe Asn Val Glu Gly Ser Glu Phe
    690                 695

<210> SEQ ID NO 10
<211> LENGTH: 697
<212> TYPE: PRT
<213> ORGANISM: Cryptococcus neoformans

<400> SEQUENCE: 10

Met Ser Glu Leu Phe Lys Asp Ile Pro Glu Phe Val Glu Thr Asp Ile
1               5                   10                  15

Gly Glu Ser Leu Ala Ala Arg Thr Glu Thr Leu Gly Ser Phe Arg Glu
            20                  25                  30

-continued

```
Leu Gly Pro Pro Asp Leu Cys His Val Met Lys Val Tyr Gly Lys Pro
            35                  40                  45

Pro Thr Gln Arg Glu Ile Gly Ser Tyr His Tyr Cys Ser Gly Ile Glu
 50                  55                  60

Ala Ser Ser Ser Ala Ser Leu Ala Ala Tyr Leu Asn Ser Leu Gln Phe
 65                  70                  75                  80

Ser Val Glu Asp Ser Ser Ala Trp Phe Gly Lys Gly Ser Ala Trp Lys
                 85                  90                  95

Val Arg Ser Gly Thr Tyr Cys Cys Phe Asn Ala Phe Ser Arg Val Asp
            100                 105                 110

Met Arg Val Glu Ala Asn Ile Pro Gly Gly Val Asp Ala Phe Val Val
            115                 120                 125

Asp Leu His Gly Gln Arg His Pro Ala Thr Pro Glu Leu Trp Gln Glu
        130                 135                 140

Thr Tyr Leu Ser Ala Ile Leu Arg Ala Ile Arg Tyr Ala Asp Asp Ala
145                 150                 155                 160

Ser Tyr Arg Leu Ala Gly Tyr Arg Lys Leu Asp Pro Ile Thr Thr Pro
                165                 170                 175

Glu Ala Glu Arg Phe Leu Lys Ala Ala Glu Ala Leu Phe Phe Lys
            180                 185                 190

Gly Trp Gln Leu Gly Ser Asp Pro Glu Ile Gln Val Ala Thr Val Val
        195                 200                 205

Thr Asn His Leu Thr Ser Ala Ile Leu Lys Tyr Phe Ser Asp Ser Phe
    210                 215                 220

Arg Leu His Arg Ala Ala Asn Leu Phe Glu Arg Met Met Asp Lys Glu
225                 230                 235                 240

Pro Glu Val Ala Ala Leu Val Ala Lys Ser Tyr Ile Gly Met Asn Glu
                245                 250                 255

Glu Ile Lys Ala Val Lys Ile Met Asn Ala Ala Leu Ala Ala Asn Pro
            260                 265                 270

Gln Ser Tyr Pro Ile Leu His Ala Gln Val Asp Phe Leu Leu Ser Lys
        275                 280                 285

His Lys Tyr Glu Trp Ala Gln Gln Val Ala Gln Gln Ala Val Asn Ser
    290                 295                 300

Ala Pro Ser Glu Phe Thr Thr Trp Ala Lys Leu Thr Glu Thr Tyr Ile
305                 310                 315                 320

Glu Leu Gly Gln Leu Asp Gln Ala Leu Leu Thr Leu Asn Ser Cys Pro
                325                 330                 335

Met Phe Thr Tyr Asn Glu Arg Asp Leu His Arg Met Pro Thr Pro Ala
            340                 345                 350

Lys Ser Asn Met Pro Val Lys Lys Phe Ile Ala Asp Ser Asn Leu Val
        355                 360                 365

Asp Glu Asp Ser Ser Arg Glu Asn Glu Ala Asp Ile Ala Leu Leu Arg
    370                 375                 380

Leu Pro Ala Pro Asn Leu Arg Gly Thr Phe Ala Lys Ala Tyr Ser Leu
385                 390                 395                 400

Leu Thr Leu Leu Val Ser Lys Ile Gly Trp Asp Glu Leu Leu Lys Ile
                405                 410                 415

Arg Ser Ser Val Phe Val Met Glu Glu Tyr Arg Leu His Lys Thr
            420                 425                 430

Asn Val Ser Val Asp Met Asn Gly Glu Ala Gly Asp Gly Ala Ser Ile
        435                 440                 445

Ala Gly Leu Lys Arg Thr Ser Ser Glu Glu Val Asn Thr Pro Ser Asp
```

```
              450                 455                 460
Ile Pro Thr Ile Arg Ile Ser Ser Glu Ser Met Arg Thr Pro Asn Thr
465                 470                 475                 480

Ala Pro Gly Pro Gly Phe Ser Glu Lys Ala Ser Thr His Lys Pro Ala
                485                 490                 495

Leu Glu Lys Pro Glu Thr Ala Gln Ala Asn Glu Asp Pro Asn Ser Pro
            500                 505                 510

Leu Gly Met Lys Ser Glu Gly Glu Gln Pro Val Ser Ala Phe Ser His
        515                 520                 525

Lys Arg Leu Cys Glu Arg Trp Leu Asp Asn Leu Phe Leu Val Leu Tyr
    530                 535                 540

Glu Asp Leu Arg Val Tyr Thr Ile Trp Arg Ala Glu Ile Ser His Phe
545                 550                 555                 560

Lys Thr Gln His Met Ser Tyr Arg Lys Thr Gly Thr Glu Trp Glu Ile
                565                 570                 575

Leu Gly Glu Leu Ala Thr Arg Leu His His Lys Glu Glu Ala Lys Asp
            580                 585                 590

Ala Tyr Gln Arg Cys Leu Asp Ser Lys Phe Ser Ala Lys Ala Leu Met
        595                 600                 605

Lys Leu Leu Glu Thr Tyr Ala Asn Glu Gly Asp Leu Gln Lys Thr Leu
    610                 615                 620

Thr Ala Ala Val Arg Leu Thr Thr Tyr His His Arg Trp Tyr Met Asp
625                 630                 635                 640

Ala Ser Tyr Pro Ser Met Val Ala His Tyr Leu Tyr Lys Val Gly Leu
                645                 650                 655

Ile His Gly His Ala Lys Leu Gln Tyr Thr Met Leu Ser Met Asn Leu
            660                 665                 670

Pro Val Gly Ile Phe Glu Ile Met Gln Gly Tyr Met Lys Tyr Gly Ala
        675                 680                 685

Thr Phe Asn Val Glu Gly Ser Glu Phe
    690                 695

<210> SEQ ID NO 11
<211> LENGTH: 1662
<212> TYPE: DNA
<213> ORGANISM: Cryptococcus neoformans
<220> FEATURE:
<221> NAME/KEY: CDS
<222> LOCATION: (1)..(1662)

<400> SEQUENCE: 11 atg tcg tta gcg gac gcc ctt ctg gca gac ctt gat ggt ctc tcg gat     48
Met Ser Leu Ala Asp Ala Leu Leu Ala Asp Leu Asp Gly Leu Ser Asp
1               5                   10                  15 gac gaa gct cga tct cct tct cct ggc ccc gag gcc tcc tcc tcg tca     96
Asp Glu Ala Arg Ser Pro Ser Pro Gly Pro Glu Ala Ser Ser Ser Ser
                20                  25                  30 atg ccg cct cct ggt ttg ccc aac aaa gga aaa cgt ccc gcc agc gct    144
Met Pro Pro Pro Gly Leu Pro Asn Lys Gly Lys Arg Pro Ala Ser Ala
            35                  40                  45 atg gaa gtc gat gat ggc gaa gga ggt gcg aat gaa gat gag gga gac    192
Met Glu Val Asp Asp Gly Glu Gly Gly Ala Asn Glu Asp Glu Gly Asp
        50                  55                  60 gat atg aag ctg gaa gac ggg acg agt gct gtg gga ttt gta cct gaa    240
Asp Met Lys Leu Glu Asp Gly Thr Ser Ala Val Gly Phe Val Pro Glu
65                  70                  75                  80 gga ggt gta agg cct gca gat gag ctg gac aag gag gaa gtg gaa aaa    288
```

-continued

```
Gly Gly Val Arg Pro Ala Asp Glu Leu Asp Lys Glu Glu Val Glu Lys
                85                  90                  95 acc gat atg aag ggt gtc gag gat gtg aag aaa gta gcc agg ttg gca      336
Thr Asp Met Lys Gly Val Glu Asp Val Lys Lys Val Ala Arg Leu Ala
            100                 105                 110 gga agc cag aag ctt cga gat gtt ctg gca gat atc ata aaa tac acc      384
Gly Ser Gln Lys Leu Arg Asp Val Leu Ala Asp Ile Ile Lys Tyr Thr
        115                 120                 125 gag tct ccc acc gat atg tct tcg tct gcc ggt ccc ctc gag gag aat      432
Glu Ser Pro Thr Asp Met Ser Ser Ser Ala Gly Pro Leu Glu Glu Asn
    130                 135                 140 cca gag tac cat ctt gtt gtc act gcg aac aac atg tcc gtc gag gtt      480
Pro Glu Tyr His Leu Val Val Thr Ala Asn Asn Met Ser Val Glu Val
145                 150                 155                 160 gac aac gag att ctc atc gtg cac aaa ttc att cgt gac cac tat gct      528
Asp Asn Glu Ile Leu Ile Val His Lys Phe Ile Arg Asp His Tyr Ala
                165                 170                 175 cct cga ttt ccg gaa ctc gaa cag ctc att gcc gaa cct tgg aca tac      576
Pro Arg Phe Pro Glu Leu Glu Gln Leu Ile Ala Glu Pro Trp Thr Tyr
            180                 185                 190 att gcc gcc gtt aat gcc atc ggt cag tct gaa gat cta acg aag gtc      624
Ile Ala Ala Val Asn Ala Ile Gly Gln Ser Glu Asp Leu Thr Lys Val
        195                 200                 205 aca ttc ccc aac acc ctc cct gcg gct act gta ctc tct atc act ctt      672
Thr Phe Pro Asn Thr Leu Pro Ala Ala Thr Val Leu Ser Ile Thr Leu
    210                 215                 220 act gct acg act tcc cgt ggt cgg ccg ctc acg cct gca gag tgg gaa      720
Thr Ala Thr Thr Ser Arg Gly Arg Pro Leu Thr Pro Ala Glu Trp Glu
225                 230                 235                 240 aca att cag cgc gcc atc gct gtc gcc caa aat ctc cgt tcg gcg cga      768
Thr Ile Gln Arg Ala Ile Ala Val Ala Gln Asn Leu Arg Ser Ala Arg
                245                 250                 255 gaa caa att ttt tcc tac gtc gag tcc cgt atg gct gct gta gca cct      816
Glu Gln Ile Phe Ser Tyr Val Glu Ser Arg Met Ala Ala Val Ala Pro
            260                 265                 270 aat ttg tct gct att gtg ggc acc ggt atc gct gcc aaa tta ctt ggt      864
Asn Leu Ser Ala Ile Val Gly Thr Gly Ile Ala Ala Lys Leu Leu Gly
        275                 280                 285 tta gca ggt ggt ctc cat gcg ttt agt cga cag ccg agt tgt aat gtg      912
Leu Ala Gly Gly Leu His Ala Phe Ser Arg Gln Pro Ser Cys Asn Val
    290                 295                 300 atg ctt ttt ggc gcg atg aag aag act ttg gcc acc tct cat ctt tct      960
Met Leu Phe Gly Ala Met Lys Lys Thr Leu Ala Thr Ser His Leu Ser
305                 310                 315                 320 gct gcc tct cag caa cga cat acc ggc ttt atc ttc caa agc tct ata     1008
Ala Ala Ser Gln Gln Arg His Thr Gly Phe Ile Phe Gln Ser Ser Ile
                325                 330                 335 gta cag agt gcc cag cct gaa gat cga aga aga gct cag cga gcg gtg     1056
Val Gln Ser Ala Gln Pro Glu Asp Arg Arg Arg Ala Gln Arg Ala Val
            340                 345                 350 tct gcc aag tgt gct ctt gcg gcc agg atc gat gca gga aag ggg tct     1104
Ser Ala Lys Cys Ala Leu Ala Ala Arg Ile Asp Ala Gly Lys Gly Ser
        355                 360                 365 agg gac gga tct tat gga aga aag tgt ttg gcg gat ttg caa aag agg     1152
Arg Asp Gly Ser Tyr Gly Arg Lys Cys Leu Ala Asp Leu Gln Lys Arg
    370                 375                 380 att gaa aag atg gcg gaa cct cct ccc aac aag atg atc aag gcg ttg     1200
Ile Glu Lys Met Ala Glu Pro Pro Pro Asn Lys Met Ile Lys Ala Leu
385                 390                 395                 400
```

```
cct atc cct cag gag act aac agg aag aag cgt ggt ggt aag aga gct    1248
Pro Ile Pro Gln Glu Thr Asn Arg Lys Lys Arg Gly Gly Lys Arg Ala
            405                 410                 415 cga aaa gcc aag gaa gcg tac gcc cag acc gaa ttg aga aag tta caa    1296
Arg Lys Ala Lys Glu Ala Tyr Ala Gln Thr Glu Leu Arg Lys Leu Gln
            420                 425                 430 aac cga atg gag ttt ggc aag gcg gaa gaa gag atc ggg gtg gac gac    1344
Asn Arg Met Glu Phe Gly Lys Ala Glu Glu Glu Ile Gly Val Asp Asp
            435                 440                 445 gag act gtt ggt ttg ggt atg atc ggt tcc gcc gga agg gtc cga ggc    1392
Glu Thr Val Gly Leu Gly Met Ile Gly Ser Ala Gly Arg Val Arg Gly
    450                 455                 460 gag atg gca gat gcg agg agt aaa gct aaa ctt tct cga gcc aac aaa    1440
Glu Met Ala Asp Ala Arg Ser Lys Ala Lys Leu Ser Arg Ala Asn Lys
465                 470                 475                 480 ctt cga act cag ctc ctt ggt cgc tca gtc aca tcc aac gac gct gcc    1488
Leu Arg Thr Gln Leu Leu Gly Arg Ser Val Thr Ser Asn Asp Ala Ala
            485                 490                 495 agc ggt atg gcc acc tcc tta tca ttc acg cct gtc caa ggt ctt gaa    1536
Ser Gly Met Ala Thr Ser Leu Ser Phe Thr Pro Val Gln Gly Leu Glu
            500                 505                 510 ata gtt aca ccc tcc ctc tct gca gcc cag aaa gta cag gct gcg aat    1584
Ile Val Thr Pro Ser Leu Ser Ala Ala Gln Lys Val Gln Ala Ala Asn
            515                 520                 525 gac aga tgg ttc tcc ggg ggt aca ttt acg cat gta agg aag ggg gga    1632
Asp Arg Trp Phe Ser Gly Gly Thr Phe Thr His Val Arg Lys Gly Gly
            530                 535                 540 agc agt att ccg gga cag gaa cag aaa tag                            1662
Ser Ser Ile Pro Gly Gln Glu Gln Lys
545                 550

<210> SEQ ID NO 12
<211> LENGTH: 553
<212> TYPE: PRT
<213> ORGANISM: Cryptococcus neoformans

<400> SEQUENCE: 12

Met Ser Leu Ala Asp Ala Leu Leu Ala Asp Leu Asp Gly Leu Ser Asp
1               5                   10                  15

Asp Glu Ala Arg Ser Pro Ser Pro Gly Pro Glu Ala Ser Ser Ser Ser
            20                  25                  30

Met Pro Pro Pro Gly Leu Pro Asn Lys Gly Lys Arg Pro Ala Ser Ala
        35                  40                  45

Met Glu Val Asp Asp Gly Glu Gly Gly Ala Asn Glu Asp Glu Gly Asp
    50                  55                  60

Asp Met Lys Leu Glu Asp Gly Thr Ser Ala Val Gly Phe Val Pro Glu
65                  70                  75                  80

Gly Gly Val Arg Pro Ala Asp Glu Leu Asp Lys Glu Val Glu Lys
                85                  90                  95

Thr Asp Met Lys Gly Val Glu Asp Val Lys Val Ala Arg Leu Ala
            100                 105                 110

Gly Ser Gln Lys Leu Arg Asp Val Leu Ala Asp Ile Lys Tyr Thr
            115                 120                 125

Glu Ser Pro Thr Asp Met Ser Ser Ala Gly Pro Leu Glu Glu Asn
            130                 135                 140

Pro Glu Tyr His Leu Val Val Thr Ala Asn Asn Met Ser Val Glu Val
145                 150                 155                 160

Asp Asn Glu Ile Leu Ile Val His Lys Phe Ile Arg Asp His Tyr Ala
```

```
                165                 170                 175
Pro Arg Phe Pro Glu Leu Glu Gln Leu Ile Ala Glu Pro Trp Thr Tyr
            180                 185                 190

Ile Ala Ala Val Asn Ala Ile Gly Gln Ser Glu Asp Leu Thr Lys Val
            195                 200                 205

Thr Phe Pro Asn Thr Leu Pro Ala Ala Thr Val Leu Ser Ile Thr Leu
    210                 215                 220

Thr Ala Thr Thr Ser Arg Gly Arg Pro Leu Thr Pro Ala Glu Trp Glu
225                 230                 235                 240

Thr Ile Gln Arg Ala Ile Ala Val Ala Gln Asn Leu Arg Ser Ala Arg
                245                 250                 255

Glu Gln Ile Phe Ser Tyr Val Glu Ser Arg Met Ala Ala Val Ala Pro
            260                 265                 270

Asn Leu Ser Ala Ile Val Gly Thr Gly Ile Ala Ala Lys Leu Leu Gly
            275                 280                 285

Leu Ala Gly Gly Leu His Ala Phe Ser Arg Gln Pro Ser Cys Asn Val
            290                 295                 300

Met Leu Phe Gly Ala Met Lys Lys Thr Leu Ala Thr Ser His Leu Ser
305                 310                 315                 320

Ala Ala Ser Gln Gln Arg His Thr Gly Phe Ile Phe Gln Ser Ser Ile
                325                 330                 335

Val Gln Ser Ala Gln Pro Glu Asp Arg Arg Ala Gln Arg Ala Val
            340                 345                 350

Ser Ala Lys Cys Ala Leu Ala Ala Arg Ile Asp Ala Gly Lys Gly Ser
            355                 360                 365

Arg Asp Gly Ser Tyr Gly Arg Lys Cys Leu Ala Asp Leu Gln Lys Arg
    370                 375                 380

Ile Glu Lys Met Ala Glu Pro Pro Asn Lys Met Ile Lys Ala Leu
385                 390                 395                 400

Pro Ile Pro Gln Glu Thr Asn Arg Lys Lys Arg Gly Gly Lys Arg Ala
                405                 410                 415

Arg Lys Ala Lys Glu Ala Tyr Ala Gln Thr Glu Leu Arg Lys Leu Gln
            420                 425                 430

Asn Arg Met Glu Phe Gly Lys Ala Glu Glu Ile Gly Val Asp Asp
            435                 440                 445

Glu Thr Val Gly Leu Gly Met Ile Gly Ser Ala Gly Arg Val Arg Gly
    450                 455                 460

Glu Met Ala Asp Ala Arg Ser Lys Ala Lys Leu Ser Arg Ala Asn Lys
465                 470                 475                 480

Leu Arg Thr Gln Leu Leu Gly Arg Ser Val Thr Ser Asn Asp Ala Ala
                485                 490                 495

Ser Gly Met Ala Thr Ser Leu Ser Phe Thr Pro Val Gln Gly Leu Glu
            500                 505                 510

Ile Val Thr Pro Ser Leu Ser Ala Ala Gln Lys Val Gln Ala Ala Asn
            515                 520                 525

Asp Arg Trp Phe Ser Gly Gly Thr Phe Thr His Val Arg Lys Gly Gly
    530                 535                 540

Ser Ser Ile Pro Gly Gln Glu Gln Lys
545                 550

<210> SEQ ID NO 13
<211> LENGTH: 759
<212> TYPE: DNA
<213> ORGANISM: Cryptococcus neoformans
```

```
<220> FEATURE:
<221> NAME/KEY: CDS
<222> LOCATION: (1)..(759)

<400> SEQUENCE: 13 atg tca tca act gat ctc gga ggc caa gct gcc gtc atc act ggc ggt      48
Met Ser Ser Thr Asp Leu Gly Gly Gln Ala Ala Val Ile Thr Gly Gly
1               5                   10                  15 ggt aag aat ctt ggt gct ttg att gcg aag act ctc gcc aag cag gga      96
Gly Lys Asn Leu Gly Ala Leu Ile Ala Lys Thr Leu Ala Lys Gln Gly
            20                  25                  30 gtc aac gtt gcg atc cat tac aac tcg gcc agt tcc aag tcc gag aca     144
Val Asn Val Ala Ile His Tyr Asn Ser Ala Ser Ser Lys Ser Glu Thr
        35                  40                  45 gaa gct aca ttg aag aca ctc gga tcg tat ggg gtc aaa gcc gct gct     192
Glu Ala Thr Leu Lys Thr Leu Gly Ser Tyr Gly Val Lys Ala Ala Ala
50                  55                  60 ttc cag gcc aat ctt acc act gag gca tca gtt gag aaa ctc ttc tca     240
Phe Gln Ala Asn Leu Thr Thr Glu Ala Ser Val Glu Lys Leu Phe Ser
65                  70                  75                  80 gac gca gca gct gct ctt gga gtg tcc aag ttc gat atc gcc atc aat     288
Asp Ala Ala Ala Ala Leu Gly Val Ser Lys Phe Asp Ile Ala Ile Asn
                85                  90                  95 acg gtc ggt aag gtt ctt aaa aag cct atc gtt gaa aca aca gag caa     336
Thr Val Gly Lys Val Leu Lys Lys Pro Ile Val Glu Thr Thr Glu Gln
            100                 105                 110 gga ttc gac gac atg ttc cta gtc aac tca aag tgt gcc ttc ttt ttt     384
Gly Phe Asp Asp Met Phe Leu Val Asn Ser Lys Cys Ala Phe Phe Phe
        115                 120                 125 atc aag cat gcg gcc aag aat ctc aac gag ggg ggc acg att ata tca     432
Ile Lys His Ala Ala Lys Asn Leu Asn Glu Gly Gly Thr Ile Ile Ser
130                 135                 140 ctc gtg act tca ctc ctt gga gca ttt gcg cct ggt tat tca act tat     480
Leu Val Thr Ser Leu Leu Gly Ala Phe Ala Pro Gly Tyr Ser Thr Tyr
145                 150                 155                 160 caa ggc agt aaa gct cct gta gag tgg ttc act aag tcg gct gcc aag     528
Gln Gly Ser Lys Ala Pro Val Glu Trp Phe Thr Lys Ser Ala Ala Lys
                165                 170                 175 gag ctt cag cct aag aat att agg gtc aac tgt gtg gct ccg ggg cca     576
Glu Leu Gln Pro Lys Asn Ile Arg Val Asn Cys Val Ala Pro Gly Pro
            180                 185                 190 atg gac act ccc ttc ttt tac ggg caa gag act gaa gat gcc gtt gct     624
Met Asp Thr Pro Phe Phe Tyr Gly Gln Glu Thr Glu Asp Ala Val Ala
        195                 200                 205 ttc cat aaa agc cag gcg ctc aca gga cgg ctc aca gat att aaa gat     672
Phe His Lys Ser Gln Ala Leu Thr Gly Arg Leu Thr Asp Ile Lys Asp
210                 215                 220 att gca cca ttg gtg gag ttc ctt tgc aag gat aag tgg att acc gga     720
Ile Ala Pro Leu Val Glu Phe Leu Cys Lys Asp Lys Trp Ile Thr Gly
225                 230                 235                 240 caa gtc atc ttc tca aat gga ggt tac acg act cgc tga                 759
Gln Val Ile Phe Ser Asn Gly Gly Tyr Thr Thr Arg
                245                 250

<210> SEQ ID NO 14
<211> LENGTH: 252
<212> TYPE: PRT
<213> ORGANISM: Cryptococcus neoformans

<400> SEQUENCE: 14

Met Ser Ser Thr Asp Leu Gly Gly Gln Ala Ala Val Ile Thr Gly Gly
```

```
              1               5                  10                 15
            Gly Lys Asn Leu Gly Ala Leu Ile Ala Lys Thr Leu Ala Lys Gln Gly
                         20                  25                  30

Val Asn Val Ala Ile His Tyr Asn Ser Ala Ser Ser Lys Ser Glu Thr
                         35                  40                  45

Glu Ala Thr Leu Lys Thr Leu Gly Ser Tyr Gly Val Lys Ala Ala Ala
                      50                  55                  60

Phe Gln Ala Asn Leu Thr Thr Glu Ala Ser Val Glu Lys Leu Phe Ser
            65                  70                  75                  80

Asp Ala Ala Ala Leu Gly Val Ser Lys Phe Asp Ile Ala Ile Asn
                             85                  90                  95

Thr Val Gly Lys Val Leu Lys Lys Pro Ile Val Glu Thr Thr Glu Gln
                         100                 105                 110

Gly Phe Asp Asp Met Phe Leu Val Asn Ser Lys Cys Ala Phe Phe
                         115                 120                 125

Ile Lys His Ala Ala Lys Asn Leu Asn Glu Gly Gly Thr Ile Ile Ser
                         130                 135                 140

Leu Val Thr Ser Leu Leu Gly Ala Phe Ala Pro Gly Tyr Ser Thr Tyr
            145                 150                 155                 160

Gln Gly Ser Lys Ala Pro Val Glu Trp Phe Thr Lys Ser Ala Ala Lys
                             165                 170                 175

Glu Leu Gln Pro Lys Asn Ile Arg Val Asn Cys Val Ala Pro Gly Pro
                         180                 185                 190

Met Asp Thr Pro Phe Phe Tyr Gly Gln Glu Thr Glu Asp Ala Val Ala
                         195                 200                 205

Phe His Lys Ser Gln Ala Leu Thr Gly Arg Leu Thr Asp Ile Lys Asp
                         210                 215                 220

Ile Ala Pro Leu Val Glu Phe Leu Cys Lys Asp Lys Trp Ile Thr Gly
            225                 230                 235                 240

Gln Val Ile Phe Ser Asn Gly Gly Tyr Thr Thr Arg
                             245                 250

<210> SEQ ID NO 15
<211> LENGTH: 2199
<212> TYPE: DNA
<213> ORGANISM: Cryptococcus neoformans
<220> FEATURE:
<221> NAME/KEY: CDS
<222> LOCATION: (1)..(2199)

<400> SEQUENCE: 15 atg cag cac cac ccc gcg gta gca gca cag ccg ggc cgc act att gcc     48
Met Gln His His Pro Ala Val Ala Ala Gln Pro Gly Arg Thr Ile Ala
1               5                   10                  15 cct atc ccg cac cac cgc cca cag caa ccc cgg atc act cct tac aca     96
Pro Ile Pro His His Arg Pro Gln Gln Pro Arg Ile Thr Pro Tyr Thr
                20                  25                  30 cca aac gta cgc gac ctc aac cca gga cct aag aac aga ctc atc ctc    144
Pro Asn Val Arg Asp Leu Asn Pro Gly Pro Lys Asn Arg Leu Ile Leu
            35                  40                  45 gcc ctc cgc tcc aac atc ccc ttt gaa gtc gac tgg gcg cta ccg cag    192
Ala Leu Arg Ser Asn Ile Pro Phe Glu Val Asp Trp Ala Leu Pro Gln
        50                  55                  60 ctt gtt gtc gca agt ttc gac cag tcg gac ggg ttc aag ctc gag gca    240
Leu Val Val Ala Ser Phe Asp Gln Ser Asp Gly Phe Lys Leu Glu Ala
65                  70                  75                  80 tgg cca gac agc att tgc gcg ttg aag gaa tgg ccg gcc aag tgg ctt    288
```

```
                Trp Pro Asp Ser Ile Cys Ala Leu Lys Glu Trp Pro Ala Lys Trp Leu
                                85                  90                  95 gaa gga cta gaa agg gaa gct gca gtg ttt gag atg aaa gct ggg cga              336
Glu Gly Leu Glu Arg Glu Ala Ala Val Phe Glu Met Lys Ala Gly Arg
                100                 105                 110 ttg gat ttt gag ggg gac gag aat gat gaa gag ggg agg atg gca aag              384
Leu Asp Phe Glu Gly Asp Glu Asn Asp Glu Glu Gly Arg Met Ala Lys
            115                 120                 125 cgc aga aaa agg gat ctg gcg ctg ggg gcg gtg gta gag tgg gag aac              432
Arg Arg Lys Arg Asp Leu Ala Leu Gly Ala Val Val Glu Trp Glu Asn
        130                 135                 140 gat ctc aag gtg gaa caa cgg gcg acc aac tct ttg ctc gtc ctc aga              480
Asp Leu Lys Val Glu Gln Arg Ala Thr Asn Ser Leu Leu Val Leu Arg
145                 150                 155                 160 aac gca tcc ttc aac gca ccc aac gca aag atc ctc tca agc tca agc              528
Asn Ala Ser Phe Asn Ala Pro Asn Ala Lys Ile Leu Ser Ser Ser Ser
                165                 170                 175 ttc ctc gct ttt cta gcc gat ttc ttc tct ttg cct cta ccg ttt ctc              576
Phe Leu Ala Phe Leu Ala Asp Phe Phe Ser Leu Pro Leu Pro Phe Leu
            180                 185                 190 cag cat ctt tgc ctg aga acc cca gag cct ata cat cat atc ctc atc              624
Gln His Leu Cys Leu Arg Thr Pro Glu Pro Ile His His Ile Leu Ile
        195                 200                 205 att gtc cag tcc atc ttc ccc cat ttg cgc gtg gac atg cca ggt atc              672
Ile Val Gln Ser Ile Phe Pro His Leu Arg Val Asp Met Pro Gly Ile
210                 215                 220 gac cgc atc aag cac atc ttt ggc gtc gtc ttc cct cag ctt ttt gtt              720
Asp Arg Ile Lys His Ile Phe Gly Val Val Phe Pro Gln Leu Phe Val
225                 230                 235                 240 gat acc cgc gat atc gca atg atg aac aac ctt atc cct ctc atg atg              768
Asp Thr Arg Asp Ile Ala Met Met Asn Asn Leu Ile Pro Leu Met Met
                245                 250                 255 atg ggc cag aca atc ccc aat aac cac cct cct ccg cct gaa ctc atc              816
Met Gly Gln Thr Ile Pro Asn Asn His Pro Pro Pro Pro Glu Leu Ile
            260                 265                 270 cct cat ctt ctc cag ctt ctc gtt ctc cgt cca gca ggc cca ctt ctc              864
Pro His Leu Leu Gln Leu Leu Val Leu Arg Pro Ala Gly Pro Leu Leu
        275                 280                 285 gat ttg act ctt gac atc ctc atc tcc ctc tcc aca aat ccc atc cac              912
Asp Leu Thr Leu Asp Ile Leu Ile Ser Leu Ser Thr Asn Pro Ile His
290                 295                 300 tcc cgt gcc ata ctt tct cat act tct ttc ccg cat cat ctc aaa tcc              960
Ser Arg Ala Ile Leu Ser His Thr Ser Phe Pro His His Leu Lys Ser
305                 310                 315                 320 atc aca gcc tta ctc gaa cat caa gct cgt ccg gtg gtg aat gcc ctt             1008
Ile Thr Ala Leu Leu Glu His Gln Ala Arg Pro Val Val Asn Ala Leu
                325                 330                 335 gac cca ccg cct tct acg aga ggg aaa atg gtg cgt aac cca gcg gga             1056
Asp Pro Pro Pro Ser Thr Arg Gly Lys Met Val Arg Asn Pro Ala Gly
            340                 345                 350 ccg agt tgc aga gca gag gaa ctt aat caa agg cgg acg aag gaa cga             1104
Pro Ser Cys Arg Ala Glu Glu Leu Asn Gln Arg Arg Thr Lys Glu Arg
        355                 360                 365 gag gcc gca ttg gga cat atg gat ccc atg gct gga ggt aga ccg gtg             1152
Glu Ala Ala Leu Gly His Met Asp Pro Met Ala Gly Gly Arg Pro Val
370                 375                 380 tac aat gag gta ggg gat aag cca ccg aca ttt agt ccg gcg acg aag             1200
Tyr Asn Glu Val Gly Asp Lys Pro Pro Thr Phe Ser Pro Ala Thr Lys
385                 390                 395                 400
```

| | | |
|---|---|---|
| aag agg ctt ttc agg atg aaa gaa ccc gaa agg tct atc gag tgg atg<br>Lys Arg Leu Phe Arg Met Lys Glu Pro Glu Arg Ser Ile Glu Trp Met<br>405 410 415 | | 1248 |
| cac cag gca ttc gtc tac tca tcg aca gcc caa gtc ctt caa gtg aca<br>His Gln Ala Phe Val Tyr Ser Ser Thr Ala Gln Val Leu Gln Val Thr<br>420 425 430 | | 1296 |
| ttc tgg cac gcc tac cga gat ttc ttc acc aac cca gct tgc gta gaa<br>Phe Trp His Ala Tyr Arg Asp Phe Phe Thr Asn Pro Ala Cys Val Glu<br>435 440 445 | | 1344 |
| cca atg ttg agt gca tct gat gtg atc aag aat gtc act gca gct ttc<br>Pro Met Leu Ser Ala Ser Asp Val Ile Lys Asn Val Thr Ala Ala Phe<br>450 455 460 | | 1392 |
| cct gga gcg agc gca aaa gtt tgg acc gat gcg agt ggt gcg caa aag<br>Pro Gly Ala Ser Ala Lys Val Trp Thr Asp Ala Ser Gly Ala Gln Lys<br>465 470 475 480 | | 1440 |
| ttt gtg att gct ggt gtc ggg ttc agg aag cga tca gat gac gat gaa<br>Phe Val Ile Ala Gly Val Gly Phe Arg Lys Arg Ser Asp Asp Asp Glu<br>485 490 495 | | 1488 |
| agg ttt aca tgt tac tgg cat gca tgc acc caa cgg tac tca gct acc<br>Arg Phe Thr Cys Tyr Trp His Ala Cys Thr Gln Arg Tyr Ser Ala Thr<br>500 505 510 | | 1536 |
| aac ccc gtc caa ctg ctc gaa cac att agc aac tac cat ctc caa acc<br>Asn Pro Val Gln Leu Leu Glu His Ile Ser Asn Tyr His Leu Gln Thr<br>515 520 525 | | 1584 |
| ttt tct gca ccc caa tgc caa tgg ggc tca tgc gat cac aac ctc tgc<br>Phe Ser Ala Pro Gln Cys Gln Trp Gly Ser Cys Asp His Asn Leu Cys<br>530 535 540 | | 1632 |
| acg tac tct cat ctc ctc acc cat atc ccc ctc ggc cag cct cca tcc<br>Thr Tyr Ser His Leu Leu Thr His Ile Pro Leu Gly Gln Pro Pro Ser<br>545 550 555 560 | | 1680 |
| tcc atc tcc gtc cct gac gcc atc tct tgc cat atc gca gac cat agt<br>Ser Ile Ser Val Pro Asp Ala Ile Ser Cys His Ile Ala Asp His Ser<br>565 570 575 | | 1728 |
| agc tcc gtc ttg cag cgc aag atc acc aat cgt acc gtc cct cct tta<br>Ser Ser Val Leu Gln Arg Lys Ile Thr Asn Arg Thr Val Pro Pro Leu<br>580 585 590 | | 1776 |
| tcc agc gtt cgt cta gcc gtt cag ggg gca ttt acc cct gtc gac gct<br>Ser Ser Val Arg Leu Ala Val Gln Gly Ala Phe Thr Pro Val Asp Ala<br>595 600 605 | | 1824 |
| cgt cga caa cct act ggc gcc gcc ctt ctc gcg gcg tta ctt atc cgt<br>Arg Arg Gln Pro Thr Gly Ala Ala Leu Leu Ala Ala Leu Leu Ile Arg<br>610 615 620 | | 1872 |
| aac ctc gcc cgt acc ctc cgt gcc gag atc tcg ctc gcc gtg ccc gaa<br>Asn Leu Ala Arg Thr Leu Arg Ala Glu Ile Ser Leu Ala Val Pro Glu<br>625 630 635 640 | | 1920 |
| ttg tct cat gct caa acg caa gaa acg gca gat gaa gct caa gcg aga<br>Leu Ser His Ala Gln Thr Gln Glu Thr Ala Asp Glu Ala Gln Ala Arg<br>645 650 655 | | 1968 |
| aaa aaa cac ctt ctc gaa gag agg tat gga ttg cca atc ccg gat tcg<br>Lys Lys His Leu Leu Glu Glu Arg Tyr Gly Leu Pro Ile Pro Asp Ser<br>660 665 670 | | 2016 |
| gtg ttg aaa gaa gaa gaa gag gag cag gcg aat gtg cag caa ggc caa<br>Val Leu Lys Glu Glu Glu Glu Gln Ala Asn Val Gln Gln Gly Gln<br>675 680 685 | | 2064 |
| gat tta gat atg agt gag gaa gag agg gag agg gcg aaa aag gcg ttt<br>Asp Leu Asp Met Ser Glu Glu Glu Arg Glu Arg Ala Lys Lys Ala Phe<br>690 695 700 | | 2112 |
| gag aat gtg gag gag agg att atg aag gtc atg ttg gag aat gtt agt<br>Glu Asn Val Glu Glu Arg Ile Met Lys Val Met Leu Glu Asn Val Ser<br>705 710 715 720 | | 2160 |

```
ggg ata acg cag tat ctt ggt gat gcg ctt ggg ctg tag          2199
Gly Ile Thr Gln Tyr Leu Gly Asp Ala Leu Gly Leu
            725                 730
```

<210> SEQ ID NO 16
<211> LENGTH: 732
<212> TYPE: PRT
<213> ORGANISM: Cryptococcus neoformans

<400> SEQUENCE: 16

```
Met Gln His His Pro Ala Val Ala Ala Gln Pro Gly Arg Thr Ile Ala
1               5                   10                  15

Pro Ile Pro His His Arg Pro Gln Gln Pro Arg Ile Thr Pro Tyr Thr
            20                  25                  30

Pro Asn Val Arg Asp Leu Asn Pro Gly Pro Lys Asn Arg Leu Ile Leu
        35                  40                  45

Ala Leu Arg Ser Asn Ile Pro Phe Glu Val Asp Trp Ala Leu Pro Gln
    50                  55                  60

Leu Val Val Ala Ser Phe Asp Gln Ser Asp Gly Phe Lys Leu Glu Ala
65                  70                  75                  80

Trp Pro Asp Ser Ile Cys Ala Leu Lys Glu Trp Pro Ala Lys Trp Leu
                85                  90                  95

Glu Gly Leu Glu Arg Glu Ala Ala Val Phe Glu Met Lys Ala Gly Arg
            100                 105                 110

Leu Asp Phe Glu Gly Asp Glu Asn Asp Glu Glu Gly Arg Met Ala Lys
        115                 120                 125

Arg Arg Lys Arg Asp Leu Ala Leu Gly Ala Val Val Glu Trp Glu Asn
    130                 135                 140

Asp Leu Lys Val Glu Gln Arg Ala Thr Asn Ser Leu Leu Val Leu Arg
145                 150                 155                 160

Asn Ala Ser Phe Asn Ala Pro Asn Ala Lys Ile Leu Ser Ser Ser Ser
                165                 170                 175

Phe Leu Ala Phe Leu Ala Asp Phe Phe Ser Leu Pro Leu Pro Phe Leu
            180                 185                 190

Gln His Leu Cys Leu Arg Thr Pro Glu Pro Ile His His Ile Leu Ile
        195                 200                 205

Ile Val Gln Ser Ile Phe Pro His Leu Arg Val Asp Met Pro Gly Ile
    210                 215                 220

Asp Arg Ile Lys His Ile Phe Gly Val Val Phe Pro Gln Leu Phe Val
225                 230                 235                 240

Asp Thr Arg Asp Ile Ala Met Met Asn Asn Leu Ile Pro Leu Met Met
                245                 250                 255

Met Gly Gln Thr Ile Pro Asn Asn His Pro Pro Pro Glu Leu Ile
            260                 265                 270

Pro His Leu Leu Gln Leu Leu Val Leu Arg Pro Ala Gly Pro Leu Leu
        275                 280                 285

Asp Leu Thr Leu Asp Ile Leu Ile Ser Leu Ser Thr Asn Pro Ile His
    290                 295                 300

Ser Arg Ala Ile Leu Ser His Thr Ser Phe Pro His His Leu Lys Ser
305                 310                 315                 320

Ile Thr Ala Leu Leu Glu His Gln Ala Arg Pro Val Val Asn Ala Leu
                325                 330                 335

Asp Pro Pro Pro Ser Thr Arg Gly Lys Met Val Arg Asn Pro Ala Gly
            340                 345                 350
```

Pro Ser Cys Arg Ala Glu Glu Leu Asn Gln Arg Arg Thr Lys Glu Arg
            355                 360                 365

Glu Ala Ala Leu Gly His Met Asp Pro Met Ala Gly Gly Arg Pro Val
        370                 375                 380

Tyr Asn Glu Val Gly Asp Lys Pro Pro Thr Phe Ser Pro Ala Thr Lys
385                 390                 395                 400

Lys Arg Leu Phe Arg Met Lys Glu Pro Glu Arg Ser Ile Glu Trp Met
                405                 410                 415

His Gln Ala Phe Val Tyr Ser Ser Thr Ala Gln Val Leu Gln Val Thr
            420                 425                 430

Phe Trp His Ala Tyr Arg Asp Phe Phe Thr Asn Pro Ala Cys Val Glu
        435                 440                 445

Pro Met Leu Ser Ala Ser Asp Val Ile Lys Asn Val Thr Ala Ala Phe
    450                 455                 460

Pro Gly Ala Ser Ala Lys Val Trp Thr Asp Ala Ser Gly Ala Gln Lys
465                 470                 475                 480

Phe Val Ile Ala Gly Val Gly Phe Arg Lys Arg Ser Asp Asp Asp Glu
                485                 490                 495

Arg Phe Thr Cys Tyr Trp His Ala Cys Thr Gln Arg Tyr Ser Ala Thr
            500                 505                 510

Asn Pro Val Gln Leu Leu Glu His Ile Ser Asn Tyr His Leu Gln Thr
        515                 520                 525

Phe Ser Ala Pro Gln Cys Gln Trp Gly Ser Cys Asp His Asn Leu Cys
    530                 535                 540

Thr Tyr Ser His Leu Leu Thr His Ile Pro Leu Gly Gln Pro Pro Ser
545                 550                 555                 560

Ser Ile Ser Val Pro Asp Ala Ile Ser Cys His Ile Ala Asp His Ser
                565                 570                 575

Ser Ser Val Leu Gln Arg Lys Ile Thr Asn Arg Thr Val Pro Pro Leu
            580                 585                 590

Ser Ser Val Arg Leu Ala Val Gln Gly Ala Phe Thr Pro Val Asp Ala
        595                 600                 605

Arg Arg Gln Pro Thr Gly Ala Ala Leu Leu Ala Leu Leu Ile Arg
    610                 615                 620

Asn Leu Ala Arg Thr Leu Arg Ala Glu Ile Ser Leu Ala Val Pro Glu
625                 630                 635                 640

Leu Ser His Ala Gln Thr Gln Glu Thr Ala Asp Glu Ala Gln Ala Arg
                645                 650                 655

Lys Lys His Leu Leu Glu Glu Arg Tyr Gly Leu Pro Ile Pro Asp Ser
            660                 665                 670

Val Leu Lys Glu Glu Glu Glu Gln Ala Asn Val Gln Gln Gly Gln
        675                 680                 685

Asp Leu Asp Met Ser Glu Glu Arg Glu Arg Ala Lys Lys Ala Phe
    690                 695                 700

Glu Asn Val Glu Glu Arg Ile Met Lys Val Met Leu Glu Asn Val Ser
705                 710                 715                 720

Gly Ile Thr Gln Tyr Leu Gly Asp Ala Leu Gly Leu
                725                 730

<210> SEQ ID NO 17
<211> LENGTH: 1305
<212> TYPE: DNA
<213> ORGANISM: Cryptococcus neoformans
<220> FEATURE:
<221> NAME/KEY: CDS

<222> LOCATION: (1)..(1305)

<400> SEQUENCE: 17

```
atg aga ctc acg att att gcc cca gac tcg gtt cat gag cac gaa gtg        48
Met Arg Leu Thr Ile Ile Ala Pro Asp Ser Val His Glu His Glu Val
1               5                   10                  15 tcc cct tcc ttg ctc atc caa gac atc atc aac atc gtt gag gca act        96
Ser Pro Ser Leu Leu Ile Gln Asp Ile Ile Asn Ile Val Glu Ala Thr
            20                  25                  30 gcc gac ctt ccc ccg gct gtt att gtt ctc aca agt gac gcc ggt aca       144
Ala Asp Leu Pro Pro Ala Val Ile Val Leu Thr Ser Asp Ala Gly Thr
        35                  40                  45 cca ctc acg gac ccc aca aga act ctc gaa agc tat ggg tta aat gga       192
Pro Leu Thr Asp Pro Thr Arg Thr Leu Glu Ser Tyr Gly Leu Asn Gly
    50                  55                  60 gag acc gcc acc atc ttc ctt aca cct aca gga cca ccc gtc gct tct       240
Glu Thr Ala Thr Ile Phe Leu Thr Pro Thr Gly Pro Pro Val Ala Ser
65                  70                  75                  80 tcg tct tcc att cca ttc cct gat gca gat gcc gac att gaa agg atg       288
Ser Ser Ser Ile Pro Phe Pro Asp Ala Asp Ala Asp Ile Glu Arg Met
                85                  90                  95 cgt tta caa gcg ctc gga aat cct tct ttg atg aat gat ttg cgt gag       336
Arg Leu Gln Ala Leu Gly Asn Pro Ser Leu Met Asn Asp Leu Arg Glu
            100                 105                 110 cgt gat ccg gaa acc ttt gcc gct att caa ggg ggt act caa agc ttc       384
Arg Asp Pro Glu Thr Phe Ala Ala Ile Gln Gly Gly Thr Gln Ser Phe
        115                 120                 125 aaa aaa gcc ctc caa ctg gcg caa tca aga caa aga gat gcc gaa ttc       432
Lys Lys Ala Leu Gln Leu Ala Gln Ser Arg Gln Arg Asp Ala Glu Phe
    130                 135                 140 gaa aag caa cgc cag att gaa gca ctc aat gcc gac cct tat gac att       480
Glu Lys Gln Arg Gln Ile Glu Ala Leu Asn Ala Asp Pro Tyr Asp Ile
145                 150                 155                 160 gaa gct cag aaa aag att gag gaa gca att cgg atg gag gcc gtt ttg       528
Glu Ala Gln Lys Lys Ile Glu Glu Ala Ile Arg Met Glu Ala Val Leu
                165                 170                 175 gag aat atg cag cac gct atg gaa tat tcc cct gag tcg ttt gga aac       576
Glu Asn Met Gln His Ala Met Glu Tyr Ser Pro Glu Ser Phe Gly Asn
            180                 185                 190 gtg acc atg ctg tat atc aat gtg gaa gta aat ggt cat cct gtt aag       624
Val Thr Met Leu Tyr Ile Asn Val Glu Val Asn Gly His Pro Val Lys
        195                 200                 205 gca ttc gtt gat tct ggt gca caa aca acg atc att tcc cct gaa tgt       672
Ala Phe Val Asp Ser Gly Ala Gln Thr Thr Ile Ile Ser Pro Glu Cys
    210                 215                 220 gcc gag caa tgt gga atc atg cgc ctg ctt gat act cgt ttc gcg ggt       720
Ala Glu Gln Cys Gly Ile Met Arg Leu Leu Asp Thr Arg Phe Ala Gly
225                 230                 235                 240 atg gcc gaa gga gta gga aca gct cgt atc ctc ggt cgt atc cac tct       768
Met Ala Glu Gly Val Gly Thr Ala Arg Ile Leu Gly Arg Ile His Ser
                245                 250                 255 gcc caa att aag ctc ggc tca ctc tac ctc cct tgt gca ttc tcc gtc       816
Ala Gln Ile Lys Leu Gly Ser Leu Tyr Leu Pro Cys Ala Phe Ser Val
            260                 265                 270 ctc gaa ggc cgt tct gtc gac ctc tta ttt ggt ctt gac atg ctt aaa       864
Leu Glu Gly Arg Ser Val Asp Leu Leu Phe Gly Leu Asp Met Leu Lys
        275                 280                 285 cgc cat caa tgc tgt atc gac ctc tcc acg aac acg ctc cgg ata aat       912
Arg His Gln Cys Cys Ile Asp Leu Ser Thr Asn Thr Leu Arg Ile Asn
    290                 295                 300
```

```
aac act gaa gta ccc ttt ttg tcg gag cac gag ctg cct gac aag gcg    960
Asn Thr Glu Val Pro Phe Leu Ser Glu His Glu Leu Pro Asp Lys Ala
305                 310                 315                 320 aga aga cgt ggg gag gcg caa gtg gcc ggg gaa atg ggt gat gcg gca   1008
Arg Arg Arg Gly Glu Ala Gln Val Ala Gly Glu Met Gly Asp Ala Ala
                325                 330                 335 ggg caa ggc gtg aaa gcg ggt gtg gcg agt ccg aag att ggg aag aag   1056
Gly Gln Gly Val Lys Ala Gly Val Ala Ser Pro Lys Ile Gly Lys Lys
            340                 345                 350 acg ttt ccg gga gag ggg cat gcg ctt ggt gcg ggc agc tcg act gga   1104
Thr Phe Pro Gly Glu Gly His Ala Leu Gly Ala Gly Ser Ser Thr Gly
                355                 360                 365 cca ggg acg gct acg ggg agt gca agt gcg aca ggt gca agg act ggg   1152
Pro Gly Thr Ala Thr Gly Ser Ala Ser Ala Thr Gly Ala Arg Thr Gly
370                 375                 380 ggg act gca agt gtc ccc tcg cct tca aat agg tgg aaa gag gac gat   1200
Gly Thr Ala Ser Val Pro Ser Pro Ser Asn Arg Trp Lys Glu Asp Asp
385                 390                 395                 400 att caa acg ctt gtg aac ctg ggt gcc cct cga gcg caa gct ata cag   1248
Ile Gln Thr Leu Val Asn Leu Gly Ala Pro Arg Ala Gln Ala Ile Gln
                405                 410                 415 cta ctt gaa gcg tca ggt gga aac gtg gat gtt gct gct tct atg ctc   1296
Leu Leu Glu Ala Ser Gly Gly Asn Val Asp Val Ala Ala Ser Met Leu
                420                 425                 430 ttt ggt tag                                                       1305
Phe Gly

<210> SEQ ID NO 18
<211> LENGTH: 434
<212> TYPE: PRT
<213> ORGANISM: Cryptococcus neoformans

<400> SEQUENCE: 18

Met Arg Leu Thr Ile Ile Ala Pro Asp Ser Val His Glu His Glu Val
1               5                   10                  15

Ser Pro Ser Leu Leu Ile Gln Asp Ile Ile Asn Ile Val Glu Ala Thr
            20                  25                  30

Ala Asp Leu Pro Pro Ala Val Ile Val Leu Thr Ser Asp Ala Gly Thr
        35                  40                  45

Pro Leu Thr Asp Pro Thr Arg Thr Leu Glu Ser Tyr Gly Leu Asn Gly
    50                  55                  60

Glu Thr Ala Thr Ile Phe Leu Thr Pro Thr Gly Pro Pro Val Ala Ser
65                  70                  75                  80

Ser Ser Ser Ile Pro Phe Pro Asp Ala Asp Ala Asp Ile Glu Arg Met
                85                  90                  95

Arg Leu Gln Ala Leu Gly Asn Pro Ser Leu Met Asn Asp Leu Arg Glu
            100                 105                 110

Arg Asp Pro Glu Thr Phe Ala Ala Ile Gln Gly Gly Thr Gln Ser Phe
        115                 120                 125

Lys Lys Ala Leu Gln Leu Ala Gln Ser Arg Gln Arg Asp Ala Glu Phe
    130                 135                 140

Glu Lys Gln Arg Gln Ile Glu Ala Leu Asn Ala Asp Pro Tyr Asp Ile
145                 150                 155                 160

Glu Ala Gln Lys Lys Ile Glu Glu Ala Ile Arg Met Glu Ala Val Leu
                165                 170                 175

Glu Asn Met Gln His Ala Met Glu Tyr Ser Pro Glu Ser Phe Gly Asn
            180                 185                 190
```

```
Val Thr Met Leu Tyr Ile Asn Val Glu Val Asn Gly His Pro Val Lys
        195                 200                 205

Ala Phe Val Asp Ser Gly Ala Gln Thr Thr Ile Ile Ser Pro Glu Cys
    210                 215                 220

Ala Glu Gln Cys Gly Ile Met Arg Leu Asp Thr Arg Phe Ala Gly
225                 230                 235                 240

Met Ala Glu Gly Val Gly Thr Ala Arg Ile Leu Gly Arg Ile His Ser
                245                 250                 255

Ala Gln Ile Lys Leu Gly Ser Leu Tyr Leu Pro Cys Ala Phe Ser Val
            260                 265                 270

Leu Glu Gly Arg Ser Val Asp Leu Leu Phe Gly Leu Asp Met Leu Lys
        275                 280                 285

Arg His Gln Cys Cys Ile Asp Leu Ser Thr Asn Thr Leu Arg Ile Asn
    290                 295                 300

Asn Thr Glu Val Pro Phe Leu Ser Glu His Glu Leu Pro Asp Lys Ala
305                 310                 315                 320

Arg Arg Arg Gly Glu Ala Gln Val Ala Gly Glu Met Gly Asp Ala Ala
                325                 330                 335

Gly Gln Gly Val Lys Ala Gly Val Ala Ser Pro Lys Ile Gly Lys Lys
            340                 345                 350

Thr Phe Pro Gly Glu Gly His Ala Leu Gly Ala Gly Ser Ser Thr Gly
        355                 360                 365

Pro Gly Thr Ala Thr Gly Ser Ala Ser Ala Thr Gly Ala Arg Thr Gly
    370                 375                 380

Gly Thr Ala Ser Val Pro Ser Pro Ser Asn Arg Trp Lys Glu Asp Asp
385                 390                 395                 400

Ile Gln Thr Leu Val Asn Leu Gly Ala Pro Arg Ala Gln Ala Ile Gln
                405                 410                 415

Leu Leu Glu Ala Ser Gly Gly Asn Val Asp Val Ala Ala Ser Met Leu
            420                 425                 430

Phe Gly

<210> SEQ ID NO 19
<211> LENGTH: 3555
<212> TYPE: DNA
<213> ORGANISM: Cryptococcus neoformans
<220> FEATURE:
<221> NAME/KEY: CDS
<222> LOCATION: (1)..(3555)

<400> SEQUENCE: 19 atg tct tcg cca gaa cca gag gag cct cgc aga ggt gca agg gtc agg    48
Met Ser Ser Pro Glu Pro Glu Glu Pro Arg Arg Gly Ala Arg Val Arg
1               5                   10                  15 aag cag gtt aat aag ttt gat gct agc cag cag aac ggg agg ggc aag    96
Lys Gln Val Asn Lys Phe Asp Ala Ser Gln Gln Asn Gly Arg Gly Lys
            20                  25                  30 aga aag cac att gaa gac agg gag gac gac gac cag gag ggt ttg ata   144
Arg Lys His Ile Glu Asp Arg Glu Asp Asp Asp Gln Glu Gly Leu Ile
        35                  40                  45 cca gac ccg gaa gac gag tct gat cac gaa cca act ccc aag aag aag   192
Pro Asp Pro Glu Asp Glu Ser Asp His Glu Pro Thr Pro Lys Lys Lys
    50                  55                  60 aag ccg gcg gca cca cga aaa tct cga gct tct gcg ggt act acc aag   240
Lys Pro Ala Ala Pro Arg Lys Ser Arg Ala Ser Ala Gly Thr Thr Lys
65                  70                  75                  80
```

| | | |
|---|---|---|
| aag gac gga cca aag aca aaa aca aag cct gca gct gaa ggc gtg agc<br>Lys Asp Gly Pro Lys Thr Lys Thr Lys Pro Ala Ala Glu Gly Val Ser<br>                85                        90                        95 | 288 |
| gaa atc gta gaa aag act gat tcg cct tta ttt aat gct ctc cag caa<br>Glu Ile Val Glu Lys Thr Asp Ser Pro Leu Phe Asn Ala Leu Gln Gln<br>        100                      105                        110 | 336 |
| ccc gat atc gcc ctt caa cct ctg att gat gag tgg atc gag acc tac<br>Pro Asp Ile Ala Leu Gln Pro Leu Ile Asp Glu Trp Ile Glu Thr Tyr<br>            115                        120                      125 | 384 |
| caa caa gcc gct ggt gat gaa ata tca gag cag aaa tcc att cac gaa<br>Gln Gln Ala Ala Gly Asp Glu Ile Ser Glu Gln Lys Ser Ile His Glu<br>130                        135                      140 | 432 |
| ctg gtt gtc ttc ttc att cga tgt tgc ggt atg act acc gag atc gag<br>Leu Val Val Phe Phe Ile Arg Cys Cys Gly Met Thr Thr Glu Ile Glu<br>145                        150                      155                      160 | 480 |
| caa gct gaa gca acg gat gac gat ggt atc ccc gat gtc atc gag cga<br>Gln Ala Glu Ala Thr Asp Asp Asp Gly Ile Pro Asp Val Ile Glu Arg<br>                165                        170                      175 | 528 |
| gtg cag gat gaa agc gtt cgc gta gcg ttg gcg act tat ccc tta att<br>Val Gln Asp Glu Ser Val Arg Val Ala Leu Ala Thr Tyr Pro Leu Ile<br>        180                      185                        190 | 576 |
| tcc aaa gca aag aat ttt aag ccc ttc aag tcc aat ttg aac gag ttc<br>Ser Lys Ala Lys Asn Phe Lys Pro Phe Lys Ser Asn Leu Asn Glu Phe<br>            195                        200                      205 | 624 |
| att tca cac ttt att tca tcg ctc gct ctc aca cct atc ctc ttt cac<br>Ile Ser His Phe Ile Ser Ser Leu Ala Leu Thr Pro Ile Leu Phe His<br>        210                      215                        220 | 672 |
| act gcc gac aat act cct cac tca tct ctg ctc atc cca ctt ctc ctc<br>Thr Ala Asp Asn Thr Pro His Ser Ser Leu Leu Ile Pro Leu Leu Leu<br>225                        230                      235                      240 | 720 |
| aac tgg ctg atg tgt atg tca tca tca act ctt cga ccc atc cgt cat<br>Asn Trp Leu Met Cys Met Ser Ser Ser Thr Leu Arg Pro Ile Arg His<br>                245                        250                      255 | 768 |
| acc tca aca tac gtg acg ctc agg atg aac tcg gct ttg tgt gac gtt<br>Thr Ser Thr Tyr Val Thr Leu Arg Met Asn Ser Ala Leu Cys Asp Val<br>            260                        265                      270 | 816 |
| gct gcg gat gtg agc aaa gac ctg agc gtt aag caa agg cag cga gat<br>Ala Ala Asp Val Ser Lys Asp Leu Ser Val Lys Gln Arg Gln Arg Asp<br>        275                      280                      285 | 864 |
| gca gaa gtc aga aaa gct gga gct aca aat gca gcg cag aag aga gtg<br>Ala Glu Val Arg Lys Ala Gly Ala Thr Asn Ala Ala Gln Lys Arg Val<br>290                        295                      300 | 912 |
| aag gct gcc gag gac agg gtc aag gaa gtg caa gaa aga aag caa act<br>Lys Ala Ala Glu Asp Arg Val Lys Glu Val Gln Glu Arg Lys Gln Thr<br>305                        310                      315                      320 | 960 |
| tta gaa gag ttg atg cag gag atc ttt gat gtg atg ttc gtc cac cga<br>Leu Glu Glu Leu Met Gln Glu Ile Phe Asp Val Met Phe Val His Arg<br>                325                        330                      335 | 1008 |
| gtt cgc gat gcc gat ccc aac att cga acc gat tgt ctg cgt gaa tta<br>Val Arg Asp Ala Asp Pro Asn Ile Arg Thr Asp Cys Leu Arg Glu Leu<br>        340                      345                      350 | 1056 |
| ggt ctg tgg gcc aaa aaa cac cca gag tac tac gtt tcg act tct tat<br>Gly Leu Trp Ala Lys Lys His Pro Glu Tyr Tyr Val Ser Thr Ser Tyr<br>            355                        360                      365 | 1104 |
| ctc tcc tac ttc acc cgt ggc tgt aac gat acc cac gct cat gcc cga<br>Leu Ser Tyr Phe Thr Arg Gly Cys Asn Asp Thr His Ala His Ala Arg<br>        370                      375                      380 | 1152 |
| ctt gag act gtc aag gct ctt gcc aac ctc tac atc cga gaa acc ttt<br>Leu Glu Thr Val Lys Ala Leu Ala Asn Leu Tyr Ile Arg Glu Thr Phe<br>385                        390                      395                      400 | 1200 |

```
atc agt aac gct cga acc ttg acg atg cgt tta gcg cct agg gtg att    1248
Ile Ser Asn Ala Arg Thr Leu Thr Met Arg Leu Ala Pro Arg Val Ile
            405                 410                 415 gag atg gcc acc agg gat gtg gat ttg aat gtg agg gta gtg gct ttg    1296
Glu Met Ala Thr Arg Asp Val Asp Leu Asn Val Arg Val Val Ala Leu
        420                 425                 430 cag gtg att aca ctt ata gac aag acg ggt att ctg caa gac gag gag    1344
Gln Val Ile Thr Leu Ile Asp Lys Thr Gly Ile Leu Gln Asp Glu Glu
            435                 440                 445 gac gag gaa aga gat aag gtg gcg aag ctt gtt ttc gac cag gag cct    1392
Asp Glu Glu Arg Asp Lys Val Ala Lys Leu Val Phe Asp Gln Glu Pro
    450                 455                 460 cga att cga aaa gct gca ggg gcg ttc atc ctt ggt ttg tgg gaa gag    1440
Arg Ile Arg Lys Ala Ala Gly Ala Phe Ile Leu Gly Leu Trp Glu Glu
465                 470                 475                 480 agg aaa gaa ggc ctc aaa gca gtc tgg tcg ggt ctg aga gcg aac aaa    1488
Arg Lys Glu Gly Leu Lys Ala Val Trp Ser Gly Leu Arg Ala Asn Lys
                485                 490                 495 aag aag cgt gca gca aac atc acc gaa gac gaa atg tcc aac tac ctc    1536
Lys Lys Arg Ala Ala Asn Ile Thr Glu Asp Glu Met Ser Asn Tyr Leu
            500                 505                 510 aac tgg aaa tcc ctc gct gca gtt ctc ctc tac acc tct aaa tcc ctg    1584
Asn Trp Lys Ser Leu Ala Ala Val Leu Leu Tyr Thr Ser Lys Ser Leu
        515                 520                 525 gac gac gac cct tct gga caa ccc tct gcc ctc aaa cca agc cta ctc    1632
Asp Asp Asp Pro Ser Gly Gln Pro Ser Ala Leu Lys Pro Ser Leu Leu
            530                 535                 540 att ccg tct tta ccc aat aca cag atg aca agg gcg act gct gcc gtc    1680
Ile Pro Ser Leu Pro Asn Thr Gln Met Thr Arg Ala Thr Ala Ala Val
545                 550                 555                 560 gag tct atc ggt gct gag cat gag ctg tgg aaa gac tgg gag agc ttg    1728
Glu Ser Ile Gly Ala Glu His Glu Leu Trp Lys Asp Trp Glu Ser Leu
                565                 570                 575 gtg gac tat ctt ttg gtg gat cac tcg act aac gaa gaa gat atg tgg    1776
Val Asp Tyr Leu Leu Val Asp His Ser Thr Asn Glu Glu Asp Met Trp
            580                 585                 590 ctg ctc cgt gaa gat gag gaa act ttc atg ttg cag gtg ctt ttg gct    1824
Leu Leu Arg Glu Asp Glu Glu Thr Phe Met Leu Gln Val Leu Leu Ala
        595                 600                 605 tgt att aag cgg gaa gaa aat gaa gag gat gag ccg gat agg acc aaa    1872
Cys Ile Lys Arg Glu Glu Asn Glu Glu Asp Glu Pro Asp Arg Thr Lys
            610                 615                 620 acg ttg ata aag gtt ttg cct cgg tta ttt gcc aag cat cag gct gat    1920
Thr Leu Ile Lys Val Leu Pro Arg Leu Phe Ala Lys His Gln Ala Asp
625                 630                 635                 640 gtt ggt cga atg act ggg att tta tct gtt ccc gga cac atg aag ctc    1968
Val Gly Arg Met Thr Gly Ile Leu Ser Val Pro Gly His Met Lys Leu
                645                 650                 655 agt ctc tat ctc gac atg cgc atg tcc tct gcc tac gag tcc ctc tgg    2016
Ser Leu Tyr Leu Asp Met Arg Met Ser Ser Ala Tyr Glu Ser Leu Trp
            660                 665                 670 gat gac atc agc aaa cag ttc cta aaa tac act tcc cct acc atc ctc    2064
Asp Asp Ile Ser Lys Gln Phe Leu Lys Tyr Thr Ser Pro Thr Ile Leu
        675                 680                 685 aca gca tcc att tct gcg atc agc cat ctc gtc ggc aac tcg tcc ctt    2112
Thr Ala Ser Ile Ser Ala Ile Ser His Leu Val Gly Asn Ser Ser Leu
            690                 695                 700 tca tcc atc aat gaa acc aag ctt tct gag ctg cac gag tct ctc ttc    2160
Ser Ser Ile Asn Glu Thr Lys Leu Ser Glu Leu His Glu Ser Leu Phe
```

-continued

|  |  |  |  |  |
|---|---|---|---|---|
| 705 | 710 | 715 | 720 | |
| gct tct cta aga gat gcg att ggc tct gaa gat gtt gcg ctt gtc act<br>Ala Ser Leu Arg Asp Ala Ile Gly Ser Glu Asp Val Ala Leu Val Thr<br>725 730 735 | | | | 2208 |
| ttg gag gac gag cag atc agc cag ctg gaa gca atc atg ctg agg ata<br>Leu Glu Asp Glu Gln Ile Ser Gln Leu Glu Ala Ile Met Leu Arg Ile<br>740 745 750 | | | | 2256 |
| acg tta ctg cag aga agt atg gat ttg gta gat gtc atg gag gat gag<br>Thr Leu Leu Gln Arg Ser Met Asp Leu Val Asp Val Met Glu Asp Glu<br>755 760 765 | | | | 2304 |
| gaa ggg cag cag agt agc ggc tgg gac att atc tgt gcg ttt gct gat<br>Glu Gly Gln Gln Ser Ser Gly Trp Asp Ile Ile Cys Ala Phe Ala Asp<br>770 775 780 | | | | 2352 |
| agg ggc aaa ttg ggg tac aag gag gaa gct act atg gta gac tat gct<br>Arg Gly Lys Leu Gly Tyr Lys Glu Glu Ala Thr Met Val Asp Tyr Ala<br>785 790 795 800 | | | | 2400 |
| gtt caa atc atc ttc ctc cac atc act tgg ctc ttc aag cgg ttc acc<br>Val Gln Ile Ile Phe Leu His Ile Thr Trp Leu Phe Lys Arg Phe Thr<br>805 810 815 | | | | 2448 |
| aag gaa gat gcg caa gat gcc acc aag att gat ctc ctt tcc acc cga<br>Lys Glu Asp Ala Gln Asp Ala Thr Lys Ile Asp Leu Leu Ser Thr Arg<br>820 825 830 | | | | 2496 |
| cgc gat acc gcc ctt cag aca ttt aac cag ctt ttc ctc gga gaa acg<br>Arg Asp Thr Ala Leu Gln Thr Phe Asn Gln Leu Phe Leu Gly Glu Thr<br>835 840 845 | | | | 2544 |
| acc aat acc gcc agt gct gta cga cgt caa gcc ttc atc tct ttc atc<br>Thr Asn Thr Ala Ser Ala Val Arg Arg Gln Ala Phe Ile Ser Phe Ile<br>850 855 860 | | | | 2592 |
| aat acg tac gta ttg ttc gcc aaa cgt gca gag ggt agg gga gga gct<br>Asn Thr Tyr Val Leu Phe Ala Lys Arg Ala Glu Gly Arg Gly Gly Ala<br>865 870 875 880 | | | | 2640 |
| cca gcg agc gac gtt tgt tct gtg acg atg ccg gaa gaa gta cag cat<br>Pro Ala Ser Asp Val Cys Ser Val Thr Met Pro Glu Glu Val Gln His<br>885 890 895 | | | | 2688 |
| aga ctg gga ggg gcg ttc caa gcg gtg att gag agg tat gct tcc gtc<br>Arg Leu Gly Gly Ala Phe Gln Ala Val Ile Glu Arg Tyr Ala Ser Val<br>900 905 910 | | | | 2736 |
| gtg gag act aga tca gca gga cgg gaa gag agt cag cag ccc ccc gaa<br>Val Glu Thr Arg Ser Ala Gly Arg Glu Glu Ser Gln Gln Pro Pro Glu<br>915 920 925 | | | | 2784 |
| ctc act cct gat gag atg cac gag gat ttc cag ttt ttc caa ctc gtt<br>Leu Thr Pro Asp Glu Met His Glu Asp Phe Gln Phe Phe Gln Leu Val<br>930 935 940 | | | | 2832 |
| tcc gtt ttt gtc ggt gcc atc cga tgt ggt gtc ctc gag gtt gaa cat<br>Ser Val Phe Val Gly Ala Ile Arg Cys Gly Val Leu Glu Val Glu His<br>945 950 955 960 | | | | 2880 |
| gcc aag gaa cct ctt gcc cat tac agt cgt ttt ggt cca acg tac gat<br>Ala Lys Glu Pro Leu Ala His Tyr Ser Arg Phe Gly Pro Thr Tyr Asp<br>965 970 975 | | | | 2928 |
| gcg atc gtc aag aag ctc gtt gat gta ctt cga gat gag ggt atc tac<br>Ala Ile Val Lys Lys Leu Val Asp Val Leu Arg Asp Glu Gly Ile Tyr<br>980 985 990 | | | | 2976 |
| aat agg gag gca gat gcg gtg cag cat gtt gcg gga agc gcc ttg cag<br>Asn Arg Glu Ala Asp Ala Val Gln His Val Ala Gly Ser Ala Leu Gln<br>995 1000 1005 | | | | 3024 |
| caa tcg ttc aac atc ttc ctc gac tct gag gaa gac gaa cca act<br>Gln Ser Phe Asn Ile Phe Leu Asp Ser Glu Glu Asp Glu Pro Thr<br>1010 1015 1020 | | | | 3069 |
| gct cct ctg gcc ctt gcc cgt gtt att gca act gcg ttc gtc atc | | | | 3114 |

-continued

```
Ala Pro Leu Ala Leu Ala Arg Val Ile Ala Thr Ala Phe Val Ile
    1025                1030                1035 cat ggt tcc caa ttc gct atc cta aga caa ttg cat cca tct gat    3159
His Gly Ser Gln Phe Ala Ile Leu Arg Gln Leu His Pro Ser Asp
    1040                1045                1050 gtt tgc gat ttc cac ctc gaa gcg ctt gac ttt gtt tct ctc aaa    3204
Val Cys Asp Phe His Leu Glu Ala Leu Asp Phe Val Ser Leu Lys
    1055                1060                1065 gtc tca acg att gtc aaa caa gaa gga aat gca agg aac aag gag    3249
Val Ser Thr Ile Val Lys Gln Glu Gly Asn Ala Arg Asn Lys Glu
    1070                1075                1080 caa aaa tcc aga cta aca agg aaa aag tgg gca gtg ctc aca ttc    3294
Gln Lys Ser Arg Leu Thr Arg Lys Lys Trp Ala Val Leu Thr Phe
    1085                1090                1095 ttc aag gtg ctc gtc cct ctt ctc gcg cct gtc aca ggt aga gat    3339
Phe Lys Val Leu Val Pro Leu Leu Ala Pro Val Thr Gly Arg Asp
    1100                1105                1110 gct ctc aag atc aag gct cat ctc gaa gat gta atc gac tct tct    3384
Ala Leu Lys Ile Lys Ala His Leu Glu Asp Val Ile Asp Ser Ser
    1115                1120                1125 ggg gtg caa ctg aca acc aac aag ggt tgg gat ggc tac cga gcg    3429
Gly Val Gln Leu Thr Thr Asn Lys Gly Trp Asp Gly Tyr Arg Ala
    1130                1135                1140 tac gaa aag aga tta gta ggg atc gca agc aag gac ccg aat gtg    3474
Tyr Glu Lys Arg Leu Val Gly Ile Ala Ser Lys Asp Pro Asn Val
    1145                1150                1155 aaa atg atg gct agc aag aag gtt gta gaa agg gag gat act gaa    3519
Lys Met Met Ala Ser Lys Lys Val Val Glu Arg Glu Asp Thr Glu
    1160                1165                1170 cag ggt gat gaa gac aat gtc ttt gca agg caa tga                3555
Gln Gly Asp Glu Asp Asn Val Phe Ala Arg Gln
    1175                1180

<210> SEQ ID NO 20
<211> LENGTH: 1184
<212> TYPE: PRT
<213> ORGANISM: Cryptococcus neoformans

<400> SEQUENCE: 20

Met Ser Ser Pro Glu Pro Glu Pro Arg Arg Gly Ala Arg Val Arg
1               5                   10                  15

Lys Gln Val Asn Lys Phe Asp Ala Ser Gln Gln Asn Gly Arg Gly Lys
            20                  25                  30

Arg Lys His Ile Glu Asp Arg Glu Asp Asp Gln Glu Gly Leu Ile
        35                  40                  45

Pro Asp Pro Glu Asp Glu Ser Asp His Glu Pro Thr Pro Lys Lys Lys
    50                  55                  60

Lys Pro Ala Ala Pro Arg Lys Ser Arg Ala Ser Ala Gly Thr Thr Lys
65                  70                  75                  80

Lys Asp Gly Pro Lys Thr Lys Thr Lys Pro Ala Ala Glu Gly Val Ser
                85                  90                  95

Glu Ile Val Glu Lys Thr Asp Ser Pro Leu Phe Asn Ala Leu Gln Gln
            100                 105                 110

Pro Asp Ile Ala Leu Gln Pro Leu Ile Asp Glu Trp Ile Glu Thr Tyr
        115                 120                 125

Gln Gln Ala Ala Gly Asp Glu Ile Ser Glu Gln Lys Ser Ile His Glu
    130                 135                 140

Leu Val Val Phe Phe Ile Arg Cys Cys Gly Met Thr Thr Glu Ile Glu
```

-continued

```
            145                 150                 155                 160
Gln Ala Glu Ala Thr Asp Asp Gly Ile Pro Asp Val Ile Glu Arg
                    165                 170                 175

Val Gln Asp Glu Ser Val Arg Val Ala Leu Ala Thr Tyr Pro Leu Ile
        180                 185                 190

Ser Lys Ala Lys Asn Phe Lys Pro Phe Lys Ser Asn Leu Asn Glu Phe
            195                 200                 205

Ile Ser His Phe Ile Ser Ser Leu Ala Leu Thr Pro Ile Leu Phe His
        210                 215                 220

Thr Ala Asp Asn Thr Pro His Ser Ser Leu Leu Ile Pro Leu Leu Leu
225                 230                 235                 240

Asn Trp Leu Met Cys Met Ser Ser Thr Leu Arg Pro Ile Arg His
                245                 250                 255

Thr Ser Thr Tyr Val Thr Leu Arg Met Asn Ser Ala Leu Cys Asp Val
                260                 265                 270

Ala Ala Asp Val Ser Lys Asp Leu Ser Val Lys Gln Arg Gln Arg Asp
        275                 280                 285

Ala Glu Val Arg Lys Ala Gly Ala Thr Asn Ala Ala Gln Lys Arg Val
        290                 295                 300

Lys Ala Ala Glu Asp Arg Val Lys Glu Val Gln Glu Arg Lys Gln Thr
305                 310                 315                 320

Leu Glu Glu Leu Met Gln Glu Ile Phe Asp Val Met Phe Val His Arg
                325                 330                 335

Val Arg Asp Ala Asp Pro Asn Ile Arg Thr Asp Cys Leu Arg Glu Leu
                340                 345                 350

Gly Leu Trp Ala Lys Lys His Pro Glu Tyr Tyr Val Ser Thr Ser Tyr
            355                 360                 365

Leu Ser Tyr Phe Thr Arg Gly Cys Asn Asp Thr His Ala His Ala Arg
        370                 375                 380

Leu Glu Thr Val Lys Ala Leu Ala Asn Leu Tyr Ile Arg Glu Thr Phe
385                 390                 395                 400

Ile Ser Asn Ala Arg Thr Leu Thr Met Arg Leu Ala Pro Arg Val Ile
                405                 410                 415

Glu Met Ala Thr Arg Asp Val Asp Leu Asn Val Arg Val Val Ala Leu
                420                 425                 430

Gln Val Ile Thr Leu Ile Asp Lys Thr Gly Ile Leu Gln Asp Glu Glu
            435                 440                 445

Asp Glu Glu Arg Asp Lys Val Ala Lys Leu Val Phe Asp Gln Glu Pro
        450                 455                 460

Arg Ile Arg Lys Ala Ala Gly Ala Phe Ile Leu Gly Leu Trp Glu Glu
465                 470                 475                 480

Arg Lys Glu Gly Leu Lys Ala Val Trp Ser Gly Leu Arg Ala Asn Lys
                485                 490                 495

Lys Lys Arg Ala Ala Asn Ile Thr Glu Asp Glu Met Ser Asn Tyr Leu
            500                 505                 510

Asn Trp Lys Ser Leu Ala Ala Val Leu Leu Tyr Thr Ser Lys Ser Leu
        515                 520                 525

Asp Asp Asp Pro Ser Gly Gln Pro Ser Ala Leu Lys Pro Ser Leu Leu
        530                 535                 540

Ile Pro Ser Leu Pro Asn Thr Gln Met Thr Arg Ala Thr Ala Ala Val
545                 550                 555                 560

Glu Ser Ile Gly Ala Glu His Glu Leu Trp Lys Asp Trp Glu Ser Leu
                565                 570                 575
```

```
Val Asp Tyr Leu Leu Val Asp His Ser Thr Asn Glu Glu Asp Met Trp
            580                 585                 590

Leu Leu Arg Glu Asp Glu Glu Thr Phe Met Leu Gln Val Leu Leu Ala
        595                 600                 605

Cys Ile Lys Arg Glu Glu Asn Glu Glu Asp Glu Pro Asp Arg Thr Lys
610                 615                 620

Thr Leu Ile Lys Val Leu Pro Arg Leu Phe Ala Lys His Gln Ala Asp
625                 630                 635                 640

Val Gly Arg Met Thr Gly Ile Leu Ser Val Pro Gly His Met Lys Leu
                645                 650                 655

Ser Leu Tyr Leu Asp Met Arg Met Ser Ser Ala Tyr Glu Ser Leu Trp
            660                 665                 670

Asp Asp Ile Ser Lys Gln Phe Leu Lys Tyr Thr Ser Pro Thr Ile Leu
        675                 680                 685

Thr Ala Ser Ile Ser Ala Ile Ser His Leu Val Gly Asn Ser Ser Leu
    690                 695                 700

Ser Ser Ile Asn Glu Thr Lys Leu Ser Glu Leu His Glu Ser Leu Phe
705                 710                 715                 720

Ala Ser Leu Arg Asp Ala Ile Gly Ser Glu Asp Val Ala Leu Val Thr
                725                 730                 735

Leu Glu Asp Glu Gln Ile Ser Gln Leu Glu Ala Ile Met Leu Arg Ile
            740                 745                 750

Thr Leu Leu Gln Arg Ser Met Asp Leu Val Asp Val Met Glu Asp Glu
        755                 760                 765

Glu Gly Gln Gln Ser Ser Gly Trp Asp Ile Ile Cys Ala Phe Ala Asp
    770                 775                 780

Arg Gly Lys Leu Gly Tyr Lys Glu Glu Ala Thr Met Val Asp Tyr Ala
785                 790                 795                 800

Val Gln Ile Ile Phe Leu His Ile Thr Trp Leu Phe Lys Arg Phe Thr
                805                 810                 815

Lys Glu Asp Ala Gln Asp Ala Thr Lys Ile Asp Leu Leu Ser Thr Arg
            820                 825                 830

Arg Asp Thr Ala Leu Gln Thr Phe Asn Gln Leu Phe Leu Gly Glu Thr
        835                 840                 845

Thr Asn Thr Ala Ser Ala Val Arg Arg Gln Ala Phe Ile Ser Phe Ile
    850                 855                 860

Asn Thr Tyr Val Leu Phe Ala Lys Arg Ala Glu Gly Arg Gly Gly Ala
865                 870                 875                 880

Pro Ala Ser Asp Val Cys Ser Val Thr Met Pro Glu Glu Val Gln His
                885                 890                 895

Arg Leu Gly Gly Ala Phe Gln Ala Val Ile Glu Arg Tyr Ala Ser Val
            900                 905                 910

Val Glu Thr Arg Ser Ala Gly Arg Glu Glu Ser Gln Gln Pro Pro Glu
        915                 920                 925

Leu Thr Pro Asp Glu Met His Glu Asp Phe Gln Phe Gln Leu Val
    930                 935                 940

Ser Val Phe Val Gly Ala Ile Arg Cys Gly Val Leu Glu Val Glu His
945                 950                 955                 960

Ala Lys Glu Pro Leu Ala His Tyr Ser Arg Phe Gly Pro Thr Tyr Asp
                965                 970                 975

Ala Ile Val Lys Lys Leu Val Asp Val Leu Arg Asp Glu Gly Ile Tyr
            980                 985                 990
```

```
Asn Arg Glu Ala Asp Ala Val Gln His Val Ala Gly Ser Ala Leu Gln
            995                 1000                1005

Gln Ser Phe Asn Ile Phe Leu Asp Ser Glu Glu Asp Glu Pro Thr
    1010                1015                1020

Ala Pro Leu Ala Leu Ala Arg Val Ile Ala Thr Ala Phe Val Ile
    1025                1030                1035

His Gly Ser Gln Phe Ala Ile Leu Arg Gln Leu His Pro Ser Asp
    1040                1045                1050

Val Cys Asp Phe His Leu Glu Ala Leu Asp Phe Val Ser Leu Lys
    1055                1060                1065

Val Ser Thr Ile Val Lys Gln Glu Gly Asn Ala Arg Asn Lys Glu
    1070                1075                1080

Gln Lys Ser Arg Leu Thr Arg Lys Lys Trp Ala Val Leu Thr Phe
    1085                1090                1095

Phe Lys Val Leu Val Pro Leu Leu Ala Pro Val Thr Gly Arg Asp
    1100                1105                1110

Ala Leu Lys Ile Lys Ala His Leu Glu Asp Val Ile Asp Ser Ser
    1115                1120                1125

Gly Val Gln Leu Thr Thr Asn Lys Gly Trp Asp Gly Tyr Arg Ala
    1130                1135                1140

Tyr Glu Lys Arg Leu Val Gly Ile Ala Ser Lys Asp Pro Asn Val
    1145                1150                1155

Lys Met Met Ala Ser Lys Lys Val Val Glu Arg Glu Asp Thr Glu
    1160                1165                1170

Gln Gly Asp Glu Asp Asn Val Phe Ala Arg Gln
    1175                1180

<210> SEQ ID NO 21
<211> LENGTH: 897
<212> TYPE: DNA
<213> ORGANISM: Cryptococcus neoformans
<220> FEATURE:
<221> NAME/KEY: CDS
<222> LOCATION: (1)..(897)

<400> SEQUENCE: 21 atg aag tac tct gct acc gca gtc gcc gtt atg ggt gcc ctc gcc att      48
Met Lys Tyr Ser Ala Thr Ala Val Ala Val Met Gly Ala Leu Ala Ile
1               5                   10                  15 caa gcc acc cca atc aag aga gat gct tac acc cca acc gac att gat      96
Gln Ala Thr Pro Ile Lys Arg Asp Ala Tyr Thr Pro Thr Asp Ile Asp
            20                  25                  30 atc cta cag tat gcg ttg act ctc gag cac ctg gag aac aac ttc tac     144
Ile Leu Gln Tyr Ala Leu Thr Leu Glu His Leu Glu Asn Asn Phe Tyr
        35                  40                  45 tcc tgc gcc ctc aac aac atg gac gct caa gcg ttc gcc gat gcc gga     192
Ser Cys Ala Leu Asn Asn Met Asp Ala Gln Ala Phe Ala Asp Ala Gly
    50                  55                  60 ttc cca gcc tgg gta cgg aac agg ttt gag cag att gcc gct cac gag     240
Phe Pro Ala Trp Val Arg Asn Arg Phe Glu Gln Ile Ala Ala His Glu
65                  70                  75                  80 gcc tcc cac gtc gcc gtt ctc tcc gat gcc ctc ggc gct gac gcc acc     288
Ala Ser His Val Ala Val Leu Ser Asp Ala Leu Gly Ala Asp Ala Thr
                85                  90                  95 aag cca tgc gag tac tcc ttc cca tac acc gac gcc aaa tcg ttc acc     336
Lys Pro Cys Glu Tyr Ser Phe Pro Tyr Thr Asp Ala Lys Ser Phe Thr
            100                 105                 110 gct ctc gct cag gtc att gag aat gtt ggt gtt tct gct tac ctc ggt     384
```

```
Ala Leu Ala Gln Val Ile Glu Asn Val Gly Val Ser Ala Tyr Leu Gly
            115                 120                 125 gcc gcc ggt ttc atc atg gac aag acc tac ttg acc gtt gct ggt tcc    432
Ala Ala Gly Phe Ile Met Asp Lys Thr Tyr Leu Thr Val Ala Gly Ser
130                 135                 140 att ctc acc acc gag gcc cgc cac cag gcc tgg atc gct tcc gcc gtt    480
Ile Leu Thr Thr Glu Ala Arg His Gln Ala Trp Ile Ala Ser Ala Val
145                 150                 155                 160 aac aag cag aac cca tgg tcc ggc cca tac gac act cct ctc ggt ctc    528
Asn Lys Gln Asn Pro Trp Ser Gly Pro Tyr Asp Thr Pro Leu Gly Leu
            165                 170                 175 tcc gat gtc tac tcc att gcc gct gcc ttc atc acc agc tgt cca tcc    576
Ser Asp Val Tyr Ser Ile Ala Ala Ala Phe Ile Thr Ser Cys Pro Ser
            180                 185                 190 tcc aac cca act ctc cca gtc aag gca ttc cca gct ctc act ctc tct    624
Ser Asn Pro Thr Leu Pro Val Lys Ala Phe Pro Ala Leu Thr Leu Ser
            195                 200                 205 tgc gac tcc gcc ggt tcg act gcc acc ctc aac tat acc ggc gct gat    672
Cys Asp Ser Ala Gly Ser Thr Ala Thr Leu Asn Tyr Thr Gly Ala Asp
210                 215                 220 tca tcc gac acc ctt att ctc tac tct ggc ctc acg acc ctc gct ctc    720
Ser Ser Asp Thr Leu Ile Leu Tyr Ser Gly Leu Thr Thr Leu Ala Leu
225                 230                 235                 240 ccc atc acc gac atg atg gtc acc atc cca tcc tct ctt cag ggc att    768
Pro Ile Thr Asp Met Met Val Thr Ile Pro Ser Ser Leu Gln Gly Ile
            245                 250                 255 gct tac gca gtc gtg tct tca acg tct aac acc acc atg gtt gac gac    816
Ala Tyr Ala Val Val Ser Ser Thr Ser Asn Thr Thr Met Val Asp Asp
            260                 265                 270 tct aac acc att gcc ggc cca gcc atc att gac ctt cct ttc gct tct    864
Ser Asn Thr Ile Ala Gly Pro Ala Ile Ile Asp Leu Pro Phe Ala Ser
            275                 280                 285 tcc gcc agc aac ccc aac ttc act ggt atg taa                        897
Ser Ala Ser Asn Pro Asn Phe Thr Gly Met
            290                 295

<210> SEQ ID NO 22
<211> LENGTH: 298
<212> TYPE: PRT
<213> ORGANISM: Cryptococcus neoformans

<400> SEQUENCE: 22

Met Lys Tyr Ser Ala Thr Ala Val Ala Val Met Gly Ala Leu Ala Ile
1               5                   10                  15

Gln Ala Thr Pro Ile Lys Arg Asp Ala Tyr Thr Pro Thr Asp Ile Asp
            20                  25                  30

Ile Leu Gln Tyr Ala Leu Thr Leu Glu His Leu Glu Asn Asn Phe Tyr
        35                  40                  45

Ser Cys Ala Leu Asn Asn Met Asp Ala Gln Ala Phe Ala Asp Ala Gly
    50                  55                  60

Phe Pro Ala Trp Val Arg Asn Arg Phe Glu Gln Ile Ala Ala His Glu
65                  70                  75                  80

Ala Ser His Val Ala Val Leu Ser Asp Ala Leu Gly Ala Asp Ala Thr
                85                  90                  95

Lys Pro Cys Glu Tyr Ser Phe Pro Tyr Thr Asp Ala Lys Ser Phe Thr
            100                 105                 110

Ala Leu Ala Gln Val Ile Glu Asn Val Gly Val Ser Ala Tyr Leu Gly
        115                 120                 125
```

```
              Ala Ala Gly Phe Ile Met Asp Lys Thr Tyr Leu Thr Val Ala Gly Ser
                  130                 135                 140

Ile Leu Thr Thr Glu Ala Arg His Gln Ala Trp Ile Ala Ser Ala Val
              145                 150                 155                 160

Asn Lys Gln Asn Pro Trp Ser Gly Pro Tyr Asp Thr Pro Leu Gly Leu
                              165                 170                 175

Ser Asp Val Tyr Ser Ile Ala Ala Phe Ile Thr Ser Cys Pro Ser
                          180                 185                 190

Ser Asn Pro Thr Leu Pro Val Lys Ala Phe Pro Ala Leu Thr Leu Ser
                      195                 200                 205

Cys Asp Ser Ala Gly Ser Thr Ala Thr Leu Asn Tyr Thr Gly Ala Asp
                  210                 215                 220

Ser Ser Asp Thr Leu Ile Leu Tyr Ser Gly Leu Thr Thr Leu Ala Leu
              225                 230                 235                 240

Pro Ile Thr Asp Met Met Val Thr Ile Pro Ser Ser Leu Gln Gly Ile
                              245                 250                 255

Ala Tyr Ala Val Val Ser Ser Thr Ser Asn Thr Thr Met Val Asp Asp
                          260                 265                 270

Ser Asn Thr Ile Ala Gly Pro Ala Ile Ile Asp Leu Pro Phe Ala Ser
                      275                 280                 285

Ser Ala Ser Asn Pro Asn Phe Thr Gly Met
                  290                 295

<210> SEQ ID NO 23
<211> LENGTH: 534
<212> TYPE: DNA
<213> ORGANISM: Cryptococcus neoformans
<220> FEATURE:
<221> NAME/KEY: CDS
<222> LOCATION: (1)..(534)

<400> SEQUENCE: 23 atg tct cta act agt gtc act cgc gtc gta tcc aaa tcc atc ctc ggc      48
Met Ser Leu Thr Ser Val Thr Arg Val Val Ser Lys Ser Ile Leu Gly
1               5                   10                  15 gct tcc ttt act agc aca act cgc agg ctt acc act acc gtt ccc aga      96
Ala Ser Phe Thr Ser Thr Thr Arg Arg Leu Thr Thr Thr Val Pro Arg
            20                  25                  30 ttt ggt aga atg cct cct cct gct cac aag atg gcc cac ttc ccg agg     144
Phe Gly Arg Met Pro Pro Pro Ala His Lys Met Ala His Phe Pro Arg
        35                  40                  45 atc aca tcc tct ctt ccc tca gaa cac tct gag ttt aga aca gtg atg     192
Ile Thr Ser Ser Leu Pro Ser Glu His Ser Glu Phe Arg Thr Val Met
50                  55                  60 tgg acg ggc gag agc agt caa ctt gtc ctc atg act atc cct gtc gga     240
Trp Thr Gly Glu Ser Ser Gln Leu Val Leu Met Thr Ile Pro Val Gly
65                  70                  75                  80 gga gaa ata ggg gaa gaa att cac cat gtt gac caa cac ttg gtt ttc     288
Gly Glu Ile Gly Glu Glu Ile His His Val Asp Gln His Leu Val Phe
                85                  90                  95 acc tct ggt act gcc aag gcc att gtt gga gga gaa gaa aaa gag atc     336
Thr Ser Gly Thr Ala Lys Ala Ile Val Gly Gly Glu Glu Lys Glu Ile
            100                 105                 110 aag gct gga gat ctt gtc atc gtt cct cag ggt acc aag cat aac ttc     384
Lys Ala Gly Asp Leu Val Ile Val Pro Gln Gly Thr Lys His Asn Phe
        115                 120                 125 gtc aat acg ggc cct acc cct ctt tgc ctt ttt act gta tat gct ccg     432
Val Asn Thr Gly Pro Thr Pro Leu Cys Leu Phe Thr Val Tyr Ala Pro
    130                 135                 140
```

```
gcc gag cat gcc gag aca aca gtc aac aaa acg aag gag gaa ggg gat    480
Ala Glu His Ala Glu Thr Thr Val Asn Lys Thr Lys Glu Glu Gly Asp
145                 150                 155                 160 aaa ttg gaa gac gag ggc aag gat gag cct cca aag tgg gca gtt agg    528
Lys Leu Glu Asp Glu Gly Lys Asp Glu Pro Pro Lys Trp Ala Val Arg
                165                 170                 175 aag tag                                                             534
Lys
```

<210> SEQ ID NO 24
<211> LENGTH: 177
<212> TYPE: PRT
<213> ORGANISM: Cryptococcus neoformans

<400> SEQUENCE: 24

```
Met Ser Leu Thr Ser Val Thr Arg Val Val Ser Lys Ser Ile Leu Gly
1               5                   10                  15

Ala Ser Phe Thr Ser Thr Thr Arg Arg Leu Thr Thr Thr Val Pro Arg
            20                  25                  30

Phe Gly Arg Met Pro Pro Ala His Lys Met Ala His Phe Pro Arg
        35                  40                  45

Ile Thr Ser Ser Leu Pro Ser Glu His Ser Glu Phe Arg Thr Val Met
    50                  55                  60

Trp Thr Gly Glu Ser Ser Gln Leu Val Leu Met Thr Ile Pro Val Gly
65                  70                  75                  80

Gly Glu Ile Gly Glu Glu Ile His Val Asp Gln His Leu Val Phe
                85                  90                  95

Thr Ser Gly Thr Ala Lys Ala Ile Val Gly Gly Glu Lys Glu Ile
            100                 105                 110

Lys Ala Gly Asp Leu Val Ile Val Pro Gln Gly Thr Lys His Asn Phe
        115                 120                 125

Val Asn Thr Gly Pro Thr Pro Leu Cys Leu Phe Thr Val Tyr Ala Pro
    130                 135                 140

Ala Glu His Ala Glu Thr Thr Val Asn Lys Thr Lys Glu Glu Gly Asp
145                 150                 155                 160

Lys Leu Glu Asp Glu Gly Lys Asp Glu Pro Pro Lys Trp Ala Val Arg
                165                 170                 175

Lys
```

<210> SEQ ID NO 25
<211> LENGTH: 1074
<212> TYPE: DNA
<213> ORGANISM: Cryptococcus neoformans
<220> FEATURE:
<221> NAME/KEY: CDS
<222> LOCATION: (1)..(1074)

<400> SEQUENCE: 25

```
atg cca act gta ctc ctc aca ggt atc acg gga ttt ctg tct gcg cac    48
Met Pro Thr Val Leu Leu Thr Gly Ile Thr Gly Phe Leu Ser Ala His
1               5                   10                  15 gtc gcc cat acc ttc ctg aag cat gac tgg ata gtg cac ggc aca ctt    96
Val Ala His Thr Phe Leu Lys His Asp Trp Ile Val His Gly Thr Leu
            20                  25                  30 cgg tcc agc tcg aag gta gcg tta atc gaa gtt att cct gaa tac tct    144
Arg Ser Ser Ser Lys Val Ala Leu Ile Glu Val Ile Pro Glu Tyr Ser
        35                  40                  45 cct tat att tcg tca ggc aaa cta aaa ctc ttc gtt gtc gga cct ctt    192
```

```
Pro Tyr Ile Ser Ser Gly Lys Leu Lys Leu Phe Val Val Gly Pro Leu
    50                  55                  60 gag aat gcc gat tac act gaa gcc atg aaa ggc gtt gat gct gtg gtc        240
Glu Asn Ala Asp Tyr Thr Glu Ala Met Lys Gly Val Asp Ala Val Val
65              70                  75                  80 cac act gcg tct ccg gta gag ttt ggt gga gac aat ttt aga gag agc        288
His Thr Ala Ser Pro Val Glu Phe Gly Gly Asp Asn Phe Arg Glu Ser
                85                  90                  95 cat ttg aaa cct gct ttg gaa gga aca agg ggt gtc ctc aga gct gta        336
His Leu Lys Pro Ala Leu Glu Gly Thr Arg Gly Val Leu Arg Ala Val
            100                 105                 110 gcc aaa gag aag aat gta aag tcc gtc gtc tac act agt act ttt gga        384
Ala Lys Glu Lys Asn Val Lys Ser Val Val Tyr Thr Ser Thr Phe Gly
        115                 120                 125 gcc gtt ggt gat cat agg tat cat ccc act gag atc aaa ggc aaa gtt        432
Ala Val Gly Asp His Arg Tyr His Pro Thr Glu Ile Lys Gly Lys Val
    130                 135                 140 atc act gag gat aac tgg aac ccg tat acc ttg gaa gag ctg gat aag        480
Ile Thr Glu Asp Asn Trp Asn Pro Tyr Thr Leu Glu Glu Leu Asp Lys
145                 150                 155                 160 atg gtg gaa tct gga gag tca ggc aac ccc aca ttt cct cca gga tat        528
Met Val Glu Ser Gly Glu Ser Gly Asn Pro Thr Phe Pro Pro Gly Tyr
                165                 170                 175 ctg ttc tat aaa gga gcc aag aag tac gcg gaa ctc gct gct tgg gaa        576
Leu Phe Tyr Lys Gly Ala Lys Lys Tyr Ala Glu Leu Ala Ala Trp Glu
            180                 185                 190 tgc cag aaa gaa gcg aga gaa cag ggt gct gaa tgg tct ttg gcc acg        624
Cys Gln Lys Glu Ala Arg Glu Gln Gly Ala Glu Trp Ser Leu Ala Thr
        195                 200                 205 atg aac tgt gtg atg atc tgg ggg cct cca att caa cct ctc aca tca        672
Met Asn Cys Val Met Ile Trp Gly Pro Pro Ile Gln Pro Leu Thr Ser
    210                 215                 220 ctc agt cat ggg ggc atg tcg acc gag ttc ctt tgg atg ctt gca gga        720
Leu Ser His Gly Gly Met Ser Thr Glu Phe Leu Trp Met Leu Ala Gly
225                 230                 235                 240 ggg aaa gat gcc cat atc atg gac agt ctc tat ccc tat tac gtc gat        768
Gly Lys Asp Ala His Ile Met Asp Ser Leu Tyr Pro Tyr Tyr Val Asp
                245                 250                 255 gtt cgg gat gct gct gaa gca cac tat caa gcc acc gtc cgt aga gcg        816
Val Arg Asp Ala Ala Glu Ala His Tyr Gln Ala Thr Val Arg Arg Ala
            260                 265                 270 caa gga agg ttt atc atc tct gcc ggc cct tat gat ttc caa gag ttc        864
Gln Gly Arg Phe Ile Ile Ser Ala Gly Pro Tyr Asp Phe Gln Glu Phe
        275                 280                 285 gca gac atg ctt agg gag ctt tat cct gag caa aaa gaa cga ttc gcc        912
Ala Asp Met Leu Arg Glu Leu Tyr Pro Glu Gln Lys Glu Arg Phe Ala
    290                 295                 300 ctt ggt gct ccc ggc aaa tat atg tac aga gat cca gga gtg tac gtg        960
Leu Gly Ala Pro Gly Lys Tyr Met Tyr Arg Asp Pro Gly Val Tyr Val
305                 310                 315                 320 ctc aca aat gaa aag agt caa agg gaa ctt ggt att act tac cgt cca       1008
Leu Thr Asn Glu Lys Ser Gln Arg Glu Leu Gly Ile Thr Tyr Arg Pro
                325                 330                 335 aaa caa gag act ctc aaa gat gca ttt gac agg ttt ttc gct ttg gag       1056
Lys Gln Glu Thr Leu Lys Asp Ala Phe Asp Arg Phe Phe Ala Leu Glu
            340                 345                 350 aaa caa gga ttg aag taa                                                1074
Lys Gln Gly Leu Lys
        355
```

<210> SEQ ID NO 26
<211> LENGTH: 357
<212> TYPE: PRT
<213> ORGANISM: Cryptococcus neoformans

<400> SEQUENCE: 26

Met Pro Thr Val Leu Leu Thr Gly Ile Thr Gly Phe Leu Ser Ala His
1               5                   10                  15

Val Ala His Thr Phe Leu Lys His Asp Trp Ile Val His Gly Thr Leu
            20                  25                  30

Arg Ser Ser Ser Lys Val Ala Leu Ile Glu Val Ile Pro Glu Tyr Ser
        35                  40                  45

Pro Tyr Ile Ser Ser Gly Lys Leu Lys Leu Phe Val Val Gly Pro Leu
    50                  55                  60

Glu Asn Ala Asp Tyr Thr Glu Ala Met Lys Gly Val Asp Ala Val Val
65                  70                  75                  80

His Thr Ala Ser Pro Val Glu Phe Gly Gly Asp Asn Phe Arg Glu Ser
                85                  90                  95

His Leu Lys Pro Ala Leu Glu Gly Thr Arg Gly Val Leu Arg Ala Val
            100                 105                 110

Ala Lys Glu Lys Asn Val Lys Ser Val Val Tyr Thr Ser Thr Phe Gly
        115                 120                 125

Ala Val Gly Asp His Arg Tyr His Pro Thr Glu Ile Lys Gly Lys Val
    130                 135                 140

Ile Thr Glu Asp Asn Trp Asn Pro Tyr Thr Leu Glu Glu Leu Asp Lys
145                 150                 155                 160

Met Val Glu Ser Gly Glu Ser Gly Asn Pro Thr Phe Pro Pro Gly Tyr
                165                 170                 175

Leu Phe Tyr Lys Gly Ala Lys Lys Tyr Ala Glu Leu Ala Ala Trp Glu
            180                 185                 190

Cys Gln Lys Glu Ala Arg Glu Gln Gly Ala Glu Trp Ser Leu Ala Thr
        195                 200                 205

Met Asn Cys Val Met Ile Trp Gly Pro Pro Ile Gln Pro Leu Thr Ser
    210                 215                 220

Leu Ser His Gly Gly Met Ser Thr Glu Phe Leu Trp Met Leu Ala Gly
225                 230                 235                 240

Gly Lys Asp Ala His Ile Met Asp Ser Leu Tyr Pro Tyr Tyr Val Asp
                245                 250                 255

Val Arg Asp Ala Ala Glu Ala His Tyr Gln Ala Thr Val Arg Arg Ala
            260                 265                 270

Gln Gly Arg Phe Ile Ile Ser Ala Gly Pro Tyr Asp Phe Gln Glu Phe
        275                 280                 285

Ala Asp Met Leu Arg Glu Leu Tyr Pro Glu Gln Lys Glu Arg Phe Ala
    290                 295                 300

Leu Gly Ala Pro Gly Lys Tyr Met Tyr Arg Asp Pro Gly Val Tyr Val
305                 310                 315                 320

Leu Thr Asn Glu Lys Ser Gln Arg Glu Leu Gly Ile Thr Tyr Arg Pro
                325                 330                 335

Lys Gln Glu Thr Leu Lys Asp Ala Phe Asp Arg Phe Phe Ala Leu Glu
            340                 345                 350

Lys Gln Gly Leu Lys
        355

<210> SEQ ID NO 27

```
<211> LENGTH: 2781
<212> TYPE: DNA
<213> ORGANISM: Cryptococcus neoformans
<220> FEATURE:
<221> NAME/KEY: CDS
<222> LOCATION: (1)..(2781)

<400> SEQUENCE: 27
```

| | | | | | | | | | | | | | | | | |
|---|---|---|---|---|---|---|---|---|---|---|---|---|---|---|---|---|
| atg | ttt | agg | aag | aga | att | ctt | tat | ctt | tct | tct | ttt | tca | atc | cct | ttg | 48 |
| Met | Phe | Arg | Lys | Arg | Ile | Leu | Tyr | Leu | Ser | Ser | Phe | Ser | Ile | Pro | Leu | |
| 1 | | | | 5 | | | | | 10 | | | | | 15 | | |
| tac | aca | gtc | cca | gcc | cac | agt | tat | tcc | tgt | act | ttt | cag | acc | aac | cag | 96 |
| Tyr | Thr | Val | Pro | Ala | His | Ser | Tyr | Ser | Cys | Thr | Phe | Gln | Thr | Asn | Gln | |
| | | | 20 | | | | | 25 | | | | | 30 | | | |
| cgc | cct | tct | act | ctc | ctc | aaa | cgc | gta | cat | tcg | ctc | gct | atg | tcc | ttc | 144 |
| Arg | Pro | Ser | Thr | Leu | Leu | Lys | Arg | Val | His | Ser | Leu | Ala | Met | Ser | Phe | |
| | | 35 | | | | | 40 | | | | | 45 | | | | |
| ccg | cca | gtt | cag | ccc | gcc | gac | aat | ggc | atg | gcg | gtc | gtt | gct | ccc | aat | 192 |
| Pro | Pro | Val | Gln | Pro | Ala | Asp | Asn | Gly | Met | Ala | Val | Val | Ala | Pro | Asn | |
| | 50 | | | | | 55 | | | | | 60 | | | | | |
| ctc | gag | tct | aac | cct | acc | act | gtt | gcg | tcc | cac | gcc | cca | caa | att | gcc | 240 |
| Leu | Glu | Ser | Asn | Pro | Thr | Thr | Val | Ala | Ser | His | Ala | Pro | Gln | Ile | Ala | |
| 65 | | | | | 70 | | | | | 75 | | | | | 80 | |
| gtc | aag | gat | gaa | aat | gat | agt | atg | agc | gag | gat | gag | cag | cct | ttg | gcg | 288 |
| Val | Lys | Asp | Glu | Asn | Asp | Ser | Met | Ser | Glu | Asp | Glu | Gln | Pro | Leu | Ala | |
| | | | | 85 | | | | | 90 | | | | | 95 | | |
| aaa | agc | aaa | gcg | aat | gga | gcg | agg | aag | aga | gtc | gaa | aac | agc | agt | gac | 336 |
| Lys | Ser | Lys | Ala | Asn | Gly | Ala | Arg | Lys | Arg | Val | Glu | Asn | Ser | Ser | Asp | |
| | | | 100 | | | | | 105 | | | | | 110 | | | |
| gag | gaa | gag | aaa | cct | ctc | agc | aaa | aag | ccc | aga | gcc | aat | ggt | gtc | aac | 384 |
| Glu | Glu | Glu | Lys | Pro | Leu | Ser | Lys | Lys | Pro | Arg | Ala | Asn | Gly | Val | Asn | |
| | | 115 | | | | | 120 | | | | | 125 | | | | |
| aag | aaa | agg | gtc | gtc | gcc | agc | agt | gat | gaa | gaa | agc | gat | gtt | tca | cct | 432 |
| Lys | Lys | Arg | Val | Val | Ala | Ser | Ser | Asp | Glu | Glu | Ser | Asp | Val | Ser | Pro | |
| | 130 | | | | | 135 | | | | | 140 | | | | | |
| cct | gct | aag | agg | cct | gtt | tcc | aag | caa | tcc | aaa | cct | gcc | acc | ccc | gat | 480 |
| Pro | Ala | Lys | Arg | Pro | Val | Ser | Lys | Gln | Ser | Lys | Pro | Ala | Thr | Pro | Asp | |
| 145 | | | | | 150 | | | | | 155 | | | | | 160 | |
| tct | gaa | tct | gat | gac | gat | caa | cct | ctc | gcc | aag | aag | gct | aac | gga | ctg | 528 |
| Ser | Glu | Ser | Asp | Asp | Asp | Gln | Pro | Leu | Ala | Lys | Lys | Ala | Asn | Gly | Leu | |
| | | | | 165 | | | | | 170 | | | | | 175 | | |
| gcc | gca | tcc | aaa | cgt | cag | gct | aaa | aaa | gcg | gag | gaa | tta | tca | gaa | gaa | 576 |
| Ala | Ala | Ser | Lys | Arg | Gln | Ala | Lys | Lys | Ala | Glu | Glu | Leu | Ser | Glu | Glu | |
| | | | 180 | | | | | 185 | | | | | 190 | | | |
| agc | tcg | gag | gaa | gaa | aag | cct | ctt | gcg | aag | gtt | gcc | aag | agg | gta | tca | 624 |
| Ser | Ser | Glu | Glu | Glu | Lys | Pro | Leu | Ala | Lys | Val | Ala | Lys | Arg | Val | Ser | |
| | | 195 | | | | | 200 | | | | | 205 | | | | |
| gca | aag | aag | atg | aag | agc | gag | act | gag | gac | tct | gag | gaa | gac | cgg | cct | 672 |
| Ala | Lys | Lys | Met | Lys | Ser | Glu | Thr | Glu | Asp | Ser | Glu | Glu | Asp | Arg | Pro | |
| | 210 | | | | | 215 | | | | | 220 | | | | | |
| ctt | gca | aag | aag | aag | gct | cct | gtt | aag | cgt | gct | cca | gca | aag | aaa | tcg | 720 |
| Leu | Ala | Lys | Lys | Lys | Ala | Pro | Val | Lys | Arg | Ala | Pro | Ala | Lys | Lys | Ser | |
| 225 | | | | | 230 | | | | | 235 | | | | | 240 | |
| gcg | aag | aag | gaa | cct | agt | gag | agt | gaa | gag | gat | gag | aag | cct | tta | gcg | 768 |
| Ala | Lys | Lys | Glu | Pro | Ser | Glu | Ser | Glu | Glu | Asp | Glu | Lys | Pro | Leu | Ala | |
| | | | | 245 | | | | | 250 | | | | | 255 | | |
| aag | aac | gct | aga | ggg | aag | gcc | aag | gcg | gcg | acg | gtg | aag | gaa | gag | aaa | 816 |
| Lys | Asn | Ala | Arg | Gly | Lys | Ala | Lys | Ala | Ala | Thr | Val | Lys | Glu | Glu | Lys | |
| | | | 260 | | | | | 265 | | | | | 270 | | | |
| ggt | aag | aag | aca | aag | aag | gag | aaa | gag | gaa | gaa | gag | gag | gaa | agg | | 864 |
| Gly | Lys | Lys | Thr | Lys | Lys | Glu | Lys | Glu | Glu | Glu | Glu | Glu | Glu | Arg | | |

-continued

| | | |
|---|---|---|
| tac aag tgg tgg gaa cag gat gct ttg ggt gat ggg tca tcc aag tgg<br>Tyr Lys Trp Trp Glu Gln Asp Ala Leu Gly Asp Gly Ser Ser Lys Trp<br>290                               295                             300 | 912 |
| acg gtc ctt gag cac aac gct gtt ctc ttc cct cct cct tat gtt cct<br>Thr Val Leu Glu His Asn Ala Val Leu Phe Pro Pro Pro Tyr Val Pro<br>305                         310                           315                    320 | 960 |
| tta ccc aag aac gtg aaa atg aag tac gat ggc gtc tca ctt acc ctc<br>Leu Pro Lys Asn Val Lys Met Lys Tyr Asp Gly Val Ser Leu Thr Leu<br>                       325                           330                         335 | 1008 |
| cct ccc gag tct gaa gaa gtc gcc ggt ttc ttc ggt gcc ctc ctt gaa<br>Pro Pro Glu Ser Glu Glu Val Ala Gly Phe Phe Gly Ala Leu Leu Glu<br>             340                           345                         350 | 1056 |
| acc gac tat gct caa gat gcc aaa ttc cgt gaa aac ttt ttc cga gac<br>Thr Asp Tyr Ala Gln Asp Ala Lys Phe Arg Glu Asn Phe Phe Arg Asp<br>                   355                       360                         365 | 1104 |
| ttt aag gct atc gtc gaa aaa tat cca ccc aag gag gac gtc aag gtt<br>Phe Lys Ala Ile Val Glu Lys Tyr Pro Pro Lys Glu Asp Val Lys Val<br>370                               375                             380 | 1152 |
| aag aag ttg gaa aag tgc gat ttt aga ccg atg ttt gag tac ttt gaa<br>Lys Lys Leu Glu Lys Cys Asp Phe Arg Pro Met Phe Glu Tyr Phe Glu<br>385                               390                           395                    400 | 1200 |
| aag gag aag gag aag aag aag gcg ttg act aag gaa gag aaa aag gcg<br>Lys Glu Lys Glu Lys Lys Lys Ala Leu Thr Lys Glu Glu Lys Lys Ala<br>                       405                           410                         415 | 1248 |
| att aaa gcg gag aag gac aag ctt gaa gca ccg tat ctc tat gcg aat<br>Ile Lys Ala Glu Lys Asp Lys Leu Glu Ala Pro Tyr Leu Tyr Ala Asn<br>             420                           425                         430 | 1296 |
| gtt gat gga agg aag gaa aag gtc ggc aac ttc cgt gca gaa cct cct<br>Val Asp Gly Arg Lys Glu Lys Val Gly Asn Phe Arg Ala Glu Pro Pro<br>                   435                       440                         445 | 1344 |
| gga ttg ttc aag ggt cgt ggt gaa cat ccc aag aag ggt act gtc aag<br>Gly Leu Phe Lys Gly Arg Gly Glu His Pro Lys Lys Gly Thr Val Lys<br>450                               455                           460 | 1392 |
| aac cgt ctc cga cct gaa gat atc att atc aac att ggc aaa gaa gct<br>Asn Arg Leu Arg Pro Glu Asp Ile Ile Ile Asn Ile Gly Lys Glu Ala<br>465                               470                           475                    480 | 1440 |
| cct atc cct gtg ccc aac att ccc ggt cag tgg aag ggt atc cag cat<br>Pro Ile Pro Val Pro Asn Ile Pro Gly Gln Trp Lys Gly Ile Gln His<br>                           485                           490                         495 | 1488 |
| gat aac aca gtg act tgg ctc gct cat tgg aag gag aat gtc aac ggt<br>Asp Asn Thr Val Thr Trp Leu Ala His Trp Lys Glu Asn Val Asn Gly<br>                     500                           505                         510 | 1536 |
| aac gcc aaa tac gtc ttc ttg agc gct ggt agt gcg tgg aaa ggt caa<br>Asn Ala Lys Tyr Val Phe Leu Ser Ala Gly Ser Ala Trp Lys Gly Gln<br>             515                           520                         525 | 1584 |
| agt gat cgt gcc aag ttt gaa aag gcc cgt gag ctt atc aaa cat gtc<br>Ser Asp Arg Ala Lys Phe Glu Lys Ala Arg Glu Leu Ile Lys His Val<br>530                               535                           540 | 1632 |
| gac aaa att cga aaa gac tac act gcc gac ctc aaa tcc aaa gtc atg<br>Asp Lys Ile Arg Lys Asp Tyr Thr Ala Asp Leu Lys Ser Lys Val Met<br>545                               550                           555                    560 | 1680 |
| gct gac cga caa cgt gcc acc gcc ctg tac ttt atc gat cgt ctg gct<br>Ala Asp Arg Gln Arg Ala Thr Ala Leu Tyr Phe Ile Asp Arg Leu Ala<br>                   565                       570                         575 | 1728 |
| ctg cga gcg ggt aat gaa aag ggt gaa gat gaa gcg gat act gtc ggc<br>Leu Arg Ala Gly Asn Glu Lys Gly Glu Asp Glu Ala Asp Thr Val Gly<br>             580                           585                         590 | 1776 |
| tgt tgt tct ctg cga tac gaa cac gtg acg ctc tct cca ccg aat act | 1824 |

```
Cys Cys Ser Leu Arg Tyr Glu His Val Thr Leu Ser Pro Pro Asn Thr
        595                 600                 605 atc atc ttt gat ttc ctc ggt aag gac tcg atg agg ttc cat cag gaa      1872
Ile Ile Phe Asp Phe Leu Gly Lys Asp Ser Met Arg Phe His Gln Glu
610                 615                 620 gtc gag gtc gat ccg caa gtg ttc aag aac ata aaa ctg ttt aag gct      1920
Val Glu Val Asp Pro Gln Val Phe Lys Asn Ile Lys Leu Phe Lys Ala
625                 630                 635                 640 gat ccg aag aag aag ggt gac gat atc ttt gac cga ctg acc acc act      1968
Asp Pro Lys Lys Lys Gly Asp Asp Ile Phe Asp Arg Leu Thr Thr Thr
                645                 650                 655 ctt ctt aac aag cac ctc aac agc atg atg cct ggt ctt acc gcc aag      2016
Leu Leu Asn Lys His Leu Asn Ser Met Met Pro Gly Leu Thr Ala Lys
                660                 665                 670 gtt ttc cgt acc tac aac gcc tca tgg act ttc caa gaa caa ctc aaa      2064
Val Phe Arg Thr Tyr Asn Ala Ser Trp Thr Phe Gln Glu Gln Leu Lys
            675                 680                 685 aac aca cct aag aac gga act gta gcc gag aag att gcg gcg tac aac      2112
Asn Thr Pro Lys Asn Gly Thr Val Ala Glu Lys Ile Ala Ala Tyr Asn
690                 695                 700 act gcc aat agg gat gtt gcc atc ttg tgt aat cac caa aag agt gtc      2160
Thr Ala Asn Arg Asp Val Ala Ile Leu Cys Asn His Gln Lys Ser Val
705                 710                 715                 720 agc aag ggt ttt gag ggc agt ttt gcc aaa gcc gag gat aag att cgt      2208
Ser Lys Gly Phe Glu Gly Ser Phe Ala Lys Ala Glu Asp Lys Ile Arg
                725                 730                 735 gcc ctc aag tat cag cgt ctc aag ctt cgt ctc caa ctt ttt tct ctt      2256
Ala Leu Lys Tyr Gln Arg Leu Lys Leu Arg Leu Gln Leu Phe Ser Leu
                740                 745                 750 aac ccc aag att aag aag aag cat ccc gag ctt gcg gag gat gag tct      2304
Asn Pro Lys Ile Lys Lys Lys His Pro Glu Leu Ala Glu Asp Glu Ser
            755                 760                 765 gat gtg gat gac gaa ttt atg gag cgc cac gaa gcc gaa tta ctc gaa      2352
Asp Val Asp Asp Glu Phe Met Glu Arg His Glu Ala Glu Leu Leu Glu
770                 775                 780 aaa gct ttg gag aac gca aag aag aaa tgg gat acg gat aat gtc aag      2400
Lys Ala Leu Glu Asn Ala Lys Lys Lys Trp Asp Thr Asp Asn Val Lys
785                 790                 795                 800 ctt gaa ggg gat ggg aag aaa aag aag acg aag gga gag ttg gat gag      2448
Leu Glu Gly Asp Gly Lys Lys Lys Lys Thr Lys Gly Glu Leu Asp Glu
                805                 810                 815 agg ttg agt gag atc aag gca gag ttt aag gag ttg aag aag gag agg      2496
Arg Leu Ser Glu Ile Lys Ala Glu Phe Lys Glu Leu Lys Lys Glu Arg
                820                 825                 830 aag gct aaa aag att gat gcc aag aga gga gcc acg gag gag aaa ctt      2544
Lys Ala Lys Lys Ile Asp Ala Lys Arg Gly Ala Thr Glu Glu Lys Leu
                835                 840                 845 ctt gct cag gtc gcc agg atc gac gaa cgt atc gct acc gcc aaa gtc      2592
Leu Ala Gln Val Ala Arg Ile Asp Glu Arg Ile Ala Thr Ala Lys Val
850                 855                 860 cag ctt caa gat cga gac aag ctc aag gat gtt gct ttg ggc aca tcc      2640
Gln Leu Gln Asp Arg Asp Lys Leu Lys Asp Val Ala Leu Gly Thr Ser
865                 870                 875                 880 aag att aac tat atc gat cca aga cta act gtc gcg tgg gcg aag aag      2688
Lys Ile Asn Tyr Ile Asp Pro Arg Leu Thr Val Ala Trp Ala Lys Lys
                885                 890                 895 ttt gat gtt cct ctc gaa aaa ctg ttc tcc aaa acc ctg cga gaa aag      2736
Phe Asp Val Pro Leu Glu Lys Leu Phe Ser Lys Thr Leu Arg Glu Lys
                900                 905                 910
```

```
ttc cct tgg gct gag gcg gag gct gga ccg gac tgg gtt ttc tag    2781
Phe Pro Trp Ala Glu Ala Glu Ala Gly Pro Asp Trp Val Phe
        915                 920                 925
```

<210> SEQ ID NO 28
<211> LENGTH: 926
<212> TYPE: PRT
<213> ORGANISM: Cryptococcus neoformans

<400> SEQUENCE: 28

```
Met Phe Arg Lys Arg Ile Leu Tyr Leu Ser Ser Phe Ser Ile Pro Leu
1               5                   10                  15

Tyr Thr Val Pro Ala His Ser Tyr Ser Cys Thr Phe Gln Thr Asn Gln
            20                  25                  30

Arg Pro Ser Thr Leu Leu Lys Arg Val His Ser Leu Ala Met Ser Phe
        35                  40                  45

Pro Pro Val Gln Pro Ala Asp Asn Gly Met Ala Val Ala Pro Asn
    50                  55                  60

Leu Glu Ser Asn Pro Thr Thr Val Ala Ser His Ala Pro Gln Ile Ala
65                  70                  75                  80

Val Lys Asp Glu Asn Asp Ser Met Ser Glu Asp Glu Gln Pro Leu Ala
                85                  90                  95

Lys Ser Lys Ala Asn Gly Ala Arg Lys Arg Val Glu Asn Ser Ser Asp
            100                 105                 110

Glu Glu Glu Lys Pro Leu Ser Lys Pro Arg Ala Asn Gly Val Asn
        115                 120                 125

Lys Lys Arg Val Val Ala Ser Ser Asp Glu Glu Ser Asp Val Ser Pro
130                 135                 140

Pro Ala Lys Arg Pro Val Ser Lys Gln Ser Lys Pro Ala Thr Pro Asp
145                 150                 155                 160

Ser Glu Ser Asp Asp Asp Gln Pro Leu Ala Lys Lys Ala Asn Gly Leu
                165                 170                 175

Ala Ala Ser Lys Arg Gln Ala Lys Ala Glu Glu Leu Ser Glu Glu
            180                 185                 190

Ser Ser Glu Glu Glu Lys Pro Leu Ala Lys Val Ala Lys Arg Val Ser
        195                 200                 205

Ala Lys Lys Met Lys Ser Glu Thr Glu Asp Ser Glu Asp Arg Pro
210                 215                 220

Leu Ala Lys Lys Lys Ala Pro Val Lys Arg Ala Pro Ala Lys Lys Ser
225                 230                 235                 240

Ala Lys Lys Glu Pro Ser Glu Ser Glu Glu Asp Glu Lys Pro Leu Ala
                245                 250                 255

Lys Asn Ala Arg Gly Lys Ala Lys Ala Ala Thr Val Lys Glu Glu Lys
            260                 265                 270

Gly Lys Lys Thr Lys Lys Glu Lys Glu Glu Glu Glu Glu Glu Arg
        275                 280                 285

Tyr Lys Trp Trp Glu Gln Asp Ala Leu Gly Asp Gly Ser Ser Lys Trp
    290                 295                 300

Thr Val Leu Glu His Asn Ala Val Leu Phe Pro Pro Tyr Val Pro
305                 310                 315                 320

Leu Pro Lys Asn Val Lys Met Lys Tyr Asp Gly Val Ser Leu Thr Leu
                325                 330                 335

Pro Pro Glu Ser Glu Glu Val Ala Gly Phe Gly Ala Leu Leu Glu
            340                 345                 350

Thr Asp Tyr Ala Gln Asp Ala Lys Phe Arg Glu Asn Phe Phe Arg Asp
```

-continued

```
                355                 360                 365
Phe Lys Ala Ile Val Glu Lys Tyr Pro Pro Lys Glu Asp Val Lys Val
370                 375                 380
Lys Lys Leu Glu Lys Cys Asp Phe Arg Pro Met Phe Glu Tyr Phe Glu
385                 390                 395                 400
Lys Glu Lys Glu Lys Lys Ala Leu Thr Lys Glu Lys Lys Ala
                405                 410                 415
Ile Lys Ala Glu Lys Asp Lys Leu Glu Ala Pro Tyr Leu Tyr Ala Asn
                420                 425                 430
Val Asp Gly Arg Lys Glu Lys Val Gly Asn Phe Arg Ala Glu Pro Pro
                435                 440                 445
Gly Leu Phe Lys Gly Arg Gly Glu His Pro Lys Lys Gly Thr Val Lys
                450                 455                 460
Asn Arg Leu Arg Pro Glu Asp Ile Ile Asn Ile Gly Lys Glu Ala
465                 470                 475                 480
Pro Ile Pro Val Pro Asn Ile Pro Gly Gln Trp Lys Gly Ile Gln His
                485                 490                 495
Asp Asn Thr Val Thr Trp Leu Ala His Trp Lys Glu Asn Val Asn Gly
                500                 505                 510
Asn Ala Lys Tyr Val Phe Leu Ser Ala Gly Ser Ala Trp Lys Gly Gln
                515                 520                 525
Ser Asp Arg Ala Lys Phe Glu Lys Ala Arg Glu Leu Ile Lys His Val
                530                 535                 540
Asp Lys Ile Arg Lys Asp Tyr Thr Ala Asp Leu Lys Ser Lys Val Met
545                 550                 555                 560
Ala Asp Arg Gln Arg Ala Thr Ala Leu Tyr Phe Ile Asp Arg Leu Ala
                565                 570                 575
Leu Arg Ala Gly Asn Glu Lys Gly Glu Asp Glu Ala Asp Thr Val Gly
                580                 585                 590
Cys Cys Ser Leu Arg Tyr Glu His Val Thr Leu Ser Pro Pro Asn Thr
                595                 600                 605
Ile Ile Phe Asp Phe Leu Gly Lys Asp Ser Met Arg Phe His Gln Glu
                610                 615                 620
Val Glu Val Asp Pro Gln Val Phe Lys Asn Ile Lys Leu Phe Lys Ala
625                 630                 635                 640
Asp Pro Lys Lys Lys Gly Asp Asp Ile Phe Asp Arg Leu Thr Thr Thr
                645                 650                 655
Leu Leu Asn Lys His Leu Asn Ser Met Met Pro Gly Leu Thr Ala Lys
                660                 665                 670
Val Phe Arg Thr Tyr Asn Ala Ser Trp Thr Phe Gln Glu Gln Leu Lys
                675                 680                 685
Asn Thr Pro Lys Asn Gly Thr Val Ala Glu Lys Ile Ala Ala Tyr Asn
                690                 695                 700
Thr Ala Asn Arg Asp Val Ala Ile Leu Cys Asn His Gln Lys Ser Val
705                 710                 715                 720
Ser Lys Gly Phe Glu Gly Ser Phe Ala Lys Ala Glu Asp Lys Ile Arg
                725                 730                 735
Ala Leu Lys Tyr Gln Arg Leu Leu Arg Leu Gln Leu Phe Ser Leu
                740                 745                 750
Asn Pro Lys Ile Lys Lys Lys His Pro Glu Leu Ala Glu Asp Glu Ser
                755                 760                 765
Asp Val Asp Asp Glu Phe Met Glu Arg His Glu Ala Glu Leu Leu Glu
770                 775                 780
```

-continued

```
Lys Ala Leu Glu Asn Ala Lys Lys Trp Asp Thr Asp Asn Val Lys
785                 790                 795                 800

Leu Glu Gly Asp Gly Lys Lys Lys Thr Lys Gly Glu Leu Asp Glu
            805                 810                 815

Arg Leu Ser Glu Ile Lys Ala Glu Phe Lys Glu Leu Lys Lys Glu Arg
        820                 825                 830

Lys Ala Lys Lys Ile Asp Ala Lys Arg Gly Ala Thr Glu Glu Lys Leu
            835                 840                 845

Leu Ala Gln Val Ala Arg Ile Asp Glu Arg Ile Ala Thr Ala Lys Val
850                 855                 860

Gln Leu Gln Asp Arg Asp Lys Leu Lys Asp Val Ala Leu Gly Thr Ser
865                 870                 875                 880

Lys Ile Asn Tyr Ile Asp Pro Arg Leu Thr Val Ala Trp Ala Lys Lys
                885                 890                 895

Phe Asp Val Pro Leu Glu Lys Leu Phe Ser Lys Thr Leu Arg Glu Lys
            900                 905                 910

Phe Pro Trp Ala Glu Ala Glu Ala Gly Pro Asp Trp Val Phe
            915                 920                 925

<210> SEQ ID NO 29
<211> LENGTH: 1125
<212> TYPE: DNA
<213> ORGANISM: Cryptococcus neoformans
<220> FEATURE:
<221> NAME/KEY: CDS
<222> LOCATION: (1)..(1125)

<400> SEQUENCE: 29 atg gcc cac cac cac ttc gta ggc ata aac ccg gca ggc ctc tcc ttc      48
Met Ala His His His Phe Val Gly Ile Asn Pro Ala Gly Leu Ser Phe
1               5                   10                  15 tcc cat ccc acc ccg cca gca gac cac ccc gcg ccc ccc tcc tcg ggc      96
Ser His Pro Thr Pro Pro Ala Asp His Pro Ala Pro Pro Ser Ser Gly
            20                  25                  30 agc atc cac acc cca gca aac ttc gcc agc att caa gaa ccc atc aca     144
Ser Ile His Thr Pro Ala Asn Phe Ala Ser Ile Gln Glu Pro Ile Thr
        35                  40                  45 gac cca tcc gct gtc gcc gcc cgc cga cgc ggt cgt cct tcc aca agg     192
Asp Pro Ser Ala Val Ala Ala Arg Arg Arg Gly Arg Pro Ser Thr Arg
    50                  55                  60 ggc gaa gct ggc gtc act ccg ccc cca gag atc gga tgg tgg gag gac     240
Gly Glu Ala Gly Val Thr Pro Pro Pro Glu Ile Gly Trp Trp Glu Asp
65                  70                  75                  80 cgt gcg ccc agc tgg cac aag gat gcc atg cag ggc ggc aag tct tct     288
Arg Ala Pro Ser Trp His Lys Asp Ala Met Gln Gly Gly Lys Ser Ser
                85                  90                  95 atg gag ctc ctg atg gaa tgg tca gag gag atg aag aat caa ggc cac     336
Met Glu Leu Leu Met Glu Trp Ser Glu Glu Met Lys Asn Gln Gly His
            100                 105                 110 tac tac tgg atg ggc gtc agg gat ggc ggc aat ctg cat caa ggt gct     384
Tyr Tyr Trp Met Gly Val Arg Asp Gly Gly Asn Leu His Gln Gly Ala
        115                 120                 125 tcg cgt ttt agg gac tac tta tat gcc cag cat ggt cct att agg cgg     432
Ser Arg Phe Arg Asp Tyr Leu Tyr Ala Gln His Gly Pro Ile Arg Arg
    130                 135                 140 tca agt aag gct atc aga aat aaa gtg gag aat att aag caa aag ttc     480
Ser Ser Lys Ala Ile Arg Asn Lys Val Glu Asn Ile Lys Gln Lys Phe
145                 150                 155                 160
```

| | | |
|---|---|---|
| ttt gaa gcc cag gaa tgg ctc aag gat ccc aat ggg gac cat acc acc<br>Phe Glu Ala Gln Glu Trp Leu Lys Asp Pro Asn Gly Asp His Thr Thr<br>                165                    170                  175 | | 528 |
| atg acc att ccg gac gtc gaa aaa aaa ctc aac aag atc tgt cgc aac<br>Met Thr Ile Pro Asp Val Glu Lys Lys Leu Asn Lys Ile Cys Arg Asn<br>           180                    185                    190 | | 576 |
| tac cgc ttc tgg gaa acc atc ttc gta gag ctt cct cca gtt gac cac<br>Tyr Arg Phe Trp Glu Thr Ile Phe Val Glu Leu Pro Pro Val Asp His<br>                195                    200                  205 | | 624 |
| gaa gct ggc cag aat gcc gaa ggg tct tca tcc aac cag act ctt cag<br>Glu Ala Gly Gln Asn Ala Glu Gly Ser Ser Ser Asn Gln Thr Leu Gln<br>210                    215                    220 | | 672 |
| tct gct tct caa act gcc gtt cga cag ggt aat ggg ccc ctc atc cgc<br>Ser Ala Ser Gln Thr Ala Val Arg Gln Gly Asn Gly Pro Leu Ile Arg<br>225                    230                    235                    240 | | 720 |
| ggt att cct gtt ccg gaa atg gga cag gca gcg gcc gat gat gcg cag<br>Gly Ile Pro Val Pro Glu Met Gly Gln Ala Ala Ala Asp Asp Ala Gln<br>                245                    250                  255 | | 768 |
| cga aat gtc cgc cga cgc ctt aat gat ggc agc tct gcc act att cct<br>Arg Asn Val Arg Arg Arg Leu Asn Asp Gly Ser Ser Ala Thr Ile Pro<br>           260                    265                    270 | | 816 |
| tcc gac tca tct ttg gtt ggt cgc gtg ctc cct gct agc tac ctc gaa<br>Ser Asp Ser Ser Leu Val Gly Arg Val Leu Pro Ala Ser Tyr Leu Glu<br>275                    280                    285 | | 864 |
| cgc acc cgt gaa gaa cgc gat cgc gaa aag cat gaa tta gcg aaa aag<br>Arg Thr Arg Glu Glu Arg Asp Arg Glu Lys His Glu Leu Ala Lys Lys<br>           290                    295                    300 | | 912 |
| cag caa gcc ctc aac agg gaa caa tat gaa ctc gag cag aag aaa gat<br>Gln Gln Ala Leu Asn Arg Glu Gln Tyr Glu Leu Glu Gln Lys Lys Asp<br>305                    310                    315                    320 | | 960 |
| gag aga gat cag aag aga ttt gag tgg gag cag act aag cat ctg gtg<br>Glu Arg Asp Gln Lys Arg Phe Glu Trp Glu Gln Thr Lys His Leu Val<br>                325                    330                    335 | | 1008 |
| gag acg gct tta aaa atc cga gaa ttg gat atc att ccg ttg gaa gcg<br>Glu Thr Ala Leu Lys Ile Arg Glu Leu Asp Ile Ile Pro Leu Glu Ala<br>           340                    345                    350 | | 1056 |
| gcg atg atc aaa gct aga gct ctt tat ggc cag gcg cga gag gaa gat<br>Ala Met Ile Lys Ala Arg Ala Leu Tyr Gly Gln Ala Arg Glu Glu Asp<br>355                    360                    365 | | 1104 |
| caa gct gaa gct act ctt taa<br>Gln Ala Glu Ala Thr Leu<br>     370 | | 1125 |

<210> SEQ ID NO 30
<211> LENGTH: 374
<212> TYPE: PRT
<213> ORGANISM: Cryptococcus neoformans

<400> SEQUENCE: 30

Met Ala His His His Phe Val Gly Ile Asn Pro Ala Gly Leu Ser Phe
1                 5                    10                    15

Ser His Pro Thr Pro Pro Ala Asp His Pro Ala Pro Ser Ser Gly
                20                    25                    30

Ser Ile His Thr Pro Ala Asn Phe Ala Ser Ile Gln Glu Pro Ile Thr
           35                    40                    45

Asp Pro Ser Ala Val Ala Ala Arg Arg Gly Arg Pro Ser Thr Arg
     50                    55                    60

Gly Glu Ala Gly Val Thr Pro Pro Glu Ile Gly Trp Trp Glu Asp
65                    70                    75                    80

```
Arg Ala Pro Ser Trp His Lys Asp Ala Met Gln Gly Gly Lys Ser Ser
                85                  90                  95

Met Glu Leu Leu Met Glu Trp Ser Glu Met Lys Asn Gln Gly His
            100                 105                 110

Tyr Tyr Trp Met Gly Val Arg Asp Gly Gly Asn Leu His Gln Gly Ala
            115                 120                 125

Ser Arg Phe Arg Asp Tyr Leu Tyr Ala Gln His Gly Pro Ile Arg Arg
        130                 135                 140

Ser Ser Lys Ala Ile Arg Asn Lys Val Glu Asn Ile Lys Gln Lys Phe
145                 150                 155                 160

Phe Glu Ala Gln Glu Trp Leu Lys Asp Pro Asn Gly Asp His Thr Thr
                165                 170                 175

Met Thr Ile Pro Asp Val Glu Lys Lys Leu Asn Lys Ile Cys Arg Asn
            180                 185                 190

Tyr Arg Phe Trp Glu Thr Ile Phe Val Glu Leu Pro Pro Val Asp His
        195                 200                 205

Glu Ala Gly Gln Asn Ala Glu Gly Ser Ser Asn Gln Thr Leu Gln
    210                 215                 220

Ser Ala Ser Gln Thr Ala Val Arg Gln Gly Asn Gly Pro Leu Ile Arg
225                 230                 235                 240

Gly Ile Pro Val Pro Glu Met Gly Gln Ala Ala Ala Asp Asp Ala Gln
                245                 250                 255

Arg Asn Val Arg Arg Leu Asn Asp Gly Ser Ser Ala Thr Ile Pro
            260                 265                 270

Ser Asp Ser Ser Leu Val Gly Arg Val Leu Pro Ala Ser Tyr Leu Glu
        275                 280                 285

Arg Thr Arg Glu Glu Arg Asp Arg Glu Lys His Glu Leu Ala Lys Lys
    290                 295                 300

Gln Gln Ala Leu Asn Arg Glu Gln Tyr Glu Leu Gln Lys Lys Asp
305                 310                 315                 320

Glu Arg Asp Gln Lys Arg Phe Glu Trp Glu Thr Lys His Leu Val
                325                 330                 335

Glu Thr Ala Leu Lys Ile Arg Glu Leu Asp Ile Ile Pro Leu Glu Ala
            340                 345                 350

Ala Met Ile Lys Ala Arg Ala Leu Tyr Gly Gln Ala Arg Glu Glu Asp
        355                 360                 365

Gln Ala Glu Ala Thr Leu
    370

<210> SEQ ID NO 31
<211> LENGTH: 1251
<212> TYPE: DNA
<213> ORGANISM: Cryptococcus neoformans
<220> FEATURE:
<221> NAME/KEY: CDS
<222> LOCATION: (1)..(1251)

<400> SEQUENCE: 31 atg gac gcc acc act ctt aca ggg cac gtc aag gag ctc aat gct gca    48
Met Asp Ala Thr Thr Leu Thr Gly His Val Lys Glu Leu Asn Ala Ala
1               5                   10                  15 aac caa gcg gga aaa tca gat gaa gtt atc tct ctg ctc aag aaa ctt    96
Asn Gln Ala Gly Lys Ser Asp Glu Val Ile Ser Leu Leu Lys Lys Leu
            20                  25                  30 cag gct gag gtt gtt cct aca gaa gat ctc ctt cga tca tcg aaa gct   144
Gln Ala Glu Val Val Pro Thr Glu Asp Leu Leu Arg Ser Ser Lys Ala
        35                  40                  45
```

```
ggt gtc gca gtc ggc aag ctt cgt acc cac gcc aca cca tca gtc tca        192
Gly Val Ala Val Gly Lys Leu Arg Thr His Ala Thr Pro Ser Val Ser
 50              55                  60 agt ctt gcc aag gag ata gtt aag aag tgg aga gat gcg gtc gag gag        240
Ser Leu Ala Lys Glu Ile Val Lys Lys Trp Arg Asp Ala Val Glu Glu
65              70                  75                  80 aca aag aag aag aga aaa aga gca gaa ggt gat gaa gga aaa gat gta        288
Thr Lys Lys Lys Arg Lys Arg Ala Glu Gly Asp Glu Gly Lys Asp Val
                85                  90                  95 aag aag gag aag gag gaa ggg aac ggg aaa cga gtc aag gcg gaa acg        336
Lys Lys Glu Lys Glu Glu Gly Asn Gly Lys Arg Val Lys Ala Glu Thr
            100                 105                 110 ggg tca tta gcg gcg aca cca tca gct agc aca ccc gcc tcg gcc tct        384
Gly Ser Leu Ala Ala Thr Pro Ser Ala Ser Thr Pro Ala Ser Ala Ser
        115                 120                 125 aca ccc gat gtc aaa gcg acc tcc cct cct gtc cgt caa cct ctt tca        432
Thr Pro Asp Val Lys Ala Thr Ser Pro Pro Val Arg Gln Pro Leu Ser
    130                 135                 140 acc att gac tca tca cgc act acg cct cga acc gcc aaa agc gat gga        480
Thr Ile Asp Ser Ser Arg Thr Thr Pro Arg Thr Ala Lys Ser Asp Gly
145                 150                 155                 160 gtg gcc gac agc ctg aga gct gat tcg agc gaa gga ggc agt gta gat        528
Val Ala Asp Ser Leu Arg Ala Asp Ser Ser Glu Gly Gly Ser Val Asp
                165                 170                 175 agc gtg agg gac aag tgt gtg atc atg att tat gac gca ttg gcg ttg        576
Ser Val Arg Asp Lys Cys Val Ile Met Ile Tyr Asp Ala Leu Ala Leu
            180                 185                 190 gat agc acg gct gaa ata aag att ttg aaa gag cgc gcc att gga att        624
Asp Ser Thr Ala Glu Ile Lys Ile Leu Lys Glu Arg Ala Ile Gly Ile
        195                 200                 205 gag cgc gca gcg aat aaa gct atg aac ttc tca aca gga aac gat tat        672
Glu Arg Ala Ala Asn Lys Ala Met Asn Phe Ser Thr Gly Asn Asp Tyr
    210                 215                 220 cgc gct aaa atg aga tca cta ttc ctc aac ttg aaa gac aag ggt aat        720
Arg Ala Lys Met Arg Ser Leu Phe Leu Asn Leu Lys Asp Lys Gly Asn
225                 230                 235                 240 ccc gct ttg aga aac gag att gtc ttg ggc tac gtc agc acc gaa aaa        768
Pro Ala Leu Arg Asn Glu Ile Val Leu Gly Tyr Val Ser Thr Glu Lys
                245                 250                 255 gtc gct agc atg tcc aaa gat gaa atg gcc tct gaa agc gtt cga atg        816
Val Ala Ser Met Ser Lys Asp Glu Met Ala Ser Glu Ser Val Arg Met
            260                 265                 270 cta aag gag aag att gcg agt gac aac ttg ttc aag gcc aag gct gtc        864
Leu Lys Glu Lys Ile Ala Ser Asp Asn Leu Phe Lys Ala Lys Ala Val
        275                 280                 285 gga gtc acc caa gct gag aca gac gcg ttc aag tgc gga cgt tgt cac        912
Gly Val Thr Gln Ala Glu Thr Asp Ala Phe Lys Cys Gly Arg Cys His
    290                 295                 300 cag agg aaa tgt act tat tac cag atg cag aca aga agc gcg gat gaa        960
Gln Arg Lys Cys Thr Tyr Tyr Gln Met Gln Thr Arg Ser Ala Asp Glu
305                 310                 315                 320 cct atg act act ttt gtt acg tat gtg tct gac ctg act cca aaa gaa       1008
Pro Met Thr Thr Phe Val Thr Tyr Val Ser Asp Leu Thr Pro Lys Glu
                325                 330                 335 tca ttg ctg act acg tgt acg act tgc tct ttt tat tca gat gta cta       1056
Ser Leu Leu Thr Thr Cys Thr Thr Cys Ser Phe Tyr Ser Asp Val Leu
            340                 345                 350 att gta aca aca ggt gga aat tca gct agt ttc gga ttt tgc ctc tgg       1104
Ile Val Thr Thr Gly Gly Asn Ser Ala Ser Phe Gly Phe Cys Leu Trp
```

```
             355                 360                 365
gga gca ttg tat ctt tcg ggt ttt ttg tca cgt cgt cta tgc agc cag      1152
Gly Ala Leu Tyr Leu Ser Gly Phe Leu Ser Arg Arg Leu Cys Ser Gln
    370                 375                 380 tat att tac gag gcg tat cgt tgt gat ttg cgt gtc aat gtc aca aag      1200
Tyr Ile Tyr Glu Ala Tyr Arg Cys Asp Leu Arg Val Asn Val Thr Lys
385                 390                 395                 400 cca tta agt gcc gta aat atg cct ttt tgc agt gtt ctg aaa ttc aaa      1248
Pro Leu Ser Ala Val Asn Met Pro Phe Cys Ser Val Leu Lys Phe Lys
            405                 410                 415 tga                                                                   1251

<210> SEQ ID NO 32
<211> LENGTH: 416
<212> TYPE: PRT
<213> ORGANISM: Cryptococcus neoformans

<400> SEQUENCE: 32

Met Asp Ala Thr Thr Leu Thr Gly His Val Lys Glu Leu Asn Ala Ala
1               5                   10                  15

Asn Gln Ala Gly Lys Ser Asp Glu Val Ile Ser Leu Leu Lys Lys Leu
            20                  25                  30

Gln Ala Glu Val Val Pro Thr Glu Asp Leu Leu Arg Ser Ser Lys Ala
        35                  40                  45

Gly Val Ala Val Gly Lys Leu Arg Thr His Ala Thr Pro Ser Val Ser
    50                  55                  60

Ser Leu Ala Lys Glu Ile Val Lys Lys Trp Arg Asp Ala Val Glu Glu
65                  70                  75                  80

Thr Lys Lys Lys Arg Lys Arg Ala Glu Gly Asp Glu Gly Lys Asp Val
                85                  90                  95

Lys Lys Glu Lys Glu Glu Gly Asn Gly Lys Arg Val Lys Ala Glu Thr
            100                 105                 110

Gly Ser Leu Ala Ala Thr Pro Ser Ala Ser Thr Pro Ala Ser Ala Ser
        115                 120                 125

Thr Pro Asp Val Lys Ala Thr Ser Pro Pro Val Arg Gln Pro Leu Ser
    130                 135                 140

Thr Ile Asp Ser Ser Arg Thr Thr Pro Arg Thr Ala Lys Ser Asp Gly
145                 150                 155                 160

Val Ala Asp Ser Leu Arg Ala Asp Ser Ser Glu Gly Gly Ser Val Asp
                165                 170                 175

Ser Val Arg Asp Lys Cys Val Ile Met Ile Tyr Asp Ala Leu Ala Leu
            180                 185                 190

Asp Ser Thr Ala Glu Ile Lys Ile Leu Lys Glu Arg Ala Ile Gly Ile
        195                 200                 205

Glu Arg Ala Ala Asn Lys Ala Met Asn Phe Ser Thr Gly Asn Asp Tyr
    210                 215                 220

Arg Ala Lys Met Arg Ser Leu Phe Leu Asn Leu Lys Asp Lys Gly Asn
225                 230                 235                 240

Pro Ala Leu Arg Asn Glu Ile Val Leu Gly Tyr Val Ser Thr Glu Lys
                245                 250                 255

Val Ala Ser Met Ser Lys Asp Glu Met Ala Ser Glu Ser Val Arg Met
            260                 265                 270

Leu Lys Glu Lys Ile Ala Ser Asp Asn Leu Phe Lys Ala Lys Ala Val
        275                 280                 285

Gly Val Thr Gln Ala Glu Thr Asp Ala Phe Lys Cys Gly Arg Cys His
```

```
                290                 295                 300
Gln Arg Lys Cys Thr Tyr Tyr Gln Met Gln Thr Arg Ser Ala Asp Glu
305                 310                 315                 320

Pro Met Thr Thr Phe Val Thr Tyr Val Ser Asp Leu Thr Pro Lys Glu
                325                 330                 335

Ser Leu Leu Thr Thr Cys Thr Thr Cys Ser Phe Tyr Ser Asp Val Leu
                340                 345                 350

Ile Val Thr Thr Gly Gly Asn Ser Ala Ser Phe Gly Phe Cys Leu Trp
                355                 360                 365

Gly Ala Leu Tyr Leu Ser Gly Phe Leu Ser Arg Arg Leu Cys Ser Gln
                370                 375                 380

Tyr Ile Tyr Glu Ala Tyr Arg Cys Asp Leu Arg Val Asn Val Thr Lys
385                 390                 395                 400

Pro Leu Ser Ala Val Asn Met Pro Phe Cys Ser Val Leu Lys Phe Lys
                405                 410                 415

<210> SEQ ID NO 33
<211> LENGTH: 657
<212> TYPE: DNA
<213> ORGANISM: Cryptococcus neoformans
<220> FEATURE:
<221> NAME/KEY: CDS
<222> LOCATION: (1)..(657)

<400> SEQUENCE: 33 atg gat tac caa aat cga gca ggt gca aac aag ggt agt ggt ggt gtc      48
Met Asp Tyr Gln Asn Arg Ala Gly Ala Asn Lys Gly Ser Gly Gly Val
1               5                   10                  15 gct ggt gca tcc gag aca gca gtg gac agg aga gaa cgt ctt cga aaa      96
Ala Gly Ala Ser Glu Thr Ala Val Asp Arg Arg Glu Arg Leu Arg Lys
                20                  25                  30 ctt gct ttg gag act att gac ttg gcc aaa gat ccc tat atc ctt agg     144
Leu Ala Leu Glu Thr Ile Asp Leu Ala Lys Asp Pro Tyr Ile Leu Arg
            35                  40                  45 acc cat ctc ggt aca tta gaa tgc cgt ctt tgt ctc act ctt cac gtc     192
Thr His Leu Gly Thr Leu Glu Cys Arg Leu Cys Leu Thr Leu His Val
        50                  55                  60 aac gag ggt tct tac ctt gcc cac act caa gga aag aaa cat caa aca     240
Asn Glu Gly Ser Tyr Leu Ala His Thr Gln Gly Lys Lys His Gln Thr
65              70                  75                  80 aac ctt gct agg cgt gca gcc aag gac aac aag gat cag aca tta atg     288
Asn Leu Ala Arg Arg Ala Ala Lys Asp Asn Lys Asp Gln Thr Leu Met
                85                  90                  95 atc caa gct ccc aca gcc gcg caa caa gtg aag aag aaa gtg ttt gtt     336
Ile Gln Ala Pro Thr Ala Ala Gln Gln Val Lys Lys Lys Val Phe Val
            100                 105                 110 aag att gga aga cct gga tac aaa atc atc aaa att cga gag cct gtc     384
Lys Ile Gly Arg Pro Gly Tyr Lys Ile Ile Lys Ile Arg Glu Pro Val
        115                 120                 125 agt caa agg atg ggt tta tta ttc act gtg tct tta cct gag ata aaa     432
Ser Gln Arg Met Gly Leu Leu Phe Thr Val Ser Leu Pro Glu Ile Lys
    130                 135                 140 gcg gga gag agg cca aga agg agg ttc atg tct gct ttt gaa caa cgg     480
Ala Gly Glu Arg Pro Arg Arg Arg Phe Met Ser Ala Phe Glu Gln Arg
145                 150                 155                 160 cga gag att ccc aat aaa gct ttc cag tac tta gtt tgt gca gcc gag     528
Arg Glu Ile Pro Asn Lys Ala Phe Gln Tyr Leu Val Leu Ala Ala Glu
                165                 170                 175 cca tac gag acc ata gca ttt gcc atc ccc tca aaa gag atg gtt gac     576
Pro Tyr Glu Thr Ile Ala Phe Ala Ile Pro Ser Lys Glu Met Val Asp
```

```
Pro Tyr Glu Thr Ile Ala Phe Ala Ile Pro Ser Lys Glu Met Val Asp
            180                 185                 190 gtt gat gaa gac ccg gag tcg aca tgg gag cac tgg gat gcc gac gag      624
Val Asp Glu Asp Pro Glu Ser Thr Trp Glu His Trp Asp Ala Asp Glu
        195                 200                 205 aag gtt tac agt tgt caa ttc ttg tat aaa taa                          657
Lys Val Tyr Ser Cys Gln Phe Leu Tyr Lys
    210                 215
```

<210> SEQ ID NO 34
<211> LENGTH: 218
<212> TYPE: PRT
<213> ORGANISM: Cryptococcus neoformans

<400> SEQUENCE: 34

```
Met Asp Tyr Gln Asn Arg Ala Gly Ala Asn Lys Gly Ser Gly Gly Val
1               5                   10                  15

Ala Gly Ala Ser Glu Thr Ala Val Asp Arg Arg Glu Arg Leu Arg Lys
            20                  25                  30

Leu Ala Leu Glu Thr Ile Asp Leu Ala Lys Asp Pro Tyr Ile Leu Arg
        35                  40                  45

Thr His Leu Gly Thr Leu Glu Cys Arg Leu Cys Leu Thr Leu His Val
    50                  55                  60

Asn Glu Gly Ser Tyr Leu Ala His Thr Gln Gly Lys Lys His Gln Thr
65                  70                  75                  80

Asn Leu Ala Arg Arg Ala Ala Lys Asp Asn Lys Asp Gln Thr Leu Met
                85                  90                  95

Ile Gln Ala Pro Thr Ala Ala Gln Val Lys Lys Val Phe Val
            100                 105                 110

Lys Ile Gly Arg Pro Gly Tyr Lys Ile Lys Ile Arg Glu Pro Val
        115                 120                 125

Ser Gln Arg Met Gly Leu Leu Phe Thr Val Ser Leu Pro Glu Ile Lys
    130                 135                 140

Ala Gly Glu Arg Pro Arg Arg Phe Met Ser Ala Phe Glu Gln Arg
145                 150                 155                 160

Arg Glu Ile Pro Asn Lys Ala Phe Gln Tyr Leu Val Leu Ala Ala Glu
                165                 170                 175

Pro Tyr Glu Thr Ile Ala Phe Ala Ile Pro Ser Lys Glu Met Val Asp
            180                 185                 190

Val Asp Glu Asp Pro Glu Ser Thr Trp Glu His Trp Asp Ala Asp Glu
        195                 200                 205

Lys Val Tyr Ser Cys Gln Phe Leu Tyr Lys
    210                 215
```

<210> SEQ ID NO 35
<211> LENGTH: 813
<212> TYPE: DNA
<213> ORGANISM: Cryptococcus neoformans
<220> FEATURE:
<221> NAME/KEY: CDS
<222> LOCATION: (1)..(813)

<400> SEQUENCE: 35

```
atg aca gtc aag gca gag caa gat ctc tat ctt gac ccc tcc att cgg      48
Met Thr Val Lys Ala Glu Gln Asp Leu Tyr Leu Asp Pro Ser Ile Arg
1               5                   10                  15 gat tgg gtc ctt atc cct atc acc cta atc atg cta ctc gtc ggt gtg      96
Asp Trp Val Leu Ile Pro Ile Thr Leu Ile Met Leu Leu Val Gly Val
            20                  25                  30
```

| | | | | | | | | | | | | | | | | |
|---|---|---|---|---|---|---|---|---|---|---|---|---|---|---|---|---|
| tta | aga | cac | tac | atc | acg | caa | ttc | ctt | aac | tct | gca | cca | aaa | aaa | caa | 144 |
| Leu | Arg | His | Tyr | Ile | Thr | Gln | Phe | Leu | Asn | Ser | Ala | Pro | Lys | Lys | Gln | |
| | | | | 35 | | | | | 40 | | | | | 45 | | |
| aca | gca | gct | gcc | gtt | cgc | gaa | caa | cgc | gca | ctt | ggt | cgc | tca | gct | ctg | 192 |
| Thr | Ala | Ala | Ala | Val | Arg | Glu | Gln | Arg | Ala | Leu | Gly | Arg | Ser | Ala | Leu | |
| | 50 | | | | | 55 | | | | | 60 | | | | | |
| ctt | cgg | gca | act | gcg | act | ctg | tcc | ccc | ctt | ccg | cct | gcc | tct | tac | aag | 240 |
| Leu | Arg | Ala | Thr | Ala | Thr | Leu | Ser | Pro | Leu | Pro | Pro | Ala | Ser | Tyr | Lys | |
| 65 | | | | | 70 | | | | | 75 | | | | | 80 | |
| gct | ctc | tcg | gga | tcc | ctt | gct | gct | tca | ctt | tct | act | ggt | gag | tat | atc | 288 |
| Ala | Leu | Ser | Gly | Ser | Leu | Ala | Ala | Ser | Leu | Ser | Thr | Gly | Glu | Tyr | Ile | |
| | | | | 85 | | | | | 90 | | | | | 95 | | |
| aag | ccc | gcc | cca | gag | tca | aag | ggg | gat | gct | tct | ccc | gcc | aat | cct | ctc | 336 |
| Lys | Pro | Ala | Pro | Glu | Ser | Lys | Gly | Asp | Ala | Ser | Pro | Ala | Asn | Pro | Leu | |
| | | | 100 | | | | | 105 | | | | | 110 | | | |
| gaa | ggt | gct | ggg | atg | gaa | aat | gcg | atg | gac | ggt | atg | aaa | aag | cag | gcc | 384 |
| Glu | Gly | Ala | Gly | Met | Glu | Asn | Ala | Met | Asp | Gly | Met | Lys | Lys | Gln | Ala | |
| | | | | 115 | | | | | 120 | | | | | 125 | | |
| gta | atg | atg | gta | ccc | aac | atg | gtt | atc | atg | cag | tat | atc | aac | gtc | ttt | 432 |
| Val | Met | Met | Val | Pro | Asn | Met | Val | Ile | Met | Gln | Tyr | Ile | Asn | Val | Phe | |
| | 130 | | | | | 135 | | | | | 140 | | | | | |
| ttt | tcc | gga | ttt | atc | ctt | atg | cgt | ctg | cca | ttt | cct | tta | acc | gca | ggc | 480 |
| Phe | Ser | Gly | Phe | Ile | Leu | Met | Arg | Leu | Pro | Phe | Pro | Leu | Thr | Ala | Gly | |
| 145 | | | | | 150 | | | | | 155 | | | | | 160 | |
| ttt | aag | tcg | ttg | ctg | tca | agg | gat | att | ccc | atg | gct | gat | ctc | gat | gtg | 528 |
| Phe | Lys | Ser | Leu | Leu | Ser | Arg | Asp | Ile | Pro | Met | Ala | Asp | Leu | Asp | Val | |
| | | | | 165 | | | | | 170 | | | | | 175 | | |
| cga | tgg | gtt | tcc | gct | ttg | tcc | tgg | tat | ttt | ctc | aac | ttg | ttt | ggc | ttg | 576 |
| Arg | Trp | Val | Ser | Ala | Leu | Ser | Trp | Tyr | Phe | Leu | Asn | Leu | Phe | Gly | Leu | |
| | | | 180 | | | | | 185 | | | | | 190 | | | |
| aac | ggt | gtt | ttc | aaa | cta | att | ctt | gga | gct | gag | aat | gct | gct | gta | gac | 624 |
| Asn | Gly | Val | Phe | Lys | Leu | Ile | Leu | Gly | Ala | Glu | Asn | Ala | Ala | Val | Asp | |
| | | 195 | | | | | 200 | | | | | 205 | | | | |
| agc | cgt | gac | ctc | acc | tcg | ctg | tct | gca | ctt | tct | ggg | gca | gga | ggc | cct | 672 |
| Ser | Arg | Asp | Leu | Thr | Ser | Leu | Ser | Ala | Leu | Ser | Gly | Ala | Gly | Gly | Pro | |
| | 210 | | | | | 215 | | | | | 220 | | | | | |
| atg | ccc | ggc | ccc | ggc | ggt | cca | cca | gac | atg | gtc | aag | ctt | ttc | aag | gcc | 720 |
| Met | Pro | Gly | Pro | Gly | Gly | Pro | Pro | Asp | Met | Val | Lys | Leu | Phe | Lys | Ala | |
| 225 | | | | | 230 | | | | | 235 | | | | | 240 | |
| gag | gtt | gag | aac | ttg | gca | ttg | gca | gaa | agt | tca | tac | aag | tgg | gtc | ggc | 768 |
| Glu | Val | Glu | Asn | Leu | Ala | Leu | Ala | Glu | Ser | Ser | Tyr | Lys | Trp | Val | Gly | |
| | | | | 245 | | | | | 250 | | | | | 255 | | |
| gac | gga | gta | gaa | gat | aga | gtt | ttg | aga | gct | tgg | ggc | aaa | gtt | taa | | 813 |
| Asp | Gly | Val | Glu | Asp | Arg | Val | Leu | Arg | Ala | Trp | Gly | Lys | Val | | | |
| | | | 260 | | | | | 265 | | | | | 270 | | | |

<210> SEQ ID NO 36
<211> LENGTH: 270
<212> TYPE: PRT
<213> ORGANISM: Cryptococcus neoformans

<400> SEQUENCE: 36

Met Thr Val Lys Ala Glu Gln Asp Leu Tyr Leu Asp Pro Ser Ile Arg
1               5                   10                  15

Asp Trp Val Leu Ile Pro Ile Thr Leu Ile Met Leu Leu Val Gly Val
                20                  25                  30

Leu Arg His Tyr Ile Thr Gln Phe Leu Asn Ser Ala Pro Lys Lys Gln
            35                  40                  45

Thr Ala Ala Ala Val Arg Glu Gln Arg Ala Leu Gly Arg Ser Ala Leu

```
                50                  55                  60
Leu Arg Ala Thr Ala Thr Leu Ser Pro Leu Pro Pro Ala Ser Tyr Lys
 65                  70                  75                  80

Ala Leu Ser Gly Ser Leu Ala Ala Ser Leu Ser Thr Gly Glu Tyr Ile
                 85                  90                  95

Lys Pro Ala Pro Glu Ser Lys Gly Asp Ala Ser Pro Ala Asn Pro Leu
                100                 105                 110

Glu Gly Ala Gly Met Glu Asn Ala Met Asp Gly Met Lys Lys Gln Ala
                115                 120                 125

Val Met Met Val Pro Asn Met Val Ile Met Gln Tyr Ile Asn Val Phe
            130                 135                 140

Phe Ser Gly Phe Ile Leu Met Arg Leu Pro Phe Pro Leu Thr Ala Gly
145                 150                 155                 160

Phe Lys Ser Leu Leu Ser Arg Asp Ile Pro Met Ala Asp Leu Asp Val
                165                 170                 175

Arg Trp Val Ser Ala Leu Ser Trp Tyr Phe Leu Asn Leu Phe Gly Leu
                180                 185                 190

Asn Gly Val Phe Lys Leu Ile Leu Gly Ala Glu Asn Ala Ala Val Asp
            195                 200                 205

Ser Arg Asp Leu Thr Ser Leu Ser Ala Leu Ser Gly Ala Gly Gly Pro
            210                 215                 220

Met Pro Gly Pro Gly Pro Pro Asp Met Val Lys Leu Phe Lys Ala
225                 230                 235                 240

Glu Val Glu Asn Leu Ala Leu Ala Glu Ser Ser Tyr Lys Trp Val Gly
                245                 250                 255

Asp Gly Val Glu Asp Arg Val Leu Arg Ala Trp Gly Lys Val
            260                 265                 270

<210> SEQ ID NO 37
<211> LENGTH: 1365
<212> TYPE: DNA
<213> ORGANISM: Cryptococcus neoformans
<220> FEATURE:
<221> NAME/KEY: CDS
<222> LOCATION: (1)..(1365)

<400> SEQUENCE: 37 atg acc gcg gtg aac agc aac cag ggc acc ggc aaa ctg agc ggc cgc      48
Met Thr Ala Val Asn Ser Asn Gln Gly Thr Gly Lys Leu Ser Gly Arg
 1               5                  10                  15 gtg ggc att gtg ggc acc ggc cat cgc gcg cgc ctg tat acc acc gcg      96
Val Gly Ile Val Gly Thr Gly His Arg Ala Arg Leu Tyr Thr Thr Ala
                20                  25                  30 gtg gcg agc cgc gcg aac acc agc ctg gtg gcg ctg tgc gat acc aac     144
Val Ala Ser Arg Ala Asn Thr Ser Leu Val Ala Leu Cys Asp Thr Asn
            35                  40                  45 gat gcg cgc atg gat tgg cat aac aaa atg ctg cgc gaa gcg ggc cgc     192
Asp Ala Arg Met Asp Trp His Asn Lys Met Leu Arg Glu Ala Gly Arg
 50                  55                  60 ccg gaa gcg aaa aaa tat gcg gcg gaa gat ttt cgc aaa atg ctg gaa     240
Pro Glu Ala Lys Lys Tyr Ala Ala Glu Asp Phe Arg Lys Met Leu Glu
 65                  70                  75                  80 cag gaa aaa ctg gat gtg ctg gtg gtg acc acc att gat tat acc cat     288
Gln Glu Lys Leu Asp Val Leu Val Val Thr Thr Ile Asp Tyr Thr His
                 85                  90                  95 gat atg tat att att ccg gcg ctg aaa gcg ggc att aaa gtg ctg agc     336
Asp Met Tyr Ile Ile Pro Ala Leu Lys Ala Gly Ile Lys Val Leu Ser
                100                 105                 110
```

```
gaa aaa ccg atg acc acc aac gtg gat aaa tgc aaa gcg att ctg aac      384
Glu Lys Pro Met Thr Thr Asn Val Asp Lys Cys Lys Ala Ile Leu Asn
        115                 120                 125 gcg gtg aac gaa agc aaa ggc agc ctg acc gtg ctg ttt aac tat cgc      432
Ala Val Asn Glu Ser Lys Gly Ser Leu Thr Val Leu Phe Asn Tyr Arg
    130                 135                 140 tat aac ccg att cat tgg aaa gtg gcg gaa gtg att gcg aaa ggc gaa      480
Tyr Asn Pro Ile His Trp Lys Val Ala Glu Val Ile Ala Lys Gly Glu
145                 150                 155                 160 att ggc gaa gtg aaa agc gtg cat ttt gaa tgg ctg ctg gat acc gtg      528
Ile Gly Glu Val Lys Ser Val His Phe Glu Trp Leu Leu Asp Thr Val
                165                 170                 175 cat ggc gcg gat tat ttt cgc cgc tgg cat cgc tat aaa gat cgc agc      576
His Gly Ala Asp Tyr Phe Arg Arg Trp His Arg Tyr Lys Asp Arg Ser
            180                 185                 190 ggc ggc ctg atg att cat aaa agc agc cat cat ttt gat ctg gtg aac      624
Gly Gly Leu Met Ile His Lys Ser Ser His His Phe Asp Leu Val Asn
        195                 200                 205 ttt tgg att cag agc gtg ccg cag agc gtg ttt ggc atg ggc agc ctg      672
Phe Trp Ile Gln Ser Val Pro Gln Ser Val Phe Gly Met Gly Ser Leu
    210                 215                 220 gcg ttt tat ggc aaa gaa aac ggc aaa aaa agc ggc tgg ggc aaa aac      720
Ala Phe Tyr Gly Lys Glu Asn Gly Lys Lys Ser Gly Trp Gly Lys Asn
225                 230                 235                 240 tat gaa cgc gcg cgc gat gcg aaa gaa gcg gaa aac gat ccg ttt gcg      768
Tyr Glu Arg Ala Arg Asp Ala Lys Glu Ala Glu Asn Asp Pro Phe Ala
                245                 250                 255 att cat ctg ggc gat gaa gaa ggc ctg aaa ggc ctg tat ttt gat gcg      816
Ile His Leu Gly Asp Glu Glu Gly Leu Lys Gly Leu Tyr Phe Asp Ala
            260                 265                 270 gaa cat att gat ggc tat cat cgc gat atg aac gtg ttt gcg gat gat      864
Glu His Ile Asp Gly Tyr His Arg Asp Met Asn Val Phe Ala Asp Asp
        275                 280                 285 att acc att gaa gat gat atg agc gtg ctg gtg cat tat gaa agc ggc      912
Ile Thr Ile Glu Asp Asp Met Ser Val Leu Val His Tyr Glu Ser Gly
    290                 295                 300 gtg aac atg acc tat cat ctg acc gcg tat agc ccg tgg gaa ggc tat      960
Val Asn Met Thr Tyr His Leu Thr Ala Tyr Ser Pro Trp Glu Gly Tyr
305                 310                 315                 320 cgc gtg atg ttt aac ggc acc cat ggc cgc ctg gaa ctg gaa gtg gtg     1008
Arg Val Met Phe Asn Gly Thr His Gly Arg Leu Glu Leu Glu Val Val
                325                 330                 335 gaa aac gcg ttt cgc ctg ccg att ccg aaa ggc agc aac aac gcg agc     1056
Glu Asn Ala Phe Arg Leu Pro Ile Pro Lys Gly Ser Asn Asn Ala Ser
            340                 345                 350 gaa cat gtg cat ggc gat agc gcg ctg ccg aac gaa ggc cat agc aaa     1104
Glu His Val His Gly Asp Ser Ala Leu Pro Asn Glu Gly His Ser Lys
        355                 360                 365 att acc ctg cat aaa ctg tgg cag cag ccg gtg aac gtg ccg tat cag     1152
Ile Thr Leu His Lys Leu Trp Gln Gln Pro Val Asn Val Pro Tyr Gln
    370                 375                 380 gaa gcg aaa ggc ggc cat ggc ggc ggc gat gaa gcg atg ctg gat gaa     1200
Glu Ala Lys Gly Gly His Gly Gly Gly Asp Glu Ala Met Leu Asp Glu
385                 390                 395                 400 att ttt ggc ccg aaa gaa ggc gaa gaa gaa cgc aaa tgc ccg gtg aac     1248
Ile Phe Gly Pro Lys Glu Gly Glu Glu Glu Arg Lys Cys Pro Val Asn
                405                 410                 415 ggc ctg agc gcg gat cag aaa gat ggc gcg ctg gcg atg gcg gtg ggc     1296
Gly Leu Ser Ala Asp Gln Lys Asp Gly Ala Leu Ala Met Ala Val Gly
```

```
                  420                425               430
ctg gcg gcg aac gaa agc ttt aaa aac ggc aaa cag gtg ttt att aaa    1344
Leu Ala Ala Asn Glu Ser Phe Lys Asn Gly Lys Gln Val Phe Ile Lys
            435                440                445 gaa ctg ctg ggc ggc acc ctg                                        1365
Glu Leu Leu Gly Gly Thr Leu
450             455

<210> SEQ ID NO 38
<211> LENGTH: 455
<212> TYPE: PRT
<213> ORGANISM: Cryptococcus neoformans

<400> SEQUENCE: 38

Met Thr Ala Val Asn Ser Asn Gln Gly Thr Gly Lys Leu Ser Gly Arg
1               5                   10                  15

Val Gly Ile Val Gly Thr Gly His Arg Ala Arg Leu Tyr Thr Thr Ala
                20                  25                  30

Val Ala Ser Arg Ala Asn Thr Ser Leu Val Ala Leu Cys Asp Thr Asn
            35                  40                  45

Asp Ala Arg Met Asp Trp His Asn Lys Met Leu Arg Glu Ala Gly Arg
50                  55                  60

Pro Glu Ala Lys Lys Tyr Ala Ala Glu Asp Phe Arg Lys Met Leu Glu
65                  70                  75                  80

Gln Glu Lys Leu Asp Val Leu Val Val Thr Ile Asp Tyr Thr His
                85                  90                  95

Asp Met Tyr Ile Ile Pro Ala Leu Lys Ala Gly Ile Lys Val Leu Ser
                100                 105                 110

Glu Lys Pro Met Thr Thr Asn Val Asp Lys Cys Lys Ala Ile Leu Asn
            115                 120                 125

Ala Val Asn Glu Ser Lys Gly Ser Leu Thr Val Leu Phe Asn Tyr Arg
130                 135                 140

Tyr Asn Pro Ile His Trp Lys Val Ala Glu Val Ile Ala Lys Gly Glu
145                 150                 155                 160

Ile Gly Glu Val Lys Ser Val His Phe Glu Trp Leu Leu Asp Thr Val
                165                 170                 175

His Gly Ala Asp Tyr Phe Arg Arg Trp His Arg Tyr Lys Asp Arg Ser
            180                 185                 190

Gly Gly Leu Met Ile His Lys Ser Ser His His Phe Asp Leu Val Asn
        195                 200                 205

Phe Trp Ile Gln Ser Val Pro Gln Ser Val Phe Gly Met Gly Ser Leu
210                 215                 220

Ala Phe Tyr Gly Lys Glu Asn Gly Lys Lys Ser Gly Trp Gly Lys Asn
225                 230                 235                 240

Tyr Glu Arg Ala Arg Asp Ala Lys Glu Ala Glu Asn Asp Pro Phe Ala
                245                 250                 255

Ile His Leu Gly Asp Glu Glu Gly Leu Lys Gly Leu Tyr Phe Asp Ala
            260                 265                 270

Glu His Ile Asp Gly Tyr His Arg Asp Met Asn Val Phe Ala Asp Asp
        275                 280                 285

Ile Thr Ile Glu Asp Asp Met Ser Val Leu Val His Tyr Glu Ser Gly
290                 295                 300

Val Asn Met Thr Tyr His Leu Thr Ala Tyr Ser Pro Trp Glu Gly Tyr
305                 310                 315                 320

Arg Val Met Phe Asn Gly Thr His Gly Arg Leu Glu Leu Glu Val Val
```

```
                    325                 330                 335
Glu Asn Ala Phe Arg Leu Pro Ile Pro Lys Gly Ser Asn Asn Ala Ser
                340                 345                 350

Glu His Val His Gly Asp Ser Ala Leu Pro Asn Glu Gly His Ser Lys
            355                 360                 365

Ile Thr Leu His Lys Leu Trp Gln Gln Pro Val Asn Val Pro Tyr Gln
    370                 375                 380

Glu Ala Lys Gly Gly His Gly Gly Asp Glu Ala Met Leu Asp Glu
385                 390                 395                 400

Ile Phe Gly Pro Lys Glu Gly Glu Glu Arg Lys Cys Pro Val Asn
                405                 410                 415

Gly Leu Ser Ala Asp Gln Lys Asp Gly Ala Leu Ala Met Ala Val Gly
                420                 425                 430

Leu Ala Ala Asn Glu Ser Phe Lys Asn Gly Lys Gln Val Phe Ile Lys
                435                 440                 445

Glu Leu Leu Gly Gly Thr Leu
    450                 455

<210> SEQ ID NO 39
<211> LENGTH: 1338
<212> TYPE: DNA
<213> ORGANISM: Cryptococcus neoformans
<220> FEATURE:
<221> NAME/KEY: CDS
<222> LOCATION: (1)..(1338)

<400> SEQUENCE: 39 atg agc gcg att cgc gcg ctg aac atg cgc aaa acc gcg agc gcg ctg        48
Met Ser Ala Ile Arg Ala Leu Asn Met Arg Lys Thr Ala Ser Ala Leu
1               5                  10                  15 aaa gcg ccg gtg gcg ttt aaa cgc acc ctg gcg acc ccg gtg aac agc        96
Lys Ala Pro Val Ala Phe Lys Arg Thr Leu Ala Thr Pro Val Asn Ser
            20                  25                  30 ctg tat acc agc gtg ctg ccg gcg aaa att ccg gcg gcg ctg cat ctg       144
Leu Tyr Thr Ser Val Leu Pro Ala Lys Ile Pro Ala Ala Leu His Leu
        35                  40                  45 aaa agc ggc cag agc tat ttt ggc agc agc ttt ggc agc gaa aac agc       192
Lys Ser Gly Gln Ser Tyr Phe Gly Ser Ser Phe Gly Ser Glu Asn Ser
    50                  55                  60 aaa ttt ggc gaa acc gtg ttt agc acc agc att acc agc tat acc gat       240
Lys Phe Gly Glu Thr Val Phe Ser Thr Ser Ile Thr Ser Tyr Thr Asp
65                  70                  75                  80 agc atg acc gat ccg agc tat ctg ggc cag att ctg gtg ttt acc agc       288
Ser Met Thr Asp Pro Ser Tyr Leu Gly Gln Ile Leu Val Phe Thr Ser
                85                  90                  95 ccg atg att ggc aac tat ggc gtg ccg agc aac acc agc agc cag ttt       336
Pro Met Ile Gly Asn Tyr Gly Val Pro Ser Asn Thr Ser Ser Gln Phe
            100                 105                 110 ccg ggc att ccg ttt ctg gaa agc gaa aaa att cag tgc acc ggc gtg       384
Pro Gly Ile Pro Phe Leu Glu Ser Glu Lys Ile Gln Cys Thr Gly Val
        115                 120                 125 gtg gtg agc gat gtg gcg ctg aaa tat agc cat tat cag gcg gtg gaa       432
Val Val Ser Asp Val Ala Leu Lys Tyr Ser His Tyr Gln Ala Val Glu
    130                 135                 140 agc ctg cat gaa tgg tgc aaa cgc tat gat gtg ccg ggc att acc ggc       480
Ser Leu His Glu Trp Cys Lys Arg Tyr Asp Val Pro Gly Ile Thr Gly
145                 150                 155                 160 gtg gat acc cgc gcg att acc agc ctg ctg cgc gat cag ggc acc acc       528
Val Asp Thr Arg Ala Ile Thr Ser Leu Leu Arg Asp Gln Gly Thr Thr
```

| | | | | | | | | | | | | | | | |
|---|---|---|---|---|---|---|---|---|---|---|---|---|---|---|---|
| | | | | 165 | | | | 170 | | | | 175 | | | |
| ctg | ggc | cgc | ctg | gcg | gtg | ggc | gat | gaa | gcg | ggc | aaa | ccg | gcg | ccg | cag | 576 |
| Leu | Gly | Arg | Leu | Ala | Val | Gly | Asp | Glu | Ala | Gly | Lys | Pro | Ala | Pro | Gln | |
| | | | 180 | | | | | 185 | | | | | 190 | | | |
| gaa | gcg | gaa | tat | tgg | gat | ccg | agc | aaa | gaa | aac | ctg | gtg | gcg | cag | gcg | 624 |
| Glu | Ala | Glu | Tyr | Trp | Asp | Pro | Ser | Lys | Glu | Asn | Leu | Val | Ala | Gln | Ala | |
| | | 195 | | | | | 200 | | | | | 205 | | | | |
| agc | acc | aaa | aaa | gcg | tat | gtg | ctg | aac | gaa | aaa | ggc | agc | ggc | ccg | cgc | 672 |
| Ser | Thr | Lys | Lys | Ala | Tyr | Val | Leu | Asn | Glu | Lys | Gly | Ser | Gly | Pro | Arg | |
| 210 | | | | | 215 | | | | | 220 | | | | | | |
| att | gcg | gtg | ctg | gat | ttt | ggc | acc | aaa | gcg | aac | att | ctg | cgc | agc | ctg | 720 |
| Ile | Ala | Val | Leu | Asp | Phe | Gly | Thr | Lys | Ala | Asn | Ile | Leu | Arg | Ser | Leu | |
| 225 | | | | | 230 | | | | | 235 | | | | | 240 | |
| att | cgc | cgc | gat | gcg | gtg | gtg | acc | gtg | ctg | ccg | tgg | gat | ttt | gat | ttt | 768 |
| Ile | Arg | Arg | Asp | Ala | Val | Val | Thr | Val | Leu | Pro | Trp | Asp | Phe | Asp | Phe | |
| | | | | 245 | | | | 250 | | | | 255 | | | | |
| aac | acc | gtg | cgc | gat | cag | ttt | gat | ggc | ctg | ttt | ctg | agc | aac | ggc | ccg | 816 |
| Asn | Thr | Val | Arg | Asp | Gln | Phe | Asp | Gly | Leu | Phe | Leu | Ser | Asn | Gly | Pro | |
| | | | 260 | | | | | 265 | | | | | 270 | | | |
| ggc | gat | ccg | aaa | atg | att | atg | gat | agc | gcg | atg | cgc | gtg | cgc | cag | acc | 864 |
| Gly | Asp | Pro | Lys | Met | Ile | Met | Asp | Ser | Ala | Met | Arg | Val | Arg | Gln | Thr | |
| | | 275 | | | | | 280 | | | | | 285 | | | | |
| att | aac | gaa | tgg | aac | aaa | ccg | att | ttt | ggc | att | tgc | atg | ggc | cat | cag | 912 |
| Ile | Asn | Glu | Trp | Asn | Lys | Pro | Ile | Phe | Gly | Ile | Cys | Met | Gly | His | Gln | |
| 290 | | | | | 295 | | | | | 300 | | | | | | |
| gtg | ctg | ggc | ctg | gcg | gcg | ggc | ctg | gaa | gcg | tat | cgc | atg | acc | ttt | ggc | 960 |
| Val | Leu | Gly | Leu | Ala | Ala | Gly | Leu | Glu | Ala | Tyr | Arg | Met | Thr | Phe | Gly | |
| 305 | | | | | 310 | | | | | 315 | | | | | 320 | |
| aac | cgc | ggc | cat | aac | cag | ccg | gtg | ctg | gcg | ctg | gcg | agc | agc | ggc | agc | 1008 |
| Asn | Arg | Gly | His | Asn | Gln | Pro | Val | Leu | Ala | Leu | Ala | Ser | Ser | Gly | Ser | |
| | | | | 325 | | | | | 330 | | | | | 335 | | |
| att | aaa | gcg | ggc | cgc | gtg | tat | gtg | acc | agc | cag | aac | cat | cag | tat | gcg | 1056 |
| Ile | Lys | Ala | Gly | Arg | Val | Tyr | Val | Thr | Ser | Gln | Asn | His | Gln | Tyr | Ala | |
| | | | 340 | | | | | 345 | | | | | 350 | | | |
| ctg | cgc | ctg | acc | gaa | gat | ttt | ccg | gaa | ggc | tgg | gcg | ccg | ttt | ttt | att | 1104 |
| Leu | Arg | Leu | Thr | Glu | Asp | Phe | Pro | Glu | Gly | Trp | Ala | Pro | Phe | Phe | Ile | |
| | | 355 | | | | | 360 | | | | | 365 | | | | |
| aac | tgc | aac | gat | agc | agc | gtg | gaa | ggc | att | att | agc | acc | ccg | gaa | agc | 1152 |
| Asn | Cys | Asn | Asp | Ser | Ser | Val | Glu | Gly | Ile | Ile | Ser | Thr | Pro | Glu | Ser | |
| 370 | | | | | 375 | | | | | 380 | | | | | | |
| ggc | aaa | cgc | att | tgg | ggc | gtg | cag | ttt | cat | ccg | gaa | agc | gcg | ggc | ggc | 1200 |
| Gly | Lys | Arg | Ile | Trp | Gly | Val | Gln | Phe | His | Pro | Glu | Ser | Ala | Gly | Gly | |
| 385 | | | | | 390 | | | | | 395 | | | | | 400 | |
| ccg | ctg | gat | acc | att | gaa | atg | ttt | acc | gat | ttt | gtg | aac | gaa | tgc | gat | 1248 |
| Pro | Leu | Asp | Thr | Ile | Glu | Met | Phe | Thr | Asp | Phe | Val | Asn | Glu | Cys | Asp | |
| | | | | 405 | | | | | 410 | | | | | 415 | | |
| gtg | agc | cgc | aaa | ggc | ttt | agc | ggc | agc | gcg | atg | att | gcg | aac | gaa | gtg | 1296 |
| Val | Ser | Arg | Lys | Gly | Phe | Ser | Gly | Ser | Ala | Met | Ile | Ala | Asn | Glu | Val | |
| | | | 420 | | | | | 425 | | | | | 430 | | | |
| aaa | gtg | gat | ggc | cat | gcg | gcg | aaa | gcg | gcg | agc | gtg | agc | gcg | | | 1338 |
| Lys | Val | Asp | Gly | His | Ala | Ala | Lys | Ala | Ala | Ser | Val | Ser | Ala | | | |
| | | | 435 | | | | | 440 | | | | | 445 | | | |

<210> SEQ ID NO 40
<211> LENGTH: 446
<212> TYPE: PRT
<213> ORGANISM: Cryptococcus neoformans

<400> SEQUENCE: 40

Met Ser Ala Ile Arg Ala Leu Asn Met Arg Lys Thr Ala Ser Ala Leu

-continued

```
1               5                   10                  15
Lys Ala Pro Val Ala Phe Lys Arg Thr Leu Ala Thr Pro Val Asn Ser
                20                  25                  30

Leu Tyr Thr Ser Val Leu Pro Ala Lys Ile Pro Ala Ala Leu His Leu
                35                  40                  45

Lys Ser Gly Gln Ser Tyr Phe Gly Ser Ser Phe Gly Ser Glu Asn Ser
                50                  55                  60

Lys Phe Gly Glu Thr Val Phe Ser Thr Ser Ile Thr Ser Tyr Thr Asp
65                  70                  75                  80

Ser Met Thr Asp Pro Ser Tyr Leu Gly Gln Ile Leu Val Phe Thr Ser
                85                  90                  95

Pro Met Ile Gly Asn Tyr Gly Val Pro Ser Asn Thr Ser Ser Gln Phe
                100                 105                 110

Pro Gly Ile Pro Phe Leu Glu Ser Glu Lys Ile Gln Cys Thr Gly Val
                115                 120                 125

Val Val Ser Asp Val Ala Leu Lys Tyr Ser His Tyr Gln Ala Val Glu
                130                 135                 140

Ser Leu His Glu Trp Cys Lys Arg Tyr Asp Val Pro Gly Ile Thr Gly
145                 150                 155                 160

Val Asp Thr Arg Ala Ile Thr Ser Leu Leu Arg Asp Gln Gly Thr Thr
                165                 170                 175

Leu Gly Arg Leu Ala Val Gly Asp Glu Ala Gly Lys Pro Ala Pro Gln
                180                 185                 190

Glu Ala Glu Tyr Trp Asp Pro Ser Lys Glu Asn Leu Val Ala Gln Ala
                195                 200                 205

Ser Thr Lys Lys Ala Tyr Val Leu Asn Glu Lys Gly Ser Gly Pro Arg
210                 215                 220

Ile Ala Val Leu Asp Phe Gly Thr Lys Ala Asn Ile Leu Arg Ser Leu
225                 230                 235                 240

Ile Arg Arg Asp Ala Val Val Thr Val Leu Pro Trp Asp Phe Asp Phe
                245                 250                 255

Asn Thr Val Arg Asp Gln Phe Asp Gly Leu Phe Leu Ser Asn Gly Pro
                260                 265                 270

Gly Asp Pro Lys Met Ile Met Asp Ser Ala Met Arg Val Arg Gln Thr
                275                 280                 285

Ile Asn Glu Trp Asn Lys Pro Ile Phe Gly Ile Cys Met Gly His Gln
                290                 295                 300

Val Leu Gly Leu Ala Ala Gly Leu Glu Ala Tyr Arg Met Thr Phe Gly
305                 310                 315                 320

Asn Arg Gly His Asn Gln Pro Val Leu Ala Leu Ala Ser Ser Gly Ser
                325                 330                 335

Ile Lys Ala Gly Arg Val Tyr Val Thr Ser Gln Asn His Gln Tyr Ala
                340                 345                 350

Leu Arg Leu Thr Glu Asp Phe Pro Glu Gly Trp Ala Pro Phe Phe Ile
                355                 360                 365

Asn Cys Asn Asp Ser Ser Val Glu Gly Ile Ile Ser Thr Pro Glu Ser
                370                 375                 380

Gly Lys Arg Ile Trp Gly Val Gln Phe His Pro Glu Ser Ala Gly Gly
385                 390                 395                 400

Pro Leu Asp Thr Ile Glu Met Phe Thr Asp Phe Val Asn Glu Cys Asp
                405                 410                 415

Val Ser Arg Lys Gly Phe Ser Gly Ser Ala Met Ile Ala Asn Glu Val
                420                 425                 430
```

```
                Lys Val Asp Gly His Ala Ala Lys Ala Ala Ser Val Ser Ala
                        435                 440                 445

<210> SEQ ID NO 41
<211> LENGTH: 843
<212> TYPE: DNA
<213> ORGANISM: Cryptococcus neoformans
<220> FEATURE:
<221> NAME/KEY: CDS
<222> LOCATION: (1)..(843)

<400> SEQUENCE: 41 atg agc gtg ccg agc ctg aaa agc gcg ctg aaa aaa ccg acc aaa agc        48
Met Ser Val Pro Ser Leu Lys Ser Ala Leu Lys Lys Pro Thr Lys Ser
1               5                   10                  15 ttt gat acc ccg ccg gcg ggc ccg agc aaa ctg agc gtg gcg gcg gcg        96
Phe Asp Thr Pro Pro Ala Gly Pro Ser Lys Leu Ser Val Ala Ala Ala
            20                  25                  30 gtg ccg gaa aaa agc aaa gcg aaa gcg aaa cag agc gtg agc att gcg       144
Val Pro Glu Lys Ser Lys Ala Lys Ala Lys Gln Ser Val Ser Ile Ala
        35                  40                  45 gaa aaa ccg cag cgc ctg cgc ggc ccg gat ctg gaa agc gaa agc gaa       192
Glu Lys Pro Gln Arg Leu Arg Gly Pro Asp Leu Glu Ser Glu Ser Glu
    50                  55                  60 ggc aac gcg agc ggc ttt gaa gat gaa agc gcg agc gaa gtg gaa gtg       240
Gly Asn Ala Ser Gly Phe Glu Asp Glu Ser Ala Ser Glu Val Glu Val
65                  70                  75                  80 gat gaa gat gaa gaa atg aac acc gat gaa gaa att gaa aaa gcg aaa       288
Asp Glu Asp Glu Glu Met Asn Thr Asp Glu Glu Ile Glu Lys Ala Lys
                85                  90                  95 gaa ggc aaa ccg aaa aaa agc acc aaa cgc aaa aaa gcg ccg acc acc       336
Glu Gly Lys Pro Lys Lys Ser Thr Lys Arg Lys Lys Ala Pro Thr Thr
            100                 105                 110 gcg gcg gat ttt ggc gcg acc ctg acc agc ctg ctg gcg gat ccg ctg       384
Ala Ala Asp Phe Gly Ala Thr Leu Thr Ser Leu Leu Ala Asp Pro Leu
        115                 120                 125 acc aaa agc aac aaa aaa gcg aaa acc gcg gat agc acc aaa aaa gcg       432
Thr Lys Ser Asn Lys Lys Ala Lys Thr Ala Asp Ser Thr Lys Lys Ala
    130                 135                 140 gcg gcg gcg ccg att ctg gcg ctg agc gcg cat aaa ctg ccg acc aaa       480
Ala Ala Ala Pro Ile Leu Ala Leu Ser Ala His Lys Leu Pro Thr Lys
145                 150                 155                 160 gcg agc gtg agc ctg gaa gcg aaa gcg aaa cgc cag ctg aaa gcg gaa       528
Ala Ser Val Ser Leu Glu Ala Lys Ala Lys Arg Gln Leu Lys Ala Glu
                165                 170                 175 aaa gaa gaa aaa gaa gat cgc gcg cgc gtg cag aac gtg ctg gaa ggc       576
Lys Glu Glu Lys Glu Asp Arg Ala Arg Val Gln Asn Val Leu Glu Gly
            180                 185                 190 tgg agc ggc gat ggc gtg gtg ggc ggc cag gaa ttt gaa cgc aac ctg       624
Trp Ser Gly Asp Gly Val Val Gly Gly Gln Glu Phe Glu Arg Asn Leu
        195                 200                 205 cgc aaa acc gcg cag aaa ggc gtg gtg aaa ctg ttt aac gcg att ctg       672
Arg Lys Thr Ala Gln Lys Gly Val Val Lys Leu Phe Asn Ala Ile Leu
    210                 215                 220 gtg gcg agc aaa aac gcg gaa gcg gcg cag acc acc ctg agc gaa aaa       720
Val Ala Ser Lys Asn Ala Glu Ala Ala Gln Thr Thr Leu Ser Glu Lys
225                 230                 235                 240 gcg cgc ctg aaa ccg gaa gcg gcg aaa aaa aaa gaa aaa gat aac att       768
Ala Arg Leu Lys Pro Glu Ala Ala Lys Lys Lys Glu Lys Asp Asn Ile
                245                 250                 255
```

```
ctg ggc cgc ggc ggc aaa gaa gat gtg ctg acc aaa gaa agc ttt ctg    816
Leu Gly Arg Gly Gly Lys Glu Asp Val Leu Thr Lys Glu Ser Phe Leu
        260                 265                 270 gaa atg gtg cgc aaa ggc agc agc aaa                                843
Glu Met Val Arg Lys Gly Ser Ser Lys
        275                 280
```

<210> SEQ ID NO 42
<211> LENGTH: 281
<212> TYPE: PRT
<213> ORGANISM: Cryptococcus neoformans

<400> SEQUENCE: 42

```
Met Ser Val Pro Ser Leu Lys Ser Ala Leu Lys Pro Thr Lys Ser
 1               5                  10                  15

Phe Asp Thr Pro Pro Ala Gly Pro Ser Lys Leu Ser Val Ala Ala
                20                  25                  30

Val Pro Glu Lys Ser Lys Ala Lys Ala Lys Gln Ser Val Ser Ile Ala
            35                  40                  45

Glu Lys Pro Gln Arg Leu Arg Gly Pro Asp Leu Glu Ser Glu Ser
    50                  55                  60

Gly Asn Ala Ser Gly Phe Glu Asp Glu Ser Ala Ser Glu Val Glu Val
65                  70                  75                  80

Asp Glu Asp Glu Glu Met Asn Thr Asp Glu Glu Ile Glu Lys Ala Lys
                85                  90                  95

Glu Gly Lys Pro Lys Lys Ser Thr Lys Arg Lys Lys Ala Pro Thr Thr
            100                 105                 110

Ala Ala Asp Phe Gly Ala Thr Leu Thr Ser Leu Leu Ala Asp Pro Leu
        115                 120                 125

Thr Lys Ser Asn Lys Lys Ala Lys Thr Ala Asp Ser Thr Lys Lys Ala
    130                 135                 140

Ala Ala Ala Pro Ile Leu Ala Leu Ser Ala His Lys Leu Pro Thr Lys
145                 150                 155                 160

Ala Ser Val Ser Leu Glu Ala Lys Ala Lys Arg Gln Leu Lys Ala Glu
                165                 170                 175

Lys Glu Glu Lys Glu Asp Arg Ala Arg Val Gln Asn Val Leu Glu Gly
            180                 185                 190

Trp Ser Gly Asp Gly Val Val Gly Gly Gln Glu Phe Glu Arg Asn Leu
        195                 200                 205

Arg Lys Thr Ala Gln Lys Gly Val Val Lys Leu Phe Asn Ala Ile Leu
    210                 215                 220

Val Ala Ser Lys Asn Ala Glu Ala Ala Gln Thr Thr Leu Ser Glu Lys
225                 230                 235                 240

Ala Arg Leu Lys Pro Glu Ala Ala Lys Lys Glu Lys Asp Asn Ile
                245                 250                 255

Leu Gly Arg Gly Gly Lys Glu Asp Val Leu Thr Lys Glu Ser Phe Leu
            260                 265                 270

Glu Met Val Arg Lys Gly Ser Ser Lys
        275                 280
```

<210> SEQ ID NO 43
<211> LENGTH: 600
<212> TYPE: DNA
<213> ORGANISM: Cryptococcus neoformans
<220> FEATURE:
<221> NAME/KEY: CDS
<222> LOCATION: (1)..(600)

```
<400> SEQUENCE: 43 atg acc tgc gcg ctg att ccg ctg ctg cgc aaa agc gat ctg cgc agc     48
Met Thr Cys Ala Leu Ile Pro Leu Leu Arg Lys Ser Asp Leu Arg Ser
1               5                   10                  15 gtg gtg att att gcg agc att gcg ggc ctg gcg aac cag cgc gcg acc     96
Val Val Ile Ile Ala Ser Ile Ala Gly Leu Ala Asn Gln Arg Ala Thr
                20                  25                  30 ggc agc gtg agc tat ggc gtg agc aaa gcg gcg gcg att cat ctg ggc    144
Gly Ser Val Ser Tyr Gly Val Ser Lys Ala Ala Ala Ile His Leu Gly
            35                  40                  45 aaa ctg ctg gcg ggc cgc ctg cat ccg ctg aaa att cgc gtg aac acc    192
Lys Leu Leu Ala Gly Arg Leu His Pro Leu Lys Ile Arg Val Asn Thr
        50                  55                  60 att tgc ccg ggc att ttt ccg agc gaa atg acc ggc aaa aac gat gcg    240
Ile Cys Pro Gly Ile Phe Pro Ser Glu Met Thr Gly Lys Asn Asp Ala
65                  70                  75                  80 ggc cag ggc ctg gaa tat gat att ggc gaa att ccg acc aaa gcg gcg    288
Gly Gln Gly Leu Glu Tyr Asp Ile Gly Glu Ile Pro Thr Lys Ala Ala
                85                  90                  95 aaa cgc agc acc gtg ggc cgc ccg ggc ctg ccg gaa gaa att gtg ggc    336
Lys Arg Ser Thr Val Gly Arg Pro Gly Leu Pro Glu Glu Ile Val Gly
            100                 105                 110 ccg gtg ctg ctg ctg agc agc aaa gcg ggc ggc tat ttt gat ggc gcg    384
Pro Val Leu Leu Leu Ser Ser Lys Ala Gly Gly Tyr Phe Asp Gly Ala
        115                 120                 125 atg ctg acc gtg gat ggc ggc cgc ctg atg gtg agc ggc ccg ttt tgc    432
Met Leu Thr Val Asp Gly Gly Arg Leu Met Val Ser Gly Pro Phe Cys
    130                 135                 140 ttt gtg ttt agc ccg agc agc ctg ccg gtg gat aac ctg cgc tgc ttt    480
Phe Val Phe Ser Pro Ser Ser Leu Pro Val Asp Asn Leu Arg Cys Phe
145                 150                 155                 160 ctg ctg ctg acc acc gtg ggc aac cgc gtg ccg gcg ttt atg atg gtg    528
Leu Leu Leu Thr Thr Val Gly Asn Arg Val Pro Ala Phe Met Met Val
                165                 170                 175 agc gat tgc ctg cgc att cgc att ttt gaa ctg aac gaa cag cgc aaa    576
Ser Asp Cys Leu Arg Ile Arg Ile Phe Glu Leu Asn Glu Gln Arg Lys
            180                 185                 190 aac gaa acc gat gtg gaa atg ggc                                    600
Asn Glu Thr Asp Val Glu Met Gly
        195                 200

<210> SEQ ID NO 44
<211> LENGTH: 200
<212> TYPE: PRT
<213> ORGANISM: Cryptococcus neoformans

<400> SEQUENCE: 44

Met Thr Cys Ala Leu Ile Pro Leu Leu Arg Lys Ser Asp Leu Arg Ser
1               5                   10                  15

Val Val Ile Ile Ala Ser Ile Ala Gly Leu Ala Asn Gln Arg Ala Thr
                20                  25                  30

Gly Ser Val Ser Tyr Gly Val Ser Lys Ala Ala Ala Ile His Leu Gly
            35                  40                  45

Lys Leu Leu Ala Gly Arg Leu His Pro Leu Lys Ile Arg Val Asn Thr
        50                  55                  60

Ile Cys Pro Gly Ile Phe Pro Ser Glu Met Thr Gly Lys Asn Asp Ala
65                  70                  75                  80

Gly Gln Gly Leu Glu Tyr Asp Ile Gly Glu Ile Pro Thr Lys Ala Ala
                85                  90                  95
```

```
Lys Arg Ser Thr Val Gly Arg Pro Gly Leu Pro Glu Ile Val Gly
            100                 105                 110

Pro Val Leu Leu Leu Ser Ser Lys Ala Gly Gly Tyr Phe Asp Gly Ala
            115                 120                 125

Met Leu Thr Val Asp Gly Gly Arg Leu Met Val Ser Gly Pro Phe Cys
130                 135                 140

Phe Val Phe Ser Pro Ser Ser Leu Pro Val Asp Asn Leu Arg Cys Phe
145                 150                 155                 160

Leu Leu Leu Thr Thr Val Gly Asn Arg Val Pro Ala Phe Met Met Val
                165                 170                 175

Ser Asp Cys Leu Arg Ile Arg Ile Phe Glu Leu Asn Glu Gln Arg Lys
            180                 185                 190

Asn Glu Thr Asp Val Glu Met Gly
            195                 200
```

<210> SEQ ID NO 45
<211> LENGTH: 1440
<212> TYPE: DNA
<213> ORGANISM: Cryptococcus neoformans
<220> FEATURE:
<221> NAME/KEY: CDS
<222> LOCATION: (1)..(1440)

<400> SEQUENCE: 45

```
atg ctg gtg aac agc agc agc atg ctg gtg acc cgc acc cat ggc ctg      48
Met Leu Val Asn Ser Ser Ser Met Leu Val Thr Arg Thr His Gly Leu
1               5                   10                  15 atg ggc gat gaa gcg tgg aaa gaa ctg gcg aaa tat ggc ctg acc cgc      96
Met Gly Asp Glu Ala Trp Lys Glu Leu Ala Lys Tyr Gly Leu Thr Arg
            20                  25                  30 tgg agc gat gat ggc gcg ttt ctg acc gtg ccg gcg cgc ggc tgc agc     144
Trp Ser Asp Asp Gly Ala Phe Leu Thr Val Pro Ala Arg Gly Cys Ser
        35                  40                  45 atg tgc gaa gtg gat ccg gtg ctg tgc gaa gaa att ggc gaa gat aac     192
Met Cys Glu Val Asp Pro Val Leu Cys Glu Glu Ile Gly Glu Asp Asn
    50                  55                  60 ctg aaa cgc agc ctg gcg ttt agc ggc acc aac cgc cgc ctg aaa cgc     240
Leu Lys Arg Ser Leu Ala Phe Ser Gly Thr Asn Arg Arg Leu Lys Arg
65                  70                  75                  80 gtg ctg gcg aaa ctg cgc cgc ggc gaa acc att aac gtg ggc gcg att     288
Val Leu Ala Lys Leu Arg Arg Gly Glu Thr Ile Asn Val Gly Ala Ile
                85                  90                  95 ggc ggc agc gtg acc aaa ggc tat ggc ctg aac cgc tat aac gaa ccg     336
Gly Gly Ser Val Thr Lys Gly Tyr Gly Leu Asn Arg Tyr Asn Glu Pro
            100                 105                 110 tat tat ccg gat acc ccg acc aac ctg cat cgc att att ttt gat cat     384
Tyr Tyr Pro Asp Thr Pro Thr Asn Leu His Arg Ile Ile Phe Asp His
        115                 120                 125 ctg gtg agc ctg tat ccg gcg ccg aac ggc gtg aaa acc gat gat agc     432
Leu Val Ser Leu Tyr Pro Ala Pro Asn Gly Val Lys Thr Asp Asp Ser
    130                 135                 140 ggc cgc aaa gaa ggc aaa cat ggc tat att aac ggc ggc cag ggc gcg     480
Gly Arg Lys Glu Gly Lys His Gly Tyr Ile Asn Gly Gly Gln Gly Ala
145                 150                 155                 160 acc ggc acc ggc tat ttt agc tat tgc tgg gaa gaa cat gtg ccg gcg     528
Thr Gly Thr Gly Tyr Phe Ser Tyr Cys Trp Glu Glu His Val Pro Ala
                165                 170                 175 gat ctg gat ctg att ttt ctg gaa cag gcg att aac gat gaa ctg ctg     576
Asp Leu Asp Leu Ile Phe Leu Glu Gln Ala Ile Asn Asp Glu Leu Leu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 180 |     |     |     |     | 185 |     |     |     |     | 190 |     |      |
| ctg | cgc | aac | att | gat | agc | tat | gaa | ctg | ctg | gtg | cgc | agc | ctg | ctg | gat | 624  |
| Leu | Arg | Asn | Ile | Asp | Ser | Tyr | Glu | Leu | Leu | Val | Arg | Ser | Leu | Leu | Asp |      |
|     |     | 195 |     |     |     |     | 200 |     |     |     |     | 205 |     |     |     |      |
| ctg | ccg | acc | agc | ccg | gcg | att | gtg | aac | ctg | cat | gtg | ttt | gcg | ctg | atg | 672  |
| Leu | Pro | Thr | Ser | Pro | Ala | Ile | Val | Asn | Leu | His | Val | Phe | Ala | Leu | Met |      |
| 210 |     |     |     |     | 215 |     |     |     |     | 220 |     |     |     |     |     |      |
| ttt | aac | agc | att | acc | ctg | ggc | ggc | gat | ctg | cat | cag | agc | att | gcg | cag | 720  |
| Phe | Asn | Ser | Ile | Thr | Leu | Gly | Gly | Asp | Leu | His | Gln | Ser | Ile | Ala | Gln |      |
| 225 |     |     |     |     | 230 |     |     |     |     | 235 |     |     |     |     | 240 |      |
| ttt | tat | gat | ctg | ccg | gtg | ctg | agc | ctg | cgc | aac | gcg | ctg | ctg | aac | gat | 768  |
| Phe | Tyr | Asp | Leu | Pro | Val | Leu | Ser | Leu | Arg | Asn | Ala | Leu | Leu | Asn | Asp |      |
|     |     |     |     | 245 |     |     |     |     | 250 |     |     |     |     | 255 |     |      |
| atg | ctg | aaa | aac | gaa | agc | ctg | att | agc | gaa | tat | ttt | ttt | gtg | cat | ccg | 816  |
| Met | Leu | Lys | Asn | Glu | Ser | Leu | Ile | Ser | Glu | Tyr | Phe | Phe | Val | His | Pro |      |
|     |     |     | 260 |     |     |     |     | 265 |     |     |     |     | 270 |     |     |      |
| gaa | ggc | gat | att | gat | ctg | cgc | cat | att | agc | cgc | aaa | ggc | cat | aac | gtg | 864  |
| Glu | Gly | Asp | Ile | Asp | Leu | Arg | His | Ile | Ser | Arg | Lys | Gly | His | Asn | Val |      |
|     |     | 275 |     |     |     |     | 280 |     |     |     |     | 285 |     |     |     |      |
| atg | ggc | cgc | att | ggc | gcg | gcg | tat | atg | gat | agc | cag | att | tgc | gaa | atg | 912  |
| Met | Gly | Arg | Ile | Gly | Ala | Ala | Tyr | Met | Asp | Ser | Gln | Ile | Cys | Glu | Met |      |
| 290 |     |     |     |     | 295 |     |     |     |     | 300 |     |     |     |     |     |      |
| gat | aaa | tat | gaa | cag | ggc | att | ccg | ggc | gcg | gat | agc | atg | agc | att | gat | 960  |
| Asp | Lys | Tyr | Glu | Gln | Gly | Ile | Pro | Gly | Ala | Asp | Ser | Met | Ser | Ile | Asp |      |
| 305 |     |     |     |     | 310 |     |     |     |     | 315 |     |     |     |     | 320 |      |
| cag | ctg | tat | ccg | gtg | gaa | ccg | att | ccg | cgc | atg | cag | att | aac | atg | aaa | 1008 |
| Gln | Leu | Tyr | Pro | Val | Glu | Pro | Ile | Pro | Arg | Met | Gln | Ile | Asn | Met | Lys |      |
|     |     |     |     | 325 |     |     |     |     | 330 |     |     |     |     | 335 |     |      |
| tat | gat | aaa | gat | ctg | gtg | ctg | ccg | acc | att | aaa | ccg | cag | tgc | ttt | agc | 1056 |
| Tyr | Asp | Lys | Asp | Leu | Val | Leu | Pro | Thr | Ile | Lys | Pro | Gln | Cys | Phe | Ser |      |
|     |     |     | 340 |     |     |     |     | 345 |     |     |     |     | 350 |     |     |      |
| gcg | aac | agc | gaa | aaa | cat | ccg | ctg | gtg | ccg | gtg | gaa | aac | aac | ggc | tgg | 1104 |
| Ala | Asn | Ser | Glu | Lys | His | Pro | Leu | Val | Pro | Val | Glu | Asn | Asn | Gly | Trp |      |
|     |     | 355 |     |     |     |     | 360 |     |     |     |     | 365 |     |     |     |      |
| cgc | aaa | tgg | aac | tgg | aaa | gaa | aaa | cat | tat | ctg | gtg | gcg | gat | gtg | ccg | 1152 |
| Arg | Lys | Trp | Asn | Trp | Lys | Glu | Lys | His | Tyr | Leu | Val | Ala | Asp | Val | Pro |      |
| 370 |     |     |     |     | 375 |     |     |     |     | 380 |     |     |     |     |     |      |
| ggc | agc | cgc | gtg | agc | ttt | aaa | ctg | aaa | acc | aac | atg | ggc | aaa | att | gaa | 1200 |
| Gly | Ser | Arg | Val | Ser | Phe | Lys | Leu | Lys | Thr | Asn | Met | Gly | Lys | Ile | Glu |      |
| 385 |     |     |     |     | 390 |     |     |     |     | 395 |     |     |     |     | 400 |      |
| gtg | cag | tat | ctg | cgc | agc | tat | cag | tat | cat | cag | ggc | agc | gcg | aaa | tgc | 1248 |
| Val | Gln | Tyr | Leu | Arg | Ser | Tyr | Gln | Tyr | His | Gln | Gly | Ser | Ala | Lys | Cys |      |
|     |     |     |     | 405 |     |     |     |     | 410 |     |     |     |     | 415 |     |      |
| tgg | gtg | gat | gaa | gaa | gtg | gaa | aaa | gcg | att | aaa | ctg | gat | ggc | tat | tgg | 1296 |
| Trp | Val | Asp | Glu | Glu | Val | Glu | Lys | Ala | Ile | Lys | Leu | Asp | Gly | Tyr | Trp |      |
|     |     |     | 420 |     |     |     |     | 425 |     |     |     |     | 430 |     |     |      |
| aaa | gaa | ccg | tat | aac | att | ggc | cgc | gcg | gtg | acc | att | cgc | gaa | ggc | ctg | 1344 |
| Lys | Glu | Pro | Tyr | Asn | Ile | Gly | Arg | Ala | Val | Thr | Ile | Arg | Glu | Gly | Leu |      |
|     |     | 435 |     |     |     |     | 440 |     |     |     |     | 445 |     |     |     |      |
| gaa | ccg | ggc | gaa | cat | acc | ctg | acc | tgc | gaa | ctg | ctg | aaa | cag | acc | gcg | 1392 |
| Glu | Pro | Gly | Glu | His | Thr | Leu | Thr | Cys | Glu | Leu | Leu | Lys | Gln | Thr | Ala |      |
| 450 |     |     |     |     | 455 |     |     |     |     | 460 |     |     |     |     |     |      |
| gat | ccg | gaa | ggc | ggc | ctg | gaa | ttt | cgc | ctg | att | agc | att | atg | agc | att | 1440 |
| Asp | Pro | Glu | Gly | Gly | Leu | Glu | Phe | Arg | Leu | Ile | Ser | Ile | Met | Ser | Ile |      |
| 465 |     |     |     |     | 470 |     |     |     |     | 475 |     |     |     |     | 480 |      |

<210> SEQ ID NO 46
<211> LENGTH: 480
<212> TYPE: PRT
<213> ORGANISM: Cryptococcus neoformans

<400> SEQUENCE: 46

| | | | | | | | | | | | | | | |
|---|---|---|---|---|---|---|---|---|---|---|---|---|---|---|
|Met|Leu|Val|Asn|Ser|Ser|Met|Leu|Val|Thr|Arg|Thr|His|Gly|Leu|
|1| | | |5| | | | |10| | | | |15|

Met Gly Asp Glu Ala Trp Lys Glu Leu Ala Lys Tyr Gly Leu Thr Arg
            20                  25                  30

Trp Ser Asp Asp Gly Ala Phe Leu Thr Val Pro Ala Arg Gly Cys Ser
        35                  40                  45

Met Cys Glu Val Asp Pro Val Leu Cys Glu Ile Gly Glu Asp Asn
50                  55                  60

Leu Lys Arg Ser Leu Ala Phe Ser Gly Thr Asn Arg Arg Leu Lys Arg
65                  70                  75                  80

Val Leu Ala Lys Leu Arg Arg Gly Glu Thr Ile Asn Val Gly Ala Ile
                85                  90                  95

Gly Gly Ser Val Thr Lys Gly Tyr Gly Leu Asn Arg Tyr Asn Glu Pro
                100                 105                 110

Tyr Tyr Pro Asp Thr Pro Thr Asn Leu His Arg Ile Ile Phe Asp His
            115                 120                 125

Leu Val Ser Leu Tyr Pro Ala Pro Asn Gly Val Lys Thr Asp Asp Ser
130                 135                 140

Gly Arg Lys Glu Gly Lys His Gly Tyr Ile Asn Gly Gly Gln Gly Ala
145                 150                 155                 160

Thr Gly Thr Gly Tyr Phe Ser Tyr Cys Trp Glu Glu His Val Pro Ala
                165                 170                 175

Asp Leu Asp Leu Ile Phe Leu Glu Gln Ala Ile Asn Asp Glu Leu Leu
            180                 185                 190

Leu Arg Asn Ile Asp Ser Tyr Glu Leu Leu Val Arg Ser Leu Leu Asp
            195                 200                 205

Leu Pro Thr Ser Pro Ala Ile Val Asn Leu His Val Phe Ala Leu Met
210                 215                 220

Phe Asn Ser Ile Thr Leu Gly Gly Asp Leu His Gln Ser Ile Ala Gln
225                 230                 235                 240

Phe Tyr Asp Leu Pro Val Leu Ser Leu Arg Asn Ala Leu Leu Asn Asp
                245                 250                 255

Met Leu Lys Asn Glu Ser Leu Ile Ser Glu Tyr Phe Phe Val His Pro
            260                 265                 270

Glu Gly Asp Ile Asp Leu Arg His Ile Ser Arg Lys Gly His Asn Val
            275                 280                 285

Met Gly Arg Ile Gly Ala Ala Tyr Met Asp Ser Gln Ile Cys Glu Met
290                 295                 300

Asp Lys Tyr Glu Gln Gly Ile Pro Gly Ala Asp Ser Met Ser Ile Asp
305                 310                 315                 320

Gln Leu Tyr Pro Val Glu Pro Ile Pro Arg Met Gln Ile Asn Met Lys
                325                 330                 335

Tyr Asp Lys Asp Leu Val Leu Pro Thr Ile Lys Pro Gln Cys Phe Ser
            340                 345                 350

Ala Asn Ser Glu Lys His Pro Leu Val Pro Val Glu Asn Asn Gly Trp
            355                 360                 365

Arg Lys Trp Asn Trp Lys Glu Lys His Tyr Leu Val Ala Asp Val Pro
            370                 375                 380

Gly Ser Arg Val Ser Phe Lys Leu Lys Thr Asn Met Gly Lys Ile Glu
385                 390                 395                 400

Val Gln Tyr Leu Arg Ser Tyr Gln Tyr His Gln Gly Ser Ala Lys Cys

```
                    405                 410                 415
Trp Val Asp Glu Glu Val Glu Lys Ala Ile Lys Leu Asp Gly Tyr Trp
                420                 425                 430

Lys Glu Pro Tyr Asn Ile Gly Arg Ala Val Thr Ile Arg Glu Gly Leu
            435                 440                 445

Glu Pro Gly Glu His Thr Leu Thr Cys Glu Leu Leu Lys Gln Thr Ala
        450                 455                 460

Asp Pro Glu Gly Leu Glu Phe Arg Leu Ile Ser Ile Met Ser Ile
465                 470                 475                 480

<210> SEQ ID NO 47
<211> LENGTH: 1176
<212> TYPE: DNA
<213> ORGANISM: Cryptococcus neoformans
<220> FEATURE:
<221> NAME/KEY: CDS
<222> LOCATION: (1)..(1176)

<400> SEQUENCE: 47 atg agc ttt gat gcg gtg gtg att ggc agc ggc gtg att ggc ctg agc      48
Met Ser Phe Asp Ala Val Val Ile Gly Ser Gly Val Ile Gly Leu Ser
1               5                   10                  15 att gcg cgc gaa ctg cat aac cgc ggc ctg aaa gtg gcg att gtg gcg      96
Ile Ala Arg Glu Leu His Asn Arg Gly Leu Lys Val Ala Ile Val Ala
                20                  25                  30 cgc gat ctg gcg gaa gat agc att agc gtg ggc ttt gcg agc ccg tgg     144
Arg Asp Leu Ala Glu Asp Ser Ile Ser Val Gly Phe Ala Ser Pro Trp
            35                  40                  45 gcg ggc tgc aac tgg ttt agc ttt gcg gaa ggc ggc acc ccg gcg gcg     192
Ala Gly Cys Asn Trp Phe Ser Phe Ala Glu Gly Gly Thr Pro Ala Ala
        50                  55                  60 gaa tgg gat acc att acc ttt ggc aaa ctg gcg aaa ctg gcg aaa gat     240
Glu Trp Asp Thr Ile Thr Phe Gly Lys Leu Ala Lys Leu Ala Lys Asp
65                  70                  75                  80 cat ccg cat att tgc cag aaa att ccg ttt tgc agc gtg tgg gat ctg     288
His Pro His Ile Cys Gln Lys Ile Pro Phe Cys Ser Val Trp Asp Leu
                85                  90                  95 ccg aaa agc gat gcg gaa agc gaa ccg tgg ttt aaa gat ctg gtg ttt     336
Pro Lys Ser Asp Ala Glu Ser Glu Pro Trp Phe Lys Asp Leu Val Phe
                100                 105                 110 gat tat aaa aac ctg aaa agc acc ccg ggc cag ccg ctg ccg ggc ggc     384
Asp Tyr Lys Asn Leu Lys Ser Thr Pro Gly Gln Pro Leu Pro Gly Gly
            115                 120                 125 aaa aaa ttt ggc cat agc ttt gcg agc tat gtg ctg cat gcg ccg aac     432
Lys Lys Phe Gly His Ser Phe Ala Ser Tyr Val Leu His Ala Pro Asn
        130                 135                 140 tat att cgc cat ctg agc agc gaa acc cgc gcg ctg ggc att ccg gtg     480
Tyr Ile Arg His Leu Ser Ser Glu Thr Arg Ala Leu Gly Ile Pro Val
145                 150                 155                 160 cat cgc tat cgc ctg agc agc ctg gat gaa gcg tat aac ctg agc ggc     528
His Arg Tyr Arg Leu Ser Ser Leu Asp Glu Ala Tyr Asn Leu Ser Gly
                165                 170                 175 att ggc aaa gtg agc ctg gtg gtg aac gcg agc ggc ctg ggc gcg aaa     576
Ile Gly Lys Val Ser Leu Val Val Asn Ala Ser Gly Leu Gly Ala Lys
                180                 185                 190 gcg ctg att ggc gtg gaa gat gaa aaa gtg tat ccg ggc cgc ggc cag     624
Ala Leu Ile Gly Val Glu Asp Glu Lys Val Tyr Pro Gly Arg Gly Gln
            195                 200                 205 acc gtg ctg gtg cgc gcg ccg ggc ttt aaa gcg tgc att atg cat acc     672
Thr Val Leu Val Arg Ala Pro Gly Phe Lys Ala Cys Ile Met His Thr
```

```
              210                 215                 220
gaa ggc ttt tat gcg gat ctg gat gaa agc ggc cgc gaa gtg acc ccg        720
Glu Gly Phe Tyr Ala Asp Leu Asp Glu Ser Gly Arg Glu Val Thr Pro
225                 230                 235                 240 ccg ccg ccg gcg tat att att ccg cgc ccg ggc ccg gaa ggc cat gtg        768
Pro Pro Pro Ala Tyr Ile Ile Pro Arg Pro Gly Pro Glu Gly His Val
            245                 250                 255 gtg ctg ggc ggc gtg tat cag cgc gat aac tgg agc acc ctg ccg gat        816
Val Leu Gly Gly Val Tyr Gln Arg Asp Asn Trp Ser Thr Leu Pro Asp
            260                 265                 270 ctg aaa gaa gcg gaa cgc att ctg aaa gat tgc tat aac ctg gcg ccg        864
Leu Lys Glu Ala Glu Arg Ile Leu Lys Asp Cys Tyr Asn Leu Ala Pro
            275                 280                 285 gaa ctg gcg ggc ccg aac ggc aaa acc tgg aaa gat att gaa att att        912
Glu Leu Ala Gly Pro Asn Gly Lys Thr Trp Lys Asp Ile Glu Ile Ile
290                 295                 300 agc cat aac gtg ggc ctg cgc ccg gcg cgc gaa ggc ggc ccg cgc ctg        960
Ser His Asn Val Gly Leu Arg Pro Ala Arg Glu Gly Gly Pro Arg Leu
305                 310                 315                 320 gaa att gaa gaa cgc gaa gtg ggc acc ggc gcg aac gaa ggc aac gcg       1008
Glu Ile Glu Glu Arg Glu Val Gly Thr Gly Ala Asn Glu Gly Asn Ala
                325                 330                 335 tat gat gtg gcg ccg atg att ggc cgc att ggc gaa cgc cgc aaa gtg       1056
Tyr Asp Val Ala Pro Met Ile Gly Arg Ile Gly Glu Arg Arg Lys Val
            340                 345                 350 gcg gtg gtg cat gcg tat ggc att ggc agc gcg ggc ttt cag gcg agc       1104
Ala Val Val His Ala Tyr Gly Ile Gly Ser Ala Gly Phe Gln Ala Ser
            355                 360                 365 ctg ggc atg gcg gaa aaa gcg agc gat ctg acc gtg aaa tat ctg agc       1152
Leu Gly Met Ala Glu Lys Ala Ser Asp Leu Thr Val Lys Tyr Leu Ser
370                 375                 380 ggc aaa cgc agc ccg gcg cgc ctg                                       1176
Gly Lys Arg Ser Pro Ala Arg Leu
385                 390

<210> SEQ ID NO 48
<211> LENGTH: 392
<212> TYPE: PRT
<213> ORGANISM: Cryptococcus neoformans

<400> SEQUENCE: 48

Met Ser Phe Asp Ala Val Val Ile Gly Ser Gly Val Ile Gly Leu Ser
1               5                   10                  15

Ile Ala Arg Glu Leu His Asn Arg Gly Leu Lys Val Ala Ile Val Ala
            20                  25                  30

Arg Asp Leu Ala Glu Asp Ser Ile Ser Val Gly Phe Ala Ser Pro Trp
        35                  40                  45

Ala Gly Cys Asn Trp Phe Ser Phe Ala Glu Gly Gly Thr Pro Ala Ala
    50                  55                  60

Glu Trp Asp Thr Ile Thr Phe Gly Lys Leu Ala Lys Leu Ala Lys Asp
65                  70                  75                  80

His Pro His Ile Cys Gln Lys Ile Pro Phe Cys Ser Val Trp Asp Leu
                85                  90                  95

Pro Lys Ser Asp Ala Glu Ser Glu Pro Trp Phe Lys Asp Leu Val Phe
            100                 105                 110

Asp Tyr Lys Asn Leu Lys Ser Thr Pro Gly Gln Pro Leu Pro Gly Gly
        115                 120                 125

Lys Lys Phe Gly His Ser Phe Ala Ser Tyr Val Leu His Ala Pro Asn
```

```
          130                 135                 140
Tyr Ile Arg His Leu Ser Ser Glu Thr Arg Ala Leu Gly Ile Pro Val
145                 150                 155                 160

His Arg Tyr Arg Leu Ser Ser Leu Asp Glu Ala Tyr Asn Leu Ser Gly
                165                 170                 175

Ile Gly Lys Val Ser Leu Val Val Asn Ala Ser Gly Leu Gly Ala Lys
                180                 185                 190

Ala Leu Ile Gly Val Glu Asp Glu Lys Val Tyr Pro Gly Arg Gly Gln
            195                 200                 205

Thr Val Leu Val Arg Ala Pro Gly Phe Lys Ala Cys Ile Met His Thr
210                 215                 220

Glu Gly Phe Tyr Ala Asp Leu Asp Glu Ser Gly Arg Glu Val Thr Pro
225                 230                 235                 240

Pro Pro Pro Ala Tyr Ile Ile Pro Arg Pro Gly Pro Glu Gly His Val
                245                 250                 255

Val Leu Gly Gly Val Tyr Gln Arg Asp Asn Trp Ser Thr Leu Pro Asp
                260                 265                 270

Leu Lys Glu Ala Glu Arg Ile Leu Lys Asp Cys Tyr Asn Leu Ala Pro
            275                 280                 285

Glu Leu Ala Gly Pro Asn Gly Lys Thr Trp Lys Asp Ile Glu Ile Ile
            290                 295                 300

Ser His Asn Val Gly Leu Arg Pro Ala Arg Glu Gly Gly Pro Arg Leu
305                 310                 315                 320

Glu Ile Glu Glu Arg Glu Val Gly Thr Gly Ala Asn Glu Gly Asn Ala
                325                 330                 335

Tyr Asp Val Ala Pro Met Ile Gly Arg Ile Gly Glu Arg Arg Lys Val
                340                 345                 350

Ala Val Val His Ala Tyr Gly Ile Gly Ser Ala Gly Phe Gln Ala Ser
            355                 360                 365

Leu Gly Met Ala Glu Lys Ala Ser Asp Leu Thr Val Lys Tyr Leu Ser
        370                 375                 380

Gly Lys Arg Ser Pro Ala Arg Leu
385                 390

<210> SEQ ID NO 49
<211> LENGTH: 198
<212> TYPE: DNA
<213> ORGANISM: Cryptococcus neoformans
<220> FEATURE:
<221> NAME/KEY: CDS
<222> LOCATION: (1)..(198)

<400> SEQUENCE: 49 atg ccg ggc ttt cag gat gtg att tat aac acc ttt ttt cgc cgc aac      48
Met Pro Gly Phe Gln Asp Val Ile Tyr Asn Thr Phe Phe Arg Arg Asn
1               5                   10                  15 agc gtg ttt gtg gcg acc acc ttt att gcg gcg ttt agc ttt agc atg      96
Ser Val Phe Val Ala Thr Thr Phe Ile Ala Ala Phe Ser Phe Ser Met
                20                  25                  30 ggc ttt gat ctg gcg acc acc gcg ttt tgg gat agc cat aac cgc ggc     144
Gly Phe Asp Leu Ala Thr Thr Ala Phe Trp Asp Ser His Asn Arg Gly
            35                  40                  45 aaa cag tgg aaa gat att cgc cat aaa tat att gaa gcg gcg ggc gat     192
Lys Gln Trp Lys Asp Ile Arg His Lys Tyr Ile Glu Ala Ala Gly Asp
        50                  55                  60 gat gaa                                                             198
Asp Glu
```

<210> SEQ ID NO 50
<211> LENGTH: 66
<212> TYPE: PRT
<213> ORGANISM: Cryptococcus neoformans

<400> SEQUENCE: 50

```
Met Pro Gly Phe Gln Asp Val Ile Tyr Asn Thr Phe Arg Arg Asn
1               5                   10                  15

Ser Val Phe Val Ala Thr Thr Phe Ile Ala Ala Phe Ser Phe Ser Met
                20                  25                  30

Gly Phe Asp Leu Ala Thr Thr Ala Phe Trp Asp Ser His Asn Arg Gly
            35                  40                  45

Lys Gln Trp Lys Asp Ile Arg His Lys Tyr Ile Glu Ala Ala Gly Asp
        50                  55                  60

Asp Glu
65
```

<210> SEQ ID NO 51
<211> LENGTH: 1368
<212> TYPE: DNA
<213> ORGANISM: Cryptococcus neoformans
<220> FEATURE:
<221> NAME/KEY: CDS
<222> LOCATION: (1)..(1368)

<400> SEQUENCE: 51

```
atg agc agc ggc aac gtg ccg aaa att gaa cgc ctg agc tgc gtg ccg      48
Met Ser Ser Gly Asn Val Pro Lys Ile Glu Arg Leu Ser Cys Val Pro
1               5                   10                  15 aac gat tat ccg tgg ggc gaa gtg ggc aac gat agc ctg gcg gcg cgc      96
Asn Asp Tyr Pro Trp Gly Glu Val Gly Asn Asp Ser Leu Ala Ala Arg
                20                  25                  30 ctg gcg agc aaa aac ggc gcg gtg agc ttt gat ctg aaa ccg gaa cag     144
Leu Ala Ser Lys Asn Gly Ala Val Ser Phe Asp Leu Lys Pro Glu Gln
            35                  40                  45 gcg tat gcg gaa ctg tgg atg ggc acc cat ccg aac aac ccg gcg cat     192
Ala Tyr Ala Glu Leu Trp Met Gly Thr His Pro Asn Asn Pro Ala His
        50                  55                  60 ctg ttt agc agc ccg gat acc ctg ctg agc acc cat ctg aaa aaa aac     240
Leu Phe Ser Ser Pro Asp Thr Leu Leu Ser Thr His Leu Lys Lys Asn
65                  70                  75                  80 ccg agc ctg ctg ggc gcg gcg aac cgc ttt agc ccg ccg ttt acc ggc     288
Pro Ser Leu Leu Gly Ala Ala Asn Arg Phe Ser Pro Pro Phe Thr Gly
                85                  90                  95 gcg aaa ggc agc ggc gcg gaa ggc cag gaa gaa ggc cat gtg ccg ttt     336
Ala Lys Gly Ser Gly Ala Glu Gly Gln Glu Glu Gly His Val Pro Phe
            100                 105                 110 ctg ttt aaa gtg ctg acc tgc aaa cag gcg ctg ccg ctg cag att cat     384
Leu Phe Lys Val Leu Thr Cys Lys Gln Ala Leu Pro Leu Gln Ile His
        115                 120                 125 ccg gat aaa gcg ctg gcg aaa aaa ctg cat gaa gaa aac ccg aaa cag     432
Pro Asp Lys Ala Leu Ala Lys Lys Leu His Glu Glu Asn Pro Lys Gln
130                 135                 140 ttt ggc gat att aac cat aaa ccg gaa att gcg gtg tgc ctg agc gat     480
Phe Gly Asp Ile Asn His Lys Pro Glu Ile Ala Val Cys Leu Ser Asp
145                 150                 155                 160 cgc ttt ctg ggc ttt gcg agc ttt cgc ccg tat gat aaa att gcg agc     528
Arg Phe Leu Gly Phe Ala Ser Phe Arg Pro Tyr Asp Lys Ile Ala Ser
                165                 170                 175
```

```
ctg ctg aaa agc gtg cag gaa att agc ctg ctg ccg agc ctg ctg cag      576
Leu Leu Lys Ser Val Gln Glu Ile Ser Leu Leu Pro Ser Leu Leu Gln
        180                 185                 190 aaa agc att aaa agc ttt att agc gcg ccg agc gcg gaa acc ctg cag      624
Lys Ser Ile Lys Ser Phe Ile Ser Ala Pro Ser Ala Glu Thr Leu Gln
            195                 200                 205 ccg acc tgg gaa ggc ttt att aaa ctg ggc gat aac gaa gaa agc gtg      672
Pro Thr Trp Glu Gly Phe Ile Lys Leu Gly Asp Asn Glu Glu Ser Val
        210                 215                 220 aaa aaa ttt agc gat cgc gtg ctg agc cag ggc ctg aaa gcg ttt gat      720
Lys Lys Phe Ser Asp Arg Val Leu Ser Gln Gly Leu Lys Ala Phe Asp
225                 230                 235                 240 agc gtg gat att gaa gat gaa gat aaa aac cgc ctg gtg cgc gcg gtg      768
Ser Val Asp Ile Glu Asp Glu Asp Lys Asn Arg Leu Val Arg Ala Val
            245                 250                 255 gaa ctg ggc aaa aaa tat aac ccg ggc gat gcg ggc ctg ttt agc agc      816
Glu Leu Gly Lys Lys Tyr Asn Pro Gly Asp Ala Gly Leu Phe Ser Ser
        260                 265                 270 ctg ctg ttt ctg aac ctg att gaa ctg aaa aaa gat cag ggc atg tat      864
Leu Leu Phe Leu Asn Leu Ile Glu Leu Lys Lys Asp Gln Gly Met Tyr
            275                 280                 285 gtg ggc gcg gat ggc ccg cat gcg tgg ctg gaa ggc gaa att gtg gaa      912
Val Gly Ala Asp Gly Pro His Ala Trp Leu Glu Gly Glu Ile Val Glu
        290                 295                 300 ctg atg gcg att agc gat aac gtg ctg aac gtg ggc ttt acc agc gat      960
Leu Met Ala Ile Ser Asp Asn Val Leu Asn Val Gly Phe Thr Ser Asp
305                 310                 315                 320 gat agc aaa gat gat ccg agc ctg gtg gcg aaa gcg gtg acc tgc acc     1008
Asp Ser Lys Asp Asp Pro Ser Leu Val Ala Lys Ala Val Thr Cys Thr
            325                 330                 335 ccg aaa gcg att aaa gat ctg ctg ctg gat gcg agc aaa tat agc aaa     1056
Pro Lys Ala Ile Lys Asp Leu Leu Leu Asp Ala Ser Lys Tyr Ser Lys
        340                 345                 350 agc cag aac ggc cgc acc acc gtg tat agc acc ccg ttt gaa gaa ttt     1104
Ser Gln Asn Gly Arg Thr Thr Val Tyr Ser Thr Pro Phe Glu Glu Phe
            355                 360                 365 agc att atg aaa att gcg ggc gat gaa att ctg agc ccg ctg gat ggc     1152
Ser Ile Met Lys Ile Ala Gly Asp Glu Ile Leu Ser Pro Leu Asp Gly
        370                 375                 380 gcg ggc gtg gcg gtg gtg ctg gaa ggc gaa tgg acc gtg gaa gat cag     1200
Ala Gly Val Ala Val Val Leu Glu Gly Glu Trp Thr Val Glu Asp Gln
385                 390                 395                 400 gaa ggc acc aaa cgc ggc ggc gaa ggc acc gat ggc gaa ggc ggc gaa     1248
Glu Gly Thr Lys Arg Gly Gly Glu Gly Thr Asp Gly Glu Gly Gly Glu
            405                 410                 415 ggc acc att tgg ttt att ggc agc gcg acc gaa acc aaa tgg acc gcg     1296
Gly Thr Ile Trp Phe Ile Gly Ser Ala Thr Glu Thr Lys Trp Thr Ala
        420                 425                 430 aaa ggc ggc aaa ggc cag att tgg att gcg ttt tat gat aaa acc gcg     1344
Lys Gly Gly Lys Gly Gln Ile Trp Ile Ala Phe Tyr Asp Lys Thr Ala
            435                 440                 445 aaa aaa gat gat gtg ggc aaa aaa                                     1368
Lys Lys Asp Asp Val Gly Lys Lys
        450                 455
```

<210> SEQ ID NO 52
<211> LENGTH: 456
<212> TYPE: PRT
<213> ORGANISM: Cryptococcus neoformans -continued

```
<400> SEQUENCE: 52

Met Ser Ser Gly Asn Val Pro Lys Ile Glu Arg Leu Ser Cys Val Pro
1               5                   10                  15

Asn Asp Tyr Pro Trp Gly Val Gly Asn Asp Ser Leu Ala Ala Arg
            20                  25                  30

Leu Ala Ser Lys Asn Gly Ala Val Ser Phe Asp Leu Lys Pro Glu Gln
                35                  40                  45

Ala Tyr Ala Glu Leu Trp Met Gly Thr His Pro Asn Asn Pro Ala His
        50                  55                  60

Leu Phe Ser Ser Pro Asp Thr Leu Leu Ser Thr His Leu Lys Lys Asn
65                  70                  75                  80

Pro Ser Leu Leu Gly Ala Ala Asn Arg Phe Ser Pro Pro Phe Thr Gly
                    85                  90                  95

Ala Lys Gly Ser Gly Ala Glu Gly Gln Glu Glu Gly His Val Pro Phe
            100                 105                 110

Leu Phe Lys Val Leu Thr Cys Lys Gln Ala Leu Pro Leu Gln Ile His
                115                 120                 125

Pro Asp Lys Ala Leu Ala Lys Lys Leu His Glu Glu Asn Pro Lys Gln
            130                 135                 140

Phe Gly Asp Ile Asn His Lys Pro Glu Ile Ala Val Cys Leu Ser Asp
145                 150                 155                 160

Arg Phe Leu Gly Phe Ala Ser Phe Arg Pro Tyr Asp Lys Ile Ala Ser
                    165                 170                 175

Leu Leu Lys Ser Val Gln Glu Ile Ser Leu Leu Pro Ser Leu Leu Gln
                180                 185                 190

Lys Ser Ile Lys Ser Phe Ile Ser Ala Pro Ser Ala Glu Thr Leu Gln
            195                 200                 205

Pro Thr Trp Glu Gly Phe Ile Lys Leu Gly Asp Asn Glu Glu Ser Val
        210                 215                 220

Lys Lys Phe Ser Asp Arg Val Leu Ser Gln Gly Leu Lys Ala Phe Asp
225                 230                 235                 240

Ser Val Asp Ile Glu Asp Glu Asp Lys Asn Arg Leu Val Arg Ala Val
                    245                 250                 255

Glu Leu Gly Lys Lys Tyr Asn Pro Gly Asp Ala Gly Leu Phe Ser Ser
                260                 265                 270

Leu Leu Phe Leu Asn Leu Ile Glu Leu Lys Lys Asp Gln Gly Met Tyr
            275                 280                 285

Val Gly Ala Asp Gly Pro His Ala Trp Leu Glu Gly Glu Ile Val Glu
        290                 295                 300

Leu Met Ala Ile Ser Asp Asn Val Leu Asn Val Gly Phe Thr Ser Asp
305                 310                 315                 320

Asp Ser Lys Asp Asp Pro Ser Leu Val Ala Lys Ala Val Thr Cys Thr
                    325                 330                 335

Pro Lys Ala Ile Lys Asp Leu Leu Leu Asp Ala Ser Lys Tyr Ser Lys
                340                 345                 350

Ser Gln Asn Gly Arg Thr Thr Val Tyr Ser Thr Pro Phe Glu Glu Phe
            355                 360                 365

Ser Ile Met Lys Ile Ala Gly Asp Glu Ile Leu Ser Pro Leu Asp Gly
        370                 375                 380

Ala Gly Val Ala Val Leu Glu Gly Glu Trp Thr Val Glu Asp Gln
385                 390                 395                 400

Glu Gly Thr Lys Arg Gly Gly Gly Thr Asp Gly Glu Gly Gly Glu
                405                 410                 415
```

```
Gly Thr Ile Trp Phe Ile Gly Ser Ala Thr Glu Thr Lys Trp Thr Ala
            420                 425                 430

Lys Gly Gly Lys Gly Gln Ile Trp Ile Ala Phe Tyr Asp Lys Thr Ala
        435                 440                 445

Lys Lys Asp Asp Val Gly Lys Lys
    450                 455

<210> SEQ ID NO 53
<211> LENGTH: 1962
<212> TYPE: DNA
<213> ORGANISM: Cryptococcus neoformans
<220> FEATURE:
<221> NAME/KEY: CDS
<222> LOCATION: (1)..(1962)

<400> SEQUENCE: 53 atg acc cgc gat ttt gat agc ctg ttt ttt acc ggc ccg att ttt gtg      48
Met Thr Arg Asp Phe Asp Ser Leu Phe Phe Thr Gly Pro Ile Phe Val
1               5                   10                  15 gat tat agc ttt acc gcg cgc cat ctg gaa agc ttt ctg agc agc ttt      96
Asp Tyr Ser Phe Thr Ala Arg His Leu Glu Ser Phe Leu Ser Ser Phe
                20                  25                  30 ccg ccg cag gtg agc cat gcg atg agc agc gcg agc acc ccg acc gcg     144
Pro Pro Gln Val Ser His Ala Met Ser Ser Ala Ser Thr Pro Thr Ala
            35                  40                  45 ccg tat ctg gaa gat ctg gtg cgc aac agc ctg gat cag acc ctg ccg     192
Pro Tyr Leu Glu Asp Leu Val Arg Asn Ser Leu Asp Gln Thr Leu Pro
        50                  55                  60 tgg gtg gtg cag aaa tat ggc ggc acc agc gtg ggc aaa agc ctg gat     240
Trp Val Val Gln Lys Tyr Gly Gly Thr Ser Val Gly Lys Ser Leu Asp
65                  70                  75                  80 aac att acc aaa att gtg ggc agc tat att gat aac ggc agc aaa gtg     288
Asn Ile Thr Lys Ile Val Gly Ser Tyr Ile Asp Asn Gly Ser Lys Val
                85                  90                  95 gcg att gtg tgc agc gcg cgc agc acc cag acc aaa agc ctg ggc acc     336
Ala Ile Val Cys Ser Ala Arg Ser Thr Gln Thr Lys Ser Leu Gly Thr
            100                 105                 110 acc aac ctg ctg ctg cag gcg agc cgc gaa gcg ctg cag ccg gcg ctg     384
Thr Asn Leu Leu Leu Gln Ala Ser Arg Glu Ala Leu Gln Pro Ala Leu
        115                 120                 125 agc agc agc ggc gat ggc cgc agc ggc agc atg agc ggc acc gcg acc     432
Ser Ser Ser Gly Asp Gly Arg Ser Gly Ser Met Ser Gly Thr Ala Thr
    130                 135                 140 ccg ttt tat ccg aaa cgc gtg ggc agc ggc ttt ttt ggc aaa gat cag     480
Pro Phe Tyr Pro Lys Arg Val Gly Ser Gly Phe Phe Gly Lys Asp Gln
145                 150                 155                 160 agc acc agc atg gtg agc agc gtg agc agc ctg agc cag ctg gaa ccg     528
Ser Thr Ser Met Val Ser Ser Val Ser Ser Leu Ser Gln Leu Glu Pro
                165                 170                 175 cag ctg ggc cgc agc ggc agc ccg agc ccg ttt cag agc agc agc agc     576
Gln Leu Gly Arg Ser Gly Ser Pro Ser Pro Phe Gln Ser Ser Ser Ser
            180                 185                 190 cgc agc ccg ccg cgc agc ccg gcg acc ccg agc cag gat agc agc gtg     624
Arg Ser Pro Pro Arg Ser Pro Ala Thr Pro Ser Gln Asp Ser Ser Val
        195                 200                 205 agc cag gaa ccg gcg ttt cat gcg acc gtg gat ctg att aaa aaa ggc     672
Ser Gln Glu Pro Ala Phe His Ala Thr Val Asp Leu Ile Lys Lys Gly
    210                 215                 220 cat ctg gaa gcg gcg cgc gcg agc ctg aaa gaa ggc ccg ctg cgc gat     720
His Leu Glu Ala Ala Arg Ala Ser Leu Lys Glu Gly Pro Leu Arg Asp
```

-continued

| | | | | |
|---|---|---|---|---|
| 225 | 230 | 235 | 240 | |

| | | |
|---|---|---|
| gaa ctg gaa gaa gaa att gaa cgc gat tgc gaa agc ctg cgc agc ttt<br>Glu Leu Glu Glu Glu Ile Glu Arg Asp Cys Glu Ser Leu Arg Ser Phe<br>245 250 255 | | 768 |
| ctg tat gcg gcg cag att att gat gaa att agc ccg cgc agc cag gat<br>Leu Tyr Ala Ala Gln Ile Ile Asp Glu Ile Ser Pro Arg Ser Gln Asp<br>260 265 270 | | 816 |
| agc att gtg ggc acc ggc gaa cgc ctg gcg tgc aaa att gtg gcg gcg<br>Ser Ile Val Gly Thr Gly Glu Arg Leu Ala Cys Lys Ile Val Ala Ala<br>275 280 285 | | 864 |
| gcg ctg cgc gat cgc ggc gtg gat agc gaa ctg gtg gtg ctg gat aac<br>Ala Leu Arg Asp Arg Gly Val Asp Ser Glu Leu Val Val Leu Asp Asn<br>290 295 300 | | 912 |
| att gtg gat gcg agc atg agc gcg gcg agc gaa gcg att agc gtg gat<br>Ile Val Asp Ala Ser Met Ser Ala Ala Ser Glu Ala Ile Ser Val Asp<br>305 310 315 320 | | 960 |
| gcg ggc gat cag ggc gtg gcg cag ctg ggc cag gaa ttt tat gat cag<br>Ala Gly Asp Gln Gly Val Ala Gln Leu Gly Gln Glu Phe Tyr Asp Gln<br>325 330 335 | | 1008 |
| ctg agc ttt cgc ctg ggc gaa cgc ctg cgc gaa tgc ggc cag cgc gtg<br>Leu Ser Phe Arg Leu Gly Glu Arg Leu Arg Glu Cys Gly Gln Arg Val<br>340 345 350 | | 1056 |
| ccg gtg gtg acc ggc tat ttt ggc ccg gtg ccg ggc agc ctg ctg gcg<br>Pro Val Val Thr Gly Tyr Phe Gly Pro Val Pro Gly Ser Leu Leu Ala<br>355 360 365 | | 1104 |
| cag att ggc cgc ggc tat acc gat ctg tgc gcg gcg ctg tgc gcg gtg<br>Gln Ile Gly Arg Gly Tyr Thr Asp Leu Cys Ala Ala Leu Cys Ala Val<br>370 375 380 | | 1152 |
| ggc ctg aaa gcg agc gaa ctg cag gtg tgg aaa gaa gtg gat ggc att<br>Gly Leu Lys Ala Ser Glu Leu Gln Val Trp Lys Glu Val Asp Gly Ile<br>385 390 395 400 | | 1200 |
| ttt acc gcg gat ccg cgc aaa gtg ccg agc gcg cgc ctg gtg ccg att<br>Phe Thr Ala Asp Pro Arg Lys Val Pro Ser Ala Arg Leu Val Pro Ile<br>405 410 415 | | 1248 |
| att acc ccg gat gaa gcg gcg gaa ctg acc tat tat ggc agc gaa gtg<br>Ile Thr Pro Asp Glu Ala Ala Glu Leu Thr Tyr Tyr Gly Ser Glu Val<br>420 425 430 | | 1296 |
| att cat ccg ttt acc atg gaa cag gtg att cgc gcg cgc att ccg att<br>Ile His Pro Phe Thr Met Glu Gln Val Ile Arg Ala Arg Ile Pro Ile<br>435 440 445 | | 1344 |
| cgc att aaa aac gtg gaa aac ccg agc ggc gcg ggc acc gtg att tat<br>Arg Ile Lys Asn Val Glu Asn Pro Ser Gly Ala Gly Thr Val Ile Tyr<br>450 455 460 | | 1392 |
| ccg gat ctg ggc ttt ccg cgc ggc ctg gat acc gaa ccg ccg aaa gcg<br>Pro Asp Leu Gly Phe Pro Arg Gly Leu Asp Thr Glu Pro Pro Lys Ala<br>465 470 475 480 | | 1440 |
| gaa cgc att gtg gaa ggc gtg gat gaa cgc atg ccg acc gcg gtg acc<br>Glu Arg Ile Val Glu Gly Val Asp Glu Arg Met Pro Thr Ala Val Thr<br>485 490 495 | | 1488 |
| att aaa gat gaa att att gtg ctg aac att cat agc aac cgc aaa acc<br>Ile Lys Asp Glu Ile Ile Val Leu Asn Ile His Ser Asn Arg Lys Thr<br>500 505 510 | | 1536 |
| ctg agc cat ggc ttt ctg gcg cgc att ttt ggc acc ctg gat cgc gcg<br>Leu Ser His Gly Phe Leu Ala Arg Ile Phe Gly Thr Leu Asp Arg Ala<br>515 520 525 | | 1584 |
| ggc gtg gtg gtg gat ctg att agc acc agc gaa gtg cat gtg agc atg<br>Gly Val Val Val Asp Leu Ile Ser Thr Ser Glu Val His Val Ser Met<br>530 535 540 | | 1632 |
| gcg atg cag gat ttt ctg aac cgc aaa cgc ctg gaa cgc ctg gtg aaa | | 1680 |

```
Ala Met Gln Asp Phe Leu Asn Arg Lys Arg Leu Glu Arg Leu Val Lys
545                 550                 555                 560 gat ctg gaa aaa att ggc gaa gtg acc gtg agc aaa gat atg gcg att      1728
Asp Leu Glu Lys Ile Gly Glu Val Thr Val Ser Lys Asp Met Ala Ile
                565                 570                 575 ctg agc ctg gtg ggc cgc aac atg cgc aac gcg att ggc agc gcg ggc      1776
Leu Ser Leu Val Gly Arg Asn Met Arg Asn Ala Ile Gly Ser Ala Gly
            580                 585                 590 ctg atg ttt gcg agc ctg gcg cgc gcg atg att aac att gaa atg att      1824
Leu Met Phe Ala Ser Leu Ala Arg Ala Met Ile Asn Ile Glu Met Ile
        595                 600                 605 agc cag ggc gcg agc gaa att aac att agc tgc gtg att gaa aac aaa      1872
Ser Gln Gly Ala Ser Glu Ile Asn Ile Ser Cys Val Ile Glu Asn Lys
    610                 615                 620 gat gcg att aaa gcg ctg aac gtg att cat gaa agc tgc ctg agc tat      1920
Asp Ala Ile Lys Ala Leu Asn Val Ile His Glu Ser Cys Leu Ser Tyr
625                 630                 635                 640 ccg cgc agc ccg gcg acc gaa atg gcg ggc ctg cag ctg cag              1962
Pro Arg Ser Pro Ala Thr Glu Met Ala Gly Leu Gln Leu Gln
                645                 650

<210> SEQ ID NO 54
<211> LENGTH: 654
<212> TYPE: PRT
<213> ORGANISM: Cryptococcus neoformans

<400> SEQUENCE: 54

Met Thr Arg Asp Phe Asp Ser Leu Phe Phe Thr Gly Pro Ile Phe Val
1               5                   10                  15

Asp Tyr Ser Phe Thr Ala Arg His Leu Glu Ser Phe Leu Ser Ser Phe
                20                  25                  30

Pro Pro Gln Val Ser His Ala Met Ser Ser Ala Ser Thr Pro Thr Ala
            35                  40                  45

Pro Tyr Leu Glu Asp Leu Val Arg Asn Ser Leu Asp Gln Thr Leu Pro
        50                  55                  60

Trp Val Val Gln Lys Tyr Gly Thr Ser Val Gly Lys Ser Leu Asp
65                  70                  75                  80

Asn Ile Thr Lys Ile Val Gly Ser Tyr Ile Asp Asn Gly Ser Lys Val
                85                  90                  95

Ala Ile Val Cys Ser Ala Arg Ser Thr Gln Thr Lys Ser Leu Gly Thr
            100                 105                 110

Thr Asn Leu Leu Leu Gln Ala Ser Arg Glu Ala Leu Gln Pro Ala Leu
        115                 120                 125

Ser Ser Ser Gly Asp Gly Arg Ser Gly Ser Met Ser Gly Thr Ala Thr
    130                 135                 140

Pro Phe Tyr Pro Lys Arg Val Gly Ser Gly Phe Phe Gly Lys Asp Gln
145                 150                 155                 160

Ser Thr Ser Met Val Ser Ser Val Ser Ser Leu Ser Gln Leu Glu Pro
                165                 170                 175

Gln Leu Gly Arg Ser Gly Ser Pro Ser Pro Phe Gln Ser Ser Ser Ser
            180                 185                 190

Arg Ser Pro Pro Arg Ser Pro Ala Thr Pro Ser Gln Asp Ser Ser Val
        195                 200                 205

Ser Gln Glu Pro Ala Phe His Ala Thr Val Asp Leu Ile Lys Lys Gly
    210                 215                 220

His Leu Glu Ala Ala Arg Ala Ser Leu Lys Glu Gly Pro Leu Arg Asp
225                 230                 235                 240
```

-continued

Glu Leu Glu Glu Glu Ile Glu Arg Asp Cys Glu Ser Leu Arg Ser Phe
            245                 250                 255

Leu Tyr Ala Ala Gln Ile Ile Asp Glu Ile Ser Pro Arg Ser Gln Asp
            260                 265                 270

Ser Ile Val Gly Thr Gly Glu Arg Leu Ala Cys Lys Ile Val Ala Ala
            275                 280                 285

Ala Leu Arg Asp Arg Gly Val Asp Ser Glu Leu Val Val Leu Asp Asn
            290                 295                 300

Ile Val Asp Ala Ser Met Ser Ala Ala Ser Glu Ala Ile Ser Val Asp
305                 310                 315                 320

Ala Gly Asp Gln Gly Val Ala Gln Leu Gly Gln Glu Phe Tyr Asp Gln
            325                 330                 335

Leu Ser Phe Arg Leu Gly Glu Arg Leu Arg Glu Cys Gly Gln Arg Val
            340                 345                 350

Pro Val Val Thr Gly Tyr Phe Gly Pro Val Pro Gly Ser Leu Leu Ala
            355                 360                 365

Gln Ile Gly Arg Gly Tyr Thr Asp Leu Cys Ala Ala Leu Cys Ala Val
            370                 375                 380

Gly Leu Lys Ala Ser Glu Leu Gln Val Trp Lys Glu Val Asp Gly Ile
385                 390                 395                 400

Phe Thr Ala Asp Pro Arg Lys Val Pro Ser Ala Arg Leu Val Pro Ile
            405                 410                 415

Ile Thr Pro Asp Glu Ala Ala Glu Leu Thr Tyr Tyr Gly Ser Glu Val
            420                 425                 430

Ile His Pro Phe Thr Met Glu Gln Val Ile Arg Ala Arg Ile Pro Ile
            435                 440                 445

Arg Ile Lys Asn Val Glu Asn Pro Ser Gly Ala Gly Thr Val Ile Tyr
450                 455                 460

Pro Asp Leu Gly Phe Pro Arg Gly Leu Asp Thr Glu Pro Pro Lys Ala
465                 470                 475                 480

Glu Arg Ile Val Glu Gly Val Asp Glu Arg Met Pro Thr Ala Val Thr
            485                 490                 495

Ile Lys Asp Glu Ile Ile Val Leu Asn Ile His Ser Asn Arg Lys Thr
            500                 505                 510

Leu Ser His Gly Phe Leu Ala Arg Ile Phe Gly Thr Leu Asp Arg Ala
            515                 520                 525

Gly Val Val Asp Leu Ile Ser Thr Ser Glu Val His Val Ser Met
            530                 535                 540

Ala Met Gln Asp Phe Leu Asn Arg Lys Arg Leu Glu Arg Leu Val Lys
545                 550                 555                 560

Asp Leu Glu Lys Ile Gly Glu Val Thr Val Ser Lys Asp Met Ala Ile
            565                 570                 575

Leu Ser Leu Val Gly Arg Asn Met Arg Asn Ala Ile Gly Ser Ala Gly
            580                 585                 590

Leu Met Phe Ala Ser Leu Ala Arg Ala Met Ile Asn Ile Glu Met Ile
            595                 600                 605

Ser Gln Gly Ala Ser Glu Ile Asn Ile Ser Cys Val Ile Glu Asn Lys
            610                 615                 620

Asp Ala Ile Lys Ala Leu Asn Val Ile His Glu Ser Cys Leu Ser Tyr
625                 630                 635                 640

Pro Arg Ser Pro Ala Thr Glu Met Ala Gly Leu Gln Leu Gln
            645                 650

```
<210> SEQ ID NO 55
<211> LENGTH: 1269
<212> TYPE: DNA
<213> ORGANISM: Cryptococcus neoformans
<220> FEATURE:
<221> NAME/KEY: CDS
<222> LOCATION: (1)..(1269)

<400> SEQUENCE: 55 atg ccg aaa cag tgg ccg acc att gtg aaa ctg gaa acc ttt att ccg      48
Met Pro Lys Gln Trp Pro Thr Ile Val Lys Leu Glu Thr Phe Ile Pro
1               5                   10                  15 agc gcg cat ggc agc ggc ggc gat tat cat cgc cag ggc ggc gat cat      96
Ser Ala His Gly Ser Gly Gly Asp Tyr His Arg Gln Gly Gly Asp His
                20                  25                  30 tgg att gtg cag ggc aac att agc tgc ccg atg cat aaa tat gaa gaa     144
Trp Ile Val Gln Gly Asn Ile Ser Cys Pro Met His Lys Tyr Glu Glu
            35                  40                  45 tat aaa gtg agc cgc acc agc tgg ggc att ggc gtg ctg ggc agc att     192
Tyr Lys Val Ser Arg Thr Ser Trp Gly Ile Gly Val Leu Gly Ser Ile
        50                  55                  60 ttt gtg aaa gtg cat gcg agc gat ggc acc gtg ggc tat gcg acc ggc     240
Phe Val Lys Val His Ala Ser Asp Gly Thr Val Gly Tyr Ala Thr Gly
65                  70                  75                  80 ttt ggc ggc ccg ccg gcg tgc tgg ctg att gaa gaa cat ttt aaa cgc     288
Phe Gly Gly Pro Pro Ala Cys Trp Leu Ile Glu Glu His Phe Lys Arg
                85                  90                  95 ttt att gtg ggc cag gat ccg cgc gat acc aac aaa atg tgg gat cag     336
Phe Ile Val Gly Gln Asp Pro Arg Asp Thr Asn Lys Met Trp Asp Gln
                100                 105                 110 atg ttt cgc gcg agc atg ttt tat ggc cgc aaa ggc ctg ccg ctg gcg     384
Met Phe Arg Ala Ser Met Phe Tyr Gly Arg Lys Gly Leu Pro Leu Ala
            115                 120                 125 gcg att agc gtg gtg gat ctg gcg att tgg gat ctg ctg ggc aaa att     432
Ala Ile Ser Val Val Asp Leu Ala Ile Trp Asp Leu Leu Gly Lys Ile
        130                 135                 140 cgc ggc gaa ccg att tat aaa atg att ggc ggc cgc acc aaa aaa gat     480
Arg Gly Glu Pro Ile Tyr Lys Met Ile Gly Gly Arg Thr Lys Lys Asp
145                 150                 155                 160 att ccg ctg tat ctg acc ggc ccg cgc ccg gaa gtg gcg aaa aaa ctg     528
Ile Pro Leu Tyr Leu Thr Gly Pro Arg Pro Glu Val Ala Lys Lys Leu
                165                 170                 175 ggc ttt tgg ggc agc aaa gtg gcg ctg ccg cat ggc ccg ccg gat ggc     576
Gly Phe Trp Gly Ser Lys Val Ala Leu Pro His Gly Pro Pro Asp Gly
                180                 185                 190 cat gaa ggc att cgc aaa aac gtg gaa tat ctg aaa gcg tgc aaa gaa     624
His Glu Gly Ile Arg Lys Asn Val Glu Tyr Leu Lys Ala Cys Lys Glu
            195                 200                 205 gcg gtg ggc ccg gat tat ccg gtg cag gtg gat tgc tat atg agc ctg     672
Ala Val Gly Pro Asp Tyr Pro Val Gln Val Asp Cys Tyr Met Ser Leu
        210                 215                 220 gat gtg ccg tat acc att gcg ctg gtg aaa gcg tgc gaa aaa gcg ggc     720
Asp Val Pro Tyr Thr Ile Ala Leu Val Lys Ala Cys Glu Lys Ala Gly
225                 230                 235                 240 gtg gaa att aac tgg tgg gaa gaa gtg ctg cat ccg gat gat ttt gat     768
Val Glu Ile Asn Trp Trp Glu Glu Val Leu His Pro Asp Asp Phe Asp
                245                 250                 255 ggc cat att aaa ctg aaa gaa gcg ctg ccg tat gtg aaa ttt acc acc     816
Gly His Ile Lys Leu Lys Glu Ala Leu Pro Tyr Val Lys Phe Thr Thr
                260                 265                 270
```

-continued

```
ggc gaa cat gaa tat agc aaa tat ggc ttt cgc aaa ctg att gaa aac    864
Gly Glu His Glu Tyr Ser Lys Tyr Gly Phe Arg Lys Leu Ile Glu Asn
        275                 280                 285 cgc gcg gtg gat att att cag ccg gat gtg atg tgg ctg ggc ggc ctg    912
Arg Ala Val Asp Ile Ile Gln Pro Asp Val Met Trp Leu Gly Gly Leu
    290                 295                 300 acc gaa ctg att aaa gtg gcg gcg atg gcg gcg gcg tat gat att ccg    960
Thr Glu Leu Ile Lys Val Ala Ala Met Ala Ala Ala Tyr Asp Ile Pro
305                 310                 315                 320 gtg gtg ccg cat ggc agc ggc ccg tat agc ttt cag gcg att atg agc   1008
Val Val Pro His Gly Ser Gly Pro Tyr Ser Phe Gln Ala Ile Met Ser
                325                 330                 335 ttt ccg aac agc gat ttt tgc gaa tat att gcg aac agc ccg gat ggc   1056
Phe Pro Asn Ser Asp Phe Cys Glu Tyr Ile Ala Asn Ser Pro Asp Gly
            340                 345                 350 aaa agc att gaa ccg agc ttt ggc aac ctg ttt ctg aac gaa gtg ctg   1104
Lys Ser Ile Glu Pro Ser Phe Gly Asn Leu Phe Leu Asn Glu Val Leu
        355                 360                 365 ccg cgc aac ggc cgc gtg gat ctg acc gat gaa ccg ggc ttt ggc ctg   1152
Pro Arg Asn Gly Arg Val Asp Leu Thr Asp Glu Pro Gly Phe Gly Leu
    370                 375                 380 gaa ctg aac ccg agc gcg gaa ctg gtg ccg tat aaa agc ttt ttt acc   1200
Glu Leu Asn Pro Ser Ala Glu Leu Val Pro Tyr Lys Ser Phe Phe Thr
385                 390                 395                 400 ccg agc aaa agc ctg ggc gcg gcg ggc gaa gtg gaa gat gat ggc aaa   1248
Pro Ser Lys Ser Leu Gly Ala Ala Gly Glu Val Glu Asp Asp Gly Lys
                405                 410                 415 gcg aaa gtg aac ggc aaa cat                                        1269
Ala Lys Val Asn Gly Lys His
            420

<210> SEQ ID NO 56
<211> LENGTH: 423
<212> TYPE: PRT
<213> ORGANISM: Cryptococcus neoformans

<400> SEQUENCE: 56

Met Pro Lys Gln Trp Pro Thr Ile Val Lys Leu Glu Thr Phe Ile Pro
1               5                   10                  15

Ser Ala His Gly Ser Gly Gly Asp Tyr His Arg Gln Gly Gly Asp His
            20                  25                  30

Trp Ile Val Gln Gly Asn Ile Ser Cys Pro Met His Lys Tyr Glu Glu
        35                  40                  45

Tyr Lys Val Ser Arg Thr Ser Trp Gly Ile Gly Val Leu Gly Ser Ile
    50                  55                  60

Phe Val Lys Val His Ala Ser Asp Gly Thr Val Gly Tyr Ala Thr Gly
65                  70                  75                  80

Phe Gly Gly Pro Pro Ala Cys Trp Leu Ile Glu Glu His Phe Lys Arg
                85                  90                  95

Phe Ile Val Gly Gln Asp Pro Arg Asp Thr Asn Lys Met Trp Asp Gln
            100                 105                 110

Met Phe Arg Ala Ser Met Phe Tyr Gly Arg Lys Gly Leu Pro Leu Ala
        115                 120                 125

Ala Ile Ser Val Val Asp Leu Ala Ile Trp Asp Leu Leu Gly Lys Ile
    130                 135                 140

Arg Gly Glu Pro Ile Tyr Lys Met Ile Gly Gly Arg Thr Lys Lys Asp
145                 150                 155                 160

Ile Pro Leu Tyr Leu Thr Gly Pro Arg Pro Glu Val Ala Lys Lys Leu
```

```
            165                 170                 175
Gly Phe Trp Gly Ser Lys Val Ala Leu Pro His Gly Pro Pro Asp Gly
            180                 185                 190

His Glu Gly Ile Arg Lys Asn Val Glu Tyr Leu Lys Ala Cys Lys Glu
        195                 200                 205

Ala Val Gly Pro Asp Tyr Pro Val Gln Val Asp Cys Tyr Met Ser Leu
    210                 215                 220

Asp Val Pro Tyr Thr Ile Ala Leu Val Lys Ala Cys Glu Lys Ala Gly
225                 230                 235                 240

Val Glu Ile Asn Trp Trp Glu Val Leu His Pro Asp Asp Phe Asp
                245                 250                 255

Gly His Ile Lys Leu Lys Glu Ala Leu Pro Tyr Val Lys Phe Thr Thr
            260                 265                 270

Gly Glu His Glu Tyr Ser Lys Tyr Gly Phe Arg Lys Leu Ile Glu Asn
        275                 280                 285

Arg Ala Val Asp Ile Ile Gln Pro Asp Val Met Trp Leu Gly Gly Leu
    290                 295                 300

Thr Glu Leu Ile Lys Val Ala Ala Met Ala Ala Ala Tyr Asp Ile Pro
305                 310                 315                 320

Val Val Pro His Gly Ser Gly Pro Tyr Ser Phe Gln Ala Ile Met Ser
                325                 330                 335

Phe Pro Asn Ser Asp Phe Cys Glu Tyr Ile Ala Asn Ser Pro Asp Gly
            340                 345                 350

Lys Ser Ile Glu Pro Ser Phe Gly Asn Leu Phe Leu Asn Glu Val Leu
        355                 360                 365

Pro Arg Asn Gly Arg Val Asp Leu Thr Asp Glu Pro Gly Phe Gly Leu
    370                 375                 380

Glu Leu Asn Pro Ser Ala Glu Leu Val Pro Tyr Lys Ser Phe Phe Thr
385                 390                 395                 400

Pro Ser Lys Ser Leu Gly Ala Ala Gly Glu Val Glu Asp Asp Gly Lys
                405                 410                 415

Ala Lys Val Asn Gly Lys His
            420

<210> SEQ ID NO 57
<211> LENGTH: 1743
<212> TYPE: DNA
<213> ORGANISM: Cryptococcus neoformans
<220> FEATURE:
<221> NAME/KEY: CDS
<222> LOCATION: (1)..(1743)

<400> SEQUENCE: 57 atg gcg aac gcg ccg cat ggc ggc gtg ctg aaa gat ctg ctg gtg cgc      48
Met Ala Asn Ala Pro His Gly Gly Val Leu Lys Asp Leu Leu Val Arg
1               5                   10                  15 gat gcg gcg ctg cat gat agc ctg ctg cag gaa gcg cgc agc ctg aac      96
Asp Ala Ala Leu His Asp Ser Leu Leu Gln Glu Ala Arg Ser Leu Asn
            20                  25                  30 gat att ttt ctg acc gaa cgc cag ctg tgc gat ctg gaa ctg att ctg     144
Asp Ile Phe Leu Thr Glu Arg Gln Leu Cys Asp Leu Glu Leu Ile Leu
        35                  40                  45 aac ggc ggc ttt agc ccg ctg gaa ggc ttt atg aac gaa cgc gat tat     192
Asn Gly Gly Phe Ser Pro Leu Glu Gly Phe Met Asn Glu Arg Asp Tyr
    50                  55                  60 acc agc gtg gtg gaa acc ctg cgc ctg gcg ccg tat aac ggc cag aaa     240
Thr Ser Val Val Glu Thr Leu Arg Leu Ala Pro Tyr Asn Gly Gln Lys
```

```
                65                  70                  75                  80
cat ggc gat gtg ttt ccg att ccg att acc ctg gat gtg agc cag gaa        288
His Gly Asp Val Phe Pro Ile Pro Ile Thr Leu Asp Val Ser Gln Glu
                    85                  90                  95 gat att aac acc ctg ggc ctg aaa cag ggc ggc cgc gtg gcg ctg cgc        336
Asp Ile Asn Thr Leu Gly Leu Lys Gln Gly Gly Arg Val Ala Leu Arg
            100                 105                 110 gat ccg cgc gat gat gcg gcg ctg gcg att ctg acc gtg agc gat att        384
Asp Pro Arg Asp Asp Ala Ala Leu Ala Ile Leu Thr Val Ser Asp Ile
        115                 120                 125 tat cgc ccg aac aaa gcg att gaa gcg gaa aaa gtg atg ggc gcg gat        432
Tyr Arg Pro Asn Lys Ala Ile Glu Ala Glu Lys Val Met Gly Ala Asp
    130                 135                 140 gat att gcg cat ccg agc gtg gcg tat ctg cgc aac aac gtg aaa gaa        480
Asp Ile Ala His Pro Ser Val Ala Tyr Leu Arg Asn Asn Val Lys Glu
145                 150                 155                 160 ttt tat gtg ggc ggc aaa gtg cag gcg att cag gcg ccg acc cat ttt        528
Phe Tyr Val Gly Gly Lys Val Gln Ala Ile Gln Ala Pro Thr His Phe
                165                 170                 175 gat tat gtg ccg ctg cgc ttt acc ccg gcg gaa ctg cgc gcg cat ttt        576
Asp Tyr Val Pro Leu Arg Phe Thr Pro Ala Glu Leu Arg Ala His Phe
            180                 185                 190 cat aaa ctg gcg tgg cgc aaa gtg gtg gcg ttt cag acc cgc aac ccg        624
His Lys Leu Ala Trp Arg Lys Val Val Ala Phe Gln Thr Arg Asn Pro
        195                 200                 205 atg cat cgc gcg cat cgc gaa ctg acc gtg cgc gcg gcg cgc cag cgc        672
Met His Arg Ala His Arg Glu Leu Thr Val Arg Ala Ala Arg Gln Arg
    210                 215                 220 cgc gcg aac gtg ctg att cat ccg gtg gtg ggc ctg acc aaa ccg ggc        720
Arg Ala Asn Val Leu Ile His Pro Val Val Gly Leu Thr Lys Pro Gly
225                 230                 235                 240 gat gtg gat cat tat acc cgc gtg cgc gcg tat cag gcg ctg atg ccg        768
Asp Val Asp His Tyr Thr Arg Val Arg Ala Tyr Gln Ala Leu Met Pro
                245                 250                 255 agc tat ccg gaa ggc atg gcg cat ctg gcg ctg ctg ccg ctg gcg atg        816
Ser Tyr Pro Glu Gly Met Ala His Leu Ala Leu Leu Pro Leu Ala Met
            260                 265                 270 cgc atg gcg ggc ccg cgc gaa gcg gtg tgg cat gcg gtg att cgc aaa        864
Arg Met Ala Gly Pro Arg Glu Ala Val Trp His Ala Val Ile Arg Lys
        275                 280                 285 aac ttt ggc gcg acc cat ttt att gtg ggc cgc gat cat gcg ggc ccg        912
Asn Phe Gly Ala Thr His Phe Ile Val Gly Arg Asp His Ala Gly Pro
    290                 295                 300 ggc aaa aac agc cag ggc cag gat ttt tat ggc ccg tat gat gcg cag        960
Gly Lys Asn Ser Gln Gly Gln Asp Phe Tyr Gly Pro Tyr Asp Ala Gln
305                 310                 315                 320 gaa ctg gtg acc cag ttt aaa gat gaa ctg cag att gaa atg gtg ccg       1008
Glu Leu Val Thr Gln Phe Lys Asp Glu Leu Gln Ile Glu Met Val Pro
                325                 330                 335 ttt cag gcg atg acc tat ctg ccg ggc agc gat gaa tat cag ccg gtg       1056
Phe Gln Ala Met Thr Tyr Leu Pro Gly Ser Asp Glu Tyr Gln Pro Val
            340                 345                 350 gat gaa gtg ccg aaa ggc acc ccg acc gcg gat att agc ggc acc gaa       1104
Asp Glu Val Pro Lys Gly Thr Pro Thr Ala Asp Ile Ser Gly Thr Glu
        355                 360                 365 ctg cgc aaa cgc ctg cgc acc ggc gcg agc att ccg gat tgg ttt agc       1152
Leu Arg Lys Arg Leu Arg Thr Gly Ala Ser Ile Pro Asp Trp Phe Ser
    370                 375                 380 tat acc ggc gtg gtg aaa gtg ctg cgc gaa agc tat ccg ccg cgc ccg       1200
```

| | | | | | | | | | | | | | | | |
|---|---|---|---|---|---|---|---|---|---|---|---|---|---|---|---|
| | Tyr | Thr | Gly | Val | Val | Lys | Val | Leu | Arg | Glu | Ser | Tyr | Pro | Pro | Arg | Pro |
| | 385 | | | | 390 | | | | | 395 | | | | | 400 |

```
cag cag ggc ttt acc att ctg ctg acc ggc ctg cat aac agc ggc aaa      1248
Gln Gln Gly Phe Thr Ile Leu Leu Thr Gly Leu His Asn Ser Gly Lys
            405                 410                 415 gat acc att gcg cgc gcg ctg cag gtg acc ctg cag cag cag ggc agc      1296
Asp Thr Ile Ala Arg Ala Leu Gln Val Thr Leu Gln Gln Gln Gly Ser
        420                 425                 430 cgc agc gtg agc ctg ctg ctg ggc gaa gaa ctg cgc agc gat ctg gat      1344
Arg Ser Val Ser Leu Leu Leu Gly Glu Glu Leu Arg Ser Asp Leu Asp
    435                 440                 445 ccg cag att ggc cgc gcg att acc ccg gaa cag aaa cat att aac ctg      1392
Pro Gln Ile Gly Arg Ala Ile Thr Pro Glu Gln Lys His Ile Asn Leu
450                 455                 460 gaa cgc att ggc ttt gtg gcg ggc gaa ctg acc aaa gcg ggc gcg gcg      1440
Glu Arg Ile Gly Phe Val Ala Gly Glu Leu Thr Lys Ala Gly Ala Ala
465                 470                 475                 480 gtg att gcg gcg ccg acc gcg ccg tat gaa cgc agc cgc cag gcg ttt      1488
Val Ile Ala Ala Pro Thr Ala Pro Tyr Glu Arg Ser Arg Gln Ala Phe
                485                 490                 495 aaa aaa cag gtg gtg ggc agc ggc ggc ggc aac tat ttt ctg gtg cat      1536
Lys Lys Gln Val Val Gly Ser Gly Gly Gly Asn Tyr Phe Leu Val His
            500                 505                 510 gtg gcg acc ccg ctg gaa tgg tgc gaa aaa gtg gat cgc cgc ggc ctg      1584
Val Ala Thr Pro Leu Glu Trp Cys Glu Lys Val Asp Arg Arg Gly Leu
        515                 520                 525 tat aaa gcg gcg cgc gcg ggc gaa att aaa aac ctg acc ggc gtg gat      1632
Tyr Lys Ala Ala Arg Ala Gly Glu Ile Lys Asn Leu Thr Gly Val Asp
    530                 535                 540 gat gtg tat gaa gcg ccg gaa gat gcg gat ctg gtg tgc gat ctg cgc      1680
Asp Val Tyr Glu Ala Pro Glu Asp Ala Asp Leu Val Cys Asp Leu Arg
545                 550                 555                 560 aac gat acc gtg ccg gaa att gtg cat agc att att atg att ctg gaa      1728
Asn Asp Thr Val Pro Glu Ile Val His Ser Ile Ile Met Ile Leu Glu
                565                 570                 575 agc cag aac ctg gtg                                                  1743
Ser Gln Asn Leu Val
            580
```

<210> SEQ ID NO 58
<211> LENGTH: 581
<212> TYPE: PRT
<213> ORGANISM: Cryptococcus neoformans

<400> SEQUENCE: 58

```
Met Ala Asn Ala Pro His Gly Gly Val Leu Lys Asp Leu Leu Val Arg
1               5                   10                  15

Asp Ala Ala Leu His Asp Ser Leu Leu Gln Glu Ala Arg Ser Leu Asn
            20                  25                  30

Asp Ile Phe Leu Thr Glu Arg Gln Leu Cys Asp Leu Glu Leu Ile Leu
        35                  40                  45

Asn Gly Gly Phe Ser Pro Leu Glu Gly Phe Met Asn Glu Arg Asp Tyr
    50                  55                  60

Thr Ser Val Val Glu Thr Leu Arg Leu Ala Pro Tyr Asn Gly Gln Lys
65                  70                  75                  80

His Gly Asp Val Phe Pro Ile Pro Ile Thr Leu Asp Val Ser Gln Glu
                85                  90                  95

Asp Ile Asn Thr Leu Gly Leu Lys Gln Gly Gly Arg Val Ala Leu Arg
            100                 105                 110
```

```
Asp Pro Arg Asp Asp Ala Ala Leu Ala Ile Leu Thr Val Ser Asp Ile
        115                 120                 125

Tyr Arg Pro Asn Lys Ala Ile Glu Ala Glu Lys Val Met Gly Ala Asp
        130                 135                 140

Asp Ile Ala His Pro Ser Val Ala Tyr Leu Arg Asn Asn Val Lys Glu
145                 150                 155                 160

Phe Tyr Val Gly Gly Lys Val Gln Ala Ile Gln Ala Pro Thr His Phe
                165                 170                 175

Asp Tyr Val Pro Leu Arg Phe Thr Pro Ala Glu Leu Arg Ala His Phe
            180                 185                 190

His Lys Leu Ala Trp Arg Lys Val Val Ala Phe Gln Thr Arg Asn Pro
        195                 200                 205

Met His Arg Ala His Arg Glu Leu Thr Val Arg Ala Ala Arg Gln Arg
    210                 215                 220

Arg Ala Asn Val Leu Ile His Pro Val Gly Leu Thr Lys Pro Gly Gly
225                 230                 235                 240

Asp Val Asp His Tyr Thr Arg Val Arg Ala Tyr Gln Ala Leu Met Pro
                245                 250                 255

Ser Tyr Pro Glu Gly Met Ala His Leu Ala Leu Leu Pro Leu Ala Met
            260                 265                 270

Arg Met Ala Gly Pro Arg Glu Ala Val Trp His Ala Val Ile Arg Lys
        275                 280                 285

Asn Phe Gly Ala Thr His Phe Ile Val Gly Arg Asp His Ala Gly Pro
    290                 295                 300

Gly Lys Asn Ser Gln Gly Gln Asp Phe Tyr Gly Pro Tyr Asp Ala Gln
305                 310                 315                 320

Glu Leu Val Thr Gln Phe Lys Asp Glu Leu Gln Ile Glu Met Val Pro
                325                 330                 335

Phe Gln Ala Met Thr Tyr Leu Pro Gly Ser Asp Glu Tyr Gln Pro Val
            340                 345                 350

Asp Glu Val Pro Lys Gly Thr Pro Thr Ala Asp Ile Ser Gly Thr Glu
        355                 360                 365

Leu Arg Lys Arg Leu Arg Thr Gly Ala Ser Ile Pro Asp Trp Phe Ser
    370                 375                 380

Tyr Thr Gly Val Val Lys Val Leu Arg Glu Ser Tyr Pro Pro Arg Pro
385                 390                 395                 400

Gln Gln Gly Phe Thr Ile Leu Leu Thr Gly Leu His Asn Ser Gly Lys
                405                 410                 415

Asp Thr Ile Ala Arg Ala Leu Gln Val Thr Leu Gln Gln Gly Ser
            420                 425                 430

Arg Ser Val Ser Leu Leu Leu Gly Glu Glu Leu Arg Ser Asp Leu Asp
        435                 440                 445

Pro Gln Ile Gly Arg Ala Ile Thr Pro Glu Gln Lys His Ile Asn Leu
    450                 455                 460

Glu Arg Ile Gly Phe Val Ala Gly Glu Leu Thr Lys Ala Gly Ala Ala
465                 470                 475                 480

Val Ile Ala Ala Pro Thr Ala Pro Tyr Glu Arg Ser Arg Gln Ala Phe
                485                 490                 495

Lys Lys Gln Val Val Gly Ser Gly Gly Asn Tyr Phe Leu Val His
            500                 505                 510

Val Ala Thr Pro Leu Glu Trp Cys Glu Lys Val Asp Arg Arg Gly Leu
        515                 520                 525
```

```
Tyr Lys Ala Ala Arg Ala Gly Glu Ile Lys Asn Leu Thr Gly Val Asp
    530             535                 540

Asp Val Tyr Glu Ala Pro Glu Asp Ala Asp Leu Val Cys Asp Leu Arg
545             550                 555                 560

Asn Asp Thr Val Pro Glu Ile Val His Ser Ile Ile Met Ile Leu Glu
                565                 570                 575

Ser Gln Asn Leu Val
            580

<210> SEQ ID NO 59
<211> LENGTH: 1716
<212> TYPE: DNA
<213> ORGANISM: Cryptococcus neoformans
<220> FEATURE:
<221> NAME/KEY: CDS
<222> LOCATION: (1)..(1716)

<400> SEQUENCE: 59
```

| | | | | | | | | | | | | | | | | |
|---|---|---|---|---|---|---|---|---|---|---|---|---|---|---|---|---|
| atg | cac | atc | gca | tac | att | ctc | ggc | ctc | gta | ccc | ctc | gct | ttc | gcc | ggt | 48 |
| Met | His | Ile | Ala | Tyr | Ile | Leu | Gly | Leu | Val | Pro | Leu | Ala | Phe | Ala | Gly | |
| 1 | | | | 5 | | | | | 10 | | | | | 15 | | |
| gtc | atc | aag | cac | gac | cct | ccc | aag | ttc | cag | cct | att | cag | tct | acc | agg | 96 |
| Val | Ile | Lys | His | Asp | Pro | Pro | Lys | Phe | Gln | Pro | Ile | Gln | Ser | Thr | Arg | |
| | | | 20 | | | | | 25 | | | | | 30 | | | |
| att | gtg | cgg | ctg | cac | cca | aac | ggg | gac | aaa | agc | aag | tgc | gtt | gac | ctc | 144 |
| Ile | Val | Arg | Leu | His | Pro | Asn | Gly | Asp | Lys | Ser | Lys | Cys | Val | Asp | Leu | |
| | | 35 | | | | | 40 | | | | | 45 | | | | |
| ctg | ggt | aat | act | cgc | cag | gat | ggt | cag | ccc | gtg | cag | att | tgc | gac | tgc | 192 |
| Leu | Gly | Asn | Thr | Arg | Gln | Asp | Gly | Gln | Pro | Val | Gln | Ile | Cys | Asp | Cys | |
| 50 | | | | | 55 | | | | | 60 | | | | | | |
| gac | ggt | acc | ccg | gct | cag | gac | tgg | gtc | ctc | aat | gcc | ggc | cgc | ggt | cag | 240 |
| Asp | Gly | Thr | Pro | Ala | Gln | Asp | Trp | Val | Leu | Asn | Ala | Gly | Arg | Gly | Gln | |
| 65 | | | | | 70 | | | | | 75 | | | | | 80 | |
| acc | aag | gtc | cag | ctc | gcc | ggc | acc | agt | ttc | tgt | ctc | gat | gcc | acc | cac | 288 |
| Thr | Lys | Val | Gln | Leu | Ala | Gly | Thr | Ser | Phe | Cys | Leu | Asp | Ala | Thr | His | |
| | | | | 85 | | | | | 90 | | | | | 95 | | |
| cct | tac | gca | gcc | gac | ggg | acc | aac | atg | aag | atc | tgg | aag | tgc | ttg | gac | 336 |
| Pro | Tyr | Ala | Ala | Asp | Gly | Thr | Asn | Met | Lys | Ile | Trp | Lys | Cys | Leu | Asp | |
| | | | 100 | | | | | 105 | | | | | 110 | | | |
| gtc | caa | cag | caa | gac | tgg | tat | tgg | acg | agt | gat | aac | aga | atc | gtt | ctc | 384 |
| Val | Gln | Gln | Gln | Asp | Trp | Tyr | Trp | Thr | Ser | Asp | Asn | Arg | Ile | Val | Leu | |
| | | | | 115 | | | | | 120 | | | | | 125 | | |
| cgc | gac | cag | ggc | aag | tgc | ctc | gac | tgg | gcc | act | ggg | gat | cgg | tct | gat | 432 |
| Arg | Asp | Gln | Gly | Lys | Cys | Leu | Asp | Trp | Ala | Thr | Gly | Asp | Arg | Ser | Asp | |
| | 130 | | | | | 135 | | | | | 140 | | | | | |
| ttc | aac | cag | ctg | cag | gtc | tgg | cgg | tgc | agc | acg | gat | aac | aac | aat | cag | 480 |
| Phe | Asn | Gln | Leu | Gln | Val | Trp | Arg | Cys | Ser | Thr | Asp | Asn | Asn | Asn | Gln | |
| 145 | | | | | 150 | | | | | 155 | | | | | 160 | |
| gtc | tgg | aca | acg | gga | ccg | gac | tac | ggt | ggg | aac | cat | ggg | ggt | gat | gct | 528 |
| Val | Trp | Thr | Thr | Gly | Pro | Asp | Tyr | Gly | Gly | Asn | His | Gly | Gly | Asp | Ala | |
| | | | | 165 | | | | | 170 | | | | | 175 | | |
| ggt | ggg | aac | ccc | gga | ggt | aat | caa | ggc | gat | gat | tca | aga | ggc | aaa | acc | 576 |
| Gly | Gly | Asn | Pro | Gly | Gly | Asn | Gln | Gly | Asp | Asp | Ser | Arg | Gly | Lys | Thr | |
| | | | 180 | | | | | 185 | | | | | 190 | | | |
| aat | act | ggt | gga | aac | ccc | gga | ggt | aat | caa | ggt | ggt | gat | tca | gga | ggg | 624 |
| Asn | Thr | Gly | Gly | Asn | Pro | Gly | Gly | Asn | Gln | Gly | Gly | Asp | Ser | Gly | Gly | |
| | | 195 | | | | | 200 | | | | | 205 | | | | |
| aaa | acc | aat | cac | atc | att | ccc | gac | ccc | cca | ggg | cca | gac | ccc | aac | agc | 672 |
| Lys | Thr | Asn | His | Ile | Ile | Pro | Asp | Pro | Pro | Gly | Pro | Asp | Pro | Asn | Ser | |
| | | 210 | | | | | 215 | | | | | 220 | | | | |

```
gag ccc ctc aac ccc gcc ctt gaa gcc att gtt aac gtc acc gag gca      720
Glu Pro Leu Asn Pro Ala Leu Glu Ala Ile Val Asn Val Thr Glu Ala
225                 230                 235                 240 gct gga ccc tgg ccg ccc atg atc aac ttc gac ggc gat tac agc aat      768
Ala Gly Pro Trp Pro Pro Met Ile Asn Phe Asp Gly Asp Tyr Ser Asn
                245                 250                 255 gac gac gtg acc gta tcg gac caa gta ccg ttc gac tac tgt atc ggg      816
Asp Asp Val Thr Val Ser Asp Gln Val Pro Phe Asp Tyr Cys Ile Gly
            260                 265                 270 gag ggg tct ggt aac ccg acg gat gat gaa gga cag cag caa gga caa      864
Glu Gly Ser Gly Asn Pro Thr Asp Asp Glu Gly Gln Gln Gln Gly Gln
        275                 280                 285 aac ttc aca gca aat gta gct ggg ata ggg aga gac ttc tgc ctg gac      912
Asn Phe Thr Ala Asn Val Ala Gly Ile Gly Arg Asp Phe Cys Leu Asp
    290                 295                 300 aat ttt ggc aat cct gac att cgg aac acc att tct ttc gac aac aac      960
Asn Phe Gly Asn Pro Asp Ile Arg Asn Thr Ile Ser Phe Asp Asn Asn
305                 310                 315                 320 acc agc att ggg aac gga gcg gac act ggg cga gcc ctt cac aag cgg     1008
Thr Ser Ile Gly Asn Gly Ala Asp Thr Gly Arg Ala Leu His Lys Arg
                325                 330                 335 aca ttt gcg gat tca ggg gcg acg ggt acg ccc aac cgg tgg aga cga     1056
Thr Phe Ala Asp Ser Gly Ala Thr Gly Thr Pro Asn Arg Trp Arg Arg
            340                 345                 350 ggg tcg gtg att tcc att tgc gtc gag agg aac aac aat tat ctg gtt     1104
Gly Ser Val Ile Ser Ile Cys Val Glu Arg Asn Asn Asn Tyr Leu Val
        355                 360                 365 cca tat gcg tcc tcc ccc gtt ccc atc cga gca tcg gct atc gtc gca     1152
Pro Tyr Ala Ser Ser Pro Val Pro Ile Arg Ala Ser Ala Ile Val Ala
    370                 375                 380 tcc gcc atg gta cgt gca atc aac ttc tgg aac gca ggt ctg aac aag     1200
Ser Ala Met Val Arg Ala Ile Asn Phe Trp Asn Ala Gly Leu Asn Lys
385                 390                 395                 400 cga ttc gtc tcg ttc gag ttt gtg gag aac tgc aac gac gcc gtg ttc     1248
Arg Phe Val Ser Phe Glu Phe Val Glu Asn Cys Asn Asp Ala Val Phe
                405                 410                 415 cat act ctt gct gtt gac cag atc aag tct gcc aaa gag cct act gtg     1296
His Thr Leu Ala Val Asp Gln Ile Lys Ser Ala Lys Glu Pro Thr Val
            420                 425                 430 ctc gcg act gcc ccc ttc cct cct cgg ggt gaa gag ggt gct agg aac     1344
Leu Ala Thr Ala Pro Phe Pro Pro Arg Gly Glu Glu Gly Ala Arg Asn
        435                 440                 445 cgc aac atc ttc gtg tgg aat acg gct ttc gag gcc aac ttt cag aac     1392
Arg Asn Ile Phe Val Trp Asn Thr Ala Phe Glu Ala Asn Phe Gln Asn
    450                 455                 460 gtc ctt acc ttt atc atg tca cat gag ctg ggg cac act ctt ggc ctg     1440
Val Leu Thr Phe Ile Met Ser His Glu Leu Gly His Thr Leu Gly Leu
465                 470                 475                 480 gcg cat gag gac tgc aaa tcc aga gac caa cct tgc gaa gtt atc act     1488
Ala His Glu Asp Cys Lys Ser Arg Asp Gln Pro Cys Glu Val Ile Thr
                485                 490                 495 gac aag gtg gct ggg tca gtc gtg gaa agc cgt atc tcc ggc agc acc     1536
Asp Lys Val Ala Gly Ser Val Val Glu Ser Arg Ile Ser Gly Ser Thr
            500                 505                 510 aca cag ctg ttc aat ggc ccc acc ccg ctt gac ata gca ggg gcg aac     1584
Thr Gln Leu Phe Asn Gly Pro Thr Pro Leu Asp Ile Ala Gly Ala Asn
        515                 520                 525 gag tac tac tca ctt gca gcg gga ccc aac acc ccg gag aac atc gta     1632
Glu Tyr Tyr Ser Leu Ala Ala Gly Pro Asn Thr Pro Glu Asn Ile Val
    530                 535                 540
```

-continued

```
ctc tgg cct gcg acg agg ggt ccg ttt atc aac tac ccg ccg cta ccg    1680
Leu Trp Pro Ala Thr Arg Gly Pro Phe Ile Asn Tyr Pro Pro Leu Pro
545                 550                 555                 560 aaa tgc aag tgg ttc ctc ggt att tgc tat tac tag                    1716
Lys Cys Lys Trp Phe Leu Gly Ile Cys Tyr Tyr
                565                 570
```

<210> SEQ ID NO 60
<211> LENGTH: 571
<212> TYPE: PRT
<213> ORGANISM: Cryptococcus neoformans

<400> SEQUENCE: 60

```
Met His Ile Ala Tyr Ile Leu Gly Leu Val Pro Leu Ala Phe Ala Gly
1               5                   10                  15

Val Ile Lys His Asp Pro Pro Lys Phe Gln Pro Ile Gln Ser Thr Arg
            20                  25                  30

Ile Val Arg Leu His Pro Asn Gly Asp Lys Ser Lys Cys Val Asp Leu
        35                  40                  45

Leu Gly Asn Thr Arg Gln Asp Gly Gln Pro Val Gln Ile Cys Asp Cys
    50                  55                  60

Asp Gly Thr Pro Ala Gln Asp Trp Val Leu Asn Ala Gly Arg Gly Gln
65                  70                  75                  80

Thr Lys Val Gln Leu Ala Gly Thr Ser Phe Cys Leu Asp Ala Thr His
                85                  90                  95

Pro Tyr Ala Ala Asp Gly Thr Asn Met Lys Ile Trp Lys Cys Leu Asp
            100                 105                 110

Val Gln Gln Gln Asp Trp Tyr Trp Thr Ser Asp Asn Arg Ile Val Leu
        115                 120                 125

Arg Asp Gln Gly Lys Cys Leu Asp Trp Ala Thr Gly Asp Arg Ser Asp
    130                 135                 140

Phe Asn Gln Leu Gln Val Trp Arg Cys Ser Thr Asp Asn Asn Asn Gln
145                 150                 155                 160

Val Trp Thr Thr Gly Pro Asp Tyr Gly Gly Asn His Gly Gly Asp Ala
                165                 170                 175

Gly Gly Asn Pro Gly Gly Asn Gln Gly Asp Asp Ser Arg Gly Lys Thr
            180                 185                 190

Asn Thr Gly Gly Asn Pro Gly Gly Asn Gln Gly Gly Asp Ser Gly Gly
        195                 200                 205

Lys Thr Asn His Ile Ile Pro Asp Pro Pro Gly Pro Asp Pro Asn Ser
    210                 215                 220

Glu Pro Leu Asn Pro Ala Leu Glu Ala Ile Val Asn Val Thr Glu Ala
225                 230                 235                 240

Ala Gly Pro Trp Pro Pro Met Ile Asn Phe Asp Gly Asp Tyr Ser Asn
                245                 250                 255

Asp Asp Val Thr Val Ser Asp Gln Val Pro Phe Asp Tyr Cys Ile Gly
            260                 265                 270

Glu Gly Ser Gly Asn Pro Thr Asp Asp Glu Gly Gln Gln Gln Gly Gln
        275                 280                 285

Asn Phe Thr Ala Asn Val Ala Gly Ile Gly Arg Asp Phe Cys Leu Asp
    290                 295                 300

Asn Phe Gly Asn Pro Asp Ile Arg Asn Thr Ile Ser Phe Asp Asn Asn
305                 310                 315                 320

Thr Ser Ile Gly Asn Gly Ala Asp Thr Gly Arg Ala Leu His Lys Arg
                325                 330                 335
```

-continued

```
Thr Phe Ala Asp Ser Gly Ala Thr Gly Thr Pro Asn Arg Trp Arg Arg
                340                 345                 350

Gly Ser Val Ile Ser Ile Cys Val Glu Arg Asn Asn Asn Tyr Leu Val
            355                 360                 365

Pro Tyr Ala Ser Ser Pro Val Pro Ile Arg Ala Ser Ala Ile Val Ala
        370                 375                 380

Ser Ala Met Val Arg Ala Ile Asn Phe Trp Asn Ala Gly Leu Asn Lys
385                 390                 395                 400

Arg Phe Val Ser Phe Glu Val Glu Asn Cys Asn Asp Ala Val Phe
                405                 410                 415

His Thr Leu Ala Val Asp Gln Ile Lys Ser Ala Lys Glu Pro Thr Val
                420                 425                 430

Leu Ala Thr Ala Pro Phe Pro Pro Arg Gly Glu Glu Gly Ala Arg Asn
            435                 440                 445

Arg Asn Ile Phe Val Trp Asn Thr Ala Phe Glu Ala Asn Phe Gln Asn
        450                 455                 460

Val Leu Thr Phe Ile Met Ser His Glu Leu Gly His Thr Leu Gly Leu
465                 470                 475                 480

Ala His Glu Asp Cys Lys Ser Arg Asp Gln Pro Cys Glu Val Ile Thr
                485                 490                 495

Asp Lys Val Ala Gly Ser Val Val Glu Ser Arg Ile Ser Gly Ser Thr
            500                 505                 510

Thr Gln Leu Phe Asn Gly Pro Thr Pro Leu Asp Ile Ala Gly Ala Asn
        515                 520                 525

Glu Tyr Tyr Ser Leu Ala Ala Gly Pro Asn Thr Pro Glu Asn Ile Val
530                 535                 540

Leu Trp Pro Ala Thr Arg Gly Pro Phe Ile Asn Tyr Pro Pro Leu Pro
545                 550                 555                 560

Lys Cys Lys Trp Phe Leu Gly Ile Cys Tyr Tyr
                565                 570
```

<210> SEQ ID NO 61
<211> LENGTH: 1500
<212> TYPE: DNA
<213> ORGANISM: Cryptococcus neoformans
<220> FEATURE:
<221> NAME/KEY: CDS
<222> LOCATION: (1)..(1500)

<400> SEQUENCE: 61

```
atg ccg agc ctg acc cag acc aaa gat ctg gcg agc ctg ctg agc gat    48
Met Pro Ser Leu Thr Gln Thr Lys Asp Leu Ala Ser Leu Leu Ser Asp
1               5                   10                  15 gcg agc cat ttt aaa cag aaa ggc tat att aac ggc gaa tgg gtg agc    96
Ala Ser His Phe Lys Gln Lys Gly Tyr Ile Asn Gly Glu Trp Val Ser
                20                  25                  30 gcg agc gat ggc gcg acc ttt ccg ctg tat aac ccg gcg acc ggc gcg   144
Ala Ser Asp Gly Ala Thr Phe Pro Leu Tyr Asn Pro Ala Thr Gly Ala
            35                  40                  45 aaa ctg gcg gat atg ccg cat atg ccg cgc agc cag gtg gcg gaa gcg   192
Lys Leu Ala Asp Met Pro His Met Pro Arg Ser Gln Val Ala Glu Ala
        50                  55                  60 att aac gcg gcg aaa gcg gcg ttt ccg gcg tgg gcg gcg ctg acc gcg   240
Ile Asn Ala Ala Lys Ala Ala Phe Pro Ala Trp Ala Ala Leu Thr Ala
65                  70                  75                  80 tat cag cgc cag aac tat ctg ctg aaa ctg ttt aaa gaa atg gaa gaa   288
Tyr Gln Arg Gln Asn Tyr Leu Leu Lys Leu Phe Lys Glu Met Glu Glu
```

```
                        85                      90                      95
cat agc gaa gat ctg gcg att att ctg tgc acc gaa aac ggc aaa ccg         336
His Ser Glu Asp Leu Ala Ile Ile Leu Cys Thr Glu Asn Gly Lys Pro
            100                     105                     110 ctg gcg gaa agc cgc gtg gaa att agc tat ggc gcg agc ttt ctg acc         384
Leu Ala Glu Ser Arg Val Glu Ile Ser Tyr Gly Ala Ser Phe Leu Thr
            115                     120                     125 tgg aac gcg gcg gaa gcg ctg cgc acc tat ggc cag acc att ccg agc         432
Trp Asn Ala Ala Glu Ala Leu Arg Thr Tyr Gly Gln Thr Ile Pro Ser
130                     135                     140 ccg ttt ccg ggc acc cgc aac acc gtg att aaa cag ccg att ggc gtg         480
Pro Phe Pro Gly Thr Arg Asn Thr Val Ile Lys Gln Pro Ile Gly Val
145                     150                     155                     160 tgc ggc ctg att acc ccg tgg aac ttt ccg aac gcg atg att acc cgc         528
Cys Gly Leu Ile Thr Pro Trp Asn Phe Pro Asn Ala Met Ile Thr Arg
                165                     170                     175 aaa atg gcg ccg gcg ctg gcg gcg ggc tgc acc gtg gtg att aaa gcg         576
Lys Met Ala Pro Ala Leu Ala Ala Gly Cys Thr Val Val Ile Lys Ala
            180                     185                     190 ccg gcg gaa acc ccg ctg agc gcg ctg gcg atg tgc gtg ctg tgc gaa         624
Pro Ala Glu Thr Pro Leu Ser Ala Leu Ala Met Cys Val Leu Cys Glu
            195                     200                     205 cgc gtg ggc att ccg ccg ggc gtg gtg aac gtg gtg acc atg gat aaa         672
Arg Val Gly Ile Pro Pro Gly Val Val Asn Val Val Thr Met Asp Lys
            210                     215                     220 ggc cag cgc gaa atg gcg gcg ggc ctg gaa ctg tgc gaa aac gtg aaa         720
Gly Gln Arg Glu Met Ala Ala Gly Leu Glu Leu Cys Glu Asn Val Lys
225                     230                     235                     240 gtg agc aaa att agc ttt acc ggc agc acc ccg gtg ggc cgc ctg ctg         768
Val Ser Lys Ile Ser Phe Thr Gly Ser Thr Pro Val Gly Arg Leu Leu
                245                     250                     255 atg aaa cag agc agc ggc acc ctg aaa aaa ctg agc ttt gaa ctg ggc         816
Met Lys Gln Ser Ser Gly Thr Leu Lys Lys Leu Ser Phe Glu Leu Gly
            260                     265                     270 ggc aac gcg gcg ttt att att ttt gat gat gcg gat ctg gat ctg gcg         864
Gly Asn Ala Ala Phe Ile Ile Phe Asp Asp Ala Asp Leu Asp Leu Ala
            275                     280                     285 gtg aac ggc gtg att ctg agc aaa ttt cgc gcg gcg ggc cag acc tgc         912
Val Asn Gly Val Ile Leu Ser Lys Phe Arg Ala Ala Gly Gln Thr Cys
            290                     295                     300 att tgc gcg aac cgc att ttt gtg cat agc aaa att tat gat gat ttt         960
Ile Cys Ala Asn Arg Ile Phe Val His Ser Lys Ile Tyr Asp Asp Phe
305                     310                     315                     320 gcg cgc cgc ctg gtg gaa cgc gtg aaa gcg ttt aaa gtg ggc aac ggc        1008
Ala Arg Arg Leu Val Glu Arg Val Lys Ala Phe Lys Val Gly Asn Gly
                325                     330                     335 att gaa gaa ggc gtg acc att ggc ccg ctg gtg agc cag cgc ggc gtg        1056
Ile Glu Glu Gly Val Thr Ile Gly Pro Leu Val Ser Gln Arg Gly Val
            340                     345                     350 gaa aaa gtg gaa cgc cat gtg cag gat gcg gtg ggc ctg ggc gcg aaa        1104
Glu Lys Val Glu Arg His Val Gln Asp Ala Val Gly Leu Gly Ala Lys
            355                     360                     365 gtg ctg gtg ggc ggc aaa cgc att gat aaa ggc gaa ggc agc tgc ttt        1152
Val Leu Val Gly Gly Lys Arg Ile Asp Lys Gly Glu Gly Ser Cys Phe
370                     375                     380 tat gaa ccg acc gtg ctg gtg gat gtg ccg cgc cag tgc gcg gtg agc        1200
Tyr Glu Pro Thr Val Leu Val Asp Val Pro Arg Gln Cys Ala Val Ser
385                     390                     395                     400 aac gaa gaa acc ttt ggc ccg ctg gcg ccg ctg ttt aaa ttt gat gat        1248
```

-continued

```
                Asn Glu Glu Thr Phe Gly Pro Leu Ala Pro Leu Phe Lys Phe Asp Asp
                                405                 410                 415 gaa gat gat gtg gtg gaa cgc gcg aac agc agc gaa gtg ggc ctg gcg      1296
Glu Asp Asp Val Val Glu Arg Ala Asn Ser Ser Glu Val Gly Leu Ala
            420                 425                 430 gcg tat ttt ttt acc aaa gat ctg gcg cgc acc cat cgc gtg gcg gaa      1344
Ala Tyr Phe Phe Thr Lys Asp Leu Ala Arg Thr His Arg Val Ala Glu
        435                 440                 445 aaa ctg gaa gtg ggc atg gtg gcg gtg aac acc ggc gcg att gcg cag      1392
Lys Leu Glu Val Gly Met Val Ala Val Asn Thr Gly Ala Ile Ala Gln
    450                 455                 460 agc tgc gtg ccg ttt ggc ggc gtg aaa cag agc ggc ttt ggc cgc gaa      1440
Ser Cys Val Pro Phe Gly Gly Val Lys Gln Ser Gly Phe Gly Arg Glu
465                 470                 475                 480 ggc ggc ccg agc ggc att gat gaa ttt atg gtg gaa aaa ctg att acc      1488
Gly Gly Pro Ser Gly Ile Asp Glu Phe Met Val Glu Lys Leu Ile Thr
                485                 490                 495 att ggc ggc ctg                                                      1500
Ile Gly Gly Leu
        500

<210> SEQ ID NO 62
<211> LENGTH: 500
<212> TYPE: PRT
<213> ORGANISM: Cryptococcus neoformans

<400> SEQUENCE: 62

Met Pro Ser Leu Thr Gln Thr Lys Asp Leu Ala Ser Leu Leu Ser Asp
1               5                   10                  15

Ala Ser His Phe Lys Gln Lys Gly Tyr Ile Asn Gly Glu Trp Val Ser
            20                  25                  30

Ala Ser Asp Gly Ala Thr Phe Pro Leu Tyr Asn Pro Ala Thr Gly Ala
        35                  40                  45

Lys Leu Ala Asp Met Pro His Met Pro Arg Ser Gln Val Ala Glu Ala
    50                  55                  60

Ile Asn Ala Ala Lys Ala Ala Phe Pro Ala Trp Ala Ala Leu Thr Ala
65                  70                  75                  80

Tyr Gln Arg Gln Asn Tyr Leu Leu Lys Leu Phe Lys Glu Met Glu Glu
                85                  90                  95

His Ser Glu Asp Leu Ala Ile Ile Leu Cys Thr Glu Asn Gly Lys Pro
            100                 105                 110

Leu Ala Glu Ser Arg Val Glu Ile Ser Tyr Gly Ala Ser Phe Leu Thr
        115                 120                 125

Trp Asn Ala Ala Glu Ala Leu Arg Thr Tyr Gly Gln Thr Ile Pro Ser
    130                 135                 140

Pro Phe Pro Gly Thr Arg Asn Thr Val Ile Lys Gln Pro Ile Gly Val
145                 150                 155                 160

Cys Gly Leu Ile Thr Pro Trp Asn Phe Pro Asn Ala Met Ile Thr Arg
                165                 170                 175

Lys Met Ala Pro Ala Leu Ala Ala Gly Cys Thr Val Val Ile Lys Ala
            180                 185                 190

Pro Ala Glu Thr Pro Leu Ser Ala Leu Ala Met Cys Val Leu Cys Glu
        195                 200                 205

Arg Val Gly Ile Pro Pro Gly Val Val Asn Val Val Thr Met Asp Lys
    210                 215                 220

Gly Gln Arg Glu Met Ala Ala Gly Leu Glu Leu Cys Glu Asn Val Lys
225                 230                 235                 240
```

```
Val Ser Lys Ile Ser Phe Thr Gly Ser Thr Pro Val Gly Arg Leu Leu
                245                 250                 255

Met Lys Gln Ser Ser Gly Thr Leu Lys Lys Leu Ser Phe Glu Leu Gly
            260                 265                 270

Gly Asn Ala Ala Phe Ile Ile Phe Asp Asp Ala Asp Leu Asp Leu Ala
        275                 280                 285

Val Asn Gly Val Ile Leu Ser Lys Phe Arg Ala Gly Gln Thr Cys
    290                 295                 300

Ile Cys Ala Asn Arg Ile Phe Val His Ser Lys Ile Tyr Asp Asp Phe
305                 310                 315                 320

Ala Arg Arg Leu Val Glu Arg Val Lys Ala Phe Lys Val Gly Asn Gly
                325                 330                 335

Ile Glu Glu Gly Val Thr Ile Gly Pro Leu Val Ser Gln Arg Gly Val
            340                 345                 350

Glu Lys Val Glu Arg His Val Gln Asp Ala Val Gly Leu Gly Ala Lys
        355                 360                 365

Val Leu Val Gly Gly Lys Arg Ile Asp Lys Gly Glu Gly Ser Cys Phe
    370                 375                 380

Tyr Glu Pro Thr Val Leu Val Asp Val Pro Arg Gln Cys Ala Val Ser
385                 390                 395                 400

Asn Glu Glu Thr Phe Gly Pro Leu Ala Pro Leu Phe Lys Phe Asp Asp
                405                 410                 415

Glu Asp Asp Val Val Glu Arg Ala Asn Ser Ser Glu Val Gly Leu Ala
            420                 425                 430

Ala Tyr Phe Phe Thr Lys Asp Leu Ala Arg Thr His Arg Val Ala Glu
        435                 440                 445

Lys Leu Glu Val Gly Met Val Ala Val Asn Thr Gly Ala Ile Ala Gln
    450                 455                 460

Ser Cys Val Pro Phe Gly Gly Val Lys Gln Ser Gly Phe Gly Arg Glu
465                 470                 475                 480

Gly Gly Pro Ser Gly Ile Asp Glu Phe Met Val Glu Lys Leu Ile Thr
                485                 490                 495

Ile Gly Gly Leu
            500

<210> SEQ ID NO 63
<211> LENGTH: 1200
<212> TYPE: DNA
<213> ORGANISM: Cryptococcus neoformans
<220> FEATURE:
<221> NAME/KEY: CDS
<222> LOCATION: (1)..(1200)

<400> SEQUENCE: 63 atg tgc agc agc cat gcg acc gcg gtg gaa agc gtg agc ccg gcg ccg      48
Met Cys Ser Ser His Ala Thr Ala Val Glu Ser Val Ser Pro Ala Pro
1               5                   10                  15 cgc aaa agc cag tat gaa gtg aaa tat gat ccg gat ctg gtg ctg aaa      96
Arg Lys Ser Gln Tyr Glu Val Lys Tyr Asp Pro Asp Leu Val Leu Lys
                20                  25                  30 agc gcg gaa ttt aaa gaa ctg aaa cag ggc gat aaa gaa ctg gaa gat     144
Ser Ala Glu Phe Lys Glu Leu Lys Gln Gly Asp Lys Glu Leu Glu Asp
            35                  40                  45 ccg aaa gcg aac ctg gcg tgc gcg tat gat gaa aaa cat aac gtg aaa     192
Pro Lys Ala Asn Leu Ala Cys Ala Tyr Asp Glu Lys His Asn Val Lys
        50                  55                  60
```

-continued

```
atg att aac aaa ccg att ccg aaa gcg cgc cag gat gaa gtg gtg gtg      240
Met Ile Asn Lys Pro Ile Pro Lys Ala Arg Gln Asp Glu Val Val Val
65                  70                  75                  80 cat att aaa gcg acc ggc att tgc ggc agc gat gtg cat ttt tgg aaa      288
His Ile Lys Ala Thr Gly Ile Cys Gly Ser Asp Val His Phe Trp Lys
                85                  90                  95 cat ggc cag att ggc ccg acc atg att gtg acc gat acc tgc ggc gcg      336
His Gly Gln Ile Gly Pro Thr Met Ile Val Thr Asp Thr Cys Gly Ala
            100                 105                 110 ggc cat gaa agc gcg ggc gaa gtg gtg gaa gtg ggc ccg ggc gtg gaa      384
Gly His Glu Ser Ala Gly Glu Val Val Glu Val Gly Pro Gly Val Glu
        115                 120                 125 cag tgg aaa gtg ggc gat cgc gtg gcg att gaa tgc ggc gtg ccg tgc      432
Gln Trp Lys Val Gly Asp Arg Val Ala Ile Glu Cys Gly Val Pro Cys
    130                 135                 140 ggc cag gcg agc tgc ggc ccg tgc gtg acc ggc cgc tat aac gcg tgc      480
Gly Gln Ala Ser Cys Gly Pro Cys Val Thr Gly Arg Tyr Asn Ala Cys
145                 150                 155                 160 ccg cag gtg gtg ttt ttt agc acc ccg ccg tat cat ggc acc ctg acc      528
Pro Gln Val Val Phe Phe Ser Thr Pro Pro Tyr His Gly Thr Leu Thr
                165                 170                 175 cgc tat cat gcg cat ccg gcg agc tgg ctg cat cgc ctg ccg gat aac      576
Arg Tyr His Ala His Pro Ala Ser Trp Leu His Arg Leu Pro Asp Asn
            180                 185                 190 ctg agc tat gaa gaa ggc gcg ctg tgc gaa ccg ttt gcg gtg gcg ctg      624
Leu Ser Tyr Glu Glu Gly Ala Leu Cys Glu Pro Phe Ala Val Ala Leu
        195                 200                 205 gcg gcg ctg gaa cgc gcg ggc aac cgc ctg ggc gat ccg gtg ctg att      672
Ala Ala Leu Glu Arg Ala Gly Asn Arg Leu Gly Asp Pro Val Leu Ile
    210                 215                 220 tgc ggc gcg ggc ccg att ggc ctg gtg acc ctg ctg gcg agc cat gcg      720
Cys Gly Ala Gly Pro Ile Gly Leu Val Thr Leu Leu Ala Ser His Ala
225                 230                 235                 240 gcg ggc tgc acc ccg att gtg att acc gat ctg cag gcg agc cgc ctg      768
Ala Gly Cys Thr Pro Ile Val Ile Thr Asp Leu Gln Ala Ser Arg Leu
                245                 250                 255 gaa gtg gcg aaa aaa ctg att ccg acc gtg aaa acc gtg cag att gaa      816
Glu Val Ala Lys Lys Leu Ile Pro Thr Val Lys Thr Val Gln Ile Glu
            260                 265                 270 cgc agc tgg acc agc aaa gaa acc agc gaa gcg att aaa gaa gcg gcg      864
Arg Ser Trp Thr Ser Lys Glu Thr Ser Glu Ala Ile Lys Glu Ala Ala
        275                 280                 285 ggc acc ggc att cgc gtg gcg att gat gcg acc ggc ttt gaa agc agc      912
Gly Thr Gly Ile Arg Val Ala Ile Asp Ala Thr Gly Phe Glu Ser Ser
    290                 295                 300 att acc gcg gcg att tat agc gtg gtg ttt ggc ggc aaa gtg ttt gtg      960
Ile Thr Ala Ala Ile Tyr Ser Val Val Phe Gly Gly Lys Val Phe Val
305                 310                 315                 320 att ggc gcg ggc ccg agc gaa cag aaa tat ccg ttt ggc tat tgc agc     1008
Ile Gly Ala Gly Pro Ser Glu Gln Lys Tyr Pro Phe Gly Tyr Cys Ser
                325                 330                 335 gcg aac gaa att gat ctg cag ttt cag tat cgc tat gcg cat cag tat     1056
Ala Asn Glu Ile Asp Leu Gln Phe Gln Tyr Arg Tyr Ala His Gln Tyr
            340                 345                 350 ccg aaa gcg ctg cgc att gtg agc ggc ggc ctg att aac ctg aaa ccg     1104
Pro Lys Ala Leu Arg Ile Val Ser Gly Gly Leu Ile Asn Leu Lys Pro
        355                 360                 365 ctg ctg acc cat acc ttt ccg ctg aac aaa gcg gtg gaa gcg ttt cat     1152
Leu Leu Thr His Thr Phe Pro Leu Asn Lys Ala Val Glu Ala Phe His
    370                 375                 380
```

```
gtg gcg gcg gat ccg acc aaa ggc gcg att aaa gtg cag att att gat      1200
Val Ala Ala Asp Pro Thr Lys Gly Ala Ile Lys Val Gln Ile Ile Asp
385                 390                 395                 400

<210> SEQ ID NO 64
<211> LENGTH: 400
<212> TYPE: PRT
<213> ORGANISM: Cryptococcus neoformans

<400> SEQUENCE: 64

Met Cys Ser Ser His Ala Thr Ala Val Glu Ser Val Ser Pro Ala Pro
1               5                   10                  15

Arg Lys Ser Gln Tyr Glu Val Lys Tyr Asp Pro Asp Leu Val Leu Lys
            20                  25                  30

Ser Ala Glu Phe Lys Glu Leu Lys Gln Gly Asp Lys Glu Leu Glu Asp
        35                  40                  45

Pro Lys Ala Asn Leu Ala Cys Ala Tyr Asp Glu Lys His Asn Val Lys
    50                  55                  60

Met Ile Asn Lys Pro Ile Pro Lys Ala Arg Gln Asp Glu Val Val Val
65                  70                  75                  80

His Ile Lys Ala Thr Gly Ile Cys Gly Ser Asp Val His Phe Trp Lys
                85                  90                  95

His Gly Gln Ile Gly Pro Thr Met Ile Val Thr Asp Thr Cys Gly Ala
            100                 105                 110

Gly His Glu Ser Ala Gly Glu Val Val Glu Val Gly Pro Gly Val Glu
        115                 120                 125

Gln Trp Lys Val Gly Asp Arg Val Ala Ile Glu Cys Gly Val Pro Cys
    130                 135                 140

Gly Gln Ala Ser Cys Gly Pro Cys Val Thr Gly Arg Tyr Asn Ala Cys
145                 150                 155                 160

Pro Gln Val Val Phe Phe Ser Thr Pro Pro Tyr His Gly Thr Leu Thr
                165                 170                 175

Arg Tyr His Ala His Pro Ala Ser Trp Leu His Arg Leu Pro Asp Asn
            180                 185                 190

Leu Ser Tyr Glu Glu Gly Ala Leu Cys Glu Pro Phe Ala Val Ala Leu
        195                 200                 205

Ala Ala Leu Glu Arg Ala Gly Asn Arg Leu Gly Asp Pro Val Leu Ile
    210                 215                 220

Cys Gly Ala Gly Pro Ile Gly Leu Val Thr Leu Leu Ala Ser His Ala
225                 230                 235                 240

Ala Gly Cys Thr Pro Ile Val Ile Thr Asp Leu Gln Ala Ser Arg Leu
                245                 250                 255

Glu Val Ala Lys Lys Leu Ile Pro Thr Val Lys Thr Val Gln Ile Glu
            260                 265                 270

Arg Ser Trp Thr Ser Lys Glu Thr Ser Glu Ala Ile Lys Glu Ala Ala
        275                 280                 285

Gly Thr Gly Ile Arg Val Ala Ile Asp Ala Thr Gly Phe Glu Ser Ser
    290                 295                 300

Ile Thr Ala Ala Ile Tyr Ser Val Val Phe Gly Gly Lys Val Phe Val
305                 310                 315                 320

Ile Gly Ala Gly Pro Ser Glu Gln Lys Tyr Pro Phe Gly Tyr Cys Ser
                325                 330                 335

Ala Asn Glu Ile Asp Leu Gln Phe Gln Tyr Arg Tyr Ala His Gln Tyr
            340                 345                 350
```

```
Pro Lys Ala Leu Arg Ile Val Ser Gly Gly Leu Ile Asn Leu Lys Pro
            355                 360                 365

Leu Leu Thr His Thr Phe Pro Leu Asn Lys Ala Val Glu Ala Phe His
    370                 375                 380

Val Ala Ala Asp Pro Thr Lys Gly Ala Ile Lys Val Gln Ile Ile Asp
385                 390                 395                 400

<210> SEQ ID NO 65
<211> LENGTH: 1689
<212> TYPE: DNA
<213> ORGANISM: Cryptococcus neoformans
<220> FEATURE:
<221> NAME/KEY: CDS
<222> LOCATION: (1)..(1689)

<400> SEQUENCE: 65 atg gtg tgc gtg att agc gat ccg gat tgg tgg cgc cag gcg gtg gtg      48
Met Val Cys Val Ile Ser Asp Pro Asp Trp Trp Arg Gln Ala Val Val
1               5                   10                  15 tat cag att tat ccg cgc agc ttt gcg gat gcg aac ggc gat ggc att      96
Tyr Gln Ile Tyr Pro Arg Ser Phe Ala Asp Ala Asn Gly Asp Gly Ile
            20                  25                  30 ggc gat ctg aaa ggc att acc gcg cgc gtg ccg tat ctg aaa gcg ctg     144
Gly Asp Leu Lys Gly Ile Thr Ala Arg Val Pro Tyr Leu Lys Ala Leu
        35                  40                  45 ggc gtg gat gcg att tgg ctg agc ccg ttt tat ccg agc gcg ctg cgc     192
Gly Val Asp Ala Ile Trp Leu Ser Pro Phe Tyr Pro Ser Ala Leu Arg
    50                  55                  60 gat ggc ggc tat gat gtg gcg gat tat cgc gat gtg gat ccg aaa att     240
Asp Gly Gly Tyr Asp Val Ala Asp Tyr Arg Asp Val Asp Pro Lys Ile
65                  70                  75                  80 ggc acc ctg gaa gaa ttt gat gaa atg acc gcg gcg ttt cag aaa gtg     288
Gly Thr Leu Glu Glu Phe Asp Glu Met Thr Ala Ala Phe Gln Lys Val
                85                  90                  95 ggc att cgc gtg att gtg gat att gtg ccg aac cat agc agc gat gat     336
Gly Ile Arg Val Ile Val Asp Ile Val Pro Asn His Ser Ser Asp Asp
            100                 105                 110 cat gaa tgg ttt cag gcg gcg ctg aaa gcg ggc aaa ggc agc ccg gaa     384
His Glu Trp Phe Gln Ala Ala Leu Lys Ala Gly Lys Gly Ser Pro Glu
        115                 120                 125 cgc gaa cgc tat att ttt cgc gat ggc ctg ggc ccg aac aaa gat cag     432
Arg Glu Arg Tyr Ile Phe Arg Asp Gly Leu Gly Pro Asn Lys Asp Gln
    130                 135                 140 ccg ccg acc gat tgg att tgc agc ttt ggc ggc agc gcg tgg agc ccg     480
Pro Pro Thr Asp Trp Ile Cys Ser Phe Gly Gly Ser Ala Trp Ser Pro
145                 150                 155                 160 agc ggc atg aac gat ggc cag tgg tat ttt cat tgg ttt gat agc agc     528
Ser Gly Met Asn Asp Gly Gln Trp Tyr Phe His Trp Phe Asp Ser Ser
                165                 170                 175 cag ccg gat tgg aac tgg gaa aac ccg gat gtg aaa gcg gat ttt ctg     576
Gln Pro Asp Trp Asn Trp Glu Asn Pro Asp Val Lys Ala Asp Phe Leu
            180                 185                 190 aaa acc ctg aaa ttt tgg ggc gat cgc ggc gtg agc ggc ttt cgc att     624
Lys Thr Leu Lys Phe Trp Gly Asp Arg Gly Val Ser Gly Phe Arg Ile
        195                 200                 205 gat gtg gcg cat ggc ctg gcg aaa gat atg agc gaa ccg ctg ccg aac     672
Asp Val Ala His Gly Leu Ala Lys Asp Met Ser Glu Pro Leu Pro Asn
    210                 215                 220 tgg gaa cag ctg acc aaa ctg acc cat cag aaa ctg acc aac ggc aac     720
Trp Glu Gln Leu Thr Lys Leu Thr His Gln Lys Leu Thr Asn Gly Asn
225                 230                 235                 240
```

```
agc gaa ctg gat cat ccg ctg ctg gat cgc aaa gaa gtg cat gat att    768
Ser Glu Leu Asp His Pro Leu Leu Asp Arg Lys Glu Val His Asp Ile
            245                 250                 255 tat cgc agc tgg cgc gaa gtg ttt aac cag ttt aac ccg ccg ctg atg    816
Tyr Arg Ser Trp Arg Glu Val Phe Asn Gln Phe Asn Pro Pro Leu Met
        260                 265                 270 gcg gtg gcg gaa gcg tgg gtg gcg ccg gat cag aaa ccg ctg tat gcg    864
Ala Val Ala Glu Ala Trp Val Ala Pro Asp Gln Lys Pro Leu Tyr Ala
    275                 280                 285 agc agc gaa ggc ctg ggc cag acc ttt agc ttt gat att ctg ctg tgc    912
Ser Ser Glu Gly Leu Gly Gln Thr Phe Ser Phe Asp Ile Leu Leu Cys
290                 295                 300 aac ttt gat gcg gaa gaa tat cgc cag tgc att aaa agc agc ctg gcg    960
Asn Phe Asp Ala Glu Glu Tyr Arg Gln Cys Ile Lys Ser Ser Leu Ala
305                 310                 315                 320 ggc agc aaa aaa agc gat agc acc acc acc tgg gtg ctg agc aac cat   1008
Gly Ser Lys Lys Ser Asp Ser Thr Thr Thr Trp Val Leu Ser Asn His
                325                 330                 335 gat gtg atg cgc cat ccg acc cgc ttt ggc ctg ccg aac gtg ccg aac   1056
Asp Val Met Arg His Pro Thr Arg Phe Gly Leu Pro Asn Val Pro Asn
            340                 345                 350 gcg aac cat gcg atg acc acc gat acc tat aac aaa ttt ctg aaa acc   1104
Ala Asn His Ala Met Thr Thr Asp Thr Tyr Asn Lys Phe Leu Lys Thr
        355                 360                 365 aaa ctg acc gat ccg aaa gtg gat att gaa cag ggc ctg cgc cgc gcg   1152
Lys Leu Thr Asp Pro Lys Val Asp Ile Glu Gln Gly Leu Arg Arg Ala
    370                 375                 380 aaa gcg gcg acc ctg atg att ctg gcg ctg ccg ggc agc acc tat ctg   1200
Lys Ala Ala Thr Leu Met Ile Leu Ala Leu Pro Gly Ser Thr Tyr Leu
385                 390                 395                 400 tat cag ggc gaa gaa ctg ggc ctg cag gaa gtg gtg gaa att ccg gat   1248
Tyr Gln Gly Glu Glu Leu Gly Leu Gln Glu Val Val Glu Ile Pro Asp
                405                 410                 415 gaa gaa cgc cag gat ccg att ttt att cgc acc aaa ggc gaa gaa gtg   1296
Glu Glu Arg Gln Asp Pro Ile Phe Ile Arg Thr Lys Gly Glu Glu Val
            420                 425                 430 ggc cgc gat ggc tgc cgc gtg ccg att ccg tgg gtg gcg gat gaa aaa   1344
Gly Arg Asp Gly Cys Arg Val Pro Ile Pro Trp Val Ala Asp Glu Lys
        435                 440                 445 aac ttt ggc tat ggc ccg ggc aaa cgc gcg cat ctg ccg cag ccg gcg   1392
Asn Phe Gly Tyr Gly Pro Gly Lys Arg Ala His Leu Pro Gln Pro Ala
    450                 455                 460 tgg ttt aaa gat tat gcg gtg gat gtg gaa gaa aaa gat gcg aac agc   1440
Trp Phe Lys Asp Tyr Ala Val Asp Val Glu Glu Lys Asp Ala Asn Ser
465                 470                 475                 480 gtg ctg agc ctg tat cgc cgc gcg ctg ggc ctg cgc aaa ggc ctg cag   1488
Val Leu Ser Leu Tyr Arg Arg Ala Leu Gly Leu Arg Lys Gly Leu Gln
                485                 490                 495 agc gcg gaa gaa ctg gaa tgg gtg gaa aac ccg aac aaa gaa gtg ctg   1536
Ser Ala Glu Glu Leu Glu Trp Val Glu Asn Pro Asn Lys Glu Val Leu
            500                 505                 510 cat ttt cgc cgc ccg ggc ggc tgg gaa gtg gtg gtg aac att ggc aaa   1584
His Phe Arg Arg Pro Gly Gly Trp Glu Val Val Val Asn Ile Gly Lys
        515                 520                 525 gat agc gtg gat ctg ccg aaa ggc agc gtg ctg att agc agc agc aac   1632
Asp Ser Val Asp Leu Pro Lys Gly Ser Val Leu Ile Ser Ser Ser Asn
    530                 535                 540 aac gcg ctg aaa ggc ggc agc att ccg ggc gaa acc acc gtg tgg ctg   1680
Asn Ala Leu Lys Gly Gly Ser Ile Pro Gly Glu Thr Thr Val Trp Leu
```

```
                545                 550                 555                 560
aaa agc gcg                                                                         1689
Lys Ser Ala
```

<210> SEQ ID NO 66
<211> LENGTH: 563
<212> TYPE: PRT
<213> ORGANISM: Cryptococcus neoformans

<400> SEQUENCE: 66

```
Met Val Cys Val Ile Ser Asp Pro Asp Trp Arg Gln Ala Val Val
1               5                   10                  15

Tyr Gln Ile Tyr Pro Arg Ser Phe Ala Asp Ala Asn Gly Asp Gly Ile
                20                  25                  30

Gly Asp Leu Lys Gly Ile Thr Ala Arg Val Pro Tyr Leu Lys Ala Leu
            35                  40                  45

Gly Val Asp Ala Ile Trp Leu Ser Pro Phe Tyr Pro Ser Ala Leu Arg
    50                  55                  60

Asp Gly Gly Tyr Asp Val Ala Asp Tyr Arg Asp Val Asp Pro Lys Ile
65                  70                  75                  80

Gly Thr Leu Glu Glu Phe Asp Glu Met Thr Ala Ala Phe Gln Lys Val
                85                  90                  95

Gly Ile Arg Val Ile Val Asp Ile Val Pro Asn His Ser Ser Asp Asp
            100                 105                 110

His Glu Trp Phe Gln Ala Ala Leu Lys Ala Gly Lys Gly Ser Pro Glu
        115                 120                 125

Arg Glu Arg Tyr Ile Phe Arg Asp Gly Leu Gly Pro Asn Lys Asp Gln
    130                 135                 140

Pro Pro Thr Asp Trp Ile Cys Ser Phe Gly Gly Ser Ala Trp Ser Pro
145                 150                 155                 160

Ser Gly Met Asn Asp Gly Gln Trp Tyr Phe His Trp Phe Asp Ser Ser
                165                 170                 175

Gln Pro Asp Trp Asn Trp Glu Asn Pro Asp Val Lys Ala Asp Phe Leu
            180                 185                 190

Lys Thr Leu Lys Phe Trp Gly Asp Arg Gly Val Ser Gly Phe Arg Ile
        195                 200                 205

Asp Val Ala His Gly Leu Ala Lys Asp Met Ser Glu Pro Leu Pro Asn
    210                 215                 220

Trp Glu Gln Leu Thr Lys Leu Thr His Gln Lys Leu Thr Asn Gly Asn
225                 230                 235                 240

Ser Glu Leu Asp His Pro Leu Leu Asp Arg Lys Glu Val His Asp Ile
                245                 250                 255

Tyr Arg Ser Trp Arg Glu Val Phe Asn Gln Phe Asn Pro Pro Leu Met
            260                 265                 270

Ala Val Ala Glu Ala Trp Val Ala Pro Asp Gln Lys Pro Leu Tyr Ala
        275                 280                 285

Ser Ser Glu Gly Leu Gly Gln Thr Phe Ser Phe Asp Ile Leu Leu Cys
    290                 295                 300

Asn Phe Asp Ala Glu Glu Tyr Arg Gln Cys Ile Lys Ser Ser Leu Ala
305                 310                 315                 320

Gly Ser Lys Lys Ser Asp Ser Thr Thr Thr Trp Val Leu Ser Asn His
                325                 330                 335

Asp Val Met Arg His Pro Thr Arg Phe Gly Leu Pro Asn Val Pro Asn
            340                 345                 350
```

| | | | | | | | | | | | | | |
|---|---|---|---|---|---|---|---|---|---|---|---|---|---|
|Ala|Asn|His|Ala|Met|Thr|Thr|Asp|Thr|Tyr|Asn|Lys|Phe|Leu|Lys|Thr
| | | |355| | | |360| | | |365| | |

Lys Leu Thr Asp Pro Lys Val Asp Ile Glu Gln Gly Leu Arg Arg Ala
    370             375             380

Lys Ala Ala Thr Leu Met Ile Leu Ala Leu Pro Gly Ser Thr Tyr Leu
385             390             395             400

Tyr Gln Gly Glu Glu Leu Gly Leu Gln Glu Val Val Glu Ile Pro Asp
            405             410             415

Glu Glu Arg Gln Asp Pro Ile Phe Ile Arg Thr Lys Gly Glu Val
        420             425             430

Gly Arg Asp Gly Cys Arg Val Pro Ile Pro Trp Val Ala Asp Glu Lys
            435             440             445

Asn Phe Gly Tyr Gly Pro Gly Lys Arg Ala His Leu Pro Gln Pro Ala
        450             455             460

Trp Phe Lys Asp Tyr Ala Val Asp Val Glu Glu Lys Asp Ala Asn Ser
465             470             475             480

Val Leu Ser Leu Tyr Arg Arg Ala Leu Gly Leu Arg Lys Gly Leu Gln
            485             490             495

Ser Ala Glu Glu Leu Glu Trp Val Glu Asn Pro Asn Lys Glu Val Leu
        500             505             510

His Phe Arg Arg Pro Gly Gly Trp Glu Val Val Val Asn Ile Gly Lys
        515             520             525

Asp Ser Val Asp Leu Pro Lys Gly Ser Val Leu Ile Ser Ser Ser Asn
        530             535             540

Asn Ala Leu Lys Gly Gly Ser Ile Pro Gly Glu Thr Thr Val Trp Leu
545             550             555             560

Lys Ser Ala

<210> SEQ ID NO 67
<211> LENGTH: 729
<212> TYPE: DNA
<213> ORGANISM: Cryptococcus neoformans
<220> FEATURE:
<221> NAME/KEY: CDS
<222> LOCATION: (1)..(729)

<400> SEQUENCE: 67

```
atg ccg agc gtg gtg ttt gat gtg gtg ggc acc tgc ttt agc tat gat     48
Met Pro Ser Val Val Phe Asp Val Val Gly Thr Cys Phe Ser Tyr Asp
1               5                   10                  15 aac ggc gcg gaa gcg ctg cag gcg cgc ctg ggc ccg aaa ctg gcg aaa     96
Asn Gly Ala Glu Ala Leu Gln Ala Arg Leu Gly Pro Lys Leu Ala Lys
            20                  25                  30 tat ggc att ccg agc aaa ctg ctg ttt tat agc tgg gtg tgc agc acc    144
Tyr Gly Ile Pro Ser Lys Leu Leu Phe Tyr Ser Trp Val Cys Ser Thr
        35                  40                  45 gaa cgc gat tat agc tat ctg agc cag att aaa cag tat aaa gcg ttt    192
Glu Arg Asp Tyr Ser Tyr Leu Ser Gln Ile Lys Gln Tyr Lys Ala Phe
    50                  55                  60 ttt gcg att ctg agc aac acc ctg acc cgc gtg ctg ttt cag gcg ggc    240
Phe Ala Ile Leu Ser Asn Thr Leu Thr Arg Val Leu Phe Gln Ala Gly
65                  70                  75                  80 gtg ccg gtg gaa gcg ctg gat gat ttt ttt acc gcg gat gat gtg gat    288
Val Pro Val Glu Ala Leu Asp Asp Phe Phe Thr Ala Asp Asp Val Asp
                85                  90                  95 tat att atg aac gaa tat aaa aaa ctg aaa gcg cgc ccg ggc ctg gcg    336
Tyr Ile Met Asn Glu Tyr Lys Lys Leu Lys Ala Arg Pro Gly Leu Ala
            100                 105                 110
```

```
gaa atg atg cag acc ctg cgc gat ggc ggc ttt gaa gtg tgg tgc tgc      384
Glu Met Met Gln Thr Leu Arg Asp Gly Gly Phe Glu Val Trp Cys Cys
        115                 120                 125 agc gat gcg aac gtg gat cgc gtg aaa ggc tat ttt gat aac gcg ggc      432
Ser Asp Ala Asn Val Asp Arg Val Lys Gly Tyr Phe Asp Asn Ala Gly
130                 135                 140 gtg gaa atg ccg ctg gat cat att ctg agc gcg gat atg gtg aaa gcg      480
Val Glu Met Pro Leu Asp His Ile Leu Ser Ala Asp Met Val Lys Ala
145                 150                 155                 160 ggc aaa ccg gaa gcg gcg gtg tat aaa ttt gcg cgc gaa aaa gcg ggc      528
Gly Lys Pro Glu Ala Ala Val Tyr Lys Phe Ala Arg Glu Lys Ala Gly
            165                 170                 175 agc gat cag ccg ggc gaa gtg agc gtg ttt gcg gcg agc cat gcg tgg      576
Ser Asp Gln Pro Gly Glu Val Ser Val Phe Ala Ala Ser His Ala Trp
        180                 185                 190 gat tgc gcg gcg gcg aaa gcg gcg ggc ttt ctg acc gcg tat acc acc      624
Asp Cys Ala Ala Ala Lys Ala Ala Gly Phe Leu Thr Ala Tyr Thr Thr
            195                 200                 205 acc tat gaa tat gat gaa tgc gaa gtg att ttt ggc aaa agc gat ctg      672
Thr Tyr Glu Tyr Asp Glu Cys Glu Val Ile Phe Gly Lys Ser Asp Leu
        210                 215                 220 gtg gcg ccg gat ctg gtg agc ctg ggc aaa ggc att gtg gaa aaa tgg      720
Val Ala Pro Asp Leu Val Ser Leu Gly Lys Gly Ile Val Glu Lys Trp
225                 230                 235                 240 ggc aaa aaa                                                          729
Gly Lys Lys <210> SEQ ID NO 68
<211> LENGTH: 243
<212> TYPE: PRT
<213> ORGANISM: Cryptococcus neoformans

<400> SEQUENCE: 68

Met Pro Ser Val Val Phe Asp Val Val Gly Thr Cys Phe Ser Tyr Asp
1               5                   10                  15

Asn Gly Ala Glu Ala Leu Gln Ala Arg Leu Gly Pro Lys Leu Ala Lys
            20                  25                  30

Tyr Gly Ile Pro Ser Lys Leu Leu Phe Tyr Ser Trp Val Cys Ser Thr
        35                  40                  45

Glu Arg Asp Tyr Ser Tyr Leu Ser Gln Ile Lys Gln Tyr Lys Ala Phe
    50                  55                  60

Phe Ala Ile Leu Ser Asn Thr Leu Thr Arg Val Leu Phe Gln Ala Gly
65                  70                  75                  80

Val Pro Val Glu Ala Leu Asp Asp Phe Phe Thr Ala Asp Asp Val Asp
                85                  90                  95

Tyr Ile Met Asn Glu Tyr Lys Lys Leu Lys Ala Arg Pro Gly Leu Ala
            100                 105                 110

Glu Met Met Gln Thr Leu Arg Asp Gly Gly Phe Glu Val Trp Cys Cys
        115                 120                 125

Ser Asp Ala Asn Val Asp Arg Val Lys Gly Tyr Phe Asp Asn Ala Gly
    130                 135                 140

Val Glu Met Pro Leu Asp His Ile Leu Ser Ala Asp Met Val Lys Ala
145                 150                 155                 160

Gly Lys Pro Glu Ala Ala Val Tyr Lys Phe Ala Arg Glu Lys Ala Gly
                165                 170                 175

Ser Asp Gln Pro Gly Glu Val Ser Val Phe Ala Ala Ser His Ala Trp
            180                 185                 190
```

```
Asp Cys Ala Ala Ala Lys Ala Ala Gly Phe Leu Thr Ala Tyr Thr Thr
        195                 200                 205

Thr Tyr Glu Tyr Asp Glu Cys Glu Val Ile Phe Gly Lys Ser Asp Leu
    210                 215                 220

Val Ala Pro Asp Leu Val Ser Leu Gly Lys Gly Ile Val Glu Lys Trp
225                 230                 235                 240

Gly Lys Lys
```